United States Patent
Pearlman et al.

(10) Patent No.: US 9,650,653 B2
(45) Date of Patent: May 16, 2017

(54) BIOCONVERSION PROCESS FOR PRODUCING NYLON-7, NYLON-7,7 AND POLYESTERS

(75) Inventors: Paul S. Pearlman, Thornton, PA (US); Changlin Chen, Cleveland (GB); Adriana L. Botes, Cleveland (GB); Alex Van Eck Conradie, Cleveland (GB); Benjamin D. Herzog, Wichita, KS (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 7 days.

(21) Appl. No.: 14/130,117

(22) PCT Filed: Jun. 29, 2012

(86) PCT No.: PCT/US2012/044984
§ 371 (c)(1),
(2), (4) Date: Apr. 3, 2014

(87) PCT Pub. No.: WO2013/003744
PCT Pub. Date: Jan. 3, 2013

(65) Prior Publication Data
US 2014/0242655 A1    Aug. 28, 2014

Related U.S. Application Data

(60) Provisional application No. 61/503,043, filed on Jun. 30, 2011, provisional application No. 61/578,265, (Continued)

(51) Int. Cl.
*C12P 7/44* (2006.01)
*C12P 13/04* (2006.01)
(Continued)

(52) U.S. Cl.
CPC ........ *C12P 7/44* (2013.01); *B29B 9/16* (2013.01); *C08G 69/14* (2013.01); *C08G 69/16* (2013.01);
(Continued)

(58) Field of Classification Search
CPC .... C13P 7/44; C12Y 102/0105; C12P 13/001; C12P 7/40; C12N 9/001
See application file for complete search history.

(56) References Cited

U.S. PATENT DOCUMENTS 2,439,513 A    4/1948 Hamblet et al.
2,557,282 A    6/1951 Hamblet et al.
(Continued)

FOREIGN PATENT DOCUMENTS

EP       2647718      10/2013
WO   WO 2008/006037    1/2008
(Continued)

OTHER PUBLICATIONS

White et al., Carboxylic acid reductase: a new tungsten enzyme catalyses the reduction of non-activated carboxylic acids to aldehydes, Eur J Biochem. (1989), vol. 184(1), pp. 89-96.*
(Continued)

*Primary Examiner* — Alexander Kim
(74) *Attorney, Agent, or Firm* — Finnegan, Henderson, Farabow, Garrett & Dunner, LLP; Carla A. Mouta-Bellum

(57) ABSTRACT

Embodiments of the present invention relate to methods for the biosynthesis of di- or trifunctional C7 alkanes in the presence of isolated enzymes or in the presence of a recombinant host cell expressing those enzymes. The di- or trifunctional C7 alkanes are useful as intermediates in the production of nylon-7, nylon-7,x, nylon-x,7, and polyesters.

42 Claims, 39 Drawing Sheets

Related U.S. Application Data filed on Dec. 21, 2011, provisional application No. 61/578,272, filed on Dec. 21, 2011, provisional application No. 61/578,289, filed on Dec. 21, 2011.

(51) Int. Cl.

| | | |
|---|---|---|
| *C12P 17/10* | (2006.01) | |
| *C12P 7/42* | (2006.01) | |
| *C12P 13/00* | (2006.01) | |
| *C12P 13/02* | (2006.01) | |
| *C08G 69/16* | (2006.01) | |
| *C08G 69/14* | (2006.01) | |
| *C08G 69/26* | (2006.01) | |
| *C08G 69/28* | (2006.01) | |
| *B29B 9/16* | (2006.01) | |
| *C12N 9/02* | (2006.01) | |
| *C12N 9/04* | (2006.01) | |
| *C12N 9/10* | (2006.01) | |
| *C12N 9/16* | (2006.01) | |
| *C12N 9/88* | (2006.01) | |
| *C12N 9/00* | (2006.01) | |
| *C12P 7/40* | (2006.01) | |
| *C12P 7/62* | (2006.01) | |

(52) U.S. Cl.
CPC ............ *C08G 69/26* (2013.01); *C08G 69/28* (2013.01); *C12N 9/001* (2013.01); *C12N 9/0006* (2013.01); *C12N 9/0008* (2013.01); *C12N 9/1025* (2013.01); *C12N 9/1096* (2013.01); *C12N 9/13* (2013.01); *C12N 9/16* (2013.01); *C12N 9/88* (2013.01); *C12N 9/93* (2013.01); *C12P 7/40* (2013.01); *C12P 7/42* (2013.01); *C12P 7/62* (2013.01); *C12P 13/001* (2013.01); *C12P 13/005* (2013.01); *C12P 13/02* (2013.01); *C12P 13/04* (2013.01); *C12P 17/10* (2013.01); *C12Y 102/0105* (2013.01)

(56) References Cited

U.S. PATENT DOCUMENTS

| | | | |
|---|---|---|---|
| 2,791,566 | A | 5/1957 | Jeffers |
| 2,840,607 | A | 6/1958 | Attane, Jr. et al. |
| 2,971,010 | A | 2/1961 | Gilby, Jr. et al. |
| 3,023,238 | A | 2/1962 | Chapman et al. |
| 3,338,959 | A | 8/1967 | Sciance et al. |
| 3,365,490 | A | 1/1968 | Arthur et al. |
| 3,515,751 | A | 6/1970 | Oberster |
| 3,719,561 | A | 3/1973 | Tanaka et al. |
| 4,058,555 | A | 11/1977 | Mims |
| 6,255,451 | B1 | 7/2001 | Koch et al. |
| 6,372,939 | B1 | 4/2002 | Bunnel et al. |
| 8,088,607 | B2 | 1/2012 | Buggard et al. |
| 8,361,769 | B1 | 1/2013 | Koch et al. |
| 2004/0054235 | A1 | 3/2004 | Fodor et al. |
| 2010/0035309 | A1 | 2/2010 | Havemen et al. |
| 2010/0151536 | A1 | 6/2010 | Baynes et al. |
| 2010/0203600 | A1 | 8/2010 | Dubois |
| 2010/0298612 | A1* | 11/2010 | Behrouzian et al. ......... 568/840 |
| 2010/0317069 | A1 | 12/2010 | Burk et al. |
| 2011/0171699 | A1 | 7/2011 | Raemakers-Franken et al. |
| 2011/0256599 | A1 | 10/2011 | Hu et al. |
| 2012/0064252 | A1 | 3/2012 | Beatty |
| 2012/0101009 | A1 | 4/2012 | Beatty |
| 2013/0065279 | A1 | 3/2013 | Burk et al. |
| 2013/0183728 | A1 | 7/2013 | Botes |
| 2013/0210090 | A1 | 8/2013 | Pearlman et al. |
| 2013/0217081 | A1 | 8/2013 | Pearlman et al. |
| 2013/0224807 | A1 | 8/2013 | Pearlman et al. |
| 2013/0267012 | A1* | 10/2013 | Steen et al. .............. 435/254.21 |
| 2014/0186902 | A1 | 7/2014 | Botes et al. |
| 2014/0186904 | A1 | 7/2014 | Botes et al. |
| 2014/0193861 | A1 | 7/2014 | Botes et al. |
| 2014/0193862 | A1 | 7/2014 | Botes et al. |
| 2014/0193863 | A1 | 7/2014 | Botes et al. |
| 2014/0193864 | A1 | 7/2014 | Botes et al. |
| 2014/0193865 | A1 | 7/2014 | Botes et al. |
| 2014/0196904 | A1 | 7/2014 | Fontenelle et al. |
| 2014/0199737 | A1 | 7/2014 | Botes et al. |
| 2014/0248673 | A1 | 9/2014 | Botes et al. |
| 2015/0111262 | A1 | 4/2015 | Botes et al. |
| 2015/0267211 | A1 | 9/2015 | Botes et al. |

FOREIGN PATENT DOCUMENTS

| | | |
|---|---|---|
| WO | WO 2008/145737 | 12/2008 |
| WO | WO 2009/121066 * | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO/2012/071439 * | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |
| WO | 2015036050 | 3/2015 |

OTHER PUBLICATIONS

KEGG Enzyme 1.2.99.6 (last viewed on Aug. 17, 2015).*
KEGG Enzyme 3.1.2.14 (last viewed on Aug. 17, 2015).*
Branden and Tooze, Introduction to Protein Structure (1999), 2nd edition, Garland Science Publisher, pp. 3-12.*
P43558, last viewed on May 24, 2016.*
P32263, last viewed on May 24, 2016.*
Q08788, last viewed on May 24, 2016.*
Q00777, last viewed on May 24, 2016.*
"Enterococcus faecalis V583 bifuntional acetaldehyde-CoA/Alcohol Dehydrogenase," biocyc.org, retrieved on Jun. 19, 2014, http://biocyc.org/EFAE226185/N EW-IMAGE?type=ENZYME &object=GH11-877-MONOMER, 9 pages.
"Information on EC 1.2.1.57—butanal dehydrogenase," brenda-enzymes.org, retrieved on Jun. 19, 2014, http://www.brenda-enzymes.org/php/result_flat.php4?ecno=1.2.1.57, 6 pages.
"BRENDA—The comprehensive Enzyme Information System," Jul. 2011, retrieved on Sep. 19, 2014, http://web.archive.org/web/20111009205602/http://www.brenda-enzymes.org/, 1 page.
Alber et al., "Malonyl-coenzyme A reductase in the modified 3-hydroxypropionate cycle for autotrophic carbon fixation in archaeal *Metallosphaera* and *Sulfolobus* spp," J. Bacteriology, 2006, 188:8551-8559.
Anton et al., Polyamides, Fibers, Encyclopedia of Polymer Science and Engineering, 2001, 11:409-445.
Azuma et al., "Naphthalene—a constituent of Magnolia flowers," Phytochemistry, 1996, 42:999-1004.

(56) References Cited

OTHER PUBLICATIONS

Barker et al., "Enzymatic reactions in the degradation of 5-aminovalerate by Clostridium aminovalercum," J Biol Chem., 1987, 262(19):8994-9003.

Becker et al., "Metabolic flux engineering of L-lysine production in Corynebacterium glutamicum—over expression and modification of G6P dehydrogenase," J Biotechnol. 2007, 132(2):99-109.

Bellmann et al., "Expression control and specificity of the basic amino acid exporter LysE of Corynebacterium glutamicum," Microbiology 2001, 147:1765-1774.

Bennett et al., "Purification and properties of ε-caprolactone hydrolases from Acinetobacter NCIB 9871 and Nocardia globevula CL1," Journal of General Microbiology, 1988 134: 161-168.

Bernstein et al., "Transfer of the high-GC cyclohexane carboxylate degradation pathway from Rhodopseudomonas palustris to *Escherichia coli* for production of biotin," Metabolic Engineering, May 2008, 10(3-4):131-140.

Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.

Binieda et al., "Purification, characterization, DNA Sequence and cloning of a pimeloyl-CoA synthetase from Pseudomonas medocin 35," Biochem J., 1999, 340:793-801.

Bond-Watts et al., "Biochemical and Structural Characterization of the trans-Enoly-CoA Reductase from Treponema denticola," Biochemistry, 2012, 51:6827-6837.

Bordes et al., "Isolation of a thermostable variant of Lip2 lipase from Yarrowia lipolytica by directed evolution and deeper insight into the denaturation mechanisms," Journal of Biotechnology, 2011, 156: 117-124.

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.

Boylan et al., "Functional identification of the fatty acid reductase components encoded in the luminescence operon of Vibrio fischeri," Journal of Bacteriology, 1985, 163(3):1186-1190.

Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.

Bramer et al., "The methylcitric acid pathway in Ralstonia eutropha: new genes identified involved in propionate metabolism," Microbiology 2001, 147:2203-2214.

Breithaupt et al., "Crystal structure of 12-oxophytodienoate reductase 3 from tomato: self-inhibition by dimerization," Proc Natl. Acad Sci. USA, 2006, 103:14337-14342.

Brigham et al., "Engineering Ralstonia eutropha for Production of Isobutanol from CO2, H2, and O2," Advanced Biofuels and Bioproducts 2013, Chapter 39, pp. 1065-1090.

Brzostowicz et al., "mRNA differential display in a microbial enrichment culture: simultaneous identification of three cyclohexanonemonooxygenases from three species," Applied and Environmental Microbiology, 2003, 69: 334-342.

Brzostowicz et al., "Identification of two gene clusters involved in cyclohexanone oxidation in Brevibacterium epidermidis strain HCU," Applied and Microbiological Biotechnology, 2002, 58:781-789.

Buckel et al., "Glutaconate CoA-transferase from Acidaminococcus fermentans," Eur J. Biochem, 1981, 118:315-321.

Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, Methanococcus jannaschii," Science, 1996, 273: 1058-1073.

Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from Pisum sativum," PNAS USA, 1984, 81(21):6613-7.

Chen et al., "Termites fumigate their nests with naphthalene," Nature, 1998, 392:558-559.

Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.

Coon, "Omega oxygenases: nonheme-iron enzymes and P450 cytochromes," Biochemical & Biophysical Research Communications, 2005,338:378-385.

Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by Muscodor vitigenus, a novel endophytic fungus," Microbiology, 2002, 148:3737-3741.

Dalby, "Optimizing enzyme function by directed evolution," Current Opinion in Structural Biology, 2003, 13, 500-505.

Davis et al., "Overproduction of acetyl-CoA carboxylase activity increases the rate of fatty acid biosynthesis in *Escherichia coli*," J. Biol. Chem., 2000, 275(37): 28593-28598.

Day et al., "Partial purification and properties of acyl-CoA reductase from *Clostridum butyricum*," Archives of Biochemistry and Biophysics, 1978, 190(1):322-331.

Deana et al., "Substrate specificity of a dicarboxyl-CoA: Dicarboxylic acid coenzyme . A transferase from rat liver mitochondria," Biochem Int., 1992, 26:767-773.

Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.

Dellomonaco et al., "Engineered reversal of the [beta]-oxidation cycle for the synthesis of fuels and chemicals," Nature, Jan. 2011, 476(7360):355-359.

Deshmukh and Mungre, "Purification and properties of 2-aminoadipate: 2-oxoglutarate aminotransferase from bovine kidney," Biochem J, 1989, 261(3):761-768.

Doan et al., "Functional expression of five Arabidopsis fatty acyl-CoA reductase genes in *Escherichia coli*," J. Plant Physiology, 2009, 166:787-796.

Dobritzsch et al., "High resolution crystal structure of pyruvate decarboxylase from Zymomonas mobilis. Implications for substrate activation in pyruvate decarboxylases," J. Biol. Chem., 1998, 273:20196-20204.

(56) References Cited

OTHER PUBLICATIONS

Donoghue and Trudgill, "The Metabolism of Cyclohexanol by Acinetobacter NCIB9871," Eur J Bochem., 1975, 60:1-7.
Drevland et al., "Enzymology and Evolution of the Pyruvate Pathway to 2-Oxobutyrate in Methanocaldococcus jannaschii," J. Bacteriol., Apr. 2007, 189(12):4391-4400.
Drevland et al., "Methanogen homoaconitase catalyzes both hydrolyase reactions in coenzyme B biosynthesis," J Biol Chem., Oct. 2008, 283: 28888-28896.
Egmond et al., "Fusarium solani pisi cutinase," Biochimie, Nov. 2000, 82(11):1015-1021.
Elkins et al., "Substrate Specificity of the RND-Type Multidrug Efflux Pumps AcrB and AcrD of *Esherichia coli* Is Determined Predominately by Two Large Periplasmic Looops," J Bacteriol. 2002, 184(23):6490-6499.
Elshahed et al., "Benzoate Fermentation by the Anaerobic bacterium Syntrophus aciditrophicus in the Absence of Hydrogen-Using Microorganisms," Applied and Environ Microbiology, 2001, 67(12):5520-5525.
Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.
Eurich et al., "Cloning and characterization of three fatty alcohol oxidase genes from Candida tropicalis strain ATCC 20336," Applied & Environmental Microbiology, 2004, 70(8): 4872-4879.
Ferreira et al. "A member of the sugar transporter family, St11p is the glycerol/H=symporter in *Saccharomyces cerevisiae*," Molecular Biology of the Cell, American Society for Cell Biology, Apr. 1, 2005, 16(4):2068-2076.
Fickers et al., "Carbon and nitrogen sources modulate lipase production in the yeast *Yarrowia lipolytica*," Journal of Applied Microbiology, 2004, 96:742-9.
Fickers et al., "The lipases from Yarrowia lipolytica: Genetics, production, regulation, biochemical characterization and biotechnological applications," Biotechnology Advances, 2011, 29: 632-644.
Fuchs et al., "Microbial degradation of aromatic compounds—from one strategy to four," Nat Rev Microbiol., Oct. 3, 2011;9(11):803-816, Oct. 2011.
Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.
Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.
Gallus and Schink, "Anaerobic degradation of pimelate by newly isolated denitrifying bacteria," Microbiology, 1994, 140:409-416.
Gasmi et al., "A molecular approach to optimize hIFN α2b expression and secretion in Yarrowia lipolytica," Appl Microbiol Biotechnol, 2011, 89:109-119.
GenBank Accession No. AAA24664.1, Mar. 25, 1993, 1 page.
GenBank Accession No. AAA24665.1, Apr. 26, 1993, 1 page.
GenBank Accession No. AAA57874.1, Nov. 21, 2011, 2 pages.
GenBank Accession No. AAA69178.1, Jul. 1, 1995, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct 23, 2009, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
GenBank Accession No. AAG08191.1, Jan. 31, 2014, 2 pages.
GenBank Accession No. AAK73167.2, retrieved May 19, 2014, 1 page.
GenBank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
GenBank Accession No. AAT43726, retrieved May 19, 2014, 1 page.
GenBank Accession No. AAW66853.1, Feb. 12, 2005, 1 page.
GenBank Accession No. AAY39893.1, Jan. 31, 2014, 2 pages.
GenBank Accession No. AB005294, Feb. 2000, 2 pages.
GenBank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
GenBank Accession No. ABE47158.1, Jan. 26, 2014, 1 page.
GenBank Accession No. ABE47159.1, Jan. 28, 2014, 2 pages.
GenBank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
GenBank Accession No. ABK71854.1, Jan. 31, 2014, 2 pages.
GenBank Accession No. ABK75684.1, Jan. 31, 2014, 2 pages.
GenBank Accession No. ACC40567.1, Jan. 31, 2014, 2 pages.
GenBank Accession No. ACJ06772.1, Dec. 4, 2009, 1 page.
GenBank Accession No. ADG98140.1, Jan. 28, 2014, 2 pages.
GenBank Accession No. ADK19581.1, Sep. 20, 2010, 2 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
GenBank Accession No. BAB91331.1, retrieved May 19, 2014, 1 page.
GenBank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
GenBank Accession No. BAF94304.1, retrieved May 19, 2014, 1 page.
GenBank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
GenBank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. EFV11917.1, Sep. 9, 2013, 2 pages.
GenBank Accession No. EIV11143.1, Jun. 19, 2012, 2 pages.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. NM_001246944, Dec. 2011, 2 pages.

(56) References Cited

OTHER PUBLICATIONS

GenBank Accession No. NM_001247852, Dec. 2011, 2 pages.
GenBank Accession No. NM_133240, Feb. 25, 2002, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus Sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast *Yarrowia lipolytica*," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism Alcaligenes eutrophus," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon Picrophilus torridus," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of Arabidopsis," Plant J., 1999, 20:1-13.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37:10108-10117.
Howell et al., "Identification of enzymes homologous to isocitrate dehydrogenase that are involved in coenzyme Band leucine biosynthesis in methanoarchaea," J Bacteriol., Sep. 2000, 182:5013-5016.
Hugler et al., "Malonyl-coenzyme A reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US 2012/069934, mailed Jun. 17, 2014, 15 pages.
International Preliminary Report on Patentability in International Application No. PCT/US 2012/042777, mailed Jan. 10, 2013, 22 pages.
International Preliminary Report on Patentability in International Application No. PCT/US 2012/044984, mailed Jan. 28, 2014, 11 pages.
International Search Report and Written Opinion for International Application No. PCT/US 2012/069934, mailed Jan. 17, 2014, 21 pages.
International Search Report and Written Opinion in International Application No. PCT/US 2012/042747, mailed Jan. 14, 2013, 19 pages.
International Search Report and Written Opinion in International Application No. PCT/US 2012/042777, mailed Sep. 11, 2012, 9 pages.
International Search Report and Written Opinion in International Application No. PCT/US 2012/044984, mailed Dec. 17, 2013, 17 pages.
International Search Report and Written Opinion in International Application No. PCT/US 2012/071472, mailed Dec. 17, 2013, 17 pages.
International Search Report and Written Opinion in International Application No. PCT/US2013/075058, mailed Sep. 15, 2014, 17 pages.
International Search Report and Written Opinion in International Application No. PCT/US2013/075087, mailed Aug. 4, 2014, 18 pages.
International Search Report and Written Opinion in International Application No. PCT/US2013/077411, mailed Sep. 24, 2014, 18 pages.
International Search Report and Written Opinion in International Application No. PCT/US2013/077413, mailed Jul. 22, 2014, 20 pages.
International Search Report and Written Opinion in International Application No. PCT/US2013/077419, mailed Jun. 16, 2014, 19 pages.

(56) References Cited

OTHER PUBLICATIONS

International Search Report and Written Opinion in International Application No. PCT/US2013/077420, mailed Jul. 21, 2014, 21 pages.
International Search Report and Written Opinion in International Application No. PCT/US2013/077423, mailed Jul. 21, 2014, 22 pages.
International Search Report and Written Opinion in International Application No. PCT/US2013/077445, mailed Sep. 15, 2014, 17 pages.
Invitation to Pay Additional Fees in International Application No. PCT/US2013/075058, mailed Jul. 7, 2014, 7 pages.
Invitation to Pay Additional Fees in International Application No. PCT/US2013/07745, mailed Jul. 7, 2014, 9 pages.
Invitation to Pay Fees in International Application No. PCT/US2013/075087, mailed May 16, 2014, 9 pages.
Invitation to Pay Fees in International Application No. PCT/US2013/077411, mailed Jul. 16, 2014, 9 pages.
Invitation to Pay Fees in International Application No. PCT/US2013/077413, mailed May 12, 2014, 9 pages.
Invitation to Pay Fees in International Application No. PCT/US2013/077419, mailed Apr. 16, 2014, 9 pages.
Invitation to Pay Fees in International Application No. PCT/US2013/077420, mailed May 13, 2014, 9 pages.
Invitation to Pay Fees in International Application No. PCT/US2013/077423, mailed May 13, 2014, 10 pages.
Invitation to Pay Fees in International Application No. PCT/US2013/077430, mailed Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbilogy, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.
Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2—C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.

Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum D5M30191 and its potential for biocatalysis," Enzyme Microb Technol. 2007, 41:628-637.
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Koch et al., "Products of Enzymatic Reduction of Benzoyl-CoA, a Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of Pseudomonas aeruginosa MCM B-407," Curr. Microbiol., 1998, 37:191-194.
Kung et al., "Cyclohexane carboxyl-coenzyme A (CoA) and cyclohex-1-ene-1-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast *Yarrowia lipolytica*," Current Genetics, 1994 26:38-44.
Lee and Meighen, "Cysteine-286 as the site of acylation of the LUX-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.

(56) References Cited

OTHER PUBLICATIONS

Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.

Lin and Cronan, "Closing in on complete pathways of biotin biosynthesis," Molecular Biosystems, 2011, 7:1811-1821.

Lin et al., "Biotin Sythesis Begins by Hijacking the Fatty Acid Synthetic Pathway," Nature Chem Biol., Sep. 2010, 6:682-688.

Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.

Lin, "Biotin Synthesis in *Escherichia coli*," PhD Dissertation, University of Illinois at Urbana-Champaign, 2012, 140 pages.

Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.

Liu et al., "Two novel metal-independent long-chain alkyl alcohol dehydrogenases from Geobacillus thermodenitrificans NG80-2," Microbiology, 2009, 155:2078-2085.

Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.

Luo et al., "Production of 3-hydroxypropionic acid through propionaldehyde dehydrogenase PduP mediated biosynthetic pathway in Klebsiella pneumoniae," Bioresource Technology, 2012, 103:1-6.

Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.

Mack and Buckel, "Conversion of glutaconate CoA-transferase from Acidaminococcus fermentans into an acyl-CoA hydrolase by site-directed mutagenesis," FEBS Letters, 1997, 405:209-212.

Maeda et al., "Purification and characterization of a biodegradable plastic-degrading enzyme from Aspergillus oryzae," Applied and Environmental Biotechnology, 2005, 67: 778-788.

Mahadik et al., "Production of acidic lipase by Aspergillus niger in solid state fermentation," Process Biochemistry, 2002, 38: 715-721.

Martin and Prather, "High-titer production of monomeric hydroxyvalerates from levulinic acide Pseudomonas putida," J. Biotechnol., 2009, 139: 61-67.

Martinez et al., "Fusarium solani cutinase is a lipolytic enzyme with a catalytic serine accessible to solvent," Nature, 1992, 356:615-618.

Matsumoto et al., "A new pathway for poly(3-hydroxybutyrate) production in *Escherichia coli and Corynebacterium glutamicum* by functional expression of a new acetoacetyl-coenzyme A synthase," Biosci. Biotechnol. Biochem., 2011, 75(2):364-366.

Mawal and Deshmukh, "Alpha-aminoadipate and kynurenine aminotransferase activities from rat kidney. Evidence for separate identity," J. Biol Chem, 1991, 266(4):2573-2575.

McAndrew et al., "Structural basis for substrate fatty acyl chain specificity: crystal structure of human very-long-chain acyl-CoA dehydrogenase," J. Biol. Chem., 2008, 283:9435-9443.

Meijnen et al., "Improved p-hydroxybenzoate production by engineered Pseudomonas putida S12 by using a mixed-substrate feeding strategy," Appl. Microbiol. Biotechnol., 2011, 90:885-893.

Mhetras et al., "Purification and characterization of acidic lipase from Aspergillus niger NCIM 1207," Bioresource Technology, 2009, 100: 1486-1490.

Millar et al., "CUT1, an Arabidopsis Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.

Miyazaki et al., "Alpha-Aminoadipate aminotransferase from an extremely thermophilic bacterium, Thermus thermophilus," Microbiology, 2004, 150(7): 2327-2334.

Mo et al., "Connecting extracellular metabolomic measurements to intracellular flux states in yeast," BMC Systems Biology, 2009, 3(37):1-17.

Mouttaki et al., "Cyclohexane Carboxylate and Benzoate Formation from Crotonate in Sytrophus aciditrophicus," Applied and Environ Microbiology, Feb. 2007, 73(3):930-938.

Murphy et al., "Fusarium polycaprolactone depolymerase is cutinase," Appl. Environm. Microbiol., 1996, 62:456-460.

Naggert et al., "Cloning, sequencing, and characterization of *Escherichia coli* thioesterase II," J. Biol. Chem., 1991, 266(17):11044-11050.

Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.

Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.

Nicol et al., "Bioconversion of crude glycerol by fungi," Applied Microbiology and Biotechnology, Feb. 10, 2012, 93(5):1865-1875.

Nieder and Shapiro, "Physiological function of the Pseudomonas putida PpG6 (Pseudomonas oleovorans) alkane hydroxylase: monoterminal oxidation of alkanes and fatty acids," J. Bacteriol., 1975, 122(1):93-98.

Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.

Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.

Ohashi et al., "Continuous production of lactic acid from molasses by perfusion culture of Lactococcus lactis using a stirred ceramic membrane reactor," J. Bioscience and Bioengineering, 1999, 87(5):647-654.

Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.

Onakunle et al., "The formation and substrate specificity of bacterial lactonases capable of enantioselective resolution of racemic lactones," Enzyme and Microbial Technology, 1997, 21: 245-251.

Oppenheim and Dickerson, "Adipic Acid," Kirk-Othmer Encyclopedia of Chemical Technology, 2003.

Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.

Palosaari and Rogers, "Purification and properties of the inducible coenzyme A-linked butyraldehyde dehydrogenase from Clostridium acetobutylicum," J. Bacteriol., 1988, 170(7):2971-2976.

Papanikolaou et al., "Citric acid production by Yarrowia lipolytica cultivated on olive-mill wastewater-based media," Bioresource Technol., 2008, 99(7):2419-2428.

Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.

Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.

Pérez-Pantoja et al., "Metabolic reconstruction of aromatic compounds degradation from the genome of the amazing pollutant-degrading bacterium Cupriavidus necator JMP134," FEMS Microbiol. Rev., 2008, 32:736-794.

Peterson et al., "The Thermal Stability of the Fusarium solani pisi Cutinase as a Function of pH," BioMed Research International, 2001, 1.2:62-69.

(56) References Cited

OTHER PUBLICATIONS

Pignede et al., "Autocloning and Amplification of LIP2 in Yarrowia lipolytica," Appl. Environ. Microbiol, 2000 66:3283-3289.
Pignede et al., "Characterization of an extracellular lipase encoded by LIP2 in Yarrowia lipolytica," Journal of Bacteriology, 2000, 182:2802-2810.
Ploux et al., "Investigation of the first step of biotin biosynthesis in Bacillus sphaericus: Purification and characterization of the pimloyl-CoA synthase, and uptake of pimelate," Biochem J., 1992, 287:685-690.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Qian et al., "Metabolic engineering of *Escherichia coli* for the production of cadaverine: a five carbon diamine," Biotechnol Bioeng, 2011, 108(1):93-103.
Qiu et al., "Crystal structure and substrate specificity of the β-ketoacyl-acyl carrier protein synthase III (FabH) from *Staphylococcus aureus*," Protein Sci, 2005, 14(8):2087-2094.
Rajashekhara et al., "Propionyl-coenzyme A synthetases of *Ralstonia solanacearum* and *Salmonella choleraesuis* display atypical kenetics," FEBS Letters, 2004, 556:143-147.
Ramsay et al., "Use of a Nylon Manufacturing Waste as an Industrial Fermentation Substrate," Applied and Environmental Microbiology, 1986, 52(1):152-156.
Ray et al., "Cocrystal structures of diaminopimelate decarboxylase: mechanism, evolution, and inhibition of an antibiotic resistance accessory factor," Structure, 2002, 10(11):1499-1508.
Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.
Rohdich et al., "Enoate reductases of Clostridia. Cloning, sequencing, and expression," J. Biol. Chem., 2001, 276:5779-5787.
Roje, "Vitamin B biosynthesis in plants," Phytochemistry, 2007, 68:1904-1921.
Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.
Ryu et al., "A novel synthesis of .beta.-trichlorostannyl ketones from siloxycyclopropanes and their facile dehydrostannation affording 2-methylene ketones," JOC, 1986, 51:2389-2391.
Salcher and Lingens, "Regulation of phospho-2-keto-3-deoxyheptonate aldolase (DAHP synthase) and anthranilate synthase of Pseudomonas aureofaciens," J Gen Microbiol., 121(2):473-476, Dec. 1980.
Sambrook et al., Molecular Cloning—a Laboratory Manual, Cold Spring Harbor Laboratory Press, 2001.
Samsonova et al., "Molecular cloning and characterization of *Escherichia coli* K12 ygjG gene," BMC Microbiology, 2003, 3:2.
Sanders et al., "Characterization of the human ω-oxidation pathway for ω-hydroxy-very-long-chain fatty acids," FASEB Journal, 2008, 22(6):2064-2071.
Sanders et al., "Evidence for two enzymatic pathways for ω-oxidation of docosanoic acid in rat liver microsomes," J. Lipid Research, 2005, 46(5):1001-1008.
Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.
Scheller et al., "Generation of the Soluble and Functional Cytosolic Domain of Microsomal Cytochrome P450 52A3," J Biol Chem., 1994, 269(17):12779-12783.
Schirmer et al., "Microbial Biosynthesis of Alkanes," Science, 2010, 329:559-562.
Schwartz et al., "A proteomic view of the facultatively chemolithoautotrophic lifestyle of Ralstonia eutropha H16," Proteomics, 2009, 9:5132-5142.
Seedorf et al., "The genome of Clostridium kluyveri, a strict anaerobe with unique metabolic features," Proc. Natl. Acad. Sci. USA, 2008, 105(6):2128-2133.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shen et al., "Driving Forces Enable High-Titer Anaerobic 1-Butanol Synthesis in *Escherichia coli*," Appl. Environ. Microbiol., 2011, 77(9):2905-2915.
Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.
Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.
Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Suzuki et al., "Antimicrobial Activity of Meropenem Against Main Bacterial Species Isolated from Patient Blood in 2006," J. Antibiot., 2007, 60(6):380-387.
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus thermophilus," Proteins, 2009, 75(2):348-359.
Tseng et al., "Biosynthesis of chiral 3-hydroxyvalerate from single propionate-unrelated carbon sources in metabolically engineered *E. coli*," Microbial Cell Factories, 2010, 9:96.
US Non-Final Office Action in U.S. Appl. No. 13/524,883, mailed Nov. 29, 2013, 13 pages.
US Non-Final Office Action in U.S. Appl. No. 13/715,981, mailed Jun. 27, 2014, 23 pages.
US Notice of Allowance in U.S. Appl. No. 13/524,883, mailed May 29, 2014, 7 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.

(56) References Cited

OTHER PUBLICATIONS

Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga Botryococcus braunii," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of non-natural alcohols," Proc Natl Acad Sci U S A., 105(52):20653-20658 Epub Dec. 8, 2008.
Zhuang et al., "Divergence of function in the hot dog fold enzyme superfamily: the bacterial thioesterase YciA," Biochemistry, 2008, 47(9):2789-2796.
Zomorrodi et al., "Improving the iMM904 S. Cerevisiae metabolic model using essentiality and synthetic lethality data," BMC Systems Biology, Dec. 2010, 4(1):1-15.
Aimin et al., "*Nocardia* sp. carboxylic acid reductase: cloning, expression, and characterization of a new aldehyde oxidoreductase family," Appl. Environ. Microbiol., 2004, 70:1874-1881.

Aloulou et al., "Purification and biochemical characterization of the LIP2 lipase from Yarrowia lipolytica," Biochim. Biophys. Acta, 2007, 1771:228-237.
Atsumi et al., "Acetolactate synthase from Bacillus subtilisserves as a 2-ketoisovalerate decarboxylase from isobutanol synthesis in *Escherichi coli*," Applied and Environ. Microbiol., 2009, 75(19):6306-6311.
Bergler et al., "Protein EnvM is the NADH-dependent enoyl-ACP reductase (FabI) of *Escherichia coli*," J. Bio Chem, 1993, 269(8):5493-5496.
Eikmanns and Buckel, "Properties of 5-hydroxyvalerate CoA-transferase from Clostridium aminovalericum," Biol. Chem, 1990, 371:1077-1082.
Fonknechten et al., "Clostridium sticklandii, a specialist in amino acid degradation: revisiting its metabolism through its genome sequence," BMC Genomics, 2010, 11:1-12.
GenBank Accession No. AAA23536, Apr. 26, 1993, 1 page.
GenBank Accession No. AAA92347.1, Mar. 15, 1996, 1 page.
GenBank Accession No. AAB99100, Aug. 27, 1996, 2 pages.
GenBank Accession No. AE000666.1, Jan. 5, 2006, 309 pages.
GenBank Accession No. D87518, Jul. 31, 1997, 2 pages.
GenBank Accession No. HQ418483.1, Apr. 4, 2011, 2 pages.
GenBank Accession No. JA114119.1, Apr. 19, 2011, 1 page.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
Horning et al., "α-Ketoglutaric Acid," Organic Syntheses, 1955, 3: 510-512.
International Search Report and Written Opinion in International Application No. PCT/US2014/052950, mailed Dec. 3, 2014, 15 pages.
International Search Report and Written Opinion in International Application No. PCT/US2014/053222, mailed Mar. 4, 2015, 18 pages.
Invitation to Pay Additional Fees in International Application No. PCT/US2014/053222, mailed Dec. 15, 2014, 8 pages.
Klatte et al., "Redox self-sufficient whole cell biotransformation for amination of alcohols," Bioorg & Medicinal Chem, May 2014, 22: 5578-5585.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Mutti et al., "Amination of ketones by employing two new (S)-selective w-transaminases and the His-tagged w-TA from Vibrio fluvialis," Eur. J. Org. Chem, 2012, 1003-1007 (Abstract).
Prabhu et al., "Lactate and Acrylate Metabolism by Megasphaera elsdenii under Batch and Steady-State Conditions," Applied and Environ. Microbiology, Sep. 2012, 78(24): 8564-8570.
Reiser and Somerville, "Isolation of mutants of *Acinetobacter cakoaceticus* deficient in wax ester synthesis and complementation of on mutation with gene encoding a fatty acyl coenzyme A reductase," J. Bacteriol., 1997, 179:2969-2975.
Rizzarelli et al., "Evidence for Selective Hydrolysis of Aliphatic Copolyesters Induced by Lipase Catalysis," Biomacromolecules, 2004, 5:433-444.
Uniprot Accession No. I5YEB8, Sep. 5, 2012, 1 page.
US Notice of Allowance in U.S. Appl. No. 13/715,981, mailed Dec. 16, 2014, 23 pages.
US Non-Final Office Action in U.S. Appl. No. 13/715,826, mailed Jan. 30, 2015, 24 pages.
US Notice of Allowance in U.S. Appl. No. 14/106,124, mailed Dec. 24, 2014, 31 pages.

(56) References Cited

OTHER PUBLICATIONS

Vyazmensky et al., "Isolation and Characterization of Subunits of Acetohydroxy Acid Synthase Isozyme III and Reconstruction of the Holoenzyme," Biochemistry, 1996, 35:10339-10346.
Zhao et al., "Prediction and characterization of enzymatic activities guided by sequence similarity and genome neighborhood networks," E-Life, Jun. 2014, 3: 1-32.
"Metabolic engineering," Wikipedia, Jun. 8, 2014 (Jun. 8, 2014), XP002744570, Retrieved from the Internet: URL:https://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," Gene, Jan. 2003, 302:185-192.
Eriksen et al., "Protein Design for Pathway Engenieering," Journal of Structural Biology, Apr. 2013, 185(2):234-242.
Invitation to Pay Fees in International Application No. PCT/US2015/036015, mailed Oct. 2, 2015, 9 pages.
Invitation to Pay Fees in International Application No. PCT/US2015/036092, mailed Sep. 21, 2015, 8 pages.
Invitation to Pay Fees in International Application No. PCT/US2015/036067, mailed Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. O32472, Jun. 11, 2014, 2 pages.
Uniprot Accession No. P69909, Jan. 4, 2005, 1 page.
Uniprot Accession No. P0A6R0, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
International Search Report and Written Opinion in International Application No. PCT/US2015/036074, mailed Sep. 9, 2015, 14 pages.
Invitation to Pay Fees in International Application No. PCT/US2015/036086, mailed Sep. 16, 2015, 7 pages.
Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.
Aursnes et al., "Total Synthesis of the Lipid Mediator PD1(n-3 DPA): Configurational Assignments and Anti-Inflammatory and Pro-resolving Actions," Journal of Natural Products, Feb. 2014, 77:910-916.
Bordeaux et al., "Catalytic, Mild, and Selective Oxyfunctionalization of Linear Alkanes: Current challenges," Angew. Chem. Int. Ed., 2012, 51:10712-10723.
Clomburg et al., "Integrated engineering of Beta-oxidation reversal and omega-oxidation pathways for the synthesis of medium chain omega-functionalized carboxylic acids," Metabolic Engineering, Jan. 2015, 28:202-212.
Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
International Preliminary Report on Patentability for International Application No. PCT/US2013/075058, mailed Jun. 25, 2015, 11 pages.
International Preliminary Report on Patentability for International Application No. PCT/US2013/075087, mailed Jun. 25, 2015, 11 pages.
International Preliminary Report on Patentability for International Application No. PCT/US2013/077445, mailed Jul. 9, 2015, 11 pages.
International Preliminary Report on Patentability for International Application No. PCT/US2013/077420, mailed Jul. 9, 2015, 14 pages.
International Preliminary Report on Patentability for International Application No. PCT/US2013/077419, mailed Jul. 9, 2015, 13 pages.
International Preliminary Report on Patentability for International Application No. PCT/US2013/077430, mailed Jul. 9, 2015, 18 pages.
International Preliminary Report on Patentability for International Application No. PCT/US2013/077413, mailed Jul. 9, 2015, 13 pages.
International Preliminary Report on Patentability for International Application No. PCT/US2013/077411, mailed Jul. 9, 2015, 12 pages.
International Preliminary Report on Patentability for International Application No. PCT/US2013/077423, mailed Jul. 9, 2015, 14 pages.
International Search Report and Written Opinion in International Application No. PCT/US2015/031227, mailed Jul. 31, 2015, 40 pages.
International Search Report and Written Opinion in International Application No. PCT/US2015/036050, mailed Aug. 14, 2015, 38 pages.
International Search Report and Written Opinion in International Application No. PCT/US2015/036057, mailed Aug. 14, 2015, 74 pages.
Kizer, "Application of Functional Genomics to Pathway Optimization for Increased Isoprenoid Production," Applied and Environmental Microbiology, 2008, 74(10)3229-3241.
Prather et al., "De novo biosynthetic pathways: rational design of microbial chemical factories," Current Opinion in Biotechnology, 2008, 19:468-474.
Scheps et al., "Synthesis of omega-hydroxy dodecanoic acid based on an engineered CYP153A fusion construct," Microbial Biotechnology, 2013, 6:694-707.
US Notice of Allowance in U.S. Appl. No. 13/715,981, mailed Apr. 6, 2015, 10 pages.
US Non-Final Office Action in U.S. Appl. No. 14/106,033, mailed Apr. 6, 2015, 37 pages.
US Non-Final Office Action in U.S. Appl. No. 14/138,827, mailed Apr. 24, 2015, 35 pages.
US Non-Final Office Action in U.S. Appl. No. 14/138,971, mailed Jun. 9, 2015, 44 pages.
US Non-Final Office Action in U.S. Appl. No. 14/138,904, mailed Jun. 9, 2015, 50 pages.
US Non-Final Office Action in U.S. Appl. No. 14/490,270, mailed Jul. 17, 2015, 49 pages.

\* cited by examiner

FIG. 11A

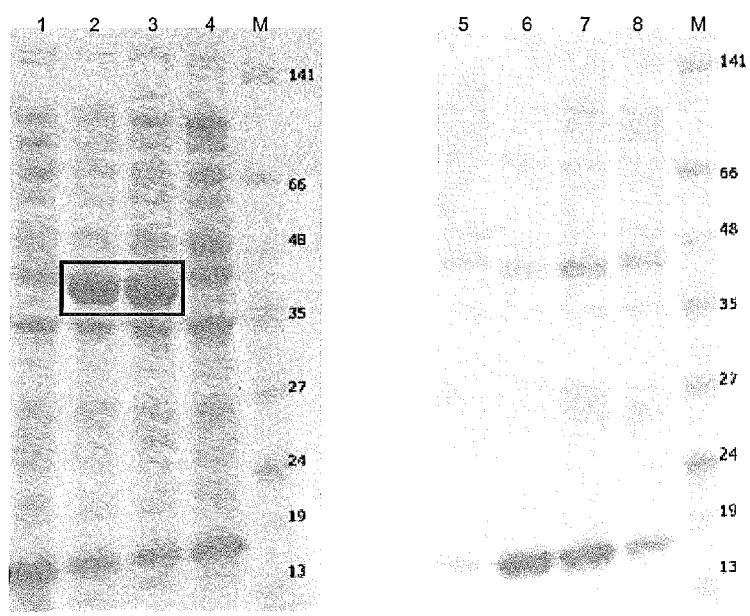

SDS-PAGE analysis on soluble and insoluble fractions from expression of the *Citrobacter amalonaticus* ammonia lyase protein (I4) (expected protein size: 45 kDa)

Lane 1. Pre-induction soluble sample; Lane 2. 4 h post-induction soluble sample; Lane 3. 24 h post-induction soluble sample; Lane 4. 24h negative control soluble sample (I17); Lane 5. Pre-induction insoluble sample; Lane 6 4 h post-induction insoluble sample; Lane 7. 24 h post-induction insoluble sample; Lane 8. 24 h negative control insoluble sample (I17); Lanes M. Marker

FIG. 11B

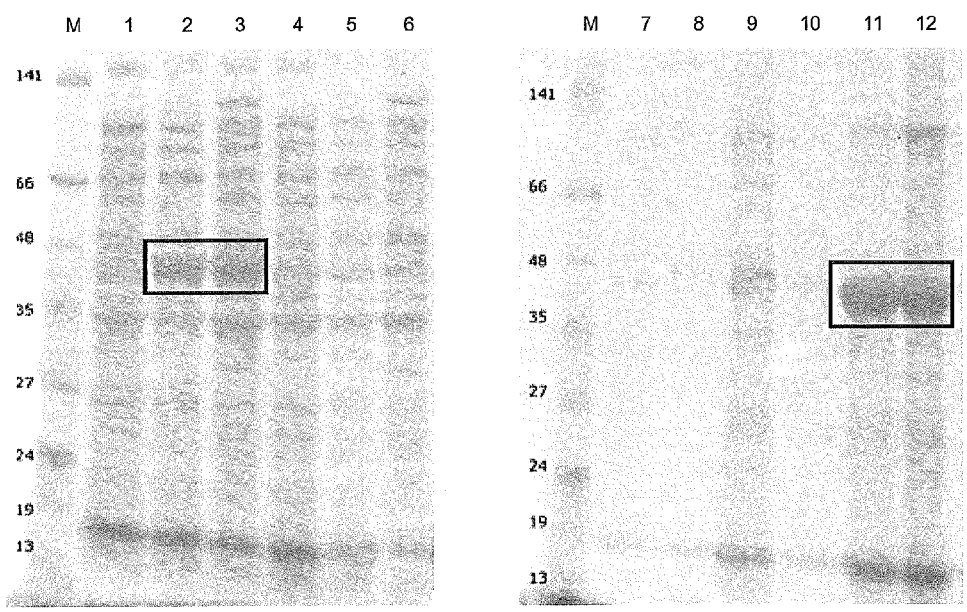

SDS-PAGE analysis on soluble and insoluble fractions from expression of the *Clostridium tetanomorphum* (I5) and *Aspergillus oryzae* (I6) ammonia lyase proteins (expected protein size: 45 kDa each)

Lane 1. Assembly I5: Pre-induction soluble sample; Lane 2. Assembly I5: 4 h post-induction soluble sample; Lane 3. Assembly I5: 24 h post-induction soluble sample; Lane 4. Assembly I6: Pre-induction soluble sample; Lane 5. Assembly I6: 4 h post-induction soluble sample; Lane 6. Assembly I6: 24 h post-induction soluble sample; Lane 7. Assembly I5: Pre-induction insoluble sample; Lane 8. Assembly I5: 4 h post-induction insoluble sample; Lane 9. Assembly I5: 24 h post-induction insoluble sample; Lane 10. Assembly I6: Pre-induction insoluble sample; Lane 11. Assembly I6: 4 h post-induction insoluble sample; Lane 12. Assembly I6: 24 h post-induction insoluble sample; Lanes M. Marker SDS-PAGE analysis on soluble and insoluble fractions from expression of the *Nocardia sp.* carboxylic acid reductase gene. (Expected protein sizes: 61 kDa for each protein)

Lane M. Marker; Lane 1. Pre-induction soluble sample; Lane 2. Pre-induction insoluble sample; Lane 3. 4 h post-induction soluble sample; Lane 4. 4 h post-induction insoluble sample.

Change in absorbance over time due to reduction of pimelic acid to pimelic acid semialdehyde by Nocardia CAR reductase activity. Benzoic acid was used as positive control, and pimleic acid without enzyme as negative control.

FIG. 14

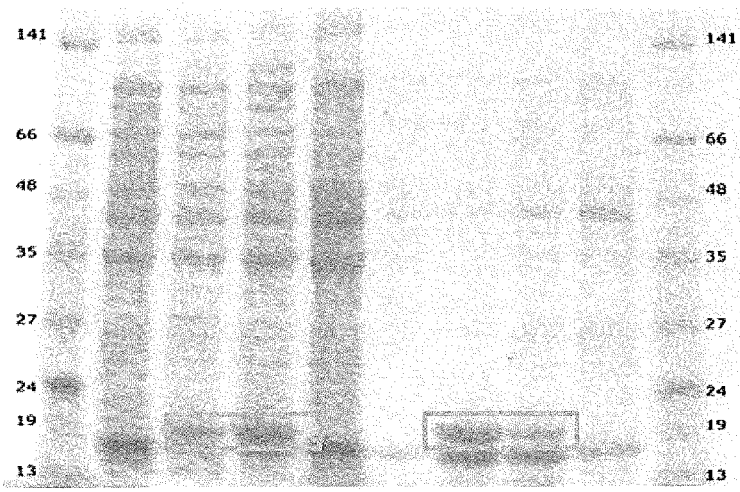

SDS-PAGE analysis on soluble fraction and insoluble fraction from expression of the *Haemophilus influenzae* YciA thioesterase protein (I8) (expected protein size: 17 kDa)

Lane 1. Pre-induction soluble sample; Lane 2. 4 h post-induction soluble sample; Lane 3. 24 h post-induction soluble sample; Lane 4. 24 h negative control soluble sample (I17); Lane 5. Pre-induction insoluble sample; Lane 6. 4 h post-induction insoluble sample; Lane 7. 24 h post-induction insoluble sample; Lane 8. 24 h negative control insoluble sample (I17); Lanes M. Marker.

FIG. 15

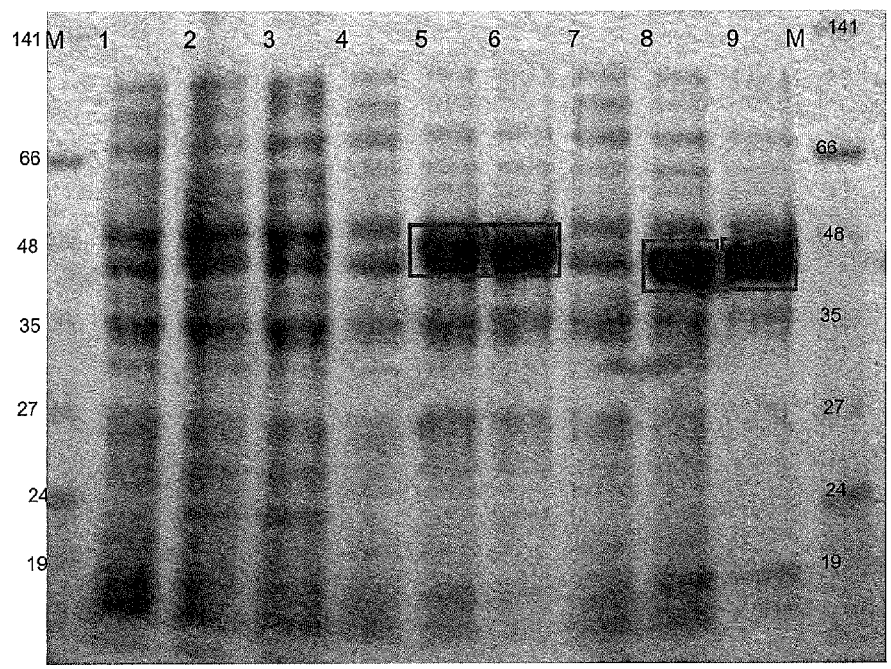

SDS-PAGE analysis of the aminotransferase IlvE-Omega Vf fusion (pING2022) and IlvE-Ad optimized omega fusion (pING2030) proteins (Expected protein sizes: 50 kDa and 47 kDa respectively)

Lane 1. Pre-induction negative control; Lane 2. 4 h post-induction negative control; Lane 3. 24 h post-induction negative control; Lane 4. pING 2022 Pre-induction; Lane 5. pING2022 4 h post-induction Lane 6. pING2022 24 h post-induction; Lane 7. pING 2030 Pre-induction; Lane 8. pING 2030 4 h post-induction; Lane 9. pING 2030 24 h post-induction; Lanes M. Marker Results of the biotransformation of sodium pyruvate and 7-aminoheptanoic acid with the measured concentrations of 7-aminoheptanoic acid substrate and L-alanine product.

Summary of the HPLC results from the L- and D-2-aminosuberic acid enantiomer concentrations in the six biotransformations after 48 and 96 hours.

FIG. 18

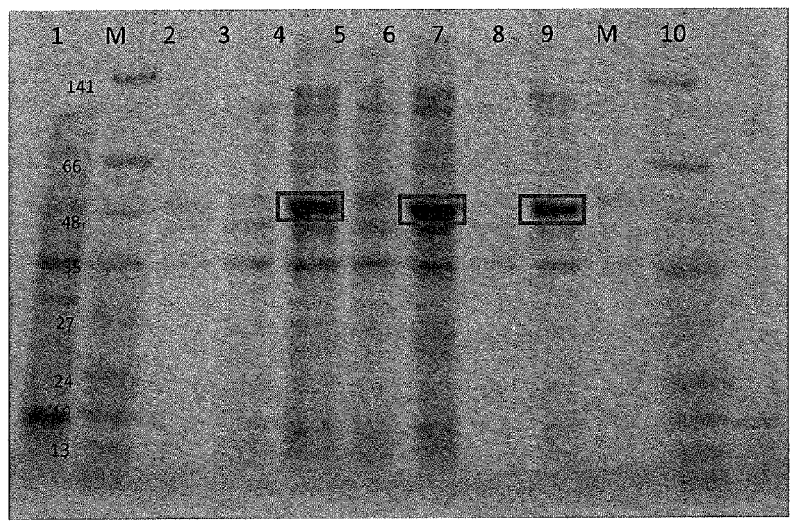

SDS-PAGE analysis on soluble and insoluble fractions from the bead lysis of expression of the *E.coli* GadA (I29), *E.coli* LysA (I30), *E.coli* GadA ilvE (I31) and *E.coli* LysA ilvE (I32) proteins.

(Expected protein sizes: 52 kDa, 46 kDa, 52 kDa and 46 kDa respectively)

Lanes M. Marker; Lane 1. Negative control 24h post-induction soluble sample; Lane 2. Assembly I29 24 h soluble sample; Lane 3. Assembly I30 4 h soluble sample;; Lane 4. Assembly I31 24h soluble sample; Lane 5. Assembly I31 24 h post-induction soluble sample; Lane 6. Assembly I29 24 h post-induction insoluble sample; Lane 7. Assembly I30 24 h post-induction insoluble sample; Lane 8. Assembly I31 24 h post-induction insoluble sample; Lane 9. Assembly I32 24 h post-induction insoluble sample; Lane 10. 24 hour negative control insoluble sample (I17).

FIG. 19

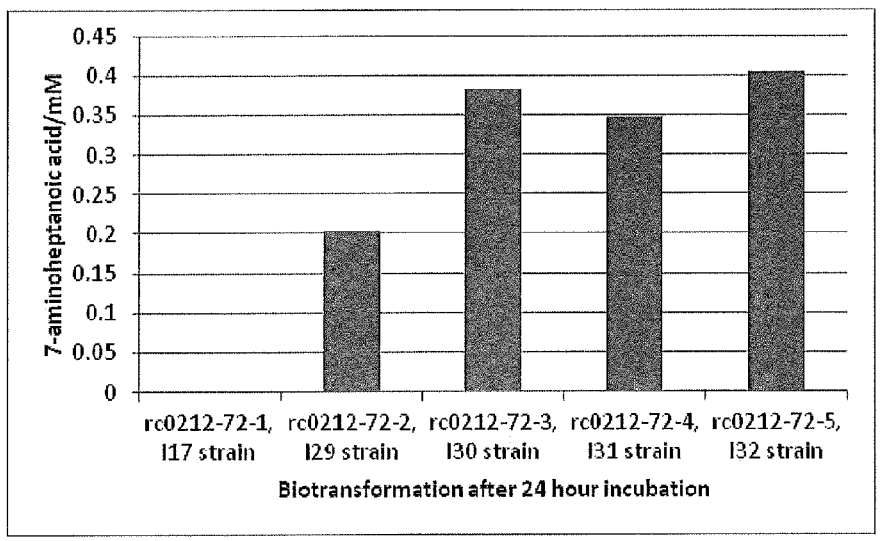

Formation of 7-aminoheptanoic acid from the decarboxylation of 2-aminosuberate.

I17 (negative control); I29 (pET21/GadA); I30 (pET21/LysA); I31 (pET21/IlvE-GadA); I32 (pET21/IlvE-LysA). GadA: *E. coli* glutamate decarboxylase; LysA: *E. coli* diaminopimelate decarboxylase; IlvE-GadA: Fusion between *E.coli* IlvE branched chain amino acid aminotransferase (N-terminus peptide: 15 residues) and E. coli glutamate decarboxylase, IlvE-LysA: Fusion between *E.coli* IlvE branched chain amino acid aminotransferase (N-terminus peptide: 15 residues) and *E. coli* diaminopimelate decarboxylase

FIG. 20

MJ0277 (SEQ ID NO:22) vs. comD (SEQ ID NO:41) and comE (SEQ ID NO:42)

```
comD     MRGSLAIYNALKDSNIDFICSVPCANLKQLLKLIEEDKNIINIPATREEEAFGICAGAYL  60
MJ0277   MKGAEAIIKALFAEGVKIIPGYPGGAMLPFYDALXDS-DLVHILTRHEQAAAHAADGFAR  59
         *:*:  :: .  .:* .* . :   .  :  .  :::* : :*: *   . * comD     AGKKTAILMQNSGIGNS--INAIASLYK--------TPQIPTLLIIS-------------  97
MJ0277   ASCEAGVCVSTSGPGATNLVTGIATAYADSSPVIALTGQVPTKLIGNDAPQEIDALGLFM 119
         *. ::.: :.,** *  .  :,,**:  *       * *:** **  .

comD     ---HRGDLKEQIFAQIP----------MCR----WIEKLIDV----------------CEI 125
MJ0277   PIYKHNFQIKKFEEIPETFRAAPEIATTGRPGPVHIDLPKDVQDGEIDIBKYPIPAKVDL 179
         : ::: : *:**       ** .     *:   **               ::

comD     PIYKPETP-------------------------EEAYKLIKYASS----- 145
MJ0277   PGYKPKTVGHPLQIKKAAKLIAESERPVILAGGGVIISGASEELLRLAEFVKIPVCTTLM 239
         * *****                                     **  :*  ::..

comD     --YMYKISYPVALLFDALY----WEYDLEK------------------------------ 169
MJ0277   GKGCPPEUHPLALGMVGMKGTKAANYAVTECDVLIAIGCRFSDRVTGDIRYFAPEAKIIHI 300
         :  . :*:** : .::        :*  :

MJ0277   DIDPAEIGKNVRADIPIVGDAKNVLRDLLAALIALEIKDKFTWLERIYELKRLSIPMMDF 360 comE                 MYPKRIDIIKKIVENVGEKEIIVSNIGIP--SKELYYVKDREPNFYMLG---- 47
MJ0277   DDKPIKPQRFVFDLMEVLNEIDSKLIQNTIIITDVGQNQMWMAHFFKTKMPRSPLASSGLG 420
             : *  :   :  ::.  :: **.:::*       :: .. *.*   * comE     --SMGLASSIGLGLALNCEDKVIVIDCDGSILMNLGSLSTIGYMNPKNYILVIIDN---- 101
MJ0277   TMGFGPPAAIGAKVAKPYAN-VISITGDGGFLMNSQELATISSYDIP-VVICIFDNRTLG 478
         . :*:,::** :*    : * * ***.;***  .*;**.  :    ::  *;**

comE     ------SAYGSTGRQKTHTGKVTNLEEIAKGGGLUTITTESLEEFEKEFKNALNEEK--- 152
MJ0277   MVYQWQNLYYGQRQSEVHLGESPDFVKLAESYGVKADRIISPDEIKKKLNEAILSNEPYL 538
         .  *  . :::.* *:,,.: ::*:. *,:       *  :*::::*:*: .::

comE     CKVIIA------KTIPYNEKCSNIEIPP------------VVLKYRFMEAIKRS 186
MJ0277   LDIVIDPAEALPMVPPGGRLTNIVQPIRVEEKIKKPQFDEIKKIRDMAAVKEF 591
          .::*       :* .: *** *              : * * * *:*,
```

FIG. 21

MJ0277 (SEQ ID NO:22) vs. LacLA (L. lactis)(SEQ ID NO:43)

```
LACLA     MSEKQFGANLVVDSLINHKVKYVFGIPGAKIDRVFDLLENEEGPQMVVTRHEQGAAFMAQ  60
MJ0277    ----MKGAEAIIKALEAEGVKIIFGYPGGAMLPFYDALYDSD-LVHILTRHEQAAAHAAD  55
                    :::.:*  .**:.** .::  ::*  .::   ;:*****.**. *;

LACLA     AVGRLTGEPGVVVTSGPGVSNLATPLLTATSEQDAILAIGGQVKRSDRLKRAHQSMDNA  120
MJ0277    GFARASGEAGVCVSTSGPGATNLVTGIATAYADSSPVIALTGQVPTKLIGNDAFQEIDAL 115
          ...;* :**.** * *****;:**:*  : **  :::..::*: ***     . ; *,*.:*

LACLA     GMMQSATRYSAEVLDPNTLSESIANAYRIAKSQHPCATPLSIPQDVTDAEVSIKAIQPLS 180
MJ0277    GLFMPITKHNFQIKKPEEIPFFRAAFEIATTGRPGPVHIDLPKDVQDGEIDIEKYPIPA  175
          *;:  .**:.. **  :.*; :.*  *;.**;*;:**,.,::.:*** *,:.:*;    :

LACLA     DPKMQ------NASIDDINYLAQAIKNAVLPVILVGAGASDAKVASSLRNLLTHVNIPVV 234
MJ0277    KVDLPGYKPKTVGHPLQIKKAAKLIAESERPVILAGQQVIISGASEELLRLAEFVKIPVC 235
          . .:       . *;*  *; *  ;; ****.*,*,  : .:.,* ,*  .*;***

LACLA     ETPQGAGVISHDLEHTFYGRIGLFNQPGDMLLKRSDLVIAVGYDPIEYEARHWN-AEID  293
MJ0277    TTLMGKSCFPEDHPLALG-MVGMHGTKAANYAVTECDVLIAIGCRFSDRVTSDIRYFAPE 294
          *; *  * :,;:*  : *  ; **;;    ,::,...*:;**;*  :   :  :

LACLA     SKIIVIDNAIAEIDTYYQPERELIGDIAATLDNLLPAVRGYKIPKGTKDYLDGLHEVAEQ 353
MJ0277    AKIIHIDIDPAEIGKNVRAQIPIVGDAKNVLRDLAALIALEIKD-KETWLERIYELKKL 353
          :;** **  ***.. ,;: ;;** . .* ;**.*: . .;*  . .:*; ::**: :

LACLA     HEFDTENTEEGRMHPLDLVSTFQEIVKDDE------TVTVDVGSLYIWMARSFKSYEPRH 407
MJ0277    SIPMMDFDDK-PIKPQRFVEDLMEVLNEIDSKLANTIITTDVGQNQWMAHFFKTKMPRS  412
          ; ;; :*  ;*, ; *:;;: *;:;;    ;*.***, ;****;.****;:  **

LACLA     LLFSNGMQTLGVALPWAITAALLRPGKKVYSHSGDGGFLFTGQELETAVRLNLPIVQIIW 467
MJ0277    FLASGGLGTMGFGFPAAIGAKVAKPYANVISFGDGGPLMNSQELATISEYDIPVVICIF  472
          ;* *.*;  *;,;: ** ** * ; :*  ;* * ;******;; .*** *     ;;:*;*  *;

LACLA     NDGHYDMVKFQEEMKYG-RSAAVDFG-YVDYVKYAEAMPAKGYRAHSKEELAEILKSIPD 525
MJ0277    DNRTLQMVYQWQNLYYGQRQSEVHLGESPDPVKLAESYGVKADRIISPDEIKEKLKEAIL 532
          :;  ,**  ;;; ** *;;.;*  *;:** **; .*,.* * *;* ** .

LACLA     TTGPVVIDVPLDYSDN------------IKLAEKLLPEEFY-----------  554
MJ0277    SNEPVLLDIVIDPAEALPMVPPGGRLTNIVQPIRVEPYIKKPQFDEIPKIRDMAAVKEF  591
          ;. * ;;*;:;*  ;;                  *;;  *;   ;*
```

FIG. 22

LACLA (*Lactococcus lactis*):

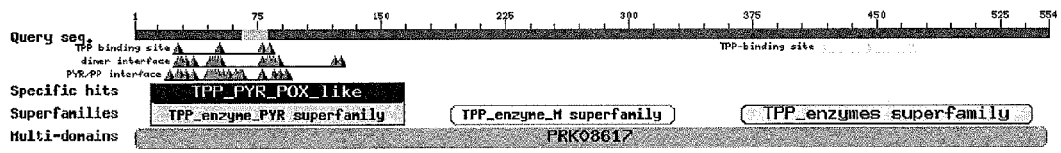

Hypothetical acetolactate synthase MJ0277 (*Methanocaldococcus jannaschii*)

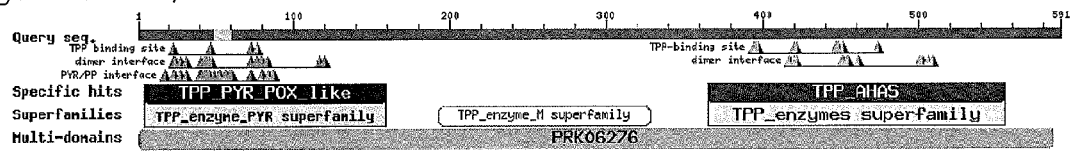

comD/comE (*Methanocellapaludicola*)

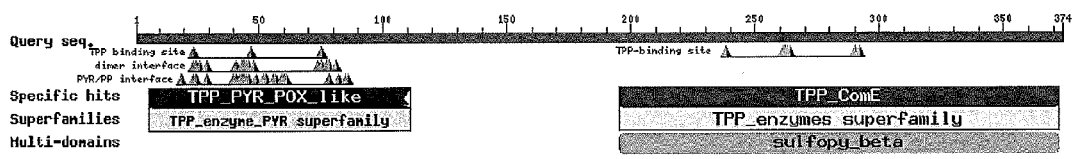

Analysis of the functional domains in LACLA acetolactate synthese, comD/comE from *Methanocella paludicola* and the hypothetical acetolactate synthase MJ0277 showed that all of them have a similar structure containing a thiamine phosphate binding site Map of pING2022 vector, containing the IlvE-Omega Vf fusion gene Map of pING2030 vector containing the IlvE-Ad optimized omega fusion gene

FIG. 25

```
   1 atgaacaaac cgcagagctg ggaggcacgc gcagaaacct acagcctgta tggtttcact
  61 gatatgccga gcttgcacca gcgcggcacg gttgttgtta ctcacggcga gggtccgtac
 121 attgtggatg tcaatggtcg tcgttatctg gacgcgaata gcggcctgtg gaatatggtc
 181 gcgggttttg accataaagg cctgattgac gcggcaaagg cacaatacga gcgctttcca
 241 ggttatcatg ctttctttgg tcgcatgagc gaccagaccg tcatgttgtc cgagaaactg
 301 gtggaagtta gcccgtttga ttcgggccgt gttttctata ccaatagcgg ctccgaggcg
 361 aatgacacca tggtgaaaat gctgtggttt ctgcatgcgg cggaaggtaa accgcagaag
 421 cgtaagatcc tgacccgttg gaacgcatac cacggtgtca ccgctgttag cgcgagcatg
 481 acgggtaaac cgtacaacag cgttttcggt ctgccgctgc cgggcttcgt ccacctgacg
 541 tgcccgcact attggcgtta cggcgaagag ggcgaaacgg aagagcaatt cgtcgcacgt
 601 ctggcacgtg agctggaaga aaccattcaa cgtgagggtg cggataccat tgccggtttc
 661 tttgccgaac cggtcatggg tgctggcggt gtaatcccgc cagcaaaggg ttactttcaa
 721 gcgatcctgc cgattttgcg taagtacgac attccggtga tcagcgacga agttatttgc
 781 ggtttcggcc gtaccggtaa tacgtggggc tgcgtcacgt atgacttcac cccggatgcg
 841 atcattagca gcaaaaacct gaccgcgggt tcttcccta tgggtgccgt gattctgggt
 901 ccggagctgt ctaagcgcct ggaaacggca attgaggcga ttgaagagtt ccgcacggt
 961 ttcactgcga gcggtcatcc tgtgggttgt gcgatcgcgc tgaaggcgat cgatgttgtg
1021 atgaatgagg gtttggccga gaacgtgcgt cgcttggctc cgcgttttga agagcgtctg
1081 aaacacatcg cggagcgccc gaacatcggc gaataccgcg gcatcggctt tatgtgggcc
1141 ttggaggcag tgaaggacaa agcgagcaaa acgccgttcg acggcaacct gagcgtgtct
1201 gagcgcattg ccaacacctg caccgatctg ggcctgatct gtcgtccgct gggtcagtcc
1261 gttgtgctgt gtccgccatt tatcctgacc gaggcccaga tggatgaaat gtttgataag
1321 ctggaaaaag ctctggacaa ggttttcgcc gaggtcgcgt aa
```

SEQ ID 1: IlvE-Omega Vf fusion Gene sequence

```
   1 MNKPQSWEAR AETYSLYGFT DMPSLHQRGT VVVTHGEGPY IVDVNGRRYL DANSGLWNMV
  61 AGFDHKGLID AAKAQYERFP GYHAFFGRMS DQTVMLSEKL VEVSPFDSGR VFYTNSGSEA
 121 NDTMVKMLWF LHAAEGKPQK RKILTRWNAY HGVTAVSASM TGKPYNSVFG LPLPGFVHLT
 181 CPHYWRYGEE GETEEQFVAR LARELEETIQ REGADTIAGF FAEPVMGAGG VIPPAKGYFQ
 241 AILPILRKYD IPVISDEVIC GFGRTGNTWG CVTYDFTPDA IISSKNLTAG FFPMGAVILG
 301 PELSKRLETA IEAIEEFPHG FTASGHPVGC AIALKAIDVV MNEGLAENVR RLAPRFEERL
 361 KHIAERPNIG EYRGIGFMWA LEAVKDKASK TPFDGNLSVS ERIANTCTDL GLICRPLGQS
 421 VVLCPPFILT EAQMDEMFDK LEKALDKVFA EVA
```

SEQ ID 2: IlvE-Omega Vf fusion protein sequence (Expected size 50132 Da)

FIG. 25 (continued)

```
   1 atgagcgccg ctaaactgcc agacctgagc cacctgtgga tgccgtttac cgccaaccgc
  61 cagtttaaag cgaatccgcg cctgttggcg agcgcaaagg gcatgtacta tacgagcttc
 121 gatgccgcc aaattctgga cggcacggca ggtctgtggt gcgtgaatgc aggccattgc
 181 cgtgaagaaa ttgttagcgc gatcgcctcc caagcgggcg tgatggatta cgcaccgggc
 241 ttccagctgg gccacccgtt ggcgttcgag gcagcgaccg ctgtcgcagg tctgatgccg
 301 caaggtctgg accgtgtatt ctttaccaac agcggcagcg agagcgtgga taccgccctg
 361 aagatcgcgc tggcgtacca tcgtgcacgt ggcgaagcgc agcgtacgcg cctgattggc
 421 cgcgagcgcg gttaccacgg tgttggtttt ggtggtatca gcgttggcgg tattagcccg
 481 aaccgcaaga cgttcagcgg cgcattgctg ccggcagtgg atcatttgcc gcacacgcac
 541 agcctggagc ataacgcgtt tacgcgtggt caaccggaat ggggtgctca cttggctgat
 601 gagctggagc gcattatcgc gctgcacgac gcgagcacca ttgcggcggt tattgtcgaa
 661 ccaatggcgg ttctaccgg cgtcttggtg ccgccgaaag gttatctgga aaaactgcgt
 721 gagatcactg cacgccacgg tatcctgctg atctttgacg aggtgattac cgcgtacggt
 781 cgtctgggtg aagcaaccgc ggcagcctac ttcggtgtta ccccggacct gatcaccatg
 841 gccaagggtg tcagcaatgc ggcggtcccg gctggtgccg tggccgttcg tcgcgaagtc
 901 cacgatgcta ttgttaatgg cccgcaaggt ggcatcgagt ttttccatgg ctatacctat
 961 tccgcgcatc ctctggcggc tgcggcggtg ctggcaactc tggacattta tcgtcgtgag
1021 gatctgttcg cccgtgctcg taaactgtcc gctgcgttcg aagaggcggc acactcgctg
1081 aaaggtgcgc cgcatgtgat tgacgtccgt aacatcggtc tggttgcggg tattgaattg
1141 agcccgcgtg agggtgcccc aggtgcgcgt gcggcggagg cattccagaa gtgttttgat
1201 accggcctga tggtccgtta cacgggcgac atcctggccg tttctccgcc gctgattgtg
1261 gacgaaaatc agatcggtca gatctttgag ggcatcggta aggttctgaa agaggtcgca
1321 taa
```

SEQ ID 3: IlvE-Ad optimized omega fusion Gene sequence

```
   1 MSAAKLPDLS HLWMPFTANR QFKANPRLLA SAKGMYYTSF DGRQILDGTA GLWCVNAGHC
  61 REEIVSAIAS QAGVMDYAPG FQLGHPLAFE AATAVAGLMP QGLDRVFFTN SGSESVDTAL
 121 KIALAYHRAR GEAQRTRLIG RERGYHGVGF GGISVGGISP NRKTFSGALL PAVDHLPHTH
 181 SLEHNAFTRG QPEWGAHLAD ELERIIALHD ASTIAAVIVE PMAGSTGVLV PPKGYLEKLR
 241 EITARHGILL IFDEVITAYG RLGEATAAAY FGVTPDLITM AKGVSNAAVP AGAVAVRREV
 301 HDAIVNGPQG GIEFFHGYTY SAHPLAAAAV LATLDIYRRE DLFARARKLS AAFEEAAHSL
 361 KGAPHVIDVR NIGLVAGIEL SPREGAPGAR AAEAFQKCFD TGLMVRYTGD ILAVSPPLIV
 421 DENQIGQIFE GIGKVLKEVA
```

SEQ ID 4: IlvE-Ad optimized omega fusion protein sequence (Expected size 46843.54Da)

FIG. 25 (continued)

```
   1 atgcaggcta ccgaacaaac ccaatctctg aaaaagactg acgaaaaata tctgtggcac
  61 gcgatgcgcg gtgcagctcc gtctccgacc aacctgatta ttaccaaagc tgaaggcgcg
 121 tgggtgaccg acattgacgg taaccgttat ctggatggca tgagcggcct gtggtgtgtt
 181 aatgtcggtt atggccgtaa ggagctggcg cgcgcggcat ttgaacaact ggaagaaatg
 241 ccgtacttcc cgctgactca aagccatgtg ccggctatca aactggcgga aaaactgaac
 301 gaatggctgg acgacgaata cgtgattttc ttctctaatt ctggctccga agcaaacgaa
 361 accgcattca aaatcgcccg tcaatatcac cagcagaaag gtgaccacgg ccgctataaa
 421 ttcatcagcc gttatcgtgc ataccatggt aattctatgg gtgcgctggc tgctaccggt
 481 caggctcagc gcaaatacaa gtacgaaccg ctgggtcagg gtttctgca cgttgcacca
 541 ccggatacct accgtaaccc ggaagacgtc cacaccctgg cttctgccga agaaatcgat
 601 cgtgttatga cctgggagct gtcccagact gttgcgggtg ttatcatgga acctattatt
 661 accggtggtg gcattctgat gccgccggac ggttatatgg gtaaagtcaa ggaaatctgc
 721 gaaaaacacg gcgcgctgct gatctgcgat gaagttatct gtggcttcgg tcgcaccggc
 781 aaaccatttg gcttcatgaa ttatggcgta aaacctgaca ttattaccat ggctaaaggc
 841 attacttccg cttatctgcc gctgagcgcg accgcagttc gccgcgaagt ttatgaagcg
 901 tttgttggtt ctgatgatta cgaccgtttc cgtcatgtaa acacgtttgg cggtaaccca
 961 gcggcatgtg cgctggcgct gaaaaacctg gaaatcatgg aaaacgaaaa gctgatcgaa
1021 cgtagcaaag aactgggtga acgtctgctg tacgaactgg aagatgtcaa agaacacccg
1081 aacgtgggcg atgttcgcgg taaaggcctg ctgctgggta ttgaactggt tgaagacaaa
1141 cagaccaagg aaccggcttc cattgaaaag atgaacaaag tgattaacgc gtgcaaagag
1201 aaaggcctga tcattggtaa gaacggtgat accgtggcag gttataacaa cattctgcag
1261 ctggcgccgc ctctgagcat cactgaagaa gatttcacct tcatcgtcaa aactatgaag
1321 gagtgcctga gccgcatcaa tggtcagtaa
```

SEQ ID 5: *Bacillus weihenstephanensis* KBAB4 Gene sequence

```
  1 MQATEQTQSL KKTDEKYLWH AMRGAAPSPT NLIITKAEGA WVTDIDGNRY LDGMSGLWCV
 61 NVGYGRKELA RAAFEQLEEM PYFPLTQSHV PAIKLAEKLN EWLDDEYVIF FSNSGSEANE
121 TAFKIARQYH QQKGDHGRYK FISRYRAYHG NSMGALAATG QAQRKYKYEP LGQGFLHVAP
181 PDTYRNPEDV HTLASAEEID RVMTWELSQT VAGVIMEPII TGGILMPPD GYMGKVKEIC
241 EKHGALLICD EVICGFGRTG KPFGFMNYGV KPDIITMAKG ITSAYLPLSA TAVRREVYEA
301 FVGSDDYDRF RHVNTFGGNP AACALALKNL EIMENEKLIE RSKELGERLL YELEDVKEHP
361 NVGDVRGKGL LLGIELVEDK QTKEPASIEK MNKVINACKE KGLIIGKNGD TVAGYNNILQ
421 LAPPLSITEE DFTFIVKTMK ECLSRINGQ
```

SEQ ID 6: *Bacillus weihenstephanensis* KBAB4 protein sequence (Expected size 50065 Da)

FIG. 25 (continued)

```
   1 atgaacgcaa gactgcacgc cacgtccccc ctcggcgacg ccgacctggt ccgtgccgac
  61 caggcccact acatgcacgg ctaccacgtg ttcgacgacc accgcgtcaa cggctcgctg
 121 aacatcgccg ccggcgacgg cgcctatatc tacgacaccg ccggcaaccg ctacctcgac
 181 gcggtgggcg gcatgtggtg caccaacatc ggcctggggc gcgaggaaat ggctcgcacc
 241 gtggccgagc agaccgcct gctggcctat tccaatccct ctgcgacat ggccaacccg
 301 cgcgccatcg aactctgccg caagctcgcc gagctggccc ccggcgacct cgaccacgtg
 361 ttcctcacca ccggcggttc caccgccgtg gacaccgcga tccgcctcat gcactactac
 421 cagaactgcc gcggcaagcg cgccaagaag cacgtcatca cgcggatcaa cgcctaccac
 481 ggctcgacct tcctcggcat gtcgctgggc ggcaagagcg ccgaccggcc ggccgagttc
 541 gacttcctcg acgagcgcat ccaccacctc gcctgtccct attactaccg cgctccggaa
 601 gggctgggcg aagccgagtt cctcgatggc ctggtggacg agttcgaacg caagatcctc
 661 gaactgggcg ccgaccgggt ggggcgttc atctccgagc cggtgttcgg ctccggcggc
 721 gtgatcgtcc cgcccgcggg ctaccacagg cggatgtggg agctgtgcca gcgctacgac
 781 gtgctgtaca tctccgacga agtggtgacc tccttcggcc gcctcggcca cttcttcgcc
 841 agccaggcgg tgttcggcgt acagccggac atcatcctca ccgccaaggg cctcacctcc
 901 ggctaccagc cgctgggcgc gtgcatcttc tcccggcgca tctgggaggt gatcgccgag
 961 ccggacaagg gccgctgctt cagccatggt ttcacctact ccggccaccc ggtggcctgc
1021 gcggcggcgc tgaagaacat cgagatcatc gagcgcgagg gcttgctcgc ccacgccgac
1081 gaggtcggcc gctacttcga ggagcgcctg caaagcctcc gcgacctgcc catcgtcggc
1141 gacgtgcgcg ggatgcgctt catggcctgt gtcgagttcg tcgccgacaa ggcgagcaag
1201 gcgctgtttc cggaaagcct gaacatcggc gagtgggtcc acctgcgggc gcagaagcgc
1261 ggcctgctgg ttcgtccgat cgtccacctg aacgtgatgt cgccgccgct gatcctcacc
1321 cgcgaacagg tcgataccgt ggtccgggtg ctgcgcgaga gcatcgagga aaccgtggag
1381 gatcttgtcc gcgccggtca ccggtaa
```

SEQ ID 7: *Pseudomonas aeruginosa* (gi9951072) Gene sequence

```
   1 MNARLHATSP LGDADLVRAD QAHYMHGYHV FDDHRVNGSL NIAAGDGAYI YDTAGNRYLD
  61 AVGGMWCTNI GLGREEMART VAEQTRLLAY SNPFCDMANP RAIELCRKLA ELAPGDLDHV
 121 FLTTGGSTAV DTAIRLMHYY QNCRGKRAKK HVITRINAYH GSTFLGMSLG GKSADRPAEF
 181 DFLDERIHHL ACPYYRAPE GLGEAEFLDG LVDEFERKIL ELGADRVGAF ISEPVFGSGG
 241 VIVPPAGYHR RMWELCQRYD VLYISDEVVT SFGRLGHFFA SQAVFGVQPD IILTAKGLTS
 301 GYQPLGACIF SRRIWEVIAE PDKGRCFSHG FTYSGHPVAC AAALKNIEII EREGLLAHAD
 361 EVGRYFEERL QSLRDLPIVG DVRGMRFMAC VEFVADKASK ALFPESLNIG EWVHLRAQKR
 421 GLLVRPIVHL NVMSPPLILT REQVDTVVRV LRESIEETVE DLVRAGHR
```

SEQ ID 8: : *Pseudomonas aeruginosa* (gi9951072) protein sequence (Expected size 52113 Da)

FIG. 25 (continued)

```
  1 atgaaggttt tagtcaatgg ccggctgatt gggcgcagtg aagcatcaat cgatttggaa
 61 gatcgcggtt atcagtttgg tgacggcatc tatgaagtga tcagggtgta caaaggagta
121 ttgttcggct tacgtgagca tgcagagcgt tttttcagaa gtgctgctga aatcggaatt
181 tcactgccat tcagtataga agatctcgag tgggacctgc aaaagcttgt acaggaaaat
241 gcggtcagtg agggagcggt atacattcag acaacaagag gtgtggcccc gcgaaaacac
301 cagtatgaag ccggcctcga gccgcagact actgcctata cgtttacggt gaaaaaaccg
361 gagcaagagc aggcatacgg agtggcggcc attacagatg aggatcttcg ctggttaaga
421 tgtgatatca aaagtctgaa tttactgtat aatgtcatga cgaagcaaag ggcctatgaa
481 gccggagcat ttgaagccat tttacttagg gacggcgttg ttacggaggg tacatcctct
541 aacgtttatg ccgttatcaa cggcacagtg cgaacacatc cggctaatcg gctcattctc
601 aatggaatta cacggatgaa tatttagga ctgattgaga agaatgggat caaactggat
661 gagactcctg tcagtgaaga agagttgaaa caggcggaag agatctttat ttcgtcaacg
721 acggcagaaa ttattccggt cgtgacgctc gatggacaat cgatcggaag cgggaaaccc
781 ggaccggtga ccaaacagct tcaggctgct tttcaagaaa gcattcaaca ggctgctagc
841 atttcataa
```

SEQ ID 9: : *Bacillus subtilis* (gi16078032) Gene sequence

```
  1 MKVLVNGRLI GRSEASIDLE DRGYQFGDGI YEVIRVYKGV LFGLREHAER FFRSAAEIGI
 61 SLPFSIEDLE WDLQKLVQEN AVSEGAVYIQ TTRGVAPRKH QYEAGLEPQT TAYTFTVKKP
121 EQEQAYGVAA ITDEDLRWLR CDIKSLNLLY NVMTKQRAYE AGAFEAILLR DGVVTEGTSS
181 NVYAVINGTV RTHPANRLIL NGITRMNILG LIEKNGIKLD ETPVSEEELK QAEEIFISST
241 TAEIIPVVTL DGQSIGSGKP GPVTKQLQAA FQESIQQAAS IS
```

SEQ ID 10: : *Bacillus subtilis* (gi16078032) protein sequence (Expected size 31182 Da)

FIG. 25 (continued)

```
   1 atgagtgcca acaacccgca aaccctcgaa tggcaggccc tgagcagcga gcatcacctg
  61 gcaccgttca gcgactacaa acaactgaaa gagaaaggcc cgcgcatcat cacccgtgcc
 121 gagggcgttt atctgtggga cagcgagggc aacaagatcc tcgatggcat gtccggcctg
 181 tggtgcgtgg ccatcggtta tggccgcgaa gaactggccg acgcagccag caaacagatg
 241 cgcgagctgc cgtactacaa cctgttcttc cagaccgccc acccgccggt gctggaactg
 301 gccaaggcca tctccgacat cgctcccgag ggcatgaacc atgtgttctt caccggttca
 361 ggctctgaag gcaatgacac gatgctgcgc atggttcgtc attactgggc gctgaaaggc
 421 cagccgaaca agaaaaccat catcagccgc gtcaatggct accacggctc caccgtcgcc
 481 ggtgccagcc tgggtggcat gacctacatg cacgaacagg gcgacctgcc gatcccgggg
 541 gtggtgcaca ttccacagcc ttactggttc ggcgaaggcg gcgacatgac gccggacgag
 601 ttcggcatct gggcggccga gcaactggaa aagaaaattc tcgagctggg cgtcgagaac
 661 gtcggtgcgt tcattgccga gccaatccag ggcgcgggcg gtgtgattgt cccgcctgat
 721 tcctactggc cgaagatcaa ggaaatcctt tcccgctacg acatcctgtt cgccgccgat
 781 gaggtgattt gtggcttcgg gcgtaccagt gagtggttcg gtagcgattt ctatggcctc
 841 aggccggaca tgatgaccat cgccaaaggc ctgacctccg gttacgtacc gatgggcggc
 901 ctgatcgtgc gcgatgaaat cgttgcggtg ctcaatgagg gtggcgattt caatcacggc
 961 tttacctact ccgggcaccc ggtggcggcc gcggttgcgc tggagaacat ccgtatcctg
1021 cgcgaagaaa agatcgtcga acgggtcagg tcggaaacgc accgtatttt gcaaaagcgt
1081 ttgcgtgagt tgagcgatca tccgctggtg ggcgaagtcc ggggtgtcgg gctgctcggg
1141 gccattgagc tggtgaagga caagaccacc cgcgagcgct ataccgacaa gggcgcggga
1201 atgatctgtc gaaccttctg cttcgacaat ggcctgatca tgcgggctgt gggcgatacc
1261 atgatcattg cgccgccact ggtgatcagt tttgcgcaaa tcgatgagct ggtagagaag
1321 gcgcgcacgt gtctggatct gacgctggcg gtgttgcagg gctga
```

SEQ ID 11: : *Pseudomonas syringae* class III Gene sequence

```
   1 atgcccggtt gcggggcgtt gcccgggaat gaaccgaaat gcggacgaga ggggaggtcg
  61 gcgatgacgc ggaatgacgc gacgaatgct gccggagcgg tgggcgcggc gatgcgggat
 121 cacatcctct tgcctgcaca ggaaatggcg aagctcggca agtccgcgca gccggtgctg
 181 actcatgccg agggcatcta tgtccatacc gaggacggcc gccgcctgat cgacgggccg
 241 gcgggcatgt ggtgcgcgca ggtgggctac ggccgccgcg agatcgtcga tgccatggcg
 301 catcaggcga tggtgctgcc ctatgcctcg ccctggtata tggccacgag ccccgcggcg
 361 cggctggcgg agaagatcgc cacgctgacg ccgggcgatc tcaaccggat cttttttcacc
 421 acgggcgggt cgaccgcggt ggacagcgcg ctgcgcttct cggaattcta caacaacgtg
 481 ctgggccggc cgcagaagaa gcgcatcatc gtgcgctacg acggctatca cggctcgacg
 541 gcgctcaccg ccgcctgcac cggccgcacc ggcaactggc cgaacttcga catcgcgcag
 601 gaccggatct cgttcctctc gagccccaat ccgcgccacg ccggcaaccg cagccaggag
 661 gcgttcctcg acgatctggt gcaggaattc gaggaccgga tcgagagcct cggccccgac
 721 acgatcgcgg ccttcctggc cgagccgatc ctcgcctcgg gcggcgtcat tattccgccc
 781 gcaggctatc atgcgcgctt caaggcgatc tgcgagaagc acgacatcct ctatatctcg
 841 gacgaggtgg tgacgggctt cggccgttgc ggcgagtggt tcgcctcgga gaaggtgttc
 901 ggggtggtgc cggacatcat caccttcgcc aagggcgtga cctcgggcta tgtgccgctc
 961 ggcggccttg cgatctccga ggcggtgctg gcgcggatct cgggcgagaa tgccaaggga
1021 agctggttca ccaacggcta tacctacagc aatcagccgg tggcctgcgc cgcggcgctt
1081 gccaacatcg agctgatgga gcgcgagggc atcgtcgatc aggcgcgcga gatggcggac
1141 tatttcgccg cggcgctggc ttcgctgcgc gatctgccgg gcgtggcgga aacccggtcg
1201 gtgggcctcg tgggttgcgt gcaatgcctg ctcgacccga cccggggcgga cggcacggcc
1261 gaggacaagg ccttcaccct gaagatcgac gagcgctgct tcgagctcgg gctgatcgtg
1321 cgcccgctgg gcgatctctg cgtgatctcg ccgccgctca tcatctcgcg cgcgcagatc
1381 gacgagatgg tcgcgatcat gcggcaggcc atcaccgaag tgagcgccgc ccacggtctg
1441 accgcgaaag aaccggccgc cgtctga
```

SEQ ID 13: *Rhodobacter sphaeroides* class III Gene sequence

```
   1 MetPGCGGLP GNEPKCGREG RSAMetTRND ATNAAGAVGA AMetRDHILL PAQEMetAKL
  61 GKSAQPVLTH AEGIYVHTED GRRLIDGPAG MetWCAQVGY GRREIVDAMe tAHQAMetVL
 121 PYASPWYMet ATSPAARLAE KIATLTPGDL NRIFFTTGGS TAVDSALRFS EFYNNVLGRP
 181 QKKRIIVRYD GYHGSTALTA ACTGRTGNWP NFDIAQDRIS FLSSPNPRHA GNRSQEAFLD
 241 DLVQEFEDRI ESLGPDTIAA FLAEPILASG GVIIPPAGYH ARFKAICEKH DILYISDEVV
 301 TGFGRCGEWF ASEKVFGVVP DIITFAKGVT SGYVPLGGLA ISEAVLARIS GENAKGSWFT
 361 NGYTYSNQPV ACAAALANIE LMetEREGIV DQAREMetAD YFAAALASLR DLPGVAETRS
 421 VGLVGCVQCL LDPTRADGTA EDKAFTLKID ERCFELGLIV RPLGDLCVIS PPLIISRAQI
 481 DEMetVAIMe tRQAITEVSA AHGLTAKEPA AV
```

SEQ ID 14: *Rhodobacter sphaeroides* class III protein sequence (Expected size 54973 Da)

FIG. 25 (continued)

```
   1 atggaccaga agctgttaac ggatttccgc tcagaactac tcgattcacg ttttggcgca
  61 aaggccattt ctactatcgc ggagtcaaaa cgatttccgc tgcacgaaat gcgcgatgat
 121 gtcgcatttc agattatcaa tgatgaatta tatcttgatg gcaacgctcg tcagaacctg
 181 gccactttct gccagacctg ggacgacgaa aacgtccata aattgatgga tttgtcgatc
 241 aataaaaact ggatcgacaa agaagaatat ccgcaatccg cagccatcga cctgcgttgc
 301 gtaaatatgg ttgccgatct gtggcatgcg cctgcgccga aaaatggtca ggccgttggc
 361 accaacacca ttggttcttc cgaggcctgt atgctcggcg ggatggcgat gaaatggcgt
 421 tggcgcaagc gtatggaagc tgcaggcaaa ccaacggata aaccaaacct ggtgtgcggt
 481 ccggtacaaa tctgctggca taaattcgcc cgctactggg atgtggagct gcgtgagatc
 541 cctatgcgcc ccggtcagtt gtttatggac ccgaaacgca tgattgaagc ctgtgacgaa
 601 aacaccatcg gcgtggtgcc gactttcggc gtgacctaca ccggtaacta tgagttccca
 661 caaccgctgc acgatgcgct ggataaattc caggccgaca ccggtatcga catcgacatg
 721 cacatcgacg ctgccagcgg tggcttcctg gcaccgttcg tcgcccggaa tatcgtctgg
 781 gacttccgcc tgccgcgtgt gaaatcgatc agtgcttcag gccataaatt cggtctggct
 841 ccgctgggct gcggctgggt tatctggcgt gacgaagaag cgctgccgca ggaactggtg
 901 ttcaacgttg actacctggg tggtcaaatt ggtacttttg ccatcaactt ctcccgcccg
 961 gcgggtcagg taattgcaca gtactatgaa ttcctgcgcc tcggtcgtga aggctatacc
1021 aaagtacaga acgcctctta ccaggttgcc gcttatctgg cggatgaaat cgccaaactg
1081 gggccgtatg agttcatctg tacgggtcgc ccggacgaag gcatcccggc ggtttgcttc
1141 aaactgaaag atggtgaaga tccgggatac accctgtacg acctctctga acgtctgcgt
1201 ctgcgcggct ggcaggttcc ggccttcact ctcggcggtg aagccaccga catcgtggtg
1261 atgcgcatta tgtgtcgtcg cggcttcgaa atggactttg ctgaactgtt gctggaagac
1321 tacaaagcct ccctgaaata tctcagcgat cacccgaaac tgcagggtat tgcccagcag
1381 aacagcttta aacacacctg a
```

SEQ ID 15: *Escherichia coli* GadA glutamate decarboxylase WT gene sequence (GeneBank NC_000913; fragment 3664203-3665603)

```
  1 MDQKLLTDFR SELLDSRFGA KAISTIAESK RFPLHEMRDD VAFQIINDEL YLDGNARQNL
 61 ATFCQTWDDE NVHKLMDLSI NKNWIDKEEY PQSAAIDLRC VNMVADLWHA PAPKNGQAVG
121 TNTIGSSEAC MLGGMAMKWR WRKRMEAAGK PTDKPNLVCG PVQICWHKFA RYWDVELREI
181 PMRPGQLFMD PKRMIEACDE NTIGVVPTFG VTYTGNYEFP QPLHDALDKF QADTGIDIDM
241 HIDAASGGFL APFVAPDIVW DFRLPRVKSI SASGHKFGLA PLGCGWVIWR DEEALPQELV
301 FNVDYLGGQI GTFAINFSRP AGQVIAQYYE FLRLGREGYT KVQNASYQVA AYLADEIAKL
361 GPYEFICTGR PDEGIPAVCF KLKDGEDPGY TLYDLSERLR LRGWQVPAFT LGGEATDIVV
421 MRIMCRRGFE MDFAELLLED YKASLKYLSD HPKLQGIAQQ NSFKHT
```

SEQ ID 16: *Escherichia coli* GadA glutamate decarboxylase protein sequence (Expected size 52685 Da)

FIG. 25 (continued)

```
   1 atgccacact ctctgttttc tactgatact gatctgactg cggaaaacct gctgcgtctg
  61 ccggctgaat tcggttgtcc ggtatgggtg tacgacgctc agattattcg tcgccagatc
 121 gcagcactga agcagttcga tgtagtgcgt tttgcacaga aggcgtgctc caacatccat
 181 atcctgcgcc tgatgcgtga gcagggcgtt aaagttgact ccgtctctct gggtgagatt
 241 gagcgcgccc tggcagccgg ctataaccca cagacccatc ctgacgacat tgtatttact
 301 gccgacgtga tcgaccaggc tactctggaa cgcgtttctg aactgcagat cccggttaat
 361 gctggttctg tggacatgct ggaccagctg ggccaggtat cccaggtca tcgtgtgtgg
 421 ctgcgtgtca acccaggttt cggccacggc cactctcaga aaactaacac tggtggtgag
 481 aactccaagc atggcatttg gtataccgat ctgccggctg cactggacgt aatccagcgt
 541 caccacctgc agctggtggg catccacatg cacattggct ccggcgtaga ctacgcccac
 601 ctggagcaag tctgcggtgc tatggtacgt caggtaatcg agttcggcca agatctgcag
 661 gcaatcagcg ctggtggcgg cctgtctgta ccttatcagc agggcgagga ggcggttgac
 721 actgagcact actacggtct gtggaacgcc gctcgtgagc aaattgcacg tcacctgggc
 781 cacccggtga aactggagat cgagccgggc cgcttcctgg tagcacagtc cggcgtactg
 841 attacccagg tacgctctgt taaacagatg ggctcccgtc actttgtgct ggtagacgca
 901 ggcttcaacg acctgatgcg tccggctatg tatggttcct atcatcacat ctctgcgctg
 961 gccgccgacg gccgctctct ggaacacgcg ccgacggttg aaacggtggt ggctggtccg
1021 ctgtgcgagt ccggcgacgt tttcactcag caggagggcg gcaatgtaga gacgcgtgcg
1081 ctgccggaag tgaaagccgg tgattatctg gtgctgcatg ataccggcgc ctatggtgcg
1141 agcatgagca gcaactacaa ctctcgcccg ctgctgccgg aggtcctgtt cgataacggc
1201 caagcccgcc tgatccgtcg tcgtcagacc atcgaggaac tgctggcact ggagctgctg
1261 taa
```

SEQ ID 17: *Escherichia coli* LysA diaminopimelate decarboxylase *E. coli* codon-optimized gene sequence (GeneBank JA114145)

```
   1 MPHSLFSTDT DLTAENLLRL PAEFGCPVWV YDAQIIRRQI AALKQFDVVR FAQKACSNIH
  61 ILRLMREQGV KVDSVSLGEI ERALAAGYNP QTHPDDIVFT ADVIDQATLE RVSELQIPVN
 121 AGSVDMLDQL GQVSPGHRVW LRVNPGFGHG HSQKTNTGGE NSKHGIWYTD LPAALDVIQR
 181 HHLQLVGIHM HIGSGVDYAH LEQVCGAMVR QVIEFGQDLQ AISAGGGLSV PYQQGEEAVD
 241 TEHYYGLWNA AREQIARHLG HPVKLEIEPG RFLVAQSGVL ITQVRSVKQM GSRHFVLVDA
 301 GFNDLMRPAM YGSYHHISAL AADGRSLEHA PTVETVVAGP LCESGDVFTQ QEGGNVETRA
 361 LPEVKAGDYL VLHDTGAYGA SMSSNYNSRP LLPEVLFDNG QARLIRRRQT IEELLALELL
```

SEQ ID 18: *Escherichia coli* LysA diaminopimelate decarboxylase protein sequence (Expected size 46177 Da)

```
>comDSulfopyruvate decarboxylase subunit alpha OS=Methanocaldococcus
jannaschii
MRGSLAIYNALKDSNIDFICSVPCANLKNLLKLIEEDKNIINIPATREEEAFGICAGAYLAGKKTAILMQNSGIG
NSINAIASLYKTFQIPTLLIISHRGDLKEQIPAQIPMGRWIEKLLDVCEIPTYKPKTPEEAYKLIKYASSYMYKI
SYPVALLFDALYWEYDLEK
```

SEQ ID 19: ComD subunit of sulfopyruvate decarboxylase (EC.4.1.1.79)

FIG. 25 (continued)

>comESulfopyruvate decarboxylase subunit beta OS=Methanocaldococcus jannaschii
MYPKRIDIIKKIVENVGEKEIIVSNIGIPSKELYYVKDRERNFYMLGSMGLASSIGLGLALNCEDKVIVIDGDGS
ILMNLGSLSTIGYMNPKNYILVIIDNSAYGSTGNQKTHTGKNTNLEEIAKGCGLDTITTESLEEFEKEFKNALNE
EKCKVIIAKTIPYNEKCSNIEIPPVVLKYRFMEAIKRS

SEQ ID 20: ComE subunit of sulfopyruvate decarboxylase (EC.4.1.1.79)

>comD/comE Methanocella paludicola
MANVEQEVIDIMKSSGIDTVLTLPCDKIKNLLAMVPSNFKEIPLTREENGIGIAAGLSMAGKRPALIIQSTGIGN
SLNVLSSLNRTYEIPLPILASWRGYYKEAIYAQTAFGKCLPAILEASDIQHIEIGAMGELDLIKKAIIASFKSNL
PTVILLSPRLWEISTERHWNPDFTPRERRFDMECHTVVPKATHTRYDMIKGITSYLSGKVVVSNIGIPSKELYAA
HDQDTNFYMTGSLGLVSAIGQGLAMGLSREVITLDGDGSILMNPNVLASVAQEKPENLTIICFDNSAHGSTGNQK
TYSESMDLELLAKAFGIENTAKASTPGELLEALEKRGKGPRFIHAIIEAKNADVPNIPLTPVEIKERFMGAVTR

SEQ ID 21: ComD/comE decarboxylase from *Methanocella paludicola*

>MJ0277 (gi|15668452|ref|NP_247250.1| acetolactate synthase catalytic subunit [Methanocaldococcus jannaschii DSM 2661])
MKGAEAIIKALEAEGVKIIFGYPGGAMLPFYDALYDSDLVHILTRHEQAAAHAADGFARASGEAGVCVSTSGPGA
TNLVTGIATAYADSSPVIALTGQVPTKLIGNDAFQEIDALGLFMPITKHNFQIKKPEEIPETFRAAFEIATTGRP
GPVHIDLPKDVQDGEIDIEKYPIPAKVDLPGYKPKTVGHPLQIKKAAKLIAESERPVILAGGGVIISGASEELLR
LAEFVKIPVCTTLMGKGCFPEDHPLALGMVGMHGTKAANYAVTECDVLIAIGCRFSDRVTGDIRYFAPEAKIIHI
DIDPAEIGKNVRADIPIVGDAKNVLRDLLAALIALEIKDKETWLERIYELKKLSIPMMDFDDKPIKPQRFVKDLM
EVLNEIDSKLKNTIITTDVGQNQMWMAHFFKTKMPRSFLASGGLGTMGFGFPAAIGAKVAKPYANVISITGDGGF
LMNSQELATISEYDIPVVICIFDNRTLGMVYQWQNLYYGQRQSEVHLGESPDFVKLAESYGVKADRIISPDEIKE
KLKEAILSNEPYLLDIVIDPAEALPMVPPGGRLTNIVQPIRVEPKIKKPQFDEIKKIRDMAAVKEF

SEQ ID 22

>MJ0663 (gi|15668844|ref|NP_247647.1| acetolactate synthase large subunit IlvB [Methanocaldococcus jannaschii DSM 2661])
MGGNIKFLEAMVDFLERNVKTIFSYPGEQILPLYNEIEGSSIKNIMVRDERGAGFMADGYARITNYIGVCLATAG
PGATNLTTPIATAYKDNSSVLAITGRCQRKYIGKNYFQEVNMDFLNFYKGYFVDKAEVSYIAKAFADCLFNKKPV
QLNIPVDLYKEEAKDINITTYTDIYKDDETPSNNIKEIDVKKPLFLIGQGIFGTLSYKEIVKISKILEKINCPIA
TTFPARGVINEKLENCIGLVGRRGDLKSLLEADKIINIGSSLSYNTYVESVREKLLSKTENIQLKPKSIKELKEF
FENLDVKNSSWIYKNSNKFQPSGDYSNKIYEIIKNIPEDAIIVTDAGKHTVFTCLLKTCVIPRNIISSHSFGTMG
FGLPASIGVKFGTIDFNIDREVVLISGDGGFLMNVEELQVVAENNLKILMVVMKNNSLAEFCKIKNPNFNKIADA
FEIDNCYIENVDEIGSEIKGYLKKNKPLLVVVETENEPLPKPNI

SEQ ID 23

FIG. 25 (continued)

>NP_247250.1 acetolactate synthase catalytic subunit [Methanocaldococcus jannaschii DSM 2661]
MKGAEAIIKALEAEGVKIIFGYPGGAMLPFYDALYDSDLVHILTRHEQAAAHAADGFARASGEAGVCVSTSGPGA
TNLVTGIATAYADSSPVIALTGQVPTKLIGNDAFQEIDALGLFMPITKHNFQIKKPEEIPETFRAAFEIATTGRP
GPVHIDLPKDVQDGEIDIEKYPIPAKVDLPGYKPKTVGHPLQIKKAAKLIAESERPVILAGGGVIISGASEELLR
LAEFVKIPVCTTLMGKGCFPEDHPLALGMVGMHGTKAANYAVTECDVLIAIGCRFSDRVTGDIRYFAPEAKIIHI
DIDPAEIGKNVRADIPIVGDAKNVLRDLLAALIALEIKDKETWLERIYELKKLSIPMMDFDDKPIKPQRFVKDLM
EVLNEIDSKLKNTIITTDVGQNQMWMAHFFKTKMPRSFLASGGLGTMGFGFPAAIGAKVAKPYANVISITGDGGF
LMNSQELATISEYDIPVVICIFDNRTLGMVYQWQNLYYGQRQSEVHLGESPDFVKLAESYGVKADRIISPDEIKE
KLKEAILSNEPYLLDIVIDPAEALPMVPPGGRLTNIVQPIRVEPKIKKPQFDEIKKIRDMAAVKEF
39SEQ ID 24

>NP_247647.1 acetolactate synthase large subunit IlvB [Methanocaldococcus jannaschii DSM 2661]
MGGNIKFLEAMVDFLERNVKTIFSYPGEQILPLYNEIEGSSIKNIMVRDERGAGFMADGYARITNYIGVCLATAG
PGATNLTTPIATAYKDNSSVLAITGRCQRKYIGKNYFQEVNMDFLNFYKGYFVDKAEVSYIAKAFADCLFNKKPV
QLNIPVDLYKEEAKDINITTYTDIYKDDETPSNNIKEIDVKKPLFLIGQGIFGTLSYKEIVKISKILEKINCPIA
TTFPARGVINEKLENCIGLVGRRGDLKSLLEADKIINIGSSLSYNTYVESVREKLLSKTENIQLKPKSIKELKEF
FENLDVKNSSWIYKNSNKFQPSGDYSNKIYEIIKNIPEDAIIVTDAGKHTVFTCLLKTCVIPRNIISSHSFGTMG
FGLPASIGVKFGTIDFNIDREVVLISGDGGFLMNVEELQVVAENNLKILMVVMKNNSLAEFCKIKNPNFNKIADA
FEIDNCYIENVDEIGSEIKGYLKKNKPLLVVVETENEPLPKPNI
SEQ ID 25

>gi|17432994|sp|P58416.1|COME_METJA RecName: Full=Sulfopyruvate decarboxylase subunit beta
MYPKRIDIIKKIVENVGEKEIIVSNIGIPSKELYYVKDRERNFYMLGSMGLASSIGLGLALNCEDKVIVIDGDGS
ILMNLGSLSTIGYMNPKNYILVIIDNSAYGSTGNQKTHTGKNTNLEEIAKGCGLDTITTESLEEFEKEFKNALNE
EKCKVIIAKTIPYNEKCSNIEIPPVVLKYRFMEAIKRS
SEQ ID 26

>gi|15668272|ref|NP_247065.1| signal recognition particle protein Srp54 [Methanocaldococcus jannaschii DSM 2661]
MLDKLGENLNKALNKLKAAAFVDKKLIKEVIKDIQRALIQADVNVKLVLKMSKEIERRALEEKTPKGLSKKEHII
KIVYEELVKLLGEEAKKLELNPKKQNVILLVGIQGSGKTTTAAKLARYIQKRGLKPALIAADTYRPAAYEQLKQL
AEKIHVPIYGDETRTKSPVDIVKEGMEKFKKADVLIIDTAGRHKEEKGLLEEMKQIKEITNPDEIILVIDGTIGQ
QAGIQAKAFKEAVGEIGSIIVTKLDGSAKGGGALSAVAETKAPIKFIGIGEGIDDLEPFDPKKFISRLLGMGDLE
SLLEKAEDMVDEKTEESIDAIMRGKFTLNELMTQLEAIENMGSMKKILSMIPGFGGAMPKELSHLTEAKIKKYKV
IISSMTKEERENPKIIKASRIRRIARGSGTTENDVREVLRYYETTKNAIDKLRKGKMLRIGGPLGQIMRQLMFKE
G
SEQ ID 27

FIG. 25 (continued)

>gi|15669612|ref|NP_248425.1| cobyrinic acid a,c-diamide synthase
[Methanocaldococcus jannaschii DSM 2661]
MIMKRVVIAGTSSEVGKTVISTGIMKALSKKYNVQGYKVGPDYIDPTYHTIATGNKSRNLDSFFMNKEQIKYLFQ
KHSKDKDISVIEGVRGLYEGISAIDDIGSTASVAKALDSPIILLVNAKSLTRSAIAIIKGFMSFDNVKIKGVIFN
FVRSENHIKKLKDAMSYYLPDIEIIGFIPRNEDFKVEGRHLGLVPTPENLKEIESKIVLWGELVEKYLDLDKIVE
IADEDFEEVDDVFLWEVNENYKKIAVAYDKAFNFYYWDNFEALKENKAKIEFFSPLKDSEVPDADILYIGGGYPE
LFKEELSRNKEMIESIKEFDGYIYGECGGLMYITKSIDNVPMVGLLNCSAVMTKHVQGLSYVKAEFLEDCLIGRK
GLKFKGHEFHYSKLVNIKEERFAYKIERGRGIINNLDGIFNGKVLAGYLHNHAVANPYFASSMVNFGE
SEQ ID 28

>gi|17432993|sp|P58415.1|COMD_METJA RecName: Full=Sulfopyruvate
decarboxylase subunit alpha
MRGSLAIYNALKDSNIDFICSVPCANLKNLLKLIEEDKNIINIPATREEEAFGICAGAYLAGKKTAILMQNSGIG
NSINAIASLYKTFQIPTLLIISHRGDLKEQIPAQIPMGRWIEKLLDVCEIPTYKPKTPEEAYKLIKYASSYMYKI
SYPVALLFDALYWEYDLEK
SEQ ID 29

>gi|15668717|ref|NP_247516.1| 2-oxoglutarate ferredoxinoxidoreductase
subunit beta [Methanocaldococcus jannaschii DSM 2661]
MHPALKYMRQDRLPHIFCSGCGNGIVMNCFLKAIEELNIKPEDYIAVSGIGCSSRVPGYLYCDSLHTTHGRPIAF
ATGIKIARPDKHVVVFTGDGDLAAIGGNHFIHGCRRNIDLTVICINNNIYGMTGGQVSPTTPYGKKATTAPYGSI
ENTMDLCKMAIAAGATYVARWTTAHPIQLVRSIKKGIQKKGFAFIEVVSQCPTYYGRFNISRKPADMIKFLKENS
IHLNKAKDMSEEELNGKIVVGEFLDIEKPEFVEELHKLIEKLKSE
SEQ ID 30

>gi|15668512|ref|NP_247310.1| hypothetical protein MJ_0337
[Methanocaldococcus jannaschii DSM 2661]
MMALNEYDAQIVEQAMKPILDSNLFSRKIFQKKKIPEDVEVYNLVQVVFDENAFKKGSMELTEVPIKTTTSPFTV
FDINLKVTKARRFVEGPNADYNKAQIFEGLAKVVARAENQYSIDALSKNNTAVGASASWNGADTTPDKIANDIID
AKTKIEQYSNAKCALVAPVDAIACFRKIGTQGFSAYDETKDFIKEIIPTNLITDKSAYLVPIDIAILQMGVAVEA
DQFIEKKATQVEFIFTEAISPMVKEKNGIIKIQKVLG
SEQ ID 31

>gi|15668717|ref|NP_247516.1| 2-oxoglutarate ferredoxinoxidoreductase
subunit beta [Methanocaldococcus jannaschii DSM 2661]
MHPALKYMRQDRLPHIFCSGCGNGIVMNCFLKAIEELNIKPEDYIAVSGIGCSSRVPGYLYCDSLHTTHGRPIAF
ATGIKIARPDKHVVVFTGDGDLAAIGGNHFIHGCRRNIDLTVICINNNIYGMTGGQVSPTTPYGKKATTAPYGSI
ENTMDLCKMAIAAGATYVARWTTAHPIQLVRSIKKGIQKKGFAFIEVVSQCPTYYGRFNISRKPADMIKFLKENS
IHLNKAKDMSEEELNGKIVVGEFLDIEKPEFVEELHKLIEKLKSE
SEQ ID 32

FIG. 25 (continued)

```
>kgd 2-ketoglutarate decarboxylase 4.1.1.71Mycobacterium leprae
MANISSPFGQNEWLVEEMYRKFRDDPSSVDPSWHEFLVDYNPESTAEPVLTDPTSTDKQPSATPQAKPAAAADPV
ASRAKPATTPTVANGTAAGSAAAPAKTTTTPPIEGDELQVLRGAAAVVVKNMSASLDVPTATSVRAVPAKLMIDN
RTVINNQLKRNRGGKISFTHLLGYALVQAVKKFPNINRHYAEIDGKPIAVTPAHTNLGLAIDLQGKDGKRSLVVA
GIKRCEELRFAQFVTAYEDIVRRARDGKLTAEDFAGVTISLTNPGTIGTVHSVPRLMTGQGAIIGVGAMEYPAEF
QGASAERIAELGIGKLITLTSTYDHRIIQGAESGDFLRTIHEMVLSDSFWDEIFRELSIPYLPVRWRTDNPDSIV
DKNARVMELIAAYRNRGHLMADIDPLRLDNTRFRSHPDLDLLTHGLTLWDLDRVFKVNGFGGWKYKKLRDVLGLL
RDAYCRHIGVEYTHILDPEQQEWLQQRVETKNVKPTVAEQKYILSKLNAAEAFETFLHTKYVGQKRFSLEGAESV
IPMMDAAIDQCAKHGLDEVVIGMPHRGRLNVLANIVGKPYSQIFTEFEGNLNPTLAHSSGDVKYHLGATGLYLQM
FGDNDIQVSLTANPSHLEAVDPVLEGLVRAKQDLLNKDTNGNQDEAFSVVPMMLHGDAAFAGQGVVAETLNLANL
PGYRVGGTIHIIVNNQIGFTTAPEYSRSSEYCTDVAKMIGAPIFHVNGDDPEACVWVAKLAVDFRQRFKKDVVID
MLCYRRRGHNEGDDPSMTNPYMYDVVDTKRGARKSYTEALIGRGDISLKEAEDALRDYQGQLERVFNEVRDLEKH
GVQPSESVESDQMIPAGLSTAVDKALLARIGDAFLAVPEGFTVHPRVQPVLEKRREMAYEGKIDWAFAELLALGS
LVAEGKLVRLSGQDTKRGTFSQRHSVIIDRHTGEEFTPLQLLANNPDGSPTGGKFLVYNSPLSEYAAVGFEYGYT
VGNPDAVVLWEAQFGDFVNGAQSIIDEFINSGEAKWGQLSTVVLLLPHGHEGQGPDHTSGRIERFLQLWAEGSMT
FAVPSTPSNYFHLLRRHALDGIKRPLIVFTPKSMLRNKAAVSDIKDFTEIKFRSVLEEPTYEDSIDDRSKVTRVL
LTCGKLYYELAARKIKDNRDDVAIVRIEQLAPLPRRRLGETLDRYENAKEFFWVQEEPANQGAWPRFGLELPELL
PRLTGIKRISRRAMSAPSSGSSKVHAVEQQEILDTAFG
SEQ ID 33

>kivd Lactococcus lactisQ684J7
MYTVGDYLLDRLHELGIEEIFGVPGDYNLQFLDQIISHKDMKWVGNANELNASYMADGYARTKKAAAFLTTFGVG
ELSAVNGLAGSYAENLPVVEIVGSPTSKVQNEGKFVHHTLADGDFKHFMKMHEPVTAARTLLTAENATVEIDRVL
SALLKERKPVYINLPVDVAAAKAEKPSLPLKKENSTSNTSDQEILNKIQESLKNAKKPIVITGHEIISFGLEKTV
TQFISKTKLPITTLNFGKSSVDEALPSFLGIYNGTLSEPNLKEFVESADFILMLGVKLTDSSTGAFTHHLNENKM
ISLNIDEGKIFNERIQNFDFESLISSLLDLSEIEYKGKYIDKKQEDFVPSNALLSQDRLWQAVENLTQSNETIVA
EQGTSFFGASSIFLKSKSHFIGQPLWGSIGYTFPAALGSQIADKESRHLLFIGDGSLQLTVQELGLAIREKINPI
CFIINNDGYTVEREIHGPNQSYNDIPMWNYSKLPESFGATEDRVVSKIVRTENEFVSVMKEAQADPNRMYWIELI
LAKEGAPKVLKKMGKLFAEQNKS
SEQ ID 34

>ARO10Transaminated amino acid decarboxylaseEC=4.1.1.-Saccharomyces
cerevisiae
MAPVTIEKFVNQEERHLVSNRSATIPFGEYIFKRLLSIDTKSVFGVPGDFNLSLLEYLYSPSVESAGLRWVGTCN
ELNAAYAADGYSRYSNKIGCLITTYGVGELSALNGIAGSFAENVKVLHIVGVAKSIDSRSSNFSDRNLHHLVPQL
HDSNFKGPNHKVYHDMVKDRVACSVAYLEDIETACDQVDNVIRDIYKYSKPGYIFVPADFADMSVTCDNLVNVPR
ISQQDCIVYPSENQLSDIINKITSWIYSSKTPAILGDVLTDRYGVSNFLNKLICKTGIWNFSTVMGKSVIDESNP
TYMGQYNGKEGLKQVYEHFELCDLVLHFGVDINEINNGHYTFTYKPNAKIIQFHPNYIRLVDTRQGNEQMFKGIN
FAPILKELYKRIDVSKLSLQYDSNVTQYTNETMRLEDPTNGQSSIITQVHLQKTMPKFLNPGDVVVCETGSFQFS
VRDFAFPSQLKYISQGFFLSIGMALPAALGVGIAMQDHSNAHINGGNVKEDYKPRLILFEGDGAAQMTIQELSTI
LKCNIPLEVIIWNNNGYTIERAIMGPTRSYNDVMSWKWTKLFEAFGDFDGKYTNSTLIQCPSKLALKLEELKNSN
KRSGIELLEVKLGELDFPEQLKCMVEAAALKRNKK
SEQ ID 35
```

FIG. 25 (continued)

```
>MdlCBenzoylformate decarboxylase 4.1.1.7 Sulfolobussolfataricus
MKVGNALFKLMSELGIRQVFGNPGTTELSFLKHMPKDFNYYLALHDGISVGMAEGYYFATRKPQIVNLHSSPGLT
NAMGFIYEALISRIPLIVLVGQQYLYRLIDEPVLYGDFIKISQGVVKSAYEIRSEKDAIKTFIRAYKESITPPYG
PVLISLPQDIPDMEVSEGEKVDIPKYFVSGTCDTSAIEFVLDKVKSASSIAIVAGYEVSIFSAHEELVRLAEKLN
APIYTEPYLSIFPIDSSNILFKGPLSRYKASDVVKELEKYDLVLVIGGWLNYVVFPDVDIRLNIVEVTSDFKEAS
KRKWDTIVCNPKDFLIKLYNMLYKGLNKNIIKRENRDLELQGDFITEVFKEMGYLDKYTIFAEIPTYRDTLIKI
IELKPSSLYITRSGLLGWALSALVGYSINGAKVLAIIGDGSFNYTPQALWSAVKYSTRLKVIVINNEGYASLSRH
GVEADWLFPSTSPWKVALAYGFEAKESRDIKNDLKWLFEDDKRKLLEIRLARH
SEQ ID 36
```

```
>aruI Pseudomonas aeruginosa 2-ketoarginine decarboxylase
MGARALRRERRLRWSPNWTRILPMQPQKTLTAGQALVRLLANYGVDTVFGIPGVHTLELYRGLPGSGIRHVLTRH
EQGAGFMADGYARVSGKPGVCFVITGPGVTNVATAIGQAYADSVPLLVISSVNHSASLGKGWGCLHETQDQRAMT
APITAFSALALSPEQLPELIARAYAVFDSERPRPVHISIPLDVLAAPVAHDWSAAVARRPGRGVPCTEALRAAAE
RLAAARRPMLIAGGGALAAGDALAALSERLAAPLFTSVAGKGLLPPDAPLNAGASLCVAPGWEMIAEADLVLAVG
TEMADTDFWRERLPLSGELIRVDIDPRKFNDFYPSAVALRGDARQTLEALLARLPQEARDAAPAAARVARLRAEI
RAAHAPLQALHQAILDRIAAALPADAFVSTDMTQLAYTGNYAFASRAPRSWLHPTGYGTLGYGLPAGIGAKLGAP
QRPGLVLVGDGGFLYTAQELATASEELDSPLVVLLWNNDALGQIRDDMLGLDIEPVGVLPRNPDFALLGRAYGCA
VRQPQDLNELERDLRAGFGQPGVTLIELRHACAR
SEQ ID 37
```

```
>fom2phosphonopyruvate decarboxylaseErwiniacarotovora subsp. atroseptica
(Pectobacteriumatrosepticum)
MIDPNKLIEFLAQRGVRFFSGVPDSLLKAFCLAIGSNNGGLAHRIASNEGCAVGMAIGHYLSTRTLPVVYMQNSG
LGNAINPLCSLATPDVYGIPLLLIIGWRGEVDDSGKQQHDEPQHVMQGRVTLPQLNVLDVPHIVLDSHNRPPWDD
IQALLQRAHDEHRPVALVVRKNTFSSPVAPANPATEPALMRREAIVAACLNVLPSTIPIVSTTGMLSRELYELRE
QRGEGHQRDFLTVGGMGLASQIALGLCDAQPQRKVVCLDGDGALLMHGGLTNTAQASNLIHIVINNGAHDSVGG
QPTVASHLPLAPIAAASGYGKTYYAETEEALQAALQQALQAQSSQFIEVQCRVGHRSDLGRPATSPAENRDAFMQ
FLNTTPKAS
SEQ ID 38
```

```
>PDC6 4.1.1.1 Pyruvate decarboxylase isozyme 3 Saccharomyces cerevisiae
MSEITLGKYLFERLKQVNVNTIFGLPGDFNLSLLDKIYEVDGLRWAGNANELNAAYAADGYARIKGLSVLVTTFG
VGELSALNGIAGSYAEHVGVLHVVGVPSISAQAKQLLLHHTLGNGDFTVFHRMSANISETTSMITDIATAPSEID
RLIRTTFITQRPSYLGLPANLVDLKVPGSLLEKPIDLSLKPNDPEAEKEVIDTVLELIQNSKNPVILSDACASRH
NVKKETQKLIDLTQFPAFVTPLGKGSIDEQHPRYGGVYVGTLSKQDVKQAVESADLILSVGALLSDFNTGSFSYS
YKTKNVVEFHSDYVKVKNATFLGVQMKFALQNLLKVIPDVVKGYKSVPVPTKTPANKGVPASTPLKQEWLWNELS
KFLQEGDVIISETGTSAFGINQTIFPKDAYGISQVLWGSIGFTTGATLGAAFAAEEIDPNKRVILFIGDGSLQLT
VQEISTMIRWGLKPYLFVLNNDGYTIEKLIHGPHAEYNEIQTWDHLALLPAFGAKKYENHKIATTGEWDALTTDS
EFQKNSVIRLIELKLPVFDAPESLIKQAQLTAATNAKQ
SEQ ID 39
```

FIG. 25 (continued)

```
>IpdC Indole-3-pyruvate decarboxylase Pantoeaananatis
    MSDFTVGDYLLARLQECGVRHLFGVPGDYNLQFLDRVIAHPDIGWVGCANELNAAYAADGYARCTGAAALL
TTFGVGELSAINGLAGSFAEYLPVIHIVGAPSSQAMQQGDCVHHTLGDGDFGHFIRMAKEVSAATAALTADNATA
EIDRVILTALQQHRPGYLMLPVDVAQRQTSAPDQPLMPTTASSDEVRIAFQQAAERLLAPAKRVSLLADFLAQRW
QQQPALAALRTGRAFPCATLLMGKGVLDEQQPGFVGTYAGEGSEGDVRQQIEEVDVTICAGVRFTDTITAGFTQQ
FSQARLIDIQPHSASVAGQTFAPLSMAEALQALLPVFERLGAGWQAACAPRAAEPVPDAALISQSAFWQAMQGFL
QPGDIILADQGTAAFGAASLRLPVGAQLLVQPLWGSIGYTLPAAFGAQTARPGQRVILIIGDGSAQLTIQELGSM
LRDQQHPLIFLLNNEGYTVERAIHGAAQRYNDIAQWNWTALPQAMSLECQAQSWRISETVQLQALMAQLTQQRRL
SFIEVVMQKDDLPPLLRKVSACLSQRNG
```

SEQ ID 40

```
                        SEQUENCE LISTING

<160> NUMBER OF SEQ ID NOS: 43

<210> SEQ ID NO 1
<211> LENGTH: 1362
<212> TYPE: DNA
<213> ORGANISM: Artificial Sequence
<220> FEATURE:
<223> OTHER INFORMATION: sequence encoding IlvE-Omega Vf fusion

<400> SEQUENCE: 1
atgaacaaac cgcagagctg ggaggcacgc gcagaaacct acagcctgta tggtttcact      60
gatatgccga gcttgcacca gcgcggcacg gttgttgtta ctcacggcga gggtccgtac     120
attgtggatg tcaatggtcg tcgttatctg gacgcgaata gcggcctgtg gaatatggtc     180
gcgggttttg accataaagg cctgattgac gcggcaaagg cacaatacga gcgctttcca     240
ggttatcatg ctttctttgg tcgcatgagc gaccagaccg tcatgttgtc cgagaaactg     300
gtggaagtta gcccgtttga ttcgggccgt gttttctata ccaatagcgg ctccgaggcg     360
aatgacacca tggtgaaaat gctgtggttt ctgcatgcgg cggaaggtaa accgcagaag     420
cgtaagatcc tgacccgttg gaacgcatac cacggtgtca ccgctgttag cgcgagcatg     480
acgggtaaac cgtacaacag cgttttcggt ctgccgctgc cgggcttcgt ccacctgacg     540
tgcccgcact attggcgtta cggcgaagag ggcgaaacgg aagagcaatt cgtcgcacgt     600
ctggcacgtg agctggaaga aaccattcaa cgtgagggtg cggataccat tgccggtttc     660
tttgccgaac cggtcatggg tgctggcggt gtaatcccgc cagcaaaggg ttactttcaa     720
gcgatcctgc cgattttgcg taagtacgac attccggtga tcagcgacga agttatttgc     780
```

```
ggtttcggcc gtaccggtaa tacgtggggc tgcgtcacgt atgacttcac cccggatgcg    840
atcattagca gcaaaaacct gaccgcgggt ttcttcccta tgggtgccgt gattctgggt    900
ccggagctgt ctaagcgcct ggaaacggca attgaggcga ttgaagagtt ccgcacggt     960 ttcactgcga gcggtcatcc tgtgggttgt gcgatcgcgc tgaaggcgat cgatgttgtg    1020
atgaatgagg gtttggccga aacgtgcgt cgcttggctc cgcgttttga gagcgtctg     1080 aaacacatcg cggagcgccc gaacatcggc gaataccgcg gcatcggctt tatgtgggcc    1140
ttggaggcag tgaaggacaa agcgagcaaa acgccgttcg acggcaacct gagcgtgtct    1200
gagcgcattg ccaacacctg caccgatctg ggcctgatct gtcgtccgct gggtcagtcc    1260
gttgtgctgt gtccgccatt tatcctgacc gaggcccaga tgatgaaat gtttgataag    1320 ctggaaaaag ctctggacaa ggttttcgcc gaggtcgcgt aa                      1362
```

<210> SEQ ID NO 2
<211> LENGTH: 453
<212> TYPE: PRT
<213> ORGANISM: Artificial Sequence
<220> FEATURE:
<223> OTHER INFORMATION: IlvE-Omega Vf fusion

<400> SEQUENCE: 2

```
Met Asn Lys Pro Gln Ser Trp Glu Ala Arg Ala Glu Thr Tyr Ser Leu
 1               5                  10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255
```

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Met Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
        450

<210> SEQ ID NO 3
<211> LENGTH: 1323
<212> TYPE: DNA
<213> ORGANISM: Artificial Sequence
<220> FEATURE:
<223> OTHER INFORMATION: sequence encoding IlvE-Ad optimized omega
      fusion

<400> SEQUENCE: 3
atgagcgccg ctaaactgcc agacctgagc cacctgtgga tgccgtttac cgccaaccgc    60
cagtttaaag cgaatccgcg cctgttggcg agcgcaaagg gcatgtacta tcgagcttc    120 gatggccgcc aaattctgga cggcacggca ggtctgtggt gcgtgaatgc aggccattgc    180
cgtgaagaaa ttgttagcgc gatcgcctcc aagcgggcg tgatggatta cgcaccgggc    240
ttccagctgg gccacccgtt ggcgttcgag gcagcgaccg ctgtcgcagg tctgatgccg    300
caaggtctgg accgtgtatt ctttaccaac agcggcagcg agagcgtgga taccgccctg    360
aagatcgcgc tggcgtacca tcgtgcacgt ggcgaagcgc agcgtacgcg cctgattggc    420
cgcgagcgcg gttaccacgg tgttggtttt ggtggtatca gcgttggcgg tattagcccg    480
aaccgcaaga cgttcagcgg cgcattgctg ccggcagtgg atcatttgcc gcacacgcac    540
agcctggagc ataacgcgtt tacgcgtggt caaccggaat ggggtgctca cttggctgat    600
gagctggagc gcattatcgc gctgcacgac gcgagcacca ttgcggcggt tattgtcgaa    660
ccaatggcgg gttctaccgg cgtcttggtg ccgccgaaag gttatctgga aaaactgcgt    720
gagatcactg cacgccacgg tatcctgctg atctttgacg aggtgattac cgcgtacggt    780
cgtctgggtg aagcaaccgc ggcagcctac ttcggtgtta ccccgaccct gatcaccatg    840
gccaagggtg tcagcaatgc ggcggtcccg gctggtgccg tggccgttcg tcgcgaagtc    900

```
cacgatgcta ttgttaatgg cccgcaaggt ggcatcgagt ttttccatgg ctatacctat    960
tccgcgcatc ctctggcggc tgcggcggtg ctggcaactc tggacattta tcgtcgtgag   1020
gatctgttcg cccgtgctcg taaactgtcc gctgcgttcg aagaggcggc acactcgctg   1080
aaaggtgcgc cgcatgtgat tgacgtccgt aacatcggtc tggttgcggg tattgaattg   1140
agcccgcgtg agggtgcccc aggtgcgcgt gcggcggagg cattccagaa gtgttttgat   1200
accggcctga tggtccgtta cacgggcgac atcctggccg tttctccgcc gctgattgtg   1260
gacgaaaatc agatcggtca gatctttgag ggcatcggta aggttctgaa agaggtcgca   1320
taa                                                                 1323

<210> SEQ ID NO 4
<211> LENGTH: 440
<212> TYPE: PRT
<213> ORGANISM: Artificial Sequence
<220> FEATURE:
<223> OTHER INFORMATION: IlvE-Ad optimized omega fusion

<400> SEQUENCE: 4

Met Ser Ala Ala Lys Leu Pro Asp Leu Ser His Leu Trp Met Pro Phe
 1               5                  10                  15

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
    50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Thr Ala Val Ala
                85                  90                  95

Gly Leu Met Pro Gln Gly Leu Asp Arg Val Phe Phe Thr Asn Ser Gly
            100                 105                 110

Ser Glu Ser Val Asp Thr Ala Leu Lys Ile Ala Leu Ala Tyr His Arg
        115                 120                 125

Ala Arg Gly Glu Ala Gln Arg Thr Arg Leu Ile Gly Arg Glu Arg Gly
    130                 135                 140

Tyr His Gly Val Gly Phe Gly Gly Ile Ser Val Gly Gly Ile Ser Pro
145                 150                 155                 160

Asn Arg Lys Thr Phe Ser Gly Ala Leu Leu Pro Ala Val Asp His Leu
                165                 170                 175

Pro His Thr His Ser Leu Glu His Asn Ala Phe Thr Arg Gly Gln Pro
            180                 185                 190

Glu Trp Gly Ala His Leu Ala Asp Glu Leu Glu Arg Ile Ile Ala Leu
        195                 200                 205

His Asp Ala Ser Thr Ile Ala Ala Val Ile Val Glu Pro Met Ala Gly
    210                 215                 220

Ser Thr Gly Val Leu Val Pro Pro Lys Gly Tyr Leu Glu Lys Leu Arg
225                 230                 235                 240

Glu Ile Thr Ala Arg His Gly Ile Leu Leu Ile Phe Asp Glu Val Ile
                245                 250                 255

Thr Ala Tyr Gly Arg Leu Gly Glu Ala Thr Ala Ala Tyr Phe Gly
            260                 265                 270

Val Thr Pro Asp Leu Ile Thr Met Ala Lys Gly Val Ser Asn Ala Ala
```

|  |  | 275 |  |  | 280 |  |  | 285 |  |  |  |
|--|--|--|--|--|--|--|--|--|--|--|--|

Val Pro Ala Gly Ala Val Ala Val Arg Arg Glu Val His Asp Ala Ile
    290                        295                        300

Val Asn Gly Pro Gln Gly Gly Ile Glu Phe Phe His Gly Tyr Thr Tyr
305                      310                      315                      320

Ser Ala His Pro Leu Ala Ala Ala Val Leu Ala Thr Leu Asp Ile
                      325                        330                      335

Tyr Arg Arg Glu Asp Leu Phe Ala Arg Ala Arg Lys Leu Ser Ala Ala
                340                      345                      350

Phe Glu Glu Ala Ala His Ser Leu Lys Gly Ala Pro His Val Ile Asp
                355                      360                      365

Val Arg Asn Ile Gly Leu Val Ala Gly Ile Glu Leu Ser Pro Arg Glu
    370                        375                        380

Gly Ala Pro Gly Ala Arg Ala Ala Glu Ala Phe Gln Lys Cys Phe Asp
385                      390                      395                      400

Thr Gly Leu Met Val Arg Tyr Thr Gly Asp Ile Leu Ala Val Ser Pro
                405                      410                      415

Pro Leu Ile Val Asp Glu Asn Gln Ile Gly Gln Ile Phe Glu Gly Ile
            420                      425                      430

Gly Lys Val Leu Lys Glu Val Ala
          435                      440

<210> SEQ ID NO 5
<211> LENGTH: 1350
<212> TYPE: DNA
<213> ORGANISM: Bacillus weihenstephanensis

<400> SEQUENCE: 5

| | | | | |
|--|--|--|--|--|
| atgcaggcta | ccgaacaaac | ccaatctctg | aaaaagactg | acgaaaaata | tctgtggcac | 60 |
| gcgatgcgcg | gtgcagctcc | gtctccgacc | aacctgatta | ttaccaaagc | tgaaggcgcg | 120 |
| tgggtgaccg | acattgacgg | taaccgttat | ctggatggca | tgagcggcct | gtggtgtgtt | 180 |
| aatgtcggtt | atggccgtaa | ggagctggcg | cgcgcggcat | ttgaacaact | ggaagaaatg | 240 |
| ccgtacttcc | gctgactca | aagccatgtg | ccggctatca | aactggcgga | aaaactgaac | 300 |
| gaatggctgg | acgacgaata | cgtgattttc | ttctctaatt | ctggctccga | agcaaacgaa | 360 |
| accgcattca | aaatcgcccg | tcaatatcac | cagcagaaag | gtgaccacgg | ccgctataaa | 420 |
| ttcatcagcc | gttatcgtgc | ataccatggt | aattctatgg | gtgcgctggc | tgctaccggt | 480 |
| caggctcagc | gcaaatacaa | gtacgaaccg | ctgggtcagg | ttttctgca | cgttgcacca | 540 |
| ccggatacct | accgtaaccc | ggaagacgtc | cacaccctgg | cttctgccga | gaaatcgat | 600 |
| cgtgttatga | cctgggagct | gtcccagact | gttgcgggtg | ttatcatgga | acctattatt | 660 |
| accggtggtg | gcattctgat | gccgccggac | ggttatatgg | gtaaagtcaa | ggaaatctgc | 720 |
| gaaaaacacg | gcgcgctgct | gatctgcgat | gaagttatct | gtggcttcgg | tcgcaccggc | 780 |
| aaaccatttg | gcttcatgaa | ttatggcgta | aaacctgaca | ttattaccat | ggctaaaggc | 840 |
| attacttccg | cttatctgcc | gctgagcgcg | accgcagttc | gccgcgaagt | ttatgaagcg | 900 |
| tttgttggtt | ctgatgatta | cgaccgtttc | cgtcatgtaa | acacgtttgg | cggtaaccca | 960 |
| gcggcatgtg | cgctggcgct | gaaaaacctg | gaaatcatgg | aaaacgaaaa | gctgatcgaa | 1020 |
| cgtagcaaag | aactgggtga | acgtctgctg | tacgaactgg | aagatgtcaa | gaacacccg | 1080 |
| aacgtgggcg | atgttcgcgg | taaaggcctg | ctgctgggta | ttgaactggt | tgaagacaaa | 1140 |
| cagaccaagg | aaccggcttc | cattgaaaag | atgaacaaag | tgattaacgc | gtgcaaagag | 1200 |

-continued

```
aaaggcctga tcattggtaa gaacggtgat accgtggcag gttataacaa cattctgcag    1260
ctggcgccgc ctctgagcat cactgaagaa gatttcacct tcatcgtcaa aactatgaag    1320
gagtgcctga gccgcatcaa tggtcagtaa                                     1350
```

<210> SEQ ID NO 6
<211> LENGTH: 449
<212> TYPE: PRT
<213> ORGANISM: Bacillus weihenstephanensis

<400> SEQUENCE: 6

```
Met Gln Ala Thr Glu Gln Thr Gln Ser Leu Lys Lys Thr Asp Glu Lys
 1               5                  10                  15

Tyr Leu Trp His Ala Met Arg Gly Ala Ala Pro Ser Pro Thr Asn Leu
            20                  25                  30

Ile Ile Thr Lys Ala Glu Gly Ala Trp Val Thr Asp Ile Asp Gly Asn
        35                  40                  45

Arg Tyr Leu Asp Gly Met Ser Gly Leu Trp Cys Val Asn Val Gly Tyr
    50                  55                  60

Gly Arg Lys Glu Leu Ala Arg Ala Ala Phe Glu Gln Leu Glu Met
65                  70                  75                  80

Pro Tyr Phe Pro Leu Thr Gln Ser His Val Pro Ala Ile Lys Leu Ala
                85                  90                  95

Glu Lys Leu Asn Glu Trp Leu Asp Asp Glu Tyr Val Ile Phe Phe Ser
            100                 105                 110

Asn Ser Gly Ser Glu Ala Asn Glu Thr Ala Phe Lys Ile Ala Arg Gln
        115                 120                 125

Tyr His Gln Gln Lys Gly Asp His Gly Arg Tyr Lys Phe Ile Ser Arg
    130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
                165                 170                 175

His Val Ala Pro Pro Asp Thr Tyr Arg Asn Pro Glu Asp Val His Thr
            180                 185                 190

Leu Ala Ser Ala Glu Glu Ile Asp Arg Val Met Thr Trp Glu Leu Ser
        195                 200                 205

Gln Thr Val Ala Gly Val Ile Met Glu Pro Ile Ile Thr Gly Gly Gly
    210                 215                 220

Ile Leu Met Pro Pro Asp Gly Tyr Met Gly Lys Val Lys Glu Ile Cys
225                 230                 235                 240

Glu Lys His Gly Ala Leu Leu Ile Cys Asp Glu Val Ile Cys Gly Phe
                245                 250                 255

Gly Arg Thr Gly Lys Pro Phe Gly Phe Met Asn Tyr Gly Val Lys Pro
            260                 265                 270

Asp Ile Ile Thr Met Ala Lys Gly Ile Thr Ser Ala Tyr Leu Pro Leu
        275                 280                 285

Ser Ala Thr Ala Val Arg Arg Glu Val Tyr Glu Ala Phe Val Gly Ser
    290                 295                 300

Asp Asp Tyr Asp Arg Phe Arg His Val Asn Thr Phe Gly Gly Asn Pro
305                 310                 315                 320

Ala Ala Cys Ala Leu Ala Leu Lys Asn Leu Glu Ile Met Glu Asn Glu
                325                 330                 335

Lys Leu Ile Glu Arg Ser Lys Glu Leu Gly Glu Arg Leu Leu Tyr Glu
```

```
                340             345             350
Leu Glu Asp Val Lys Glu His Pro Asn Val Gly Asp Val Arg Gly Lys
            355                 360                 365

Gly Leu Leu Gly Ile Glu Leu Val Glu Asp Lys Gln Thr Lys Glu
    370                 375                 380

Pro Ala Ser Ile Glu Lys Met Asn Lys Val Ile Asn Ala Cys Lys Glu
385                 390                 395                 400

Lys Gly Leu Ile Ile Gly Lys Asn Gly Asp Thr Val Ala Gly Tyr Asn
                405                 410                 415

Asn Ile Leu Gln Leu Ala Pro Pro Leu Ser Ile Thr Glu Glu Asp Phe
                420                 425                 430

Thr Phe Ile Val Lys Thr Met Lys Glu Cys Leu Ser Arg Ile Asn Gly
            435                 440                 445

Gln

<210> SEQ ID NO 7
<211> LENGTH: 1407
<212> TYPE: DNA
<213> ORGANISM: Pseudomonas aeruginosa

<400> SEQUENCE: 7
```

| | | | | | |
|---|---|---|---|---|---|
| atgaacgcaa | gactgcacgc | cacgtccccc | ctcggcgacg | ccgacctggt | ccgtgccgac | 60 |
| caggcccact | acatgcacgg | ctaccacgtg | ttcgacgacc | accgcgtcaa | cggctcgctg | 120 |
| aacatcgccg | ccggcgacgg | cgcctatatc | tacgacaccg | ccggcaaccg | ctacctcgac | 180 |
| gcggtgggcg | catgtggtg | caccaacatc | ggcctgggc | gcgaggaaat | ggctcgcacc | 240 |
| gtggccgagc | agaccgcct | gctggcctat | tccaatccct | tctgcgacat | ggccaacccg | 300 |
| cgcgccatcg | aactctgccg | caagctcgcc | gagctggccc | ccggcgaccct | cgaccacgtg | 360 |
| ttcctcacca | ccggcggttc | caccgccgtg | acaccgcga | tccgcctcat | gcactactac | 420 |
| cagaactgcc | gcggcaagcg | cgccaagaag | cacgtcatca | gcggatcaa | cgcctaccac | 480 |
| ggctcgacct | tcctcggcat | gtcgctgggc | ggcaagagcg | ccgaccggcc | ggccgagttc | 540 |
| gacttcctcg | acgagcgcat | ccaccacctc | gcctgtccct | attactaccg | cgctccggaa | 600 |
| gggctgggcg | aagccgagtt | cctcgatggc | ctggtggacg | agttcgaacg | caagatcctc | 660 |
| gaactgggcg | ccgaccgggt | gggggcgttc | atctccgagc | cggtgttcgg | ctccggcggc | 720 |
| gtgatcgtcc | cgcccgcggg | ctaccacagg | cggatgtggg | agctgtgcca | gcgctacgac | 780 |
| gtgctgtaca | tctccgacga | agtggtgacc | tccttcggcc | gcctcggcca | cttcttcgcc | 840 |
| agccaggcgg | tgttcggcgt | acagccggac | atcatcctca | ccgccaaggg | cctcacctcc | 900 |
| ggctaccagc | cgctgggcgc | gtgcatcttc | tcccggcgca | tctgggaggt | gatcgccgag | 960 |
| ccggacaagg | gccgctgctt | cagccatggt | ttcacctact | ccggccaccc | ggtggcctgc | 1020 |
| gcggcggcgc | tgaagaacat | cgagatcatc | gagcgcgagg | gcttgctcgc | ccacgccgac | 1080 |
| gaggtcggcc | gctacttcga | ggagcgcctg | caaagcctcc | gcgacctgcc | catcgtcggc | 1140 |
| gacgtgcgcg | ggatgcgctt | catggcctgt | gtcgagttcg | tcgccgacaa | ggcgagcaag | 1200 |
| gcgctgtttc | cggaaagcct | gaacatcggc | gagtgggtcc | acctgcgggc | gcagaagcgc | 1260 |
| ggcctgctgg | ttcgtccgat | cgtccacctg | aacgtgatgt | cgccgccgct | gatcctcacc | 1320 |
| cgcgaacagg | tcgataccgt | ggtccgggtg | ctgcgcgaga | gcatcgagga | aaccgtggag | 1380 |
| gatcttgtcc | gcgccggtca | ccggtaa | | | | 1407 |

```
<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
 1               5                  10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380
```

```
Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
            405                 410                 415

Ala Gln Lys Arg Gly Leu Leu Val Arg Pro Ile Val His Leu Asn Val
        420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 9
<211> LENGTH: 849
<212> TYPE: DNA
<213> ORGANISM: Bacillus subtilis

<400> SEQUENCE: 9
atgaaggttt tagtcaatgg ccggctgatt gggcgcagtg aagcatcaat cgatttggaa       60
gatcgcggtt atcagtttgg tgacggcatc tatgaagtga tcagggtgta caaggagta      120
ttgttcggct acgtgagca tgcagagcgt tttttcagaa gtgctgctga atcggaatt       180
tcactgccat tcagtataga agatctcgag tgggacctgc aaaagcttgt acaggaaaat     240
gcggtcagtg agggagcggt atacattcag acaacaagag gtgtggcccc gcgaaaacac     300
cagtatgaag ccggcctcga gccgcagact actgcctata cgtttacggt gaaaaaaccg     360
gagcaagagc aggcatacgg agtggcggcc attacagatg aggatcttcg ctggttaaga     420
tgtgatatca aaagtctgaa tttactgtat aatgtcatga cgaagcaaag ggcctatgaa     480
gccggagcat tgaagccat tttacttagg gacggcgttg ttacgagggg tacatcctct     540
aacgtttatg ccgttatcaa cggcacagtg cgaacacatc cggctaatcg gctcattctc     600
aatggaatta cacggatgaa atattttagga ctgattgaga agaatgggat caaactggat     660
gagactcctg tcagtgaaga agagttgaaa caggcggaag agatcttttat ttcgtcaacg     720
acggcagaaa ttattccggt cgtgacgctc gatggacaat cgatcggaag cgggaaaccc     780
ggaccggtga ccaaacagct tcaggctgct tttcaagaaa gcattcaaca ggctgctagc     840
atttcataa                                                             849

<210> SEQ ID NO 10
<211> LENGTH: 282
<212> TYPE: PRT
<213> ORGANISM: Bacillus subtilis

<400> SEQUENCE: 10

Met Lys Val Leu Val Asn Gly Arg Leu Ile Gly Arg Ser Glu Ala Ser
1               5                   10                  15

Ile Asp Leu Glu Asp Arg Gly Tyr Gln Phe Gly Asp Gly Ile Tyr Glu
            20                  25                  30

Val Ile Arg Val Tyr Lys Gly Val Leu Phe Gly Leu Arg Glu His Ala
        35                  40                  45

Glu Arg Phe Phe Arg Ser Ala Ala Glu Ile Gly Ile Ser Leu Pro Phe
    50                  55                  60

Ser Ile Glu Asp Leu Glu Trp Asp Leu Gln Lys Leu Val Gln Glu Asn
65                  70                  75                  80
```

```
Ala Val Ser Glu Gly Ala Val Tyr Ile Gln Thr Thr Arg Gly Val Ala
                85                  90                  95
Pro Arg Lys His Gln Tyr Glu Ala Gly Leu Glu Pro Gln Thr Thr Ala
            100                 105                 110
Tyr Thr Phe Thr Val Lys Lys Pro Glu Gln Glu Gln Ala Tyr Gly Val
        115                 120                 125
Ala Ala Ile Thr Asp Glu Asp Leu Arg Trp Leu Arg Cys Asp Ile Lys
    130                 135                 140
Ser Leu Asn Leu Leu Tyr Asn Val Met Thr Lys Gln Arg Ala Tyr Glu
145                 150                 155                 160
Ala Gly Ala Phe Glu Ala Ile Leu Leu Arg Asp Gly Val Val Thr Glu
                165                 170                 175
Gly Thr Ser Ser Asn Val Tyr Ala Val Ile Asn Gly Thr Val Arg Thr
            180                 185                 190
His Pro Ala Asn Arg Leu Ile Leu Asn Gly Ile Thr Arg Met Asn Ile
        195                 200                 205
Leu Gly Leu Ile Glu Lys Asn Gly Ile Lys Leu Asp Glu Thr Pro Val
    210                 215                 220
Ser Glu Glu Leu Lys Gln Ala Glu Ile Phe Ile Ser Ser Thr
225                 230                 235                 240
Thr Ala Glu Ile Ile Pro Val Val Thr Leu Asp Gly Gln Ser Ile Gly
                245                 250                 255
Ser Gly Lys Pro Gly Pro Val Thr Lys Gln Leu Gln Ala Ala Phe Gln
            260                 265                 270
Glu Ser Ile Gln Gln Ala Ala Ser Ile Ser
        275                 280
```

<210> SEQ ID NO 11
<211> LENGTH: 1365
<212> TYPE: DNA
<213> ORGANISM: Pseudomonas syringae

<400> SEQUENCE: 11

```
atgagtgcca acaacccgca aaccctcgaa tggcaggccc tgagcagcga gcatcacctg     60
gcaccgttca gcgactacaa caactgaaa gagaaaggcc gcgcatcat cacccgtgcc    120
gagggcgttt atctgtggga cagcgagggc aacaagatcc tcgatggcat gtccggcctg    180
tggtgcgtgg ccatcggtta tggccgcgaa gaactggccg acgcagccag caaacagatg    240
cgcgagctgc cgtactacaa cctgttcttc cagaccgccc accgccggt gctggaactg    300
gccaaggcca tctccgacat cgctcccgag ggcatgaacc atgtgttctt caccggttca    360
ggctctgaag gcaatgacac gatgctgcgc atggttcgtc attactgggc gctgaaaggc    420
cagccgaaca agaaaaccat catcagccgc gtcaatggct accacggctc caccgtcgcc    480
ggtgccagcc tgggtggcat gacctacatg cacgaacagg gcgacctgcc gatcccgggg    540
gtggtgcaca ttccacagcc ttactggttc ggcaaggcg gcgacatgac gccgacgag    600
ttcggcatct gggcggccga gcaactggaa agaaaaattc tcgagctggg cgtcgagaac    660
gtcggtgcgt tcattgccga gccaatccag ggcgcgggcg tgtgattgt cccgcctgat    720
tcctactggc cgaagatcaa ggaaatcctt tcccgctacg acatcctgtt cgccgccgat    780
gaggtgattt gtggcttcgg cgtaccagt gagtggttcg gtagcgattt ctatggcctc    840
aggccggaca tgatgaccat cgccaaaggc ctgacctccg gttacgtacc gatgggcggc    900
ctgatcgtgc gcgatgaaat cgttgcggtg ctcaatgagg gtggcgattt caatcacggc    960
```

```
tttacctact ccgggcaccc ggtggcggcc gcggttgcgc tggagaacat ccgtatcctg    1020
cgcgaagaaa agatcgtcga acgggtcagg tcggaaacgg caccgtattt gcaaaagcgt    1080
ttgcgtgagt tgagcgatca tccgctggtg ggcgaagtcc ggggtgtcgg gctgctcggg    1140
gccattgagc tggtgaagga caagaccacc cgcgagcgct ataccgacaa gggcgcggga    1200
atgatctgtc gaaccttctg cttcgacaat ggcctgatca tgcgggctgt gggcgatacc    1260
atgatcattg cgccgccact ggtgatcagt tttgcgcaaa tcgatgagct ggtagagaag    1320
gcgcgcacgt gtctggatct gacgctggcg gtgttgcagg gctga                   1365
```

<210> SEQ ID NO 12
<211> LENGTH: 454
<212> TYPE: PRT
<213> ORGANISM: Pseudomonas syringae

<400> SEQUENCE: 12

```
Met Ser Ala Asn Asn Pro Gln Thr Leu Glu Trp Gln Ala Leu Ser Ser
 1               5                  10                  15

Glu His His Leu Ala Pro Phe Ser Asp Tyr Lys Gln Leu Lys Glu Lys
                20                  25                  30

Gly Pro Arg Ile Ile Thr Arg Ala Glu Gly Val Tyr Leu Trp Asp Ser
            35                  40                  45

Glu Gly Asn Lys Ile Leu Asp Gly Met Ser Gly Leu Trp Cys Val Ala
        50                  55                  60

Ile Gly Tyr Gly Arg Glu Glu Leu Ala Asp Ala Ala Ser Lys Gln Met
 65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
           100                 105                 110

Asn His Val Phe Phe Thr Gly Ser Gly Ser Glu Gly Asn Asp Thr Met
       115                 120                 125

Leu Arg Met Val Arg His Tyr Trp Ala Leu Lys Gly Gln Pro Asn Lys
   130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
               165                 170                 175

Pro Ile Pro Gly Val Val His Ile Pro Gln Pro Tyr Trp Phe Gly Glu
           180                 185                 190

Gly Gly Asp Met Thr Pro Asp Glu Phe Gly Ile Trp Ala Ala Glu Gln
       195                 200                 205

Leu Glu Lys Lys Ile Leu Glu Leu Gly Val Glu Asn Val Gly Ala Phe
   210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
               245                 250                 255

Phe Ala Ala Asp Glu Val Ile Cys Gly Phe Gly Arg Thr Ser Glu Trp
           260                 265                 270

Phe Gly Ser Asp Phe Tyr Gly Leu Arg Pro Asp Met Met Thr Ile Ala
       275                 280                 285

Lys Gly Leu Thr Ser Gly Tyr Val Pro Met Gly Gly Leu Ile Val Arg
   290                 295                 300
```

```
Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
            325                 330                 335

Ile Arg Ile Leu Arg Glu Glu Lys Ile Val Glu Arg Val Arg Ser Glu
                340                 345                 350

Thr Ala Pro Tyr Leu Gln Lys Arg Leu Arg Glu Leu Ser Asp His Pro
            355                 360                 365

Leu Val Gly Glu Val Arg Gly Val Gly Leu Leu Gly Ala Ile Glu Leu
        370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
                435                 440                 445

Leu Ala Val Leu Gln Gly
    450
```

```
<210> SEQ ID NO 13
<211> LENGTH: 1467
<212> TYPE: DNA
<213> ORGANISM: Rhodobacter sphaeroides

<400> SEQUENCE: 13
atgcccggtt gcgggggctt gcccgggaat gaaccgaaat gcggacgaga ggggaggtcg      60
gcgatgacgc ggaatgacgc gacgaatgct gccggagcgg tgggcgcggc gatgcgggat     120
cacatcctct tgcctgcaca ggaaatggcg aagctcggca agtccgcgca gccggtgctg     180
actcatgccg agggcatcta tgtccatacc gaggacggcc gccgcctgat cgacgggccg     240
gcgggcatgt ggtgcgcgca ggtgggctac ggccgccgcg agatcgtcga tgccatggcg     300
catcaggcga tggtgctgcc ctatgcctcg ccctggtata tggccacgag ccccgcggcg     360
cggctggcgg agaagatcgc cacgctgacg ccgggcgatc tcaaccggat cttttttcacc     420 acgggcgggt cgaccgcggt ggacagcgcg ctgcgcttct cggaattcta caacaacgtg     480
ctgggccggc cgcagaagaa gcgcatcatc gtgcgctacg acggctatca cggctcgacg     540
gcgctcaccg ccgcctgcac cggccgcacc ggcaactggc cgaacttcga catcgcgcag     600
gaccggatct cgttcctctc gagccccaat ccgcgccacg ccggcaaccg cagccaggag     660
gcgttcctcg acgatctggt gcaggaattc gaggaccgga tcgagagcct cggccccgac     720
acgatcgcgg ccttcctggc cgagccgatc ctcgcctcgg gcggcgtcat tattccgccc     780
gcaggctatc atgcgcgctt caaggcgatc tgcgagaagc acgacatcct ctatatctcg     840
gacgaggtgg tgacgggctt cggccgttgc ggcgagtggt cgcctcgga gaaggtgttc     900 gggtggtgc cggacatcat caccttcgcc aagggcgtga cctcgggcta tgtgccgctc     960
ggcggccttg cgatctccga gcggtgctg cgcggatct cggcgagaa tgccaaggga    1020 agctggttca ccaacggcta tacctacagc aatcagccgg tggcctgcgc cgcggcgctt    1080
gccaacatcg agctgatgga gcgcgagggc atcgtcgatc aggcgcgcga gatggcggac    1140
tatttcgccg cggcgctggc ttcgctgcgc gatctgccgg gcgtggcgga aaccggtcg    1200 gtgggcctcg tgggttgcgt gcaatgcctg ctcgacccga cccgggcgga cggcacggcc    1260
```

```
gaggacaagg ccttcaccct gaagatcgac gagcgctgct tcgagctcgg gctgatcgtg   1320
cgcccgctgg gcgatctctg cgtgatctcg ccgccgctca tcatctcgcg cgcgcagatc   1380
gacgagatgg tcgcgatcat gcggcaggcc atcaccgaag tgagcgccgc ccacggtctg   1440
accgcgaaag aaccggccgc cgtctga                                        1467
```

<210> SEQ ID NO 14
<211> LENGTH: 488
<212> TYPE: PRT
<213> ORGANISM: Rhodobacter sphaeroides

<400> SEQUENCE: 14

```
Met Pro Gly Cys Gly Gly Leu Pro Gly Asn Glu Pro Lys Cys Gly Arg
 1               5                  10                  15

Glu Gly Arg Ser Ala Met Thr Arg Asn Asp Ala Thr Asn Ala Ala Gly
            20                  25                  30

Ala Val Gly Ala Ala Met Arg Asp His Ile Leu Leu Pro Ala Gln Glu
        35                  40                  45

Met Ala Lys Leu Gly Lys Ser Ala Gln Pro Val Leu Thr His Ala Glu
    50                  55                  60

Gly Ile Tyr Val His Thr Glu Asp Gly Arg Arg Leu Ile Asp Gly Pro
65                  70                  75                  80

Ala Gly Met Trp Cys Ala Gln Val Gly Tyr Gly Arg Arg Glu Ile Val
                85                  90                  95

Asp Ala Met Ala His Gln Ala Met Val Leu Pro Tyr Ala Ser Pro Trp
            100                 105                 110

Tyr Met Ala Thr Ser Pro Ala Ala Arg Leu Ala Glu Lys Ile Ala Thr
        115                 120                 125

Leu Thr Pro Gly Asp Leu Asn Arg Ile Phe Phe Thr Thr Gly Gly Ser
    130                 135                 140

Thr Ala Val Asp Ser Ala Leu Arg Phe Ser Glu Phe Tyr Asn Asn Val
145                 150                 155                 160

Leu Gly Arg Pro Gln Lys Lys Arg Ile Ile Val Arg Tyr Asp Gly Tyr
                165                 170                 175

His Gly Ser Thr Ala Leu Thr Ala Ala Cys Thr Gly Arg Thr Gly Asn
            180                 185                 190

Trp Pro Asn Phe Asp Ile Ala Gln Asp Arg Ile Ser Phe Leu Ser Ser
        195                 200                 205

Pro Asn Pro Arg His Ala Gly Asn Arg Ser Gln Glu Ala Phe Leu Asp
    210                 215                 220

Asp Leu Val Gln Glu Phe Glu Asp Arg Ile Glu Ser Leu Gly Pro Asp
225                 230                 235                 240

Thr Ile Ala Ala Phe Leu Ala Glu Pro Ile Leu Ala Ser Gly Gly Val
                245                 250                 255

Ile Ile Pro Pro Ala Gly Tyr His Ala Arg Phe Lys Ala Ile Cys Glu
            260                 265                 270

Lys His Asp Ile Leu Tyr Ile Ser Asp Glu Val Val Thr Gly Phe Gly
        275                 280                 285

Arg Cys Gly Glu Trp Phe Ala Ser Glu Lys Val Phe Gly Val Val Pro
    290                 295                 300

Asp Ile Ile Thr Phe Ala Lys Gly Val Thr Ser Gly Tyr Val Pro Leu
305                 310                 315                 320

Gly Gly Leu Ala Ile Ser Glu Ala Val Leu Ala Arg Ile Ser Gly Glu
                325                 330                 335
```

```
Asn Ala Lys Gly Ser Trp Phe Thr Asn Gly Tyr Thr Tyr Ser Asn Gln
                340                 345                 350

Pro Val Ala Cys Ala Ala Ala Leu Ala Asn Ile Glu Leu Met Glu Arg
            355                 360                 365

Glu Gly Ile Val Asp Gln Ala Arg Glu Met Ala Asp Tyr Phe Ala Ala
        370                 375                 380

Ala Leu Ala Ser Leu Arg Asp Leu Pro Gly Val Ala Glu Thr Arg Ser
385                 390                 395                 400

Val Gly Leu Val Gly Cys Val Gln Cys Leu Leu Asp Pro Thr Arg Ala
                405                 410                 415

Asp Gly Thr Ala Glu Asp Lys Ala Phe Thr Leu Lys Ile Asp Glu Arg
            420                 425                 430

Cys Phe Glu Leu Gly Leu Ile Val Arg Pro Leu Gly Asp Leu Cys Val
        435                 440                 445

Ile Ser Pro Pro Leu Ile Ile Ser Arg Ala Gln Ile Asp Glu Met Val
        450                 455                 460

Ala Ile Met Arg Gln Ala Ile Thr Glu Val Ser Ala Ala His Gly Leu
465                 470                 475                 480

Thr Ala Lys Glu Pro Ala Ala Val
                485

<210> SEQ ID NO 15
<211> LENGTH: 1401
<212> TYPE: DNA
<213> ORGANISM: Escherichia coli

<400> SEQUENCE: 15
atggaccaga agctgttaac ggatttccgc tcagaactac tcgattcacg ttttggcgca      60
aaggccattt ctactatcgc ggagtcaaaa cgatttccgc tgcacgaaat gcgcgatgat     120
gtcgcatttc agattatcaa tgatgaatta tatcttgatg caacgctcg tcagaacctg      180 gccactttct gccagacctg ggacgacgaa acgtccata aattgatgga tttgtcgatc      240
aataaaaact ggatcgacaa agaagaatat ccgcaatccg cagccatcga cctgcgttgc     300
gtaaatatgg ttgccgatct gtggcatgcg cctgcgccga aaatggtca ggccgttggc      360 accaacacca ttggttcttc cgaggcctgt atgctcggcg ggatggcgat gaaatggcgt     420
tggcgcaagc gtatggaagc tgcaggcaaa ccaacggata aaccaaacct ggtgtgcggt     480
ccggtacaaa tctgctggca taaattcgcc cgctactggg atgtggagct cgtgagatc     540 cctatgcgcc ccggtcagtt gtttatggac ccgaaacgca tgattgaagc ctgtgacgaa     600
aacaccatcg gcgtggtgcc gactttcggc gtgacctaca ccggtaacta tgagttccca     660
caaccgctgc acgatgcgct ggataaattc caggccgaca ccggtatcga catcgacatg     720
cacatcgacg ctgccagcgg tggcttcctg gcaccgttcg tcgcccccga tatcgtctgg     780
gacttccgcc tgccgcgtgt gaaatcgatc agtgcttcag gccataaatt cggtctggct     840
ccgctgggct gcggctgggt tatctggcgt gacgaagaag cgctgccgca ggaactggtg     900
ttcaacgttg actacctggg tggtcaaatt ggtactttg ccatcaactt ctcccgcccg      960
gcgggtcagg taattgcaca gtactatgaa ttcctgcgcc tcggtcgtga aggctatacc    1020
aaagtacaga acgcctctta ccaggttgcc gcttatctgg cggatgaaat cgccaaactg    1080
gggccgtatg agttcatctg tacgggtcgc cggacgaag gcatcccggc ggtttgcttc     1140
aaactgaaag atggtgaaga tccgggatac accctgtacg acctctctga acgtctgcgt    1200
```

-continued

```
ctgcgcggct ggcaggttcc ggccttcact ctcggcggtg aagccaccga catcgtggtg    1260
atgcgcatta tgtgtcgtcg cggcttcgaa atggactttg ctgaactgtt gctggaagac    1320
tacaaagcct ccctgaaata tctcagcgat cacccgaaac tgcagggtat tgcccagcag    1380
aacagcttta aacacacctg a                                              1401
```

<210> SEQ ID NO 16
<211> LENGTH: 466
<212> TYPE: PRT
<213> ORGANISM: Escherichia coli

<400> SEQUENCE: 16

```
Met Asp Gln Lys Leu Leu Thr Asp Phe Arg Ser Glu Leu Leu Asp Ser
  1               5                  10                  15

Arg Phe Gly Ala Lys Ala Ile Ser Thr Ile Ala Glu Ser Lys Arg Phe
                 20                  25                  30

Pro Leu His Glu Met Arg Asp Asp Val Ala Phe Gln Ile Ile Asn Asp
             35                  40                  45

Glu Leu Tyr Leu Asp Gly Asn Ala Arg Gln Asn Leu Ala Thr Phe Cys
         50                  55                  60

Gln Thr Trp Asp Asp Glu Asn Val His Lys Leu Met Asp Leu Ser Ile
 65                  70                  75                  80

Asn Lys Asn Trp Ile Asp Lys Glu Glu Tyr Pro Gln Ser Ala Ala Ile
                 85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
            115                 120                 125

Ala Cys Met Leu Gly Gly Met Ala Met Lys Trp Arg Trp Arg Lys Arg
        130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335
```

```
Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465

<210> SEQ ID NO 17
<211> LENGTH: 1263
<212> TYPE: DNA
<213> ORGANISM: Escherichia coli

<400> SEQUENCE: 17
atgccacact ctctgttttc tactgatact gatctgactg cggaaaacct gctgcgtctg      60
ccggctgaat tcggttgtcc ggtatgggtg tacgacgctc agattattcg tcgccagatc     120
gcagcactga agcagttcga gtagtgcgt tttgcacaga aggcgtgctc aacatccat     180 atcctgcgcc tgatgcgtga gcagggcgtt aaagttgact ccgtctctct gggtgagatt     240
gagcgcgccc tggcagccgg ctataaccca cagacccatc ctgacgacat tgtatttact     300
gccgacgtga tcgaccaggc tactctggaa cgcgtttctg aactgcagat cccggttaat     360
gctggttctg tggacatgct ggaccagctg ggccaggtat ccccaggtca tcgtgtgtgg     420
ctgcgtgtca acccaggttt cggccacggc cactctcaga aaactaacac tggtggtgag     480
aactccaagc atggcatttg gtataccgat ctgccggctg cactggacgt aatccagcgt     540
caccacctgc agctggtggg catccacatg cacattggct ccggcgtaga ctacgcccac     600
ctggagcaag tctgcggtgc tatggtacgt caggtaatcg agttcggcca agatctgcag     660
gcaatcagcg ctggtggcgg cctgtctgta cctttatcagc agggcgagga ggcggttgac     720
actgagcact actacggtct gtggaacgcc gctcgtgagc aaattgcacg tcacctgggc     780
cacccggtga aactggagat cgagccgggc cgcttcctgg tagcacagtc cggcgtactg     840
attacccagg tacgctctgt taaacagatg ggctcccgtc actttgtgct ggtagacgca     900
ggcttcaacg acctgatgcg tccggctatg tatggttcct atcatcacat ctctgcgctg     960
gccgccgacg gccgctctct ggaacacgcg ccgacggttg aaacggtggt ggctggtccg    1020
ctgtgcgagt ccggcgacgt tttcactcag caggagggcg gcaatgtaga gacgcgtgcg    1080
ctgccggaag tgaaagccgg tgattatctg gtgctgcatg ataccggcgc ctatggtgcg    1140
agcatgagca gcaactacaa ctctcgcccg ctgctgccgg aggtcctgtt cgataacggc    1200
caagcccgcc tgatccgtcg tcgtcagacc atcgaggaac tgctggcact ggagctgctg    1260
taa                                                                  1263
```

```
<210> SEQ ID NO 18
<211> LENGTH: 420
<212> TYPE: PRT
<213> ORGANISM: Escherichia coli

<400> SEQUENCE: 18

Met Pro His Ser Leu Phe Ser Thr Asp Thr Asp Leu Thr Ala Glu Asn
 1               5                  10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
    370                 375                 380
```

```
Asn Tyr Asn Ser Arg Pro Leu Leu Pro Glu Val Leu Phe Asp Asn Gly
385                 390                 395                 400

Gln Ala Arg Leu Ile Arg Arg Arg Gln Thr Ile Glu Glu Leu Leu Ala
                405                 410                 415

Leu Glu Leu Leu
            420

<210> SEQ ID NO 19
<211> LENGTH: 169
<212> TYPE: PRT
<213> ORGANISM: Methanocaldococcus jannaschii

<400> SEQUENCE: 19

Met Arg Gly Ser Leu Ala Ile Tyr Asn Ala Leu Lys Asp Ser Asn Ile
1               5                   10                  15

Asp Phe Ile Cys Ser Val Pro Cys Ala Asn Leu Lys Asn Leu Leu Lys
                20                  25                  30

Leu Ile Glu Glu Asp Lys Asn Ile Ile Asn Ile Pro Ala Thr Arg Glu
            35                  40                  45

Glu Glu Ala Phe Gly Ile Cys Ala Gly Ala Tyr Leu Ala Gly Lys Lys
50                  55                  60

Thr Ala Ile Leu Met Gln Asn Ser Gly Ile Gly Asn Ser Ile Asn Ala
65                  70                  75                  80

Ile Ala Ser Leu Tyr Lys Thr Phe Gln Ile Pro Thr Leu Leu Ile Ile
                85                  90                  95

Ser His Arg Gly Asp Leu Lys Gly Gln Ile Pro Ala Gln Ile Pro Met
            100                 105                 110

Gly Arg Trp Ile Glu Lys Leu Leu Asp Val Cys Glu Ile Pro Thr Tyr
        115                 120                 125

Lys Pro Lys Thr Pro Glu Glu Ala Tyr Lys Leu Ile Lys Tyr Ala Ser
130                 135                 140

Ser Tyr Met Tyr Lys Ile Ser Tyr Pro Val Ala Leu Leu Phe Asp Ala
145                 150                 155                 160

Leu Tyr Trp Glu Tyr Asp Leu Glu Lys
                165

<210> SEQ ID NO 20
<211> LENGTH: 188
<212> TYPE: PRT
<213> ORGANISM: Methanocaldococcus jannaschii

<400> SEQUENCE: 20

Met Tyr Pro Lys Arg Ile Asp Ile Ile Lys Lys Ile Val Glu Asn Val
1               5                   10                  15

Gly Glu Lys Glu Ile Ile Val Ser Asn Ile Gly Ile Pro Ser Lys Glu
                20                  25                  30

Leu Tyr Tyr Val Lys Asp Arg Glu Arg Asn Phe Tyr Met Leu Gly Ser
            35                  40                  45

Met Gly Leu Ala Ser Ser Ile Gly Leu Gly Leu Ala Leu Asn Cys Glu
50                  55                  60

Asp Lys Val Ile Val Ile Asp Gly Asp Gly Ser Ile Leu Met Asn Leu
65                  70                  75                  80

Gly Ser Leu Ser Thr Ile Gly Tyr Met Asn Pro Lys Asn Tyr Ile Leu
                85                  90                  95

Val Ile Ile Asp Asn Ser Ala Tyr Gly Ser Thr Gly Asn Gln Lys Thr
            100                 105                 110
```

```
His Thr Gly Lys Asn Thr Asn Leu Glu Glu Ile Ala Lys Gly Cys Gly
        115                 120                 125

Leu Asp Thr Ile Thr Thr Glu Ser Leu Glu Glu Phe Glu Lys Glu Phe
    130                 135                 140

Lys Asn Ala Leu Asn Glu Glu Lys Cys Lys Val Ile Ile Ala Lys Thr
145                 150                 155                 160

Ile Pro Tyr Asn Glu Lys Cys Ser Asn Ile Glu Ile Pro Pro Val Val
                165                 170                 175

Leu Lys Tyr Arg Phe Met Glu Ala Ile Lys Arg Ser
            180                 185

<210> SEQ ID NO 21
<211> LENGTH: 374
<212> TYPE: PRT
<213> ORGANISM: Methanocella paludicola

<400> SEQUENCE: 21

Met Ala Asn Val Glu Gln Glu Val Ile Asp Ile Met Lys Ser Ser Gly
  1               5                  10                  15

Ile Asp Thr Val Leu Thr Leu Pro Cys Asp Lys Ile Lys Asn Leu Leu
                20                  25                  30

Ala Met Val Pro Ser Asn Phe Lys Glu Ile Pro Leu Thr Arg Glu Glu
            35                  40                  45

Asn Gly Ile Gly Ile Ala Ala Gly Leu Ser Met Ala Gly Lys Arg Pro
     50                  55                  60

Ala Leu Ile Ile Gln Ser Thr Gly Ile Gly Asn Ser Leu Asn Val Leu
 65                  70                  75                  80

Ser Ser Leu Asn Arg Thr Tyr Glu Ile Pro Leu Pro Ile Leu Ala Ser
                 85                  90                  95

Trp Arg Gly Tyr Tyr Lys Glu Ala Ile Tyr Ala Gln Thr Ala Phe Gly
            100                 105                 110

Lys Cys Leu Pro Ala Ile Leu Glu Ala Ser Asp Ile Gln His Ile Glu
        115                 120                 125

Ile Gly Ala Met Gly Glu Leu Asp Leu Ile Lys Lys Ala Ile Ile Ala
    130                 135                 140

Ser Phe Lys Ser Asn Leu Pro Thr Val Ile Leu Leu Ser Pro Arg Leu
145                 150                 155                 160

Trp Glu Ile Ser Thr Glu Arg His Trp Asn Pro Asp Phe Thr Pro Arg
                165                 170                 175

Glu Arg Arg Phe Asp Met Glu Cys His Thr Val Val Pro Lys Ala Thr
            180                 185                 190

His Thr Arg Tyr Asp Met Ile Lys Gly Ile Thr Ser Tyr Leu Ser Gly
        195                 200                 205

Lys Val Val Ser Asn Ile Gly Ile Pro Ser Lys Glu Leu Tyr Ala
    210                 215                 220

Ala His Asp Gln Asp Thr Asn Phe Tyr Met Thr Gly Ser Leu Gly Leu
225                 230                 235                 240

Val Ser Ala Ile Gly Gln Gly Leu Ala Met Gly Leu Ser Arg Glu Val
                245                 250                 255

Ile Thr Leu Asp Gly Asp Gly Ser Ile Leu Met Asn Pro Asn Val Leu
            260                 265                 270

Ala Ser Val Ala Gln Glu Lys Pro Glu Asn Leu Thr Ile Ile Cys Phe
        275                 280                 285

Asp Asn Ser Ala His Gly Ser Thr Gly Asn Gln Lys Thr Tyr Ser Glu
```

```
            290                 295                 300
Ser Met Asp Leu Glu Leu Leu Ala Lys Ala Phe Gly Ile Glu Asn Thr
305                 310                 315                 320

Ala Lys Ala Ser Thr Pro Gly Glu Leu Leu Glu Ala Leu Glu Lys Arg
                325                 330                 335

Gly Lys Gly Pro Arg Phe Ile His Ala Ile Ile Glu Ala Lys Asn Ala
            340                 345                 350

Asp Val Pro Asn Ile Pro Leu Thr Pro Val Glu Ile Lys Glu Arg Phe
            355                 360                 365

Met Gly Ala Val Thr Arg
    370

<210> SEQ ID NO 22
<211> LENGTH: 591
<212> TYPE: PRT
<213> ORGANISM: Methanocaldococcus jannaschii

<400> SEQUENCE: 22

Met Lys Gly Ala Glu Ala Ile Ile Lys Ala Leu Glu Ala Glu Gly Val
1               5                   10                  15

Lys Ile Ile Phe Gly Tyr Pro Gly Gly Ala Met Leu Pro Phe Tyr Asp
            20                  25                  30

Ala Leu Tyr Asp Ser Asp Leu Val His Ile Leu Thr Arg His Glu Gln
        35                  40                  45

Ala Ala His Ala Ala Asp Gly Phe Ala Arg Ala Ser Gly Glu Ala
    50                  55                  60

Gly Val Cys Val Ser Thr Ser Gly Pro Gly Ala Thr Asn Leu Val Thr
65                  70                  75                  80

Gly Ile Ala Thr Ala Tyr Ala Asp Ser Ser Pro Val Ile Ala Leu Thr
                85                  90                  95

Gly Gln Val Pro Thr Lys Leu Ile Gly Asn Asp Ala Phe Gln Glu Ile
            100                 105                 110

Asp Ala Leu Gly Leu Phe Met Pro Ile Thr Lys His Asn Phe Gln Ile
        115                 120                 125

Lys Lys Pro Glu Glu Ile Pro Glu Thr Phe Arg Ala Ala Phe Glu Ile
130                 135                 140

Ala Thr Thr Gly Arg Pro Gly Pro Val His Ile Asp Leu Pro Lys Asp
145                 150                 155                 160

Val Gln Asp Gly Glu Ile Asp Ile Glu Lys Tyr Pro Ile Pro Ala Lys
                165                 170                 175

Val Asp Leu Pro Gly Tyr Lys Pro Lys Thr Val Gly His Pro Leu Gln
            180                 185                 190

Ile Lys Lys Ala Ala Lys Leu Ile Ala Glu Ser Glu Arg Pro Val Ile
        195                 200                 205

Leu Ala Gly Gly Gly Val Ile Ile Ser Gly Ala Ser Glu Glu Leu Leu
210                 215                 220

Arg Leu Ala Glu Phe Val Lys Ile Pro Val Cys Thr Thr Leu Met Gly
225                 230                 235                 240

Lys Gly Cys Phe Pro Glu Asp His Pro Leu Ala Leu Gly Met Val Gly
                245                 250                 255

Met His Gly Thr Lys Ala Ala Asn Tyr Ala Val Thr Glu Cys Asp Val
            260                 265                 270

Leu Ile Ala Ile Gly Cys Arg Phe Ser Asp Arg Val Thr Gly Asp Ile
        275                 280                 285
```

```
Arg Tyr Phe Ala Pro Glu Ala Lys Ile Ile His Ile Asp Ile Asp Pro
            290                 295                 300

Ala Glu Ile Gly Lys Asn Val Arg Ala Asp Ile Pro Ile Val Gly Asp
305                 310                 315                 320

Ala Lys Asn Val Leu Arg Asp Leu Leu Ala Ala Leu Ile Ala Leu Glu
                325                 330                 335

Ile Lys Asp Lys Glu Thr Trp Leu Glu Arg Ile Tyr Glu Leu Lys Lys
            340                 345                 350

Leu Ser Ile Pro Met Met Asp Phe Asp Lys Pro Ile Lys Pro Gln
            355                 360                 365

Arg Phe Val Lys Asp Leu Met Glu Val Leu Asn Glu Ile Asp Ser Lys
370                 375                 380

Leu Lys Asn Thr Ile Ile Thr Thr Asp Val Gly Gln Asn Gln Met Trp
385                 390                 395                 400

Met Ala His Phe Phe Lys Thr Lys Met Pro Arg Ser Phe Leu Ala Ser
                405                 410                 415

Gly Gly Leu Gly Thr Met Gly Phe Gly Phe Pro Ala Ala Ile Gly Ala
            420                 425                 430

Lys Val Ala Lys Pro Tyr Ala Asn Val Ile Ser Ile Thr Gly Asp Gly
                435                 440                 445

Gly Phe Leu Met Asn Ser Gln Glu Leu Ala Thr Ile Ser Glu Tyr Asp
450                 455                 460

Ile Pro Val Val Ile Cys Ile Phe Asp Asn Arg Thr Leu Gly Met Val
465                 470                 475                 480

Tyr Gln Trp Gln Asn Leu Tyr Tyr Gly Gln Arg Gln Ser Glu Val His
                485                 490                 495

Leu Gly Glu Ser Pro Asp Phe Val Lys Leu Ala Glu Ser Tyr Gly Val
            500                 505                 510

Lys Ala Asp Arg Ile Ile Ser Pro Asp Glu Ile Lys Glu Lys Leu Lys
            515                 520                 525

Glu Ala Ile Leu Ser Asn Glu Pro Tyr Leu Leu Asp Ile Val Ile Asp
530                 535                 540

Pro Ala Glu Ala Leu Pro Met Val Pro Pro Gly Gly Arg Leu Thr Asn
545                 550                 555                 560

Ile Val Gln Pro Ile Arg Val Glu Pro Lys Ile Lys Lys Pro Gln Phe
                565                 570                 575

Asp Glu Ile Lys Lys Ile Arg Asp Met Ala Ala Val Lys Glu Phe
            580                 585                 590

<210> SEQ ID NO 23
<211> LENGTH: 494
<212> TYPE: PRT
<213> ORGANISM: Methanocaldococcus jannaschii

<400> SEQUENCE: 23

Met Gly Gly Asn Ile Lys Phe Leu Glu Ala Met Val Asp Phe Leu Glu
1               5                   10                  15

Arg Asn Val Lys Thr Ile Phe Ser Tyr Pro Gly Glu Gln Ile Leu Pro
            20                  25                  30

Leu Tyr Asn Glu Ile Glu Gly Ser Ser Ile Lys Asn Ile Met Val Arg
        35                  40                  45

Asp Glu Arg Gly Ala Gly Phe Met Ala Asp Gly Tyr Ala Arg Ile Thr
    50                  55                  60

Asn Tyr Ile Gly Val Cys Leu Ala Thr Ala Gly Pro Gly Ala Thr Asn
65                  70                  75                  80
```

```
Leu Thr Thr Pro Ile Ala Thr Ala Tyr Lys Asp Asn Ser Ser Val Leu
                85                  90                  95

Ala Ile Thr Gly Arg Cys Gln Arg Lys Tyr Ile Gly Lys Asn Tyr Phe
                100                 105                 110

Gln Glu Val Asn Met Asp Phe Leu Asn Phe Tyr Lys Gly Tyr Phe Val
        115                 120                 125

Asp Lys Ala Glu Val Ser Tyr Ile Ala Lys Ala Phe Ala Asp Cys Leu
    130                 135                 140

Phe Asn Lys Lys Pro Val Gln Leu Asn Ile Pro Val Asp Leu Tyr Lys
145                 150                 155                 160

Glu Glu Ala Lys Asp Ile Asn Ile Thr Thr Tyr Thr Asp Ile Tyr Lys
                165                 170                 175

Asp Asp Glu Thr Pro Ser Asn Asn Ile Lys Glu Ile Asp Val Lys Lys
                180                 185                 190

Pro Leu Phe Leu Ile Gly Gln Gly Ile Phe Gly Thr Leu Ser Tyr Lys
            195                 200                 205

Glu Ile Val Lys Ile Ser Lys Ile Leu Glu Lys Ile Asn Cys Pro Ile
    210                 215                 220

Ala Thr Thr Phe Pro Ala Arg Gly Val Ile Asn Glu Lys Leu Glu Asn
225                 230                 235                 240

Cys Ile Gly Leu Val Gly Arg Arg Gly Asp Leu Lys Ser Leu Leu Glu
                245                 250                 255

Ala Asp Lys Ile Ile Asn Ile Gly Ser Ser Leu Ser Tyr Asn Thr Tyr
                260                 265                 270

Val Glu Ser Val Arg Glu Lys Leu Leu Ser Lys Thr Glu Asn Ile Gln
            275                 280                 285

Leu Lys Pro Lys Ser Ile Lys Glu Leu Lys Glu Phe Phe Glu Asn Leu
    290                 295                 300

Asp Val Lys Asn Ser Ser Trp Ile Tyr Lys Asn Ser Asn Lys Phe Gln
305                 310                 315                 320

Pro Ser Gly Asp Tyr Ser Asn Lys Ile Tyr Glu Ile Ile Lys Asn Ile
                325                 330                 335

Pro Glu Asp Ala Ile Ile Val Thr Asp Ala Gly Lys His Thr Val Phe
                340                 345                 350

Thr Cys Leu Leu Lys Thr Cys Val Ile Pro Arg Asn Ile Ile Ser Ser
            355                 360                 365

His Ser Phe Gly Thr Met Gly Phe Gly Leu Pro Ala Ser Ile Gly Val
    370                 375                 380

Lys Phe Gly Thr Ile Asp Phe Asn Ile Asp Arg Glu Val Val Leu Ile
385                 390                 395                 400

Ser Gly Asp Gly Gly Phe Leu Met Asn Val Glu Glu Leu Gln Val Val
                405                 410                 415

Ala Glu Asn Asn Leu Lys Ile Leu Met Val Val Met Lys Asn Asn Ser
                420                 425                 430

Leu Ala Glu Phe Cys Lys Ile Lys Asn Pro Asn Phe Asn Lys Ile Ala
            435                 440                 445

Asp Ala Phe Glu Ile Asp Asn Cys Tyr Ile Glu Asn Val Asp Glu Ile
    450                 455                 460

Gly Ser Glu Ile Lys Gly Tyr Leu Lys Lys Asn Lys Pro Leu Leu Val
465                 470                 475                 480

Val Val Glu Thr Glu Asn Glu Pro Leu Pro Lys Pro Asn Ile
                485                 490
```

<210> SEQ ID NO 24
<211> LENGTH: 591
<212> TYPE: PRT
<213> ORGANISM: Methanocaldococcus jannaschii

<400> SEQUENCE: 24

```
Met Lys Gly Ala Glu Ala Ile Ile Lys Ala Leu Glu Ala Glu Gly Val
  1               5                  10                  15

Lys Ile Ile Phe Gly Tyr Pro Gly Gly Ala Met Leu Pro Phe Tyr Asp
                 20                  25                  30

Ala Leu Tyr Asp Ser Asp Leu Val His Ile Leu Thr Arg His Glu Gln
             35                  40                  45

Ala Ala His Ala Ala Asp Gly Phe Ala Arg Ala Ser Gly Glu Ala
     50                  55                  60

Gly Val Cys Val Ser Thr Ser Gly Pro Gly Ala Thr Asn Leu Val Thr
 65                  70                  75                  80

Gly Ile Ala Thr Ala Tyr Ala Asp Ser Ser Pro Val Ile Ala Leu Thr
                 85                  90                  95

Gly Gln Val Pro Thr Lys Leu Ile Gly Asn Asp Ala Phe Gln Glu Ile
            100                 105                 110

Asp Ala Leu Gly Leu Phe Met Pro Ile Thr Lys His Asn Phe Gln Ile
        115                 120                 125

Lys Lys Pro Glu Glu Ile Pro Glu Thr Phe Arg Ala Ala Phe Glu Ile
130                 135                 140

Ala Thr Thr Gly Arg Pro Gly Pro Val His Ile Asp Leu Pro Lys Asp
145                 150                 155                 160

Val Gln Asp Gly Glu Ile Asp Ile Glu Lys Tyr Pro Ile Pro Ala Lys
                165                 170                 175

Val Asp Leu Pro Gly Tyr Lys Pro Lys Thr Val Gly His Pro Leu Gln
            180                 185                 190

Ile Lys Lys Ala Ala Lys Leu Ile Ala Glu Ser Glu Arg Pro Val Ile
        195                 200                 205

Leu Ala Gly Gly Gly Val Ile Ile Ser Gly Ala Ser Glu Glu Leu Leu
210                 215                 220

Arg Leu Ala Glu Phe Val Lys Ile Pro Val Cys Thr Thr Leu Met Gly
225                 230                 235                 240

Lys Gly Cys Phe Pro Glu Asp His Pro Leu Ala Leu Gly Met Val Gly
                245                 250                 255

Met His Gly Thr Lys Ala Ala Asn Tyr Ala Val Thr Glu Cys Asp Val
            260                 265                 270

Leu Ile Ala Ile Gly Cys Arg Phe Ser Asp Arg Val Thr Gly Asp Ile
        275                 280                 285

Arg Tyr Phe Ala Pro Glu Ala Lys Ile Ile His Ile Asp Ile Asp Pro
290                 295                 300

Ala Glu Ile Gly Lys Asn Val Arg Ala Asp Ile Pro Ile Val Gly Asp
305                 310                 315                 320

Ala Lys Asn Val Leu Arg Asp Leu Leu Ala Leu Ile Ala Leu Glu
                325                 330                 335

Ile Lys Asp Lys Glu Thr Trp Leu Glu Arg Ile Tyr Leu Lys Lys
        340                 345                 350

Leu Ser Ile Pro Met Met Asp Phe Asp Lys Pro Ile Lys Pro Gln
355                 360                 365

Arg Phe Val Lys Asp Leu Met Glu Val Leu Asn Glu Ile Asp Ser Lys
370                 375                 380
```

```
Leu Lys Asn Thr Ile Ile Thr Thr Asp Val Gly Gln Asn Gln Met Trp
385                 390                 395                 400

Met Ala His Phe Phe Lys Thr Lys Met Pro Arg Ser Phe Leu Ala Ser
            405                 410                 415

Gly Gly Leu Gly Thr Met Gly Phe Gly Phe Pro Ala Ala Ile Gly Ala
        420                 425                 430

Lys Val Ala Lys Pro Tyr Ala Asn Val Ile Ser Ile Thr Gly Asp Gly
            435                 440                 445

Gly Phe Leu Met Asn Ser Gln Glu Leu Ala Thr Ile Ser Glu Tyr Asp
        450                 455                 460

Ile Pro Val Val Ile Cys Ile Phe Asp Asn Arg Thr Leu Gly Met Val
465                 470                 475                 480

Tyr Gln Trp Gln Asn Leu Tyr Tyr Gly Gln Arg Gln Ser Glu Val His
                485                 490                 495

Leu Gly Glu Ser Pro Asp Phe Val Lys Leu Ala Glu Ser Tyr Gly Val
            500                 505                 510

Lys Ala Asp Arg Ile Ile Ser Pro Asp Glu Ile Lys Glu Lys Leu Lys
            515                 520                 525

Glu Ala Ile Leu Ser Asn Glu Pro Tyr Leu Leu Asp Ile Val Ile Asp
        530                 535                 540

Pro Ala Glu Ala Leu Pro Met Val Pro Pro Gly Gly Arg Leu Thr Asn
545                 550                 555                 560

Ile Val Gln Pro Ile Arg Val Glu Pro Lys Ile Lys Lys Pro Gln Phe
                565                 570                 575

Asp Glu Ile Lys Lys Ile Arg Asp Met Ala Ala Val Lys Glu Phe
            580                 585                 590

<210> SEQ ID NO 25
<211> LENGTH: 494
<212> TYPE: PRT
<213> ORGANISM: Methanocaldococcus jannaschii

<400> SEQUENCE: 25

Met Gly Gly Asn Ile Lys Phe Leu Glu Ala Met Val Asp Phe Leu Glu
1               5                   10                  15

Arg Asn Val Lys Thr Ile Phe Ser Tyr Pro Gly Glu Gln Ile Leu Pro
            20                  25                  30

Leu Tyr Asn Glu Ile Glu Gly Ser Ser Ile Lys Asn Ile Met Val Arg
        35                  40                  45

Asp Glu Arg Gly Ala Gly Phe Met Ala Asp Gly Tyr Ala Arg Ile Thr
    50                  55                  60

Asn Tyr Ile Gly Val Cys Leu Ala Thr Ala Gly Pro Gly Ala Thr Asn
65                  70                  75                  80

Leu Thr Thr Pro Ile Ala Thr Ala Tyr Lys Asp Asn Ser Ser Val Leu
                85                  90                  95

Ala Ile Thr Gly Arg Cys Gln Arg Lys Tyr Ile Gly Lys Asn Tyr Phe
            100                 105                 110

Gln Glu Val Asn Met Asp Phe Leu Asn Phe Tyr Lys Gly Tyr Phe Val
        115                 120                 125

Asp Lys Ala Glu Val Ser Tyr Ile Ala Lys Ala Phe Ala Asp Cys Leu
    130                 135                 140

Phe Asn Lys Lys Pro Val Gln Leu Asn Ile Pro Val Asp Leu Tyr Lys
145                 150                 155                 160

Glu Glu Ala Lys Asp Ile Asn Ile Thr Thr Tyr Thr Asp Ile Tyr Lys
```

165                 170                 175
Asp Asp Glu Thr Pro Ser Asn Asn Ile Lys Glu Ile Asp Val Lys Lys
                180                 185                 190

Pro Leu Phe Leu Ile Gly Gln Gly Ile Phe Gly Thr Leu Ser Tyr Lys
            195                 200                 205

Glu Ile Val Lys Ile Ser Lys Ile Leu Glu Lys Ile Asn Cys Pro Ile
        210                 215                 220

Ala Thr Thr Phe Pro Ala Arg Gly Val Ile Asn Glu Lys Leu Glu Asn
225                 230                 235                 240

Cys Ile Gly Leu Val Gly Arg Arg Gly Asp Leu Lys Ser Leu Leu Glu
                245                 250                 255

Ala Asp Lys Ile Ile Asn Ile Gly Ser Ser Leu Ser Tyr Asn Thr Tyr
            260                 265                 270

Val Glu Ser Val Arg Glu Lys Leu Leu Ser Lys Thr Glu Asn Ile Gln
        275                 280                 285

Leu Lys Pro Lys Ser Ile Lys Glu Leu Lys Glu Phe Phe Glu Asn Leu
    290                 295                 300

Asp Val Lys Asn Ser Ser Trp Ile Tyr Lys Asn Ser Asn Lys Phe Gln
305                 310                 315                 320

Pro Ser Gly Asp Tyr Ser Asn Lys Ile Tyr Glu Ile Ile Lys Asn Ile
                325                 330                 335

Pro Glu Asp Ala Ile Ile Val Thr Asp Ala Gly Lys His Thr Val Phe
            340                 345                 350

Thr Cys Leu Leu Lys Thr Cys Val Ile Pro Arg Asn Ile Ile Ser Ser
        355                 360                 365

His Ser Phe Gly Thr Met Gly Phe Gly Leu Pro Ala Ser Ile Gly Val
    370                 375                 380

Lys Phe Gly Thr Ile Asp Phe Asn Ile Asp Arg Glu Val Val Leu Ile
385                 390                 395                 400

Ser Gly Asp Gly Gly Phe Leu Met Asn Val Glu Glu Leu Gln Val Val
                405                 410                 415

Ala Glu Asn Asn Leu Lys Ile Leu Met Val Val Met Lys Asn Asn Ser
            420                 425                 430

Leu Ala Glu Phe Cys Lys Ile Lys Asn Pro Asn Phe Asn Lys Ile Ala
        435                 440                 445

Asp Ala Phe Glu Ile Asp Asn Cys Tyr Ile Glu Asn Val Asp Glu Ile
    450                 455                 460

Gly Ser Glu Ile Lys Gly Tyr Leu Lys Lys Asn Lys Pro Leu Leu Val
465                 470                 475                 480

Val Val Glu Thr Glu Asn Glu Pro Leu Pro Lys Pro Asn Ile
                485                 490

<210> SEQ ID NO 26
<211> LENGTH: 188
<212> TYPE: PRT
<213> ORGANISM: Methanocaldococcus jannaschii

<400> SEQUENCE: 26

Met Tyr Pro Lys Arg Ile Asp Ile Ile Lys Lys Ile Val Glu Asn Val
1               5                   10                  15

Gly Glu Lys Glu Ile Ile Val Ser Asn Ile Gly Ile Pro Ser Lys Glu
                20                  25                  30

Leu Tyr Tyr Val Lys Asp Arg Glu Arg Asn Phe Tyr Met Leu Gly Ser
            35                  40                  45

```
Met Gly Leu Ala Ser Ser Ile Gly Leu Gly Leu Ala Leu Asn Cys Glu
     50                  55                  60

Asp Lys Val Ile Val Ile Asp Gly Asp Gly Ser Ile Leu Met Asn Leu
 65                  70                  75                  80

Gly Ser Leu Ser Thr Ile Gly Tyr Met Asn Pro Lys Asn Tyr Ile Leu
                 85                  90                  95

Val Ile Ile Asp Asn Ser Ala Tyr Gly Ser Thr Gly Asn Gln Lys Thr
                100                 105                 110

His Thr Gly Lys Asn Thr Asn Leu Glu Glu Ile Ala Lys Gly Cys Gly
            115                 120                 125

Leu Asp Thr Ile Thr Thr Glu Ser Leu Glu Glu Phe Glu Lys Glu Phe
130                 135                 140

Lys Asn Ala Leu Asn Glu Glu Lys Cys Lys Val Ile Ala Lys Thr
145                 150                 155                 160

Ile Pro Tyr Asn Glu Lys Cys Ser Asn Ile Glu Ile Pro Pro Val Val
                165                 170                 175

Leu Lys Tyr Arg Phe Met Glu Ala Ile Lys Arg Ser
            180                 185
```

<210> SEQ ID NO 27
<211> LENGTH: 451
<212> TYPE: PRT
<213> ORGANISM: Methanocaldococcus jannaschii

<400> SEQUENCE: 27

```
Met Leu Asp Lys Leu Gly Glu Asn Leu Asn Lys Ala Leu Asn Lys Leu
 1               5                  10                  15

Lys Ala Ala Ala Phe Val Asp Lys Lys Leu Ile Lys Glu Val Ile Lys
                 20                  25                  30

Asp Ile Gln Arg Ala Leu Ile Gln Ala Asp Val Asn Val Lys Leu Val
             35                  40                  45

Leu Lys Met Ser Lys Glu Ile Glu Arg Arg Ala Leu Glu Glu Lys Thr
 50                  55                  60

Pro Lys Gly Leu Ser Lys Lys Glu His Ile Ile Lys Ile Val Tyr Glu
 65                  70                  75                  80

Glu Leu Val Lys Leu Leu Gly Glu Gly Ala Lys Lys Leu Glu Leu Asn
                 85                  90                  95

Pro Lys Lys Gln Asn Val Ile Leu Leu Val Gly Ile Gln Gly Ser Gly
                100                 105                 110

Lys Thr Thr Thr Ala Ala Lys Leu Ala Arg Tyr Ile Gln Lys Arg Gly
            115                 120                 125

Leu Lys Pro Ala Leu Ile Ala Ala Asp Thr Tyr Arg Pro Ala Ala Tyr
130                 135                 140

Glu Gln Leu Lys Gln Leu Ala Glu Lys Ile His Val Pro Ile Tyr Gly
145                 150                 155                 160

Asp Glu Thr Arg Thr Lys Ser Pro Val Asp Ile Val Lys Glu Gly Met
                165                 170                 175

Glu Lys Phe Lys Lys Ala Asp Val Leu Ile Ile Asp Thr Ala Gly Arg
                180                 185                 190

His Lys Glu Glu Lys Gly Leu Leu Glu Glu Met Lys Gln Ile Lys Glu
            195                 200                 205

Ile Thr Asn Pro Asp Glu Ile Ile Leu Val Ile Asp Gly Thr Ile Gly
210                 215                 220

Gln Gln Ala Gly Ile Gln Ala Lys Ala Phe Lys Glu Ala Val Gly Glu
225                 230                 235                 240
```

-continued

```
Ile Gly Ser Ile Ile Val Thr Lys Leu Asp Gly Ser Ala Lys Gly Gly
                245                 250                 255
Gly Ala Leu Ser Ala Val Ala Glu Thr Lys Ala Pro Ile Lys Phe Ile
            260                 265                 270
Gly Ile Gly Glu Gly Ile Asp Asp Leu Glu Pro Phe Asp Pro Lys Lys
        275                 280                 285
Phe Ile Ser Arg Leu Leu Gly Met Gly Asp Leu Glu Ser Leu Leu Glu
    290                 295                 300
Lys Ala Glu Asp Met Val Asp Glu Lys Thr Glu Ser Ile Asp Ala
305                 310                 315                 320
Ile Met Arg Gly Lys Phe Thr Leu Asn Glu Leu Met Thr Gln Leu Glu
                325                 330                 335
Ala Ile Glu Asn Met Gly Ser Met Lys Lys Ile Leu Ser Met Ile Pro
            340                 345                 350
Gly Phe Gly Gly Ala Met Pro Lys Glu Leu Ser His Leu Thr Glu Ala
        355                 360                 365
Lys Ile Lys Lys Tyr Lys Val Ile Ser Ser Met Thr Lys Glu Glu
    370                 375                 380
Arg Glu Asn Pro Lys Ile Ile Lys Ala Ser Arg Ile Arg Ile Ala
385                 390                 395                 400
Arg Gly Ser Gly Thr Thr Glu Asn Asp Val Arg Glu Val Leu Arg Tyr
                405                 410                 415
Tyr Glu Thr Thr Lys Asn Ala Ile Asp Lys Leu Arg Lys Gly Lys Met
            420                 425                 430
Leu Arg Ile Gly Gly Pro Leu Gly Gln Ile Met Arg Gln Leu Met Phe
        435                 440                 445
Lys Glu Gly
    450

<210> SEQ ID NO 28
<211> LENGTH: 443
<212> TYPE: PRT
<213> ORGANISM: Methanocaldococcus jannaschii

<400> SEQUENCE: 28

Met Ile Met Lys Arg Val Val Ile Ala Gly Thr Ser Ser Glu Val Gly
1               5                   10                  15
Lys Thr Val Ile Ser Thr Gly Ile Met Lys Ala Leu Ser Lys Lys Tyr
            20                  25                  30
Asn Val Gln Gly Tyr Lys Val Gly Pro Asp Tyr Ile Asp Pro Thr Tyr
        35                  40                  45
His Thr Ile Ala Thr Gly Asn Lys Ser Arg Asn Leu Asp Ser Phe Phe
    50                  55                  60
Met Asn Lys Glu Gln Ile Lys Tyr Leu Phe Gln Lys His Ser Lys Asp
65                  70                  75                  80
Lys Asp Ile Ser Val Ile Glu Gly Val Arg Gly Leu Tyr Glu Gly Ile
                85                  90                  95
Ser Ala Ile Asp Asp Ile Gly Ser Thr Ala Ser Val Ala Lys Ala Leu
            100                 105                 110
Asp Ser Pro Ile Ile Leu Leu Val Asn Ala Lys Ser Leu Thr Arg Ser
        115                 120                 125
Ala Ile Ala Ile Ile Lys Gly Phe Met Ser Phe Asp Asn Val Lys Ile
    130                 135                 140
Lys Gly Val Ile Phe Asn Phe Val Arg Ser Glu Asn His Ile Lys Lys
```

```
                145                 150                 155                 160
Leu Lys Asp Ala Met Ser Tyr Tyr Leu Pro Asp Ile Glu Ile Ile Gly
                    165                 170                 175

Phe Ile Pro Arg Asn Glu Asp Phe Lys Val Glu Gly Arg His Leu Gly
                180                 185                 190

Leu Val Pro Thr Pro Glu Asn Leu Lys Glu Ile Ser Lys Ile Val
            195                 200                 205

Leu Trp Gly Glu Leu Val Glu Lys Tyr Leu Asp Leu Asp Lys Ile Val
    210                 215                 220

Glu Ile Ala Asp Glu Asp Phe Glu Val Asp Asp Val Phe Leu Trp
225                 230                 235                 240

Glu Val Asn Glu Asn Tyr Lys Lys Ile Ala Val Ala Tyr Asp Lys Ala
                245                 250                 255

Phe Asn Phe Tyr Tyr Trp Asp Asn Phe Glu Ala Leu Lys Glu Asn Lys
                260                 265                 270

Ala Lys Ile Glu Phe Phe Ser Pro Leu Lys Asp Ser Glu Val Pro Asp
            275                 280                 285

Ala Asp Ile Leu Tyr Ile Gly Gly Tyr Pro Glu Leu Phe Lys Glu
    290                 295                 300

Glu Leu Ser Arg Asn Lys Glu Met Ile Glu Ser Ile Lys Glu Phe Asp
305                 310                 315                 320

Gly Tyr Ile Tyr Gly Glu Cys Gly Gly Leu Met Tyr Ile Thr Lys Ser
                325                 330                 335

Ile Asp Asn Val Pro Met Val Gly Leu Leu Asn Cys Ser Ala Val Met
            340                 345                 350

Thr Lys His Val Gln Gly Leu Ser Tyr Val Lys Ala Glu Phe Leu Glu
    355                 360                 365

Asp Cys Leu Ile Gly Arg Lys Gly Leu Lys Phe Lys Gly His Glu Phe
370                 375                 380

His Tyr Ser Lys Leu Val Asn Ile Lys Glu Glu Arg Phe Ala Tyr Lys
385                 390                 395                 400

Ile Glu Arg Gly Arg Gly Ile Ile Asn Asn Leu Asp Gly Ile Phe Asn
                405                 410                 415

Gly Lys Val Leu Ala Gly Tyr Leu His Asn His Ala Val Ala Asn Pro
            420                 425                 430

Tyr Phe Ala Ser Ser Met Val Asn Phe Gly Glu
            435                 440

<210> SEQ ID NO 29
<211> LENGTH: 169
<212> TYPE: PRT
<213> ORGANISM: Methanocaldococcus jannaschii

<400> SEQUENCE: 29

Met Arg Gly Ser Leu Ala Ile Tyr Asn Ala Leu Lys Asp Ser Asn Ile
1               5                   10                  15

Asp Phe Ile Cys Ser Val Pro Cys Ala Asn Leu Lys Asn Leu Leu Lys
                20                  25                  30

Leu Ile Glu Glu Asp Lys Asn Ile Ile Asn Ile Pro Ala Thr Arg Glu
            35                  40                  45

Glu Glu Ala Phe Gly Ile Cys Ala Gly Ala Tyr Leu Ala Gly Lys Lys
        50                  55                  60

Thr Ala Ile Leu Met Gln Asn Ser Gly Ile Gly Asn Ser Ile Asn Ala
65                  70                  75                  80
```

```
Ile Ala Ser Leu Tyr Lys Thr Phe Gln Ile Pro Thr Leu Leu Ile Ile
                85                  90                  95
Ser His Arg Gly Asp Leu Lys Glu Gln Ile Pro Ala Gln Ile Pro Met
                100                 105                 110
Gly Arg Trp Ile Glu Lys Leu Leu Asp Val Cys Glu Ile Pro Thr Tyr
                115                 120                 125
Lys Pro Lys Thr Pro Glu Glu Ala Tyr Lys Leu Ile Lys Tyr Ala Ser
                130                 135                 140
Ser Tyr Met Tyr Lys Ile Ser Tyr Pro Val Ala Leu Leu Phe Asp Ala
145                 150                 155                 160
Leu Tyr Trp Glu Tyr Asp Leu Glu Lys
                165
```

<210> SEQ ID NO 30
<211> LENGTH: 270
<212> TYPE: PRT
<213> ORGANISM: Methanocaldococcus jannaschii

<400> SEQUENCE: 30

```
Met His Pro Ala Leu Lys Tyr Met Arg Gln Asp Arg Leu Pro His Ile
1               5                   10                  15
Phe Cys Ser Gly Cys Gly Asn Gly Ile Val Met Asn Cys Phe Leu Lys
                20                  25                  30
Ala Ile Glu Glu Leu Asn Ile Lys Pro Glu Asp Tyr Ile Ala Val Ser
                35                  40                  45
Gly Ile Gly Cys Ser Ser Arg Val Pro Gly Tyr Leu Tyr Cys Asp Ser
            50                  55                  60
Leu His Thr Thr His Gly Arg Pro Ile Ala Phe Ala Thr Gly Ile Lys
65              70                  75                  80
Ile Ala Arg Pro Asp Lys His Val Val Val Phe Thr Gly Asp Gly Asp
                85                  90                  95
Leu Ala Ala Ile Gly Gly Asn His Phe Ile His Gly Cys Arg Arg Asn
                100                 105                 110
Ile Asp Leu Thr Val Ile Cys Ile Asn Asn Asn Ile Tyr Gly Met Thr
                115                 120                 125
Gly Gly Gln Val Ser Pro Thr Thr Pro Tyr Gly Lys Lys Ala Thr Thr
            130                 135                 140
Ala Pro Tyr Gly Ser Ile Glu Asn Thr Met Asp Leu Cys Lys Met Ala
145                 150                 155                 160
Ile Ala Ala Gly Ala Thr Tyr Val Ala Arg Trp Thr Thr Ala His Pro
                165                 170                 175
Ile Gln Leu Val Arg Ser Ile Lys Lys Gly Ile Gln Lys Lys Gly Phe
                180                 185                 190
Ala Phe Ile Glu Val Val Ser Gln Cys Pro Thr Tyr Tyr Gly Arg Phe
                195                 200                 205
Asn Ile Ser Arg Lys Pro Ala Asp Met Ile Lys Phe Leu Lys Glu Asn
            210                 215                 220
Ser Ile His Leu Asn Lys Ala Lys Asp Met Ser Glu Glu Leu Asn
225                 230                 235                 240
Gly Lys Ile Val Val Gly Glu Phe Leu Asp Ile Glu Lys Pro Glu Phe
                245                 250                 255
Val Glu Glu Leu His Lys Leu Ile Glu Lys Leu Lys Ser Glu
                260                 265                 270
```

<210> SEQ ID NO 31

```
<211> LENGTH: 262
<212> TYPE: PRT
<213> ORGANISM: Methanocaldococcus jannaschii

<400> SEQUENCE: 31

Met Met Ala Leu Asn Glu Tyr Asp Ala Gln Ile Val Glu Gln Ala Met
1               5                   10                  15

Lys Pro Ile Leu Asp Ser Asn Leu Phe Ser Arg Lys Ile Phe Gln Lys
            20                  25                  30

Lys Lys Ile Pro Glu Asp Val Glu Val Tyr Asn Leu Gln Val Val
        35                  40                  45

Phe Asp Glu Asn Ala Phe Lys Lys Gly Ser Met Glu Leu Thr Glu Val
50                  55                  60

Pro Ile Lys Thr Thr Thr Ser Pro Phe Thr Val Phe Asp Ile Asn Leu
65                  70                  75                  80

Lys Val Thr Lys Ala Arg Arg Phe Val Glu Gly Pro Asn Ala Asp Tyr
                85                  90                  95

Asn Lys Ala Gln Ile Phe Glu Gly Leu Ala Lys Val Val Ala Arg Ala
            100                 105                 110

Glu Asn Gln Tyr Ser Ile Asp Ala Leu Ser Lys Asn Asn Thr Ala Val
        115                 120                 125

Gly Ala Ser Ala Ser Trp Asn Gly Ala Asp Thr Thr Pro Asp Lys Ile
130                 135                 140

Ala Asn Asp Ile Ile Asp Ala Lys Thr Lys Ile Glu Gln Tyr Ser Asn
145                 150                 155                 160

Ala Lys Cys Ala Leu Val Ala Pro Val Asp Ala Ile Ala Cys Phe Arg
                165                 170                 175

Lys Ile Gly Thr Gln Gly Phe Ser Ala Tyr Asp Glu Thr Lys Asp Phe
            180                 185                 190

Ile Lys Glu Ile Ile Pro Thr Asn Leu Ile Thr Asp Lys Ser Ala Tyr
        195                 200                 205

Leu Val Pro Ile Asp Ile Ala Ile Leu Gln Met Gly Val Ala Val Glu
210                 215                 220

Ala Asp Gln Phe Ile Glu Lys Lys Ala Thr Gln Val Glu Phe Ile Phe
225                 230                 235                 240

Thr Glu Ala Ile Ser Pro Met Val Lys Glu Lys Asn Gly Ile Ile Lys
                245                 250                 255

Ile Gln Lys Val Leu Gly
            260

<210> SEQ ID NO 32
<211> LENGTH: 270
<212> TYPE: PRT
<213> ORGANISM: Methanocaldococcus jannaschii

<400> SEQUENCE: 32

Met His Pro Ala Leu Lys Tyr Met Arg Gln Asp Arg Leu Pro His Ile
1               5                   10                  15

Phe Cys Ser Gly Cys Gly Asn Gly Ile Val Met Asn Cys Phe Leu Lys
            20                  25                  30

Ala Ile Glu Glu Leu Asn Ile Lys Pro Glu Asp Tyr Ile Ala Val Ser
        35                  40                  45

Gly Ile Gly Cys Ser Ser Arg Val Pro Gly Tyr Leu Tyr Cys Asp Ser
50                  55                  60

Leu His Thr His Gly Arg Pro Ile Ala Phe Ala Thr Gly Ile Lys
65                  70                  75                  80
```

```
Ile Ala Arg Pro Asp Lys His Val Val Phe Thr Gly Asp Gly Asp
                85                  90                  95

Leu Ala Ala Ile Gly Gly Asn His Phe Ile His Gly Cys Arg Arg Asn
                100                 105                 110

Ile Asp Leu Thr Val Ile Cys Ile Asn Asn Ile Tyr Gly Met Thr
            115                 120                 125

Gly Gly Gln Val Ser Pro Thr Thr Pro Tyr Gly Lys Lys Ala Thr Thr
130                 135                 140

Ala Pro Tyr Gly Ser Ile Glu Asn Thr Met Asp Leu Cys Lys Met Ala
145                 150                 155                 160

Ile Ala Ala Gly Ala Thr Tyr Val Ala Arg Trp Thr Thr Ala His Pro
                165                 170                 175

Ile Gln Leu Val Arg Ser Ile Lys Lys Gly Ile Gln Lys Lys Gly Phe
            180                 185                 190

Ala Phe Ile Glu Val Val Ser Gln Cys Pro Thr Tyr Tyr Gly Arg Phe
        195                 200                 205

Asn Ile Ser Arg Lys Pro Ala Asp Met Ile Lys Phe Leu Lys Glu Asn
    210                 215                 220

Ser Ile His Leu Asn Lys Ala Lys Asp Met Ser Glu Glu Leu Asn
225                 230                 235                 240

Gly Lys Ile Val Val Gly Glu Phe Leu Asp Ile Glu Lys Pro Glu Phe
                245                 250                 255

Val Glu Glu Leu His Lys Leu Ile Glu Lys Leu Lys Ser Glu
            260                 265                 270
```

<210> SEQ ID NO 33
<211> LENGTH: 1238
<212> TYPE: PRT
<213> ORGANISM: Mycobacterium leprae

<400> SEQUENCE: 33

```
Met Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
                20                  25                  30

Trp His Glu Phe Leu Val Asp Tyr Asn Pro Glu Ser Thr Ala Glu Pro
            35                  40                  45

Val Leu Thr Asp Pro Thr Ser Thr Asp Lys Gln Pro Ser Ala Thr Pro
    50                  55                  60

Gln Ala Lys Pro Ala Ala Ala Asp Pro Val Ala Ser Arg Ala Lys
65                  70                  75                  80

Pro Ala Thr Thr Pro Thr Val Ala Asn Gly Thr Ala Ala Gly Ser Ala
                85                  90                  95

Ala Ala Pro Ala Lys Thr Thr Thr Pro Pro Ile Glu Gly Asp Glu
                100                 105                 110

Leu Gln Val Leu Arg Gly Ala Ala Ala Val Val Lys Asn Met Ser
            115                 120                 125

Ala Ser Leu Asp Val Pro Thr Ala Thr Ser Val Arg Ala Val Pro Ala
        130                 135                 140

Lys Leu Met Ile Asp Asn Arg Thr Val Ile Asn Asn Gln Leu Lys Arg
145                 150                 155                 160

Asn Arg Gly Gly Lys Ile Ser Phe Thr His Leu Leu Gly Tyr Ala Leu
                165                 170                 175

Val Gln Ala Val Lys Lys Phe Pro Asn Ile Asn Arg His Tyr Ala Glu
```

```
              180                 185                 190
Ile Asp Gly Lys Pro Ile Ala Val Thr Pro Ala His Thr Asn Leu Gly
            195                 200                 205
Leu Ala Ile Asp Leu Gln Gly Lys Asp Gly Lys Arg Ser Leu Val Val
210                 215                 220
Ala Gly Ile Lys Arg Cys Glu Glu Leu Arg Phe Ala Gln Phe Val Thr
225                 230                 235                 240
Ala Tyr Glu Asp Ile Val Arg Ala Arg Asp Gly Lys Leu Thr Ala
                245                 250                 255
Glu Asp Phe Ala Gly Val Thr Ile Ser Leu Thr Asn Pro Gly Thr Ile
                260                 265                 270
Gly Thr Val His Ser Val Pro Arg Leu Met Thr Gly Gln Gly Ala Ile
            275                 280                 285
Ile Gly Val Gly Ala Met Glu Tyr Pro Ala Glu Phe Gln Gly Ala Ser
            290                 295                 300
Ala Glu Arg Ile Ala Glu Leu Gly Ile Gly Lys Leu Ile Thr Leu Thr
305                 310                 315                 320
Ser Thr Tyr Asp His Arg Ile Ile Gln Gly Ala Glu Ser Gly Asp Phe
                325                 330                 335
Leu Arg Thr Ile His Glu Met Val Leu Ser Asp Ser Phe Trp Asp Glu
                340                 345                 350
Ile Phe Arg Glu Leu Ser Ile Pro Tyr Leu Pro Val Arg Trp Arg Thr
            355                 360                 365
Asp Asn Pro Asp Ser Ile Val Asp Lys Asn Ala Arg Val Met Glu Leu
            370                 375                 380
Ile Ala Ala Tyr Arg Asn Arg Gly His Leu Met Ala Asp Ile Asp Pro
385                 390                 395                 400
Leu Arg Leu Asp Asn Thr Arg Phe Arg Ser His Pro Asp Leu Asp Leu
                405                 410                 415
Leu Thr His Gly Leu Thr Leu Trp Asp Leu Asp Arg Val Phe Lys Val
            420                 425                 430
Asn Gly Phe Gly Gly Trp Lys Tyr Lys Lys Leu Arg Asp Val Leu Gly
            435                 440                 445
Leu Leu Arg Asp Ala Tyr Cys Arg His Ile Gly Val Glu Tyr Thr His
            450                 455                 460
Ile Leu Asp Pro Glu Gln Gln Glu Trp Leu Gln Gln Arg Val Glu Thr
465                 470                 475                 480
Lys Asn Val Lys Pro Thr Val Ala Glu Gln Lys Tyr Ile Leu Ser Lys
                485                 490                 495
Leu Asn Ala Ala Glu Ala Phe Glu Thr Phe Leu His Thr Lys Tyr Val
            500                 505                 510
Gly Gln Lys Arg Phe Ser Leu Glu Gly Ala Glu Ser Val Ile Pro Met
            515                 520                 525
Met Asp Ala Ala Ile Asp Gln Cys Ala Lys His Gly Leu Asp Glu Val
            530                 535                 540
Val Ile Gly Met Pro His Arg Gly Arg Leu Asn Val Leu Ala Asn Ile
545                 550                 555                 560
Val Gly Lys Pro Tyr Ser Gln Ile Phe Thr Glu Phe Glu Gly Asn Leu
                565                 570                 575
Asn Pro Thr Leu Ala His Ser Ser Gly Asp Val Lys Tyr His Leu Gly
            580                 585                 590
Ala Thr Gly Leu Tyr Leu Gln Met Phe Gly Asp Asn Asp Ile Gln Val
            595                 600                 605
```

```
Ser Leu Thr Ala Asn Pro Ser His Leu Glu Ala Val Asp Pro Val Leu
    610                 615                 620

Glu Gly Leu Val Arg Ala Lys Gln Asp Leu Leu Asn Lys Asp Thr Asn
625                 630                 635                 640

Gly Asn Gln Asp Glu Ala Phe Ser Val Val Pro Met Met Leu His Gly
                645                 650                 655

Asp Ala Ala Phe Ala Gly Gln Gly Val Val Ala Glu Thr Leu Asn Leu
                660                 665                 670

Ala Asn Leu Pro Gly Tyr Arg Val Gly Gly Thr Ile His Ile Ile Val
        675                 680                 685

Asn Asn Gln Ile Gly Phe Thr Thr Ala Pro Glu Tyr Ser Arg Ser Ser
    690                 695                 700

Glu Tyr Cys Thr Asp Val Ala Lys Met Ile Gly Ala Pro Ile Phe His
705                 710                 715                 720

Val Asn Gly Asp Asp Pro Glu Ala Cys Val Trp Val Ala Lys Leu Ala
                725                 730                 735

Val Asp Phe Arg Gln Arg Phe Lys Lys Asp Val Val Ile Asp Met Leu
                740                 745                 750

Cys Tyr Arg Arg Arg Gly His Asn Glu Gly Asp Asp Pro Ser Met Thr
        755                 760                 765

Asn Pro Tyr Met Tyr Asp Val Val Asp Thr Lys Arg Gly Ala Arg Lys
    770                 775                 780

Ser Tyr Thr Glu Ala Leu Ile Gly Arg Gly Asp Ile Ser Leu Lys Glu
785                 790                 795                 800

Ala Glu Asp Ala Leu Arg Asp Tyr Gln Gly Gln Leu Glu Arg Val Phe
                805                 810                 815

Asn Glu Val Arg Asp Leu Glu Lys His Gly Val Gln Pro Ser Glu Ser
                820                 825                 830

Val Glu Ser Asp Gln Met Ile Pro Ala Gly Leu Ser Thr Ala Val Asp
        835                 840                 845

Lys Ala Leu Leu Ala Arg Ile Gly Asp Ala Phe Leu Ala Val Pro Glu
    850                 855                 860

Gly Phe Thr Val His Pro Arg Val Gln Pro Val Leu Glu Lys Arg Arg
865                 870                 875                 880

Glu Met Ala Tyr Glu Gly Lys Ile Asp Trp Ala Phe Ala Glu Leu Leu
                885                 890                 895

Ala Leu Gly Ser Leu Val Ala Glu Gly Lys Leu Val Arg Leu Ser Gly
                900                 905                 910

Gln Asp Thr Lys Arg Gly Thr Phe Ser Gln Arg His Ser Val Ile Ile
        915                 920                 925

Asp Arg His Thr Gly Glu Glu Phe Thr Pro Leu Gln Leu Leu Ala Asn
    930                 935                 940

Asn Pro Asp Gly Ser Pro Thr Gly Gly Lys Phe Leu Val Tyr Asn Ser
945                 950                 955                 960

Pro Leu Ser Glu Tyr Ala Ala Val Gly Phe Glu Tyr Gly Tyr Thr Val
                965                 970                 975

Gly Asn Pro Asp Ala Val Val Leu Trp Glu Ala Gln Phe Gly Asp Phe
                980                 985                 990

Val Asn Gly Ala Gln Ser Ile Ile Asp Glu Phe Ile Asn Ser Gly Glu
        995                 1000                1005

Ala Lys Trp Gly Gln Leu Ser Thr Val Val Leu Leu Leu Pro His Gly
    1010                1015                1020
```

His Glu Gly Gln Gly Pro Asp His Thr Ser Gly Arg Ile Glu Arg Phe
1025                1030                1035                1040

Leu Gln Leu Trp Ala Glu Gly Ser Met Thr Phe Ala Val Pro Ser Thr
            1045                1050                1055

Pro Ser Asn Tyr Phe His Leu Leu Arg Arg His Ala Leu Asp Gly Ile
        1060                1065                1070

Lys Arg Pro Leu Ile Val Phe Thr Pro Lys Ser Met Leu Arg Asn Lys
    1075                1080                1085

Ala Ala Val Ser Asp Ile Lys Asp Phe Thr Glu Ile Lys Phe Arg Ser
        1090                1095                1100

Val Leu Glu Glu Pro Thr Tyr Glu Asp Ser Ile Asp Asp Arg Ser Lys
1105                1110                1115                1120

Val Thr Arg Val Leu Leu Thr Cys Gly Lys Leu Tyr Tyr Glu Leu Ala
            1125                1130                1135

Ala Arg Lys Ile Lys Asp Asn Arg Asp Asp Val Ala Ile Val Arg Ile
        1140                1145                1150

Glu Gln Leu Ala Pro Leu Pro Arg Arg Arg Leu Gly Glu Thr Leu Asp
            1155                1160                1165

Arg Tyr Glu Asn Ala Lys Glu Phe Phe Trp Val Gln Glu Pro Ala
1170                1175                1180

Asn Gln Gly Ala Trp Pro Arg Phe Gly Leu Glu Leu Pro Glu Leu Leu
1185                1190                1195                1200

Pro Arg Leu Thr Gly Ile Lys Arg Ile Ser Arg Arg Ala Met Ser Ala
            1205                1210                1215

Pro Ser Ser Gly Ser Ser Lys Val His Ala Val Glu Gln Gln Glu Ile
            1220                1225                1230

Leu Asp Thr Ala Phe Gly
        1235

<210> SEQ ID NO 34
<211> LENGTH: 548
<212> TYPE: PRT
<213> ORGANISM: Lactococcus lactis

<400> SEQUENCE: 34

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

```
Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
                210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 35
<211> LENGTH: 635
```

<212> TYPE: PRT
<213> ORGANISM: Saccharomyces cerevisiae

<400> SEQUENCE: 35

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
    210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
    290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
    370                 375                 380

Lys Arg Ile Asp Val Ser Lys Leu Ser Leu Gln Tyr Asp Ser Asn Val
385                 390                 395                 400

-continued

```
Thr Gln Tyr Thr Asn Glu Thr Met Arg Leu Glu Asp Pro Thr Asn Gly
                405                 410                 415

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
        435                 440                 445

Phe Ser Val Arg Asp Phe Ala Phe Pro Ser Gln Leu Lys Tyr Ile Ser
    450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
        515                 520                 525

Asn Ile Pro Leu Glu Val Ile Ile Trp Asn Asn Gly Tyr Thr Ile
    530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Glu Leu Asp Phe Pro Gln Leu Lys Cys Met
    610                 615                 620

Val Glu Ala Ala Ala Leu Lys Arg Asn Lys Lys
625                 630                 635

<210> SEQ ID NO 36
<211> LENGTH: 503
<212> TYPE: PRT
<213> ORGANISM: Sulfolobus solfataricus

<400> SEQUENCE: 36

Met Lys Val Gly Asn Ala Leu Phe Lys Leu Met Ser Glu Leu Gly Ile
1               5                   10                  15

Arg Gln Val Phe Gly Asn Pro Gly Thr Thr Glu Leu Ser Phe Leu Lys
            20                  25                  30

His Met Pro Lys Asp Phe Asn Tyr Tyr Leu Ala Leu His Asp Gly Ile
        35                  40                  45

Ser Val Gly Met Ala Glu Gly Tyr Tyr Phe Ala Thr Arg Lys Pro Gln
    50                  55                  60

Ile Val Asn Leu His Ser Ser Pro Gly Leu Thr Asn Ala Met Gly Phe
65                  70                  75                  80

Ile Tyr Glu Ala Leu Ile Ser Arg Ile Pro Leu Ile Val Leu Val Gly
                85                  90                  95

Gln Gln Tyr Leu Tyr Arg Leu Ile Asp Glu Pro Val Leu Tyr Gly Asp
            100                 105                 110

Phe Ile Lys Ile Ser Gln Gly Val Val Lys Ser Ala Tyr Glu Ile Arg
        115                 120                 125

Ser Glu Lys Asp Ala Ile Lys Thr Phe Ile Arg Ala Tyr Lys Glu Ser
```

```
            130                 135                 140
Ile Thr Pro Pro Tyr Gly Pro Val Leu Ile Ser Leu Pro Gln Asp Ile
145                 150                 155                 160

Pro Asp Met Glu Val Ser Glu Gly Lys Val Asp Ile Pro Lys Tyr
                165                 170                 175

Phe Val Ser Gly Thr Cys Asp Thr Ser Ala Ile Glu Phe Val Leu Asp
                180                 185                 190

Lys Val Lys Ser Ala Ser Ser Ile Ala Ile Val Ala Gly Tyr Glu Val
                195                 200                 205

Ser Ile Phe Ser Ala His Glu Glu Leu Val Arg Leu Ala Glu Lys Leu
            210                 215                 220

Asn Ala Pro Ile Tyr Thr Glu Pro Tyr Leu Ser Ile Phe Pro Ile Asp
225                 230                 235                 240

Ser Ser Asn Ile Leu Phe Lys Gly Pro Leu Ser Arg Tyr Lys Ala Ser
                245                 250                 255

Asp Val Val Lys Glu Leu Glu Lys Tyr Asp Leu Val Leu Val Ile Gly
                260                 265                 270

Gly Trp Leu Asn Tyr Val Val Phe Pro Asp Val Asp Ile Arg Leu Asn
            275                 280                 285

Ile Val Glu Val Thr Ser Asp Phe Lys Glu Ala Ser Lys Arg Lys Trp
290                 295                 300

Asp Thr Ile Val Cys Asn Pro Lys Asp Phe Leu Ile Lys Leu Tyr Asn
305                 310                 315                 320

Met Leu Tyr Lys Gly Leu Asn Lys Asn Ile Ile Lys Arg Glu Asn Arg
                325                 330                 335

Asp Leu Glu Leu Gln Gly Asp Phe Ile Thr Glu Val Phe Lys Glu Met
                340                 345                 350

Lys Gly Tyr Leu Asp Lys Tyr Thr Ile Phe Ala Glu Ile Pro Thr Tyr
                355                 360                 365

Arg Asp Thr Leu Ile Lys Ile Ile Glu Leu Lys Pro Ser Ser Leu Tyr
            370                 375                 380

Ile Thr Arg Ser Gly Leu Leu Gly Trp Ala Leu Ser Ala Leu Val Gly
385                 390                 395                 400

Tyr Ser Ile Asn Gly Ala Lys Val Leu Ala Ile Ile Gly Asp Gly Ser
                405                 410                 415

Phe Asn Tyr Thr Pro Gln Ala Leu Trp Ser Ala Val Lys Tyr Ser Thr
                420                 425                 430

Arg Leu Lys Val Ile Val Asn Asn Glu Gly Tyr Ala Ser Leu Ser
            435                 440                 445

Arg His Gly Val Glu Ala Asp Trp Leu Phe Pro Ser Thr Ser Pro Trp
        450                 455                 460

Lys Val Ala Leu Ala Tyr Gly Phe Glu Ala Lys Glu Ser Arg Asp Ile
465                 470                 475                 480

Lys Asn Asp Leu Lys Trp Leu Phe Glu Asp Asp Lys Arg Lys Leu Leu
                485                 490                 495

Glu Ile Arg Leu Ala Arg His
            500

<210> SEQ ID NO 37
<211> LENGTH: 559
<212> TYPE: PRT
<213> ORGANISM: Pseudomonas aeruginosa

<400> SEQUENCE: 37
```

```
Met Gly Ala Arg Ala Leu Arg Arg Glu Arg Leu Arg Trp Ser Pro
 1               5                  10                  15

Asn Trp Thr Arg Ile Leu Pro Met Gln Pro Gln Lys Thr Leu Thr Ala
             20                  25                  30

Gly Gln Ala Leu Val Arg Leu Leu Ala Asn Tyr Gly Val Asp Thr Val
         35                  40                  45

Phe Gly Ile Pro Gly Val His Thr Leu Glu Leu Tyr Arg Gly Leu Pro
     50                  55                  60

Gly Ser Gly Ile Arg His Val Leu Thr Arg His Glu Gln Gly Ala Gly
65                  70                  75                  80

Phe Met Ala Asp Gly Tyr Ala Arg Val Ser Gly Lys Pro Gly Val Cys
                 85                  90                  95

Phe Val Ile Thr Gly Pro Gly Val Thr Asn Val Ala Thr Ala Ile Gly
             100                 105                 110

Gln Ala Tyr Ala Asp Ser Val Pro Leu Leu Val Ile Ser Ser Val Asn
         115                 120                 125

His Ser Ala Ser Leu Gly Lys Gly Trp Gly Cys Leu His Glu Thr Gln
130                 135                 140

Asp Gln Arg Ala Met Thr Ala Pro Ile Thr Ala Phe Ser Ala Leu Ala
145                 150                 155                 160

Leu Ser Pro Glu Gln Leu Pro Glu Leu Ile Ala Arg Ala Tyr Ala Val
                 165                 170                 175

Phe Asp Ser Glu Arg Pro Arg Pro Val His Ile Ser Ile Pro Leu Asp
             180                 185                 190

Val Leu Ala Ala Pro Val Ala His Asp Trp Ser Ala Ala Val Ala Arg
         195                 200                 205

Arg Pro Gly Arg Gly Val Pro Cys Thr Glu Ala Leu Arg Ala Ala Ala
210                 215                 220

Glu Arg Leu Ala Ala Ala Arg Arg Pro Met Leu Ile Ala Gly Gly Gly
225                 230                 235                 240

Ala Leu Ala Ala Gly Asp Ala Leu Ala Ala Leu Ser Glu Arg Leu Ala
                 245                 250                 255

Ala Pro Leu Phe Thr Ser Val Ala Gly Lys Gly Leu Leu Pro Pro Asp
             260                 265                 270

Ala Pro Leu Asn Ala Gly Ala Ser Leu Cys Val Ala Pro Gly Trp Glu
         275                 280                 285

Met Ile Ala Glu Ala Asp Leu Val Leu Ala Val Gly Thr Glu Met Ala
290                 295                 300

Asp Thr Asp Phe Trp Arg Glu Arg Leu Pro Leu Ser Gly Glu Leu Ile
305                 310                 315                 320

Arg Val Asp Ile Asp Pro Arg Lys Phe Asn Asp Phe Tyr Pro Ser Ala
                 325                 330                 335

Val Ala Leu Arg Gly Asp Ala Arg Gln Thr Leu Glu Ala Leu Leu Ala
             340                 345                 350

Arg Leu Pro Gln Glu Ala Arg Asp Ala Pro Ala Ala Ala Arg Val
         355                 360                 365

Ala Arg Leu Arg Ala Glu Ile Arg Ala Ala His Ala Pro Leu Gln Ala
370                 375                 380

Leu His Gln Ala Ile Leu Asp Arg Ile Ala Ala Ala Leu Pro Ala Asp
385                 390                 395                 400

Ala Phe Val Ser Thr Asp Met Thr Gln Leu Ala Tyr Thr Gly Asn Tyr
                 405                 410                 415

Ala Phe Ala Ser Arg Ala Pro Arg Ser Trp Leu His Pro Thr Gly Tyr
```

-continued

```
            420                 425                 430

Gly Thr Leu Gly Tyr Gly Leu Pro Ala Gly Ile Gly Ala Lys Leu Gly
        435                 440                 445

Ala Pro Gln Arg Pro Gly Leu Val Leu Val Gly Asp Gly Gly Phe Leu
    450                 455                 460

Tyr Thr Ala Gln Glu Leu Ala Thr Ala Ser Glu Glu Leu Asp Ser Pro
465                 470                 475                 480

Leu Val Val Leu Leu Trp Asn Asn Asp Ala Leu Gly Gln Ile Arg Asp
                485                 490                 495

Asp Met Leu Gly Leu Asp Ile Glu Pro Val Gly Val Leu Pro Arg Asn
            500                 505                 510

Pro Asp Phe Ala Leu Leu Gly Arg Ala Tyr Gly Cys Ala Val Arg Gln
        515                 520                 525

Pro Gln Asp Leu Asn Glu Leu Glu Arg Asp Leu Arg Ala Gly Phe Gly
    530                 535                 540

Gln Pro Gly Val Thr Leu Ile Glu Leu Arg His Ala Cys Ala Arg
545                 550                 555

<210> SEQ ID NO 38
<211> LENGTH: 384
<212> TYPE: PRT
<213> ORGANISM: Erwinia carotovora subsp. atroseptica

<400> SEQUENCE: 38

Met Ile Asp Pro Asn Lys Leu Ile Glu Phe Leu Ala Gln Arg Gly Val
 1               5                  10                  15

Arg Phe Phe Ser Gly Val Pro Asp Ser Leu Leu Lys Ala Phe Cys Leu
            20                  25                  30

Ala Ile Gly Ser Asn Asn Gly Gly Leu Ala His Arg Ile Ala Ser Asn
        35                  40                  45

Glu Gly Cys Ala Val Gly Met Ala Ile Gly His Tyr Leu Ser Thr Arg
    50                  55                  60

Thr Leu Pro Val Val Tyr Met Gln Asn Ser Gly Leu Gly Asn Ala Ile
65                  70                  75                  80

Asn Pro Leu Cys Ser Leu Ala Thr Pro Asp Val Tyr Gly Ile Pro Leu
                85                  90                  95

Leu Leu Ile Ile Gly Trp Arg Gly Glu Val Asp Asp Ser Gly Lys Gln
            100                 105                 110

Gln His Asp Glu Pro Gln His Val Met Gln Gly Arg Val Thr Leu Pro
        115                 120                 125

Gln Leu Asn Val Leu Asp Val Pro His Ile Val Leu Asp Ser His Asn
    130                 135                 140

Arg Pro Pro Trp Asp Asp Ile Gln Ala Leu Leu Gln Arg Ala His Asp
145                 150                 155                 160

Glu His Arg Pro Val Ala Leu Val Val Arg Lys Asn Thr Phe Ser Ser
                165                 170                 175

Pro Val Ala Pro Ala Asn Pro Ala Thr Glu Pro Ala Leu Met Arg Arg
            180                 185                 190

Glu Ala Ile Val Ala Ala Cys Leu Asn Val Leu Pro Ser Thr Ile Pro
        195                 200                 205

Ile Val Ser Thr Thr Gly Met Leu Ser Arg Glu Leu Tyr Glu Leu Arg
    210                 215                 220

Glu Gln Arg Gly Glu Gly His Gln Arg Asp Phe Leu Thr Val Gly Gly
225                 230                 235                 240
```

```
Met Gly Leu Ala Ser Gln Ile Ala Leu Gly Leu Cys Asp Ala Gln Pro
            245                 250                 255

Gln Arg Lys Val Val Cys Leu Asp Gly Asp Gly Ala Leu Leu Met His
        260                 265                 270

Met Gly Gly Leu Thr Asn Thr Ala Gln Ala Ser Asn Leu Ile His Ile
            275                 280                 285

Val Ile Asn Asn Gly Ala His Asp Ser Val Gly Gly Gln Pro Thr Val
        290                 295                 300

Ala Ser His Leu Pro Leu Ala Pro Ile Ala Ala Ser Gly Tyr Gly
305                 310                 315                 320

Lys Thr Tyr Tyr Ala Glu Thr Glu Ala Leu Gln Ala Ala Leu Gln
                325                 330                 335

Gln Ala Leu Gln Ala Gln Ser Ser Gln Phe Ile Glu Val Gln Cys Arg
        340                 345                 350

Val Gly His Arg Ser Asp Leu Gly Arg Pro Ala Thr Ser Pro Ala Glu
        355                 360                 365

Asn Arg Asp Ala Phe Met Gln Phe Leu Asn Thr Thr Pro Lys Ala Ser
        370                 375                 380

<210> SEQ ID NO 39
<211> LENGTH: 563
<212> TYPE: PRT
<213> ORGANISM: Saccharomyces cerevisiae

<400> SEQUENCE: 39

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240
```

```
Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 40
<211> LENGTH: 549
<212> TYPE: PRT
<213> ORGANISM: Pantoea ananatis

<400> SEQUENCE: 40

Met Ser Asp Phe Thr Val Gly Asp Tyr Leu Leu Ala Arg Leu Gln Glu
1               5                   10                  15

Cys Gly Val Arg His Leu Phe Gly Val Pro Gly Asp Tyr Asn Leu Gln
            20                  25                  30

Phe Leu Asp Arg Val Ile Ala His Pro Asp Ile Gly Trp Val Gly Cys
        35                  40                  45
```

-continued

```
Ala Asn Glu Leu Asn Ala Ala Tyr Ala Ala Asp Gly Tyr Ala Arg Cys
     50                  55                  60

Thr Gly Ala Ala Ala Leu Leu Thr Thr Phe Gly Val Gly Glu Leu Ser
 65                  70                  75                  80

Ala Ile Asn Gly Leu Ala Gly Ser Phe Ala Glu Tyr Leu Pro Val Ile
                 85                  90                  95

His Ile Val Gly Ala Pro Ser Ser Gln Ala Met Gln Gln Gly Asp Cys
             100                 105                 110

Val His His Thr Leu Gly Asp Gly Asp Phe Gly His Phe Ile Arg Met
         115                 120                 125

Ala Lys Glu Val Ser Ala Ala Thr Ala Ala Leu Thr Ala Asp Asn Ala
     130                 135                 140

Thr Ala Glu Ile Asp Arg Val Ile Leu Thr Ala Leu Gln Gln His Arg
145                 150                 155                 160

Pro Gly Tyr Leu Met Leu Pro Val Asp Val Ala Gln Arg Gln Thr Ser
                165                 170                 175

Ala Pro Asp Gln Pro Leu Met Pro Thr Thr Ala Ser Ser Asp Glu Val
            180                 185                 190

Arg Ile Ala Phe Gln Gln Ala Ala Glu Arg Leu Leu Ala Pro Ala Lys
        195                 200                 205

Arg Val Ser Leu Leu Ala Asp Phe Leu Ala Gln Arg Trp Gln Gln Gln
    210                 215                 220

Pro Ala Leu Ala Ala Leu Arg Thr Gly Arg Ala Phe Pro Cys Ala Thr
225                 230                 235                 240

Leu Leu Met Gly Lys Gly Val Leu Asp Glu Gln Pro Gly Phe Val
                245                 250                 255

Gly Thr Tyr Ala Gly Glu Gly Ser Glu Gly Asp Val Arg Gln Gln Ile
                260                 265                 270

Glu Glu Val Asp Val Thr Ile Cys Ala Gly Val Arg Phe Thr Asp Thr
            275                 280                 285

Ile Thr Ala Gly Phe Thr Gln Gln Phe Ser Gln Ala Arg Leu Ile Asp
        290                 295                 300

Ile Gln Pro His Ser Ala Ser Val Ala Gly Gln Thr Phe Ala Pro Leu
305                 310                 315                 320

Ser Met Ala Glu Ala Leu Gln Ala Leu Leu Pro Val Phe Glu Arg Leu
                325                 330                 335

Gly Ala Gly Trp Gln Ala Ala Cys Ala Pro Arg Ala Ala Glu Pro Val
                340                 345                 350

Pro Asp Ala Ala Leu Ile Ser Gln Ser Ala Phe Trp Gln Ala Met Gln
            355                 360                 365

Gly Phe Leu Gln Pro Gly Asp Ile Ile Leu Ala Asp Gln Gly Thr Ala
        370                 375                 380

Ala Phe Gly Ala Ala Ser Leu Arg Leu Pro Val Gly Ala Gln Leu Leu
385                 390                 395                 400

Val Gln Pro Leu Trp Gly Ser Ile Gly Tyr Thr Leu Pro Ala Ala Phe
                405                 410                 415

Gly Ala Gln Thr Ala Arg Pro Gly Gln Arg Val Ile Leu Ile Ile Gly
                420                 425                 430

Asp Gly Ser Ala Gln Leu Thr Ile Gln Glu Leu Gly Ser Met Leu Arg
            435                 440                 445

Asp Gln Gln His Pro Leu Ile Phe Leu Leu Asn Asn Glu Gly Tyr Thr
450                 455                 460
```

```
Val Glu Arg Ala Ile His Gly Ala Ala Gln Arg Tyr Asn Asp Ile Ala
465                 470                 475                 480

Gln Trp Asn Trp Thr Ala Leu Pro Gln Ala Met Ser Leu Glu Cys Gln
                485                 490                 495

Ala Gln Ser Trp Arg Ile Ser Glu Thr Val Gln Leu Gln Ala Leu Met
            500                 505                 510

Ala Gln Leu Thr Gln Gln Arg Arg Leu Ser Phe Ile Glu Val Val Met
        515                 520                 525

Gln Lys Asp Asp Leu Pro Pro Leu Leu Arg Lys Val Ser Ala Cys Leu
    530                 535                 540

Ser Gln Arg Asn Gly
545
```

<210> SEQ ID NO 41
<211> LENGTH: 169
<212> TYPE: PRT
<213> ORGANISM: Methanocella paludicola

<400> SEQUENCE: 41

```
Met Arg Gly Ser Leu Ala Ile Tyr Asn Ala Leu Lys Asp Ser Asn Ile
1               5                   10                  15

Asp Phe Ile Cys Ser Val Pro Cys Ala Asn Leu Lys Asn Leu Leu Lys
            20                  25                  30

Leu Ile Glu Glu Asp Lys Asn Ile Ile Asn Ile Pro Ala Thr Arg Glu
        35                  40                  45

Glu Glu Ala Phe Gly Ile Cys Ala Gly Ala Tyr Leu Ala Gly Lys Lys
    50                  55                  60

Thr Ala Ile Leu Met Gln Asn Ser Gly Ile Gly Asn Ser Ile Asn Ala
65                  70                  75                  80

Ile Ala Ser Leu Tyr Lys Thr Phe Gln Ile Pro Thr Leu Leu Ile Ile
                85                  90                  95

Ser His Arg Gly Asp Leu Lys Glu Gln Ile Pro Ala Gln Ile Pro Met
            100                 105                 110

Gly Arg Trp Ile Glu Lys Leu Leu Asp Val Cys Glu Ile Pro Thr Tyr
        115                 120                 125

Lys Pro Lys Thr Pro Glu Glu Ala Tyr Lys Leu Ile Lys Tyr Ala Ser
    130                 135                 140

Ser Tyr Met Tyr Lys Ile Ser Tyr Pro Val Ala Leu Leu Phe Asp Ala
145                 150                 155                 160

Leu Tyr Trp Glu Tyr Asp Leu Glu Lys
                165
```

<210> SEQ ID NO 42
<211> LENGTH: 188
<212> TYPE: PRT
<213> ORGANISM: Methanocella paludicola

<400> SEQUENCE: 42

```
Met Tyr Pro Lys Arg Ile Asp Ile Ile Lys Lys Ile Val Glu Asn Val
1               5                   10                  15

Gly Glu Lys Glu Ile Ile Val Ser Asn Ile Gly Ile Pro Ser Lys Glu
            20                  25                  30

Leu Tyr Tyr Val Lys Asp Arg Glu Arg Asn Phe Tyr Met Leu Gly Ser
        35                  40                  45

Met Gly Leu Ala Ser Ser Ile Gly Leu Gly Leu Ala Leu Asn Cys Glu
    50                  55                  60
```

```
Asp Lys Val Ile Val Ile Asp Gly Asp Gly Ser Ile Leu Met Asn Leu
 65                  70                  75                  80

Gly Ser Leu Ser Thr Ile Gly Tyr Met Asn Pro Lys Asn Tyr Ile Leu
                 85                  90                  95

Val Ile Ile Asp Asn Ser Ala Tyr Gly Ser Thr Gly Asn Gln Lys Thr
            100                 105                 110

His Thr Gly Lys Asn Thr Asn Leu Glu Glu Ile Ala Lys Gly Cys Gly
        115                 120                 125

Leu Asp Thr Ile Thr Thr Glu Ser Leu Glu Glu Phe Glu Lys Glu Phe
    130                 135                 140

Lys Asn Ala Leu Asn Glu Glu Lys Cys Lys Val Ile Ile Ala Lys Thr
145                 150                 155                 160

Ile Pro Tyr Asn Glu Lys Cys Ser Asn Ile Glu Ile Pro Pro Val Val
                165                 170                 175

Leu Lys Tyr Arg Phe Met Glu Ala Ile Lys Arg Ser
            180                 185
```

<210> SEQ ID NO 43
<211> LENGTH: 554
<212> TYPE: PRT
<213> ORGANISM: Lactococcus lactis

<400> SEQUENCE: 43

```
Met Ser Glu Lys Gln Phe Gly Ala Asn Leu Val Val Asp Ser Leu Ile
  1               5                  10                  15

Asn His Lys Val Lys Tyr Val Phe Gly Ile Pro Gly Ala Lys Ile Asp
                 20                  25                  30

Arg Val Phe Asp Leu Leu Glu Asn Glu Glu Gly Pro Gln Met Val Val
             35                  40                  45

Thr Arg His Glu Gln Gly Ala Ala Phe Met Ala Gln Ala Val Gly Arg
         50                  55                  60

Leu Thr Gly Glu Pro Gly Val Val Val Thr Ser Gly Pro Gly Val
 65                  70                  75                  80

Ser Asn Leu Ala Thr Pro Leu Leu Thr Ala Thr Ser Glu Gly Asp Ala
                 85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
    130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Ala Lys Val Ala Ser Ser Leu Arg Asn
    210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255
```

-continued

```
Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
        275                 280                 285

Asn Ala Glu Ile Asp Ser Arg Ile Ile Val Ile Asp Asn Ala Ile Ala
        290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
            355                 360                 365

Leu Asp Leu Val Ser Thr Phe Gln Glu Ile Val Lys Asp Asp Glu Thr
        370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
                420                 425                 430

Gly Lys Lys Val Tyr Ser His Ser Gly Asp Gly Gly Phe Leu Phe Thr
            435                 440                 445

Gly Gln Glu Leu Glu Thr Ala Val Arg Leu Asn Leu Pro Ile Val Gln
    450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                485                 490                 495

Val Lys Tyr Ala Glu Ala Met Arg Ala Lys Gly Tyr Arg Ala His Ser
            500                 505                 510

Lys Glu Glu Leu Ala Glu Ile Leu Lys Ser Ile Pro Asp Thr Thr Gly
            515                 520                 525

Pro Val Val Ile Asp Val Pro Leu Asp Tyr Ser Asp Asn Ile Lys Leu
            530                 535                 540

Ala Glu Lys Leu Leu Pro Glu Glu Phe Tyr
545                 550
```

US 9,650,653 B2

BIOCONVERSION PROCESS FOR PRODUCING NYLON-7, NYLON-7,7 AND POLYESTERS

CROSS-REFERENCE TO RELATED APPLICATIONS

This application claims the benefit of U.S. Provisional Appl. Ser. No. 61/503,043, filed Jun. 30, 2011, and U.S. Provisional Appl. Ser. Nos. 61/578,265; 61/578,272; and 61/578,289, all of which were filed Dec. 21, 2011, the entireties of all of which are incorporated by reference as if fully set forth herein.

FIELD OF THE INVENTION

Embodiments of the present invention relate to methods for the biosynthetic production of di- or trifunctional C7 alkanes in the presence of one or more isolated enzymes or in the presence of a recombinant host cell expressing one or more enzymes. The di- or trifunctional C7 alkanes are useful as intermediates in the production, for example, of nylon-7, nylon-7,x and/or nylon-x,7.

BACKGROUND OF THE INVENTION

The promotion of sustainable practices by the chemical industry is focused on lowering energy usage, recycling raw materials, and reducing by-products produced during the production of goods. However, the chemical industry vitally depends upon petroleum and natural gas as basic feedstocks. Given the state of optimization associated with major petrochemical processes, a significant shift in feedstock use and manufacturing designs will be required to lower energy, emissions, and costs to below their current level. Biotechnology offers a new approach for the production of industrial chemical intermediates and end-products from renewable carbohydrates, such as plant derived sugars, or other renewable feedstocks such as fatty acids. In addition, biotechnology also offers a way to utilize waste or low value streams such as glycerol from biodiesel production, or to transform petrochemical-derived feedstocks such as benzene, toluene, and polycyclic aromatic hydrocarbons (PAHs) to useful products in bioprocesses that are more benign to the environment than existing chemical processes.

US2010/0203600 and WO2011/031147 are incorporated by reference in their entirety. There is a need in the art for cost-effective biosynthetic routes to chemical intermediates to nylon-7, nylon-7,x nylon-x,7, and polyesters and the end-products nylon-7, nylon-7,x nylon-x,7, and polyesters especially from a variety renewable and non-renewable feedstocks.

SUMMARY OF THE INVENTION

This disclosure is based at least in part of the development of enzymatic systems and recombinant hosts for biosynthesizing di- or trifunctional C7 alkanes that are useful intermediates (monomers) for producing nylon-7, nylon-x,7, nylon-7,x, and polyesters. In particular, as described herein, intermediates useful in the production of nylon-7, and nylon-7,x, nylon-x,7, and polyesters can be biosynthetically produced from renewable feedstocks, such as plant-derived sugars and glycerol, or from petrochemical-derived feedstocks such as benzene or cyclohexane carboxylate. In some embodiments, production of the di- or trifunctional C7 alkanes ultimately proceeds through a common intermediate, pimelic acid semialdehyde (also known as 7-oxoheptanoate), even though there are a number of different feedstocks that can be used and a number of ways to produce pimelic acid semialdehyde. FIG. 1 is a schematic depicting the biotransformation of pimelic acid semialdehyde to various difunctional C7 alkanes.

For example, pimelic acid semialdehyde can be derived from pimeloyl-coenzyme A (CoA), pimeloyl-[acyl carrier protein (acp)], pimelic acid (also known as heptane 1,7-dioate), or α-ketosuberate. As described herein, pimeloyl-CoA and pimeloyl-[acp] can be derived from a number of sources, including from a diverse number of naturally occurring metabolic pathways that form pimeloyl-CoA or pimeloyl-[acp] as an intermediate in the naturally occurring metabolic pathway.

In addition, pimeloyl-CoA and pimelic acid also can be derived from the corresponding enoate 2-heptene-dioic acid or its corresponding CoA ester. In some embodiments, these C7 2-enoates are derived from D,L-diaminopimelate. In some embodiments, the production of difunctional C7 alkanes (e.g., 7 amino heptanoic acid) proceeds through α-ketosuberate or α-aminosuberate, which can be derived from D,L-diaminopimelate. In other embodiments, the α-ketosuberate or α-aminosuberate is derived from α-ketopimelate.

More specifically, the present document provides a variety of methods of converting compounds in order to produce intermediates useful for the manufacture of nylon-7, nylon-7,7, and polyester. It is not required that at all possible steps of any one method be performed and any of the methods can be terminated when a desired compound is obtained. Thus, any method can be terminated after the production of, for example, pimelic acid, 7-amino-heptanoic acid, enantholactam, 1,7-diaminoheptane, or 7-hydroxy-heptanoic acid.

A first method of converting a compound can include contacting a compound selected from 2,6 diaminopimelate (2,6 DAP) and α-amino-pimelate (AAP) with an enzyme that catalyzes the reductive deamination of 2,6 DAP to 6-amino-2-heptenedioic acid (6A2HA) or the reductive deamination of AAP to 2-heptene dioic acid (2 HDA), such that 6A2HA or 2 HDA is produced.

The compound can be 2,6 DAP and the first method can further involve contacting the 6A2HA with an enzyme that catalyzes the enoate reduction of the 6A2HA to AAP, such that AAP is produced.

The AAP can be contacted with an enzyme that catalyzes the reductive deamination of the AAP to 2 HDA, such that 2 HDA is produced.

The 2 HDA can be contacted with an enzyme that catalyzes the enoate reduction of the 2 HDA to pimelic acid (PA), such that PA is produced.

The PA can be contacted with an enzyme that catalyzes the carboxylic acid reduction of the PA to pimelic acid semialdehyde (PAS), such that PAS is produced.

The PAS can be contacted with an enzyme that catalyzes the semialdehyde amination of the PAS to 7-amino-heptanoic acid (7 AHA), such that 7 AHA is produced.

The 7 AHA can be contacted with an enzyme that catalyzes the amide hydrolysis of the 7 AHA to enatholactam (ENTL), such that ENTL is produced.

A second method of converting compound can include, after performing all the steps of the first method up to the production of 7 AHA, contacting the 7 AHA with an enzyme that catalyzes the aldehyde dehydrogenation of the 7 AHA to 7-amino-heptanal (7 AHT), such that AHT is produced.

The 7 AHT can be contacted with an enzyme that catalyzes the transfer of an amino group to the 7 AHT to produce 1,7-diaminoheptane (1,7 DAH), such that 1,7 DAH is produced.

A third method of converting compound can include, after performing all the steps of the first method up to the production of 2 HDA, contacting the 2 HDA with an enzyme that catalyzes the transfer of Coenzyme A (CoA) to the 2 HDA to produce 2-heptene diacid-CoA (2 HDA-CoA), such that 2 HDA-CoA is produced.

The 2 HDA-CoA can be contacted with an enzyme that catalyzes the enoate reduction of the 2 HDA-CoA to pimeloyl-CoA (PCoA), such that PCoA is produced.

The PCoA can be contacted with an enzyme that catalyzes the thioester hydrolysis of the PCoA to PA, such that PA is produced.

The PA can be contacted with an enzyme that catalyzes the carboxylic acid reduction of the PA to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

A fourth method of converting a compound can include, after performing all the steps of the third method up to production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A fifth method of converting a compound can include, after performing all the steps of the first method up to the production of AAP, contacting the AAP with an enzyme that catalyzes the transfer of an amino group to the AAP to produce α-keto-pimelate (AKP), such that AKP is produced.

The AKP can be contacted with one or more enzymes that catalyze the ketone reduction of the AKP to α-hydroxy-pimelate (AHP), such that AHP is produced.

The AHP can be contacted with an enzyme that catalyzes the transfer of CoA to the AHP to produce α-hydroxy-pimelate (AHP-CoA), such that AHP-CoA is produced.

The AHP-CoA can be contacted with an enzyme that catalyzes the dehydration of the AHP-CoA to 2 HDA-CoA, such that 2 HDA-CoA is produced.

The 2 HDA-CoA can be contacted with an enzyme that catalyzes the enoate reduction of the 2 HDA-CoA to PCoA, such that PCoA is produced.

The PCoA can be contacted with an enzyme that catalyzes the thioester hydrolysis of the PCoA to PA, such that PA is produced.

The PA can be contacted with an enzyme that catalyzes the carboxylic acid reduction of the PA to PAS, such that PAS is produced.

The PAS with can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, wherein ENTL is produced.

A sixth method of converting a compound can include, after performing all the steps of the fifth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A seventh method of converting a compound can include, after performing all the steps of the fifth method up to the production of AHP, contacting the AHP with an enzyme that catalyzes the dehydration of the AHP to 2 HDA, such that 2 HDA is produced.

The 2 HDA can be contacted with an enzyme that catalyzes the enoate reduction of the 2 HDA to pimelic acid (PA), such that PA is produced.

The PA can be contacted with an enzyme that catalyzes the carboxylic acid reduction of the PA to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

An eighth method of converting a compound can include, after performing all the steps of the fifth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A ninth method of converting a compound can include, after performing all the steps of the seventh method up to the production of 2 HDA, contacting the 2 HDA with an enzyme that catalyzes the transfer of CoA to 2 HDA to produce 2 HDA-CoA, such that 2 HDA-CoA is produced.

The 2 HDA-CoA can be contacted with an enzyme that catalyzes the enoate reduction of the 2 HDA-CoA to PCoA, such that PCoA is produced.

The PCoA can be contacted with an enzyme that catalyzes the thioester hydrolysis of the PCoA to PA, such that PA is produced.

The PA can be contacted with an enzyme that catalyzes the carboxylic acid reduction of the PA to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

A tenth method of converting a compound can include, after performing all the steps of the ninth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

An eleventh method of converting a compound can include, after performing all the steps of the fifth method up to the production of AKP, contacting the AKP with an enzyme that catalyzes the α-keto acid chain elongation of the AKP to α-keto-suberate (AKS), such that AKS is produced.

The AKS can be contacted with an enzyme that catalyzes the transfer of an amino group to the AKS to produce α-amino suberate (AAS), such that AAS is produced. The AAS can be contacted with an enzyme that catalyzes the α-keto acid decarboxylation of the AAS to 7 AHA, such that 7 AHA is produced.

The 7 AHA can be contacted with an enzyme that catalyzes the amide hydrolysis of the 7 AHA to ENTL, such that ENTL is produced.

A twelfth method of converting a compound can include, after performing all the steps of the eleventh method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A thirteenth method of converting a compound can include, after performing all the steps of the eleventh method up to the production of AKS, contacting the AKS with an enzyme that catalyzes the α-keto acid decarboxylation of the AKS to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

A fourteenth method of converting a compound can include, after performing all the steps of the thirteenth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A fifteenth method of converting a compound can include, after performing all the steps of the fifth method up to the production of PCoA, contacting the PCoA with an enzyme that catalyzes the reduction of the PCoA to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

A sixteenth method of converting a compound can include, after performing all the steps of the fifteenth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A seventeenth method of converting a compound can include, after performing all the steps of the ninth method up to the production of PCoA, contacting the PCoA with an enzyme that catalyzes the reduction of the PCoA to PAS, such that PAS is produced.

The PAS can be contacted with an enzyme that catalyzes the semialdehyde amination of the PAS to 7 AHA, such that 7 AHA is produced.

The 7 AHA can be contacted with an enzyme that catalyzes the amide hydrolysis of the 7 AHA to ENTL, such that ENTL is produced.

An eighteenth method of converting a compound can include, after performing all the steps of the seventeenth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A nineteenth method of converting a compound can include contacting a compound selected from 6A2HA and 2 HDA with an enzyme that catalyzes the enoate reduction of 6A2HA to AAP or for the enoate reduction of 2 HDA to PA, such that AAP or PA is produced. It is understood that, following the production of AAP or PA, any of the steps after the production of AAP or PA described above in the first to eighteenth methods can be performed.

A twentieth method of converting a compound can include contacting a compound selected from PCoA and pimeloyl [acp] (PACP) with an enzyme that catalyzes the thioesterase hydrolysis PCoA or PACP to PA, wherein PA is produced.

The PA can be contacted with an enzyme that catalyzes the carboxylic acid reduction of the PA to PAS, such that PAS is produced.

The PAS can be contacted with an enzyme that catalyzes the semialdehyde amination of the PAS to 7 AHA, such that 7 AHA is produced.

The 7 AHA with an enzyme that catalyzes the amide hydrolysis of the 7 AHA to ENTL, such that ENTL is produced.

A twenty first method of converting a compound can include, after performing all the steps of the twentieth method up to the production of 7 AHA, contacting the 7 AHA with an enzyme that catalyzes the aldehyde dehydrogenation of the 7 AHA to 7 AHT, such that 7 AHT is produced.

The 7 AHT can be contacted with an enzyme that catalyzes the transfer of an amino group to the 7 AHT to produce 1,7 DAH, such that 1,7 DAH is produced.

A twenty second method of converting a compound can include contacting AKP with one or more enzymes that catalyze the ketone reduction of AKP to AHP, such that AHP is produced. The AKP can have been produced by chain elongation of α-keto adipate or α-keto glutarate. The AHP can then be converted to PA or to PCoA. It is understood that, following the production of PA or PCoA, any of the steps after the production of PA or PCoA described above in the first to eighteenth methods can be performed.

A twenty third method of converting a compound can include converting AKP to AKS by α-keto acid chain elongation. The AKP can have been produced by chain elongation of α-keto adipate or α-keto glutarate. It is understood that, following the production of AKS, any of the steps after the production of AKS described above in the first to eighteenth methods can be performed.

A twenty fourth method of converting a compound can include contacting PAS with an enzyme that catalyzes the semialdehyde amination of PAS to 7 AHA, such that 7 AHA is produced. The PAS can have been obtained by conversion from 2,6 DAP, AKG, PCoA, or PACP. It is understood that, following the production of AHA, any of the steps after the production of AHA described above in the first to eighteenth methods can be performed.

A twenty fifth method of converting a compound can include contacting a compound selected from PCoA and PACP with an enzyme that catalyzes the reduction of the compound to PAS, such that PAS is produced. It is understood that, following the production of PAS, any of the steps after the production of PAS described above in the first to eighteenth methods can be performed. Moreover, any of the steps described in the first to eighteenth and the twenty second method leading to the production of PCoA can be performed prior to the twenty fifth method.

A twenty sixth method of converting a compound can include contacting PAS with an enzyme that catalyzes the alcohol dehydrogenation of PAS to 7-hydroxy-heptanoic acid (7 HHA), such that 7 HHA is produced. It is understood that any of the steps described in the first to eighteenth and the twentieth, twenty second, twenty third, and twenty fifth methods leading to the production of PAS can be performed prior to the twenty sixth method.

In any of the described methods the enzyme(s) can be used in purified form. Alternatively, the enzyme(s) can be used in the form of a cell lysate or a partially purified cell lysate. In addition, the enzyme(s) can be in a cell recombinantly expressing it/them.

In the described methods, an enzyme that catalyzes reductive deamination can include an ammonia lyase. The ammonia lyase can be in EC 4.3.1, e.g., EC 4.3.1.1; EC 4.3.1.2; EC 4.3.1.3; EC 4.3.1.12; EC 43.1.13; or EC 4.3.1.24.

In the described methods, an enzyme that catalyzes enoate reduction can include an enoate reductase. The enoate reductase can be in EC 1.3.1, e.g., EC 1.3.1.31.

In the described methods, an enzyme that catalyzes carboxylic acid reduction can include a carboxylic acid reductase. The carboxylic acid reductase can be in EC 1.2.99, e.g., EC 1.2.99.6.

In the described methods, an enzyme that catalyzes semi-aldehyde amination can include an ω transaminase. The ω transaminase can be in EC 2.6.1, e.g., EC 2.6.1.18; EC 2.6.1.19; EC 2.6.1.2; EC 2.6.1.7; EC 2.6.1.29; EC 2.6.1.36; EC 2.6.1.39; EC 2.6.1.42; or EC 2.6.1.68.

In the described methods, an enzyme that catalyzes thioester hydrolysis can include a thioesterase, an acid-thiol ligase, or a CoA transferase. The thioesterase can be in EC 3.1.2, e.g., EC 3.1.2.18; EC 3.1.2.19; or EC 3.1.2.20. The acid-thiol ligase can be in EC 6.2.1, e.g., EC 6.2.1.3; EC 6.2.1.14; or EC 6.2.1.23. The CoA transferase can be in EC 2.8.3, e.g., EC 2.8.3.12 or EC 2.8.3.13.

In the described methods, an enzyme that catalyzes the transfer of an amino group can include an aminotransferase. The aminotransferase can be in EC 2.6.1, e.g., EC 2.6.1.67.

In the described methods, an enzyme that catalyzes ketone reduction can be a carbonyl reductase. The carbonyl reductase can include EC.1.1.1.184.

In the described methods, an enzyme that catalyzes α-keto acid decarboxylation can be an α-keto acid decarboxylase.

In the described methods, an enzyme that catalyzes reduction (of, for example, PCoA to PAS) can be a fatty-acyl-CoA reductase. The fatty-acyl-CoA reductase can be in EC 1.2.1, e.g., EC 1.2.1.50.

In the described methods, an enzyme that catalyzes aldehyde dehydrogenation can be an aldehyde dehydrogenase. The aldehyde dehydrogenase can be in EC 1.2.1, e.g., EC 1.2.1.4 or EC 1.2.1.63.

In the described methods, an enzyme that catalyzes the transfer of CoA can include a CoA transferase. The CoA transferase can be in EC 2.8.3, e.g., EC 2.8.3.12 or EC 2.8.3.13.

In the described methods, an enzyme that catalyzes amide hydrolysis can be an amino hydrolase.

In the described methods, an enzyme that catalyzes dehydration (of, for example, AHP or AHP-CoA) can be a hydro-lyase. The hydro-lyase can be in EC 4.2.1, e.g., EC 4.2.1.2; EC 4.2.1.59; 4.2.1.61; 4.1.2.17 or 4.1.2.18.

In the described methods, enzymes that catalyzes α-keto acid chain elongation can include one of more of the set of enzymes including AksA, AksD, AksE and AksF. The AksA can be in EC 2.3.3, e.g., EC 2.3.3.13 or 2.3.3.14. The AksD can be in EC 4.2.1, e.g., EC 4.2.1.33. The AksF can be in EC 1.1.1, e.g., EC 1.1.1.85. One or more (e.g., two or more, three or more, four or more, five or more, six or more, seven or more, eight or more, nine or more, ten or more, 12 or more, 14 or more, 18, or more, or 20 or more) of the α-keto acid chain elongation enzymes can be from methanogenic bacteria.

In the described methods, an enzyme that catalyzes alcohol dehydrogenation can include an alcohol dehydrogenase. The alcohol dehydrogenase can include EC. 1.1.1.1 or EC 1.1.1.2. It can also be, for example, adhA from *Zymomonas mobilis*, adhB from *Zymomonas mobilis*, butanol dehydrogenase from *Clostridium acetobutylicum*, Saccharomyces ADHIV, and ADH6 from *S. cerevisiae*.

PCoA or PACP used in the methods of the document can be derived from acetyl-CoA or benzoyl-CoA. The acetyl-CoA can be derived from renewable feedstocks comprising cellulosic feedstocks, sugars, glycerol, or fatty acids. Moreover, the acetyl-CoA can be derived from SynGas, methane or methanol. The benzoyl-CoA can be derived from polycyclic aromatic hydrocarbons.

The 2,6 DAP used in the methods of the document can be produced by a lysine-producing organism lacking diaminopimelate decarboxylase. The 2,6 DAP is derived from renewable feedstocks, which can contain sugars.

The present document features a bioderived nylon-7, nylon-7, x nylon-x,7, and polyester. It also includes a Nylon-7 produced by a process that includes polymerizing 7 AHA, where the 7 AHA is derived from PAS or AAS. Also provided by the document is a nylon-7,7 produced by a process that includes polymerizing PA and 1,7 DHA, where the PA is derived from PCoA; PACP; or 2 HDA and the 1,7 DHA is derived from 7 AHA. The document also embodies nylon-7 produced by a process that includes polymerizing 7 AHA made by any of the methods described above that lead to the production of 7 AHA. Another aspect of the invention is a nylon 7,7 produced by a process comprising polymerizing 1,7 DHA and PA, where the 1,7 DHA is made by any of the methods described above that lead to the production of 1,7 DHA and the PA is made by any of the methods described above that lead to the production of PA.

The present document also provides a substantially pure culture of host cells, a substantial number of which comprise and express one or more exogenous nucleic acids encoding one or more enzymes involved in the biosynthesis of one or more polymer monomers selected from 7 AHA; PA; 1,7 DAH; ENTL; and 7 HHA. These enzymes include acyl-CoA reductases, acyl-[acp] reductases, thioester hydrolases, ammonia lyases, enoate reductases, aminotransferases, CoA transferases, thioesterases, acid-thiol ligases, hydro-lyases, carbonyl reductases, carboxylic acid reductases, fatty-acyl CoA reductases, ω-transaminases, α-keto acid decarboxylases, aldehyde dehydrogenases, alcohol dehydrogenases, and enzymes catalyzing α-keto acid chain elongation. As used herein, a "substantial number" is at least 10% (e.g., at least: 20%; 30%; 40%; 50%; 60%; 70%; 75%; 80%; 85%; 90%; 95%; 97%; 98%; 99%; or even 100%) of the cells in the culture.

The cells of the culture can be prokaryotic cells, such as, without limitation, *Escherichia coli*, *Rhodopseudomonas palustris*, sphingomonads, pseudomonads, methanogenic bacteria (e.g., *Methanobacterium autotrophicum*), *Corynebacterium, Salmonella, Burkholderia, Moraxella, Alcaligenes, Psychrobacter, Thermotoga, Acinetobacteria, Rhodobacter, Azoarcus, Rhodospirillum, Brevibacterium*, streptococci, lactobacilli, *Nocardia, Bacillus, Rhodococcus, Clostridium, Streptomyces*, and *Arthobacter*.

Alternatively, the cells of the culture can be eukaryotic cells, e.g., fungal cells such as yeast cells. The yeast cells can be of a yeast such as, without limitation, *Yarrowia lipolytica, Candida, Rhodotorula, Rhizopus, Saccharomyces, Pichia, Trichosporon, Issatchenka, Kluyveromyces, Debaryomyces, Hansenula, Schizosaccharomyces, Schwanniomyces*, and *Lipomyces*. The *Candida* cells can be of a yeast such as, without limitation, *C. tropicalis, C. albicans, C. cloacae, C. guillermondii, C. intermedia, C. maltosa, C. parapsilosis*, and *C. zeylenoides*. Other fungal cells can be of a fungus such as, without limitation, *Aspergillus, Exophiala, Mucor, Trichoderma, Cladosporium, Phanerochaete, Cladophialophora, Paecilomyces, Scedosporium*, and *Ophiostoma*.

Exogenous enzymes that can be expressed by the cells are as follows. The ammonia lyases can include an ammonia lyase in EC 4.3.1, e.g., EC 4.3.1.1; EC 4.3.1.2; EC 4.3.1.3; EC 4.3.1.12; EC 4.3.1.13; or EC 4.3.1.24. The enoate reductases can include an enoate reductase in EC 1.3.1, e.g., EC 1.3.1.31. The carboxylic acid reductases include a carboxylic acid reductase in EC 1.2.99, e.g., EC 1.2.99.6. The ω-transaminases can include a transaminase in EC 2.6.1, e.g., EC 2.6.1.18; EC 2.6.1.19; EC 2.6.1.2; EC 2.6.1.7; EC 2.6.1.29; EC 2.6.1.36; EC 2.6.1.39; EC 2.6.1.42; or EC 2.6.1.68. The thioesterases can include a thioesterase in EC 3.1.2, e.g., EC 3.1.2.18; EC 3.1.2.19; or EC 3.1.2.20. The acid-thiol ligases can include an acid-thiol ligase in EC 6.2.1, e.g., EC 6.2.1.3; EC 6.2.1.14; or EC 6.2.1.23. The CoA transferases can include a CoA transferase in EC 2.8.3, e.g., EC 2.8.3.12 or EC 2.8.3.13. The aminotransferases can include an aminotransferase in EC 2.6.1, e.g., EC 2.6.1.67. The carbonyl reductases can include EC.1.1.1.184. The fatty-acyl-CoA reductases can include a fatty-acyl-CoA reductase in EC 1.2.1, e.g., EC 1.2.1.50. The aldehyde dehydrogenases can include an aldehyde dehydrogenase in EC 1.2.1, e.g., EC 1.2.1.4 or EC 1.2.1.63. The hydro-lyases include a hydro-lyase in EC 4.2.1, e.g., EC 4.2.1.2; EC 4.2.1.59; 4.2.1.61; 4.1.2.17 or 4.1.2.18. The enzymes catalyzing α-keto acid chain elongation can include one or more enzymes of the set including AksA, AksD, AksE and AksF enzymes. The AksA can include an AksA enzyme in EC 2.3.3, e.g., EC 2.3.3.13 or 2.3.3.14. The AksD can include an AksD enzyme in EC 4.2.1, e.g., EC 4.2.1.33. The AksF can include an AksF enzyme in EC 1.1.1, e.g., EC 1.1.1.85. The alcohol dehydrogenases can include, e.g., EC. 1.1.1.1 or EC 1.1.1.2. In addition the alcohol dehydrogenases can include, for example, adhA from *Zymomonas mobilis*, adhB from *Zymomonas mobilis*, butanol dehydrogenase from *Clostridium acetobutylicum, Saccharomyces* ADHIV, and ADH6 from *S. cerevisiae*.

Another aspect of the present document is an isolated host cell comprising and expressing one or more exogenous nucleic acids encoding one or exogenous nucleic acids involved in the biosynthesis of one or more polymer monomers selected from 7 AHA; PA; 1,7 DAH; ENTL; and 7 HHA. The enzymes include acyl-CoA reductases, acyl-[acp] reductases, thioester hydrolases, ammonia lyases, enoate reductases, aminotransferases, CoA transferases, thioesterases, acid-thiol ligases, hydro-lyases, carbonyl reductases, carboxylic acid reductases, fatty-acyl CoA reductases, ω-transaminases, α-keto acid decarboxylases, aldehyde dehydrogenases, alcohol dehydrogenases, and enzymes catalyzing α-keto acid chain elongation. The cell and enzymes can be any of those described above for a substantially pure culture of host cells.

Other objects and advantages will become apparent to those skilled in the art from a consideration of the ensuing detailed descriptions set forth herein.

These reactions are analogous to the reactions catalyzed by citrate synthase, aconitase, and isocitrate dehydrogenase in the TCA cycle I (prokaryotic) and the reactions catalyzed by (R)-homocitrate synthase, homoaconitase and (−)-threo-isohomocitrate dehydrogenase in lysine biosynthesis V [Howell, 1998, supra].

Figure 4:
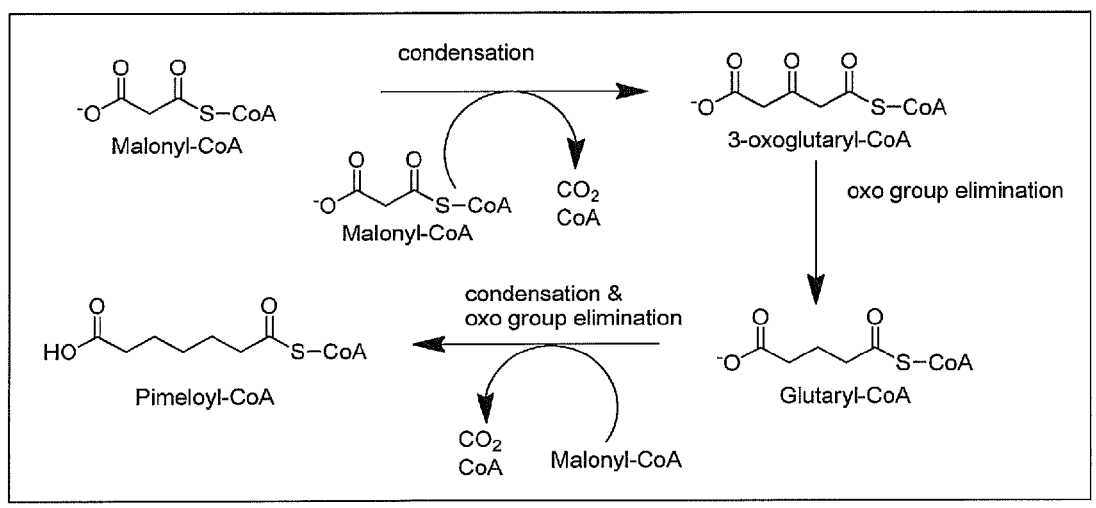

FIG. 4 is a schematic of the formation of pimeloyl-CoA through condensation of three malonyl-CoAs.

Figure 5:
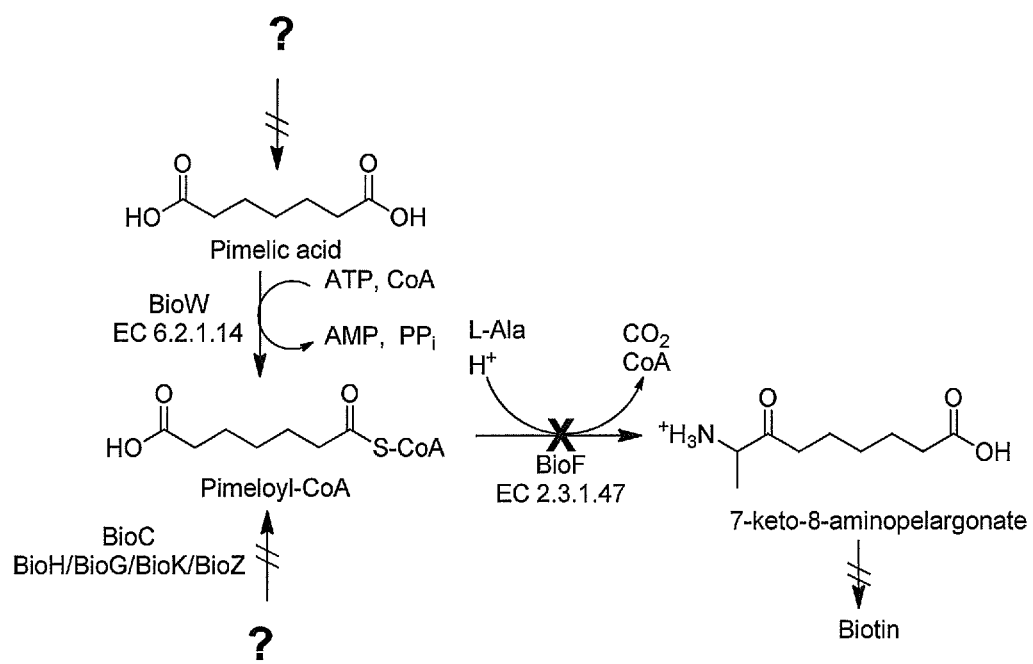

FIG. 5 is a schematic of the formation of pimeloyl-CoA from pimelic acid or other precursors in 7-keto-8-aminopelargonate biosynthesis in biotin biosynthesis pathway II. 7-keto-8-aminopelargonate is the key intermediate for biotin biosynthesis. Degradation of pimeloyl-CoA in the host organism can be prevented by deletion or inactivation of BioF, the gene encoding 7-keto-8-aminopelargonic acid synthetase (E.C. 2.3.1.47).

Figure 6:
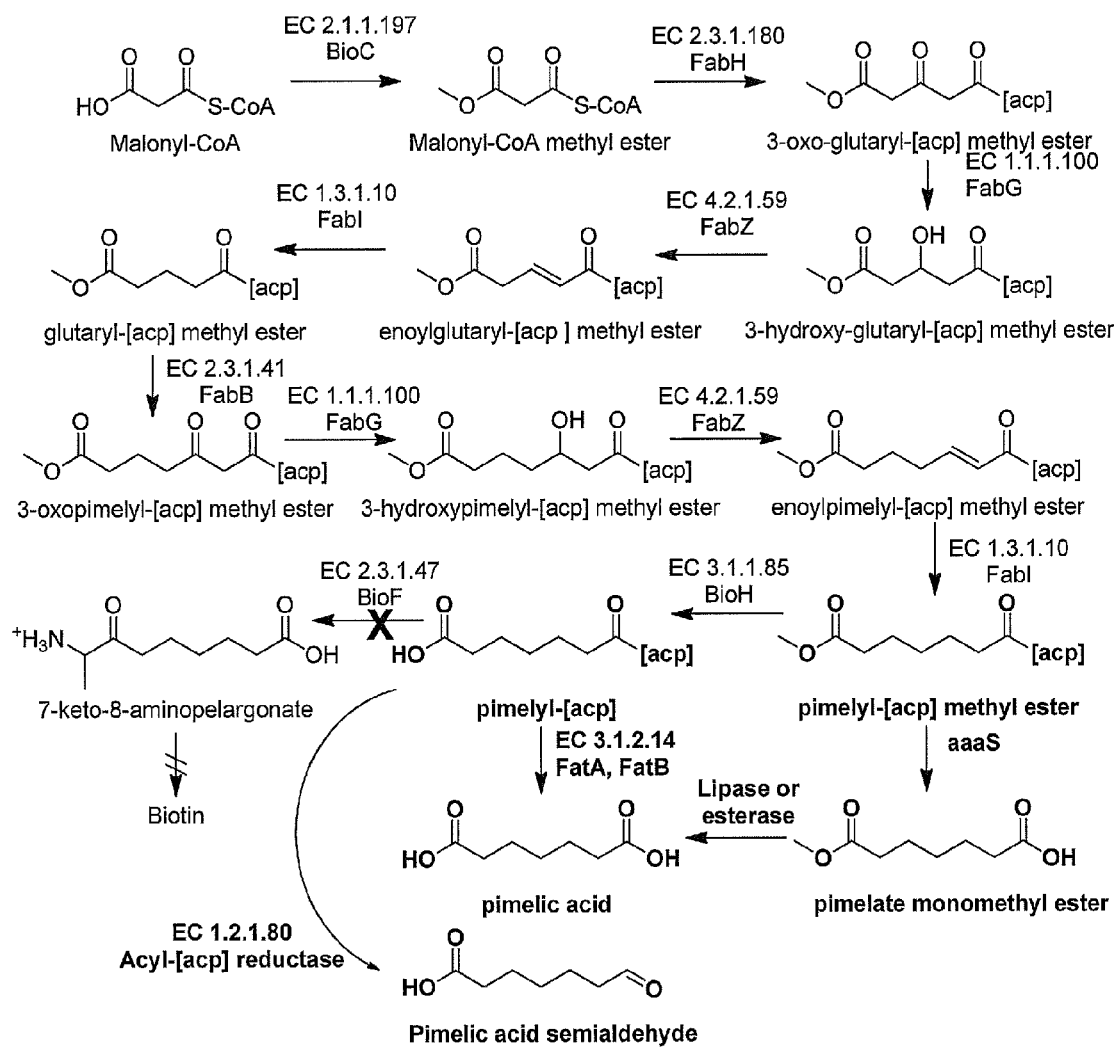

FIG. 6 is a schematic of the formation of pimeloyl-[acp] or its methyl ester in 7-keto-8-aminopelargonate biosynthesis in biotin biosynthesis pathway I. The key intermediate in biotin biosynthesis. Pimelic acid or pimelic acid semialdehyde can be prepared from these precursors by the action of aaaS (acyl-ACP synthetase), FatA (fatty acyl-ACP thioesterase A), FatB (fatty acyl-ACP thioesterase B), or acyl-[acp] reductase as shown in bold text.

Figure 7:
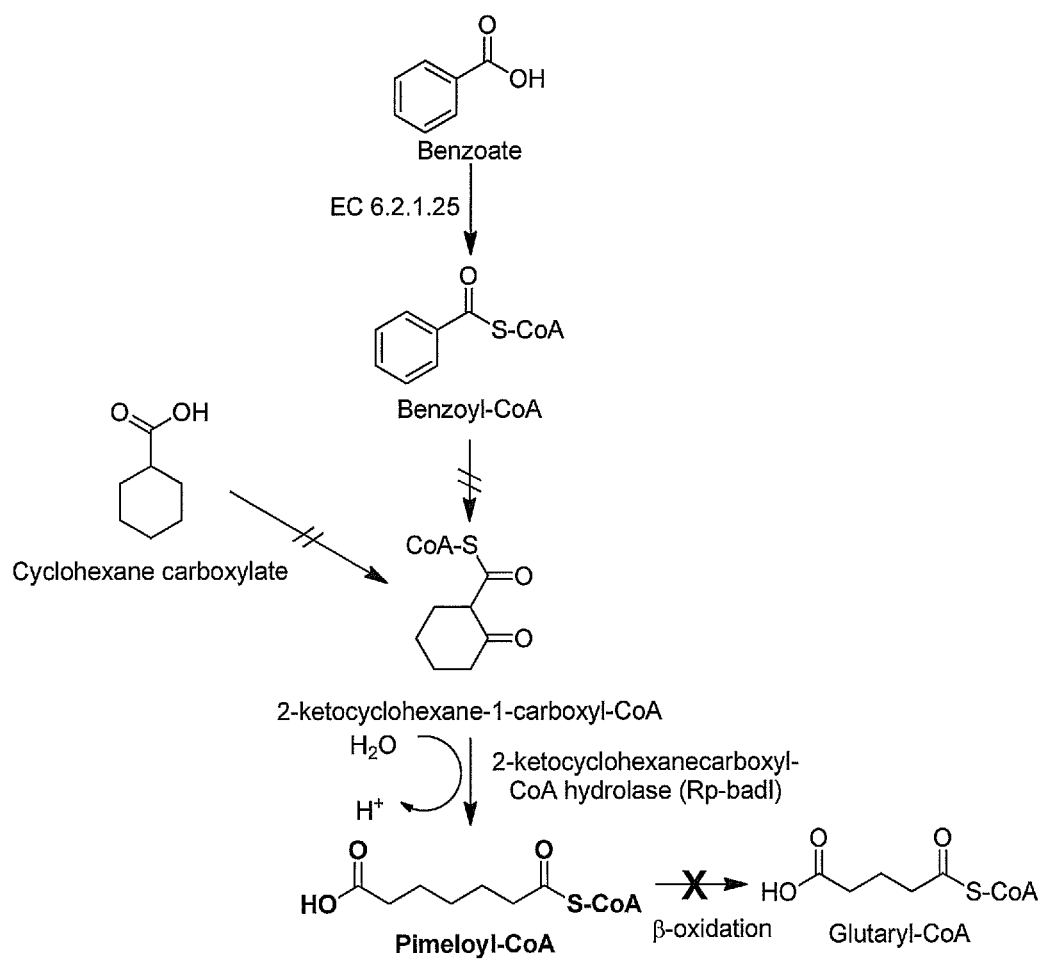

FIG. 7 is a scheme showing formation of pimeloyl-CoA from benzoate or cyclohexane carboxylate degradation.

Figure 8:
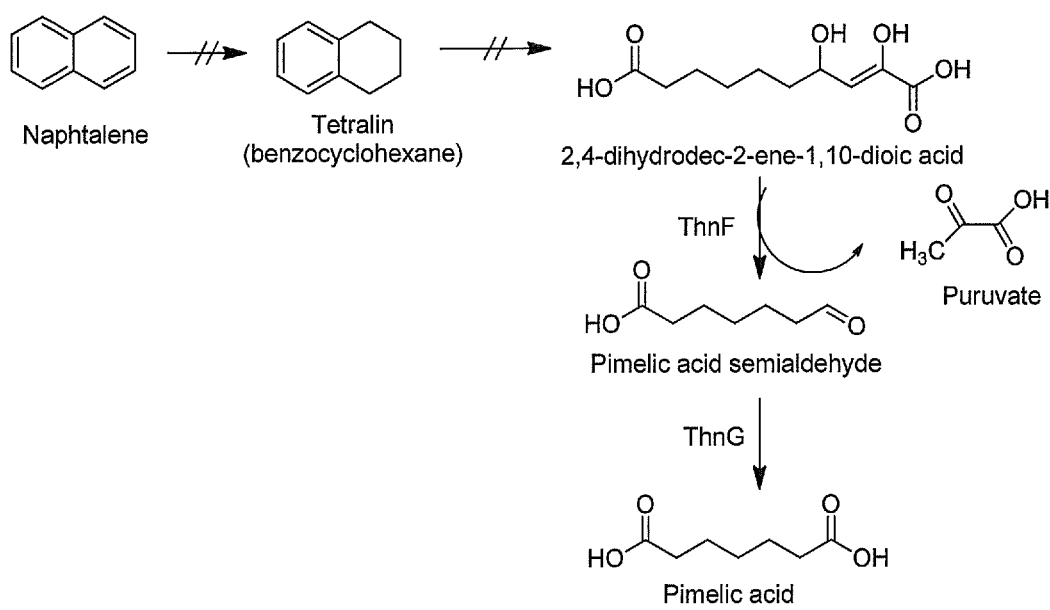

FIG. 8 is a scheme showing the formation of pimelic acid semialdehyde in the tetralin degradation pathway in *Sphingomonas* and *Corynebacterium* spp.

Figure 9:
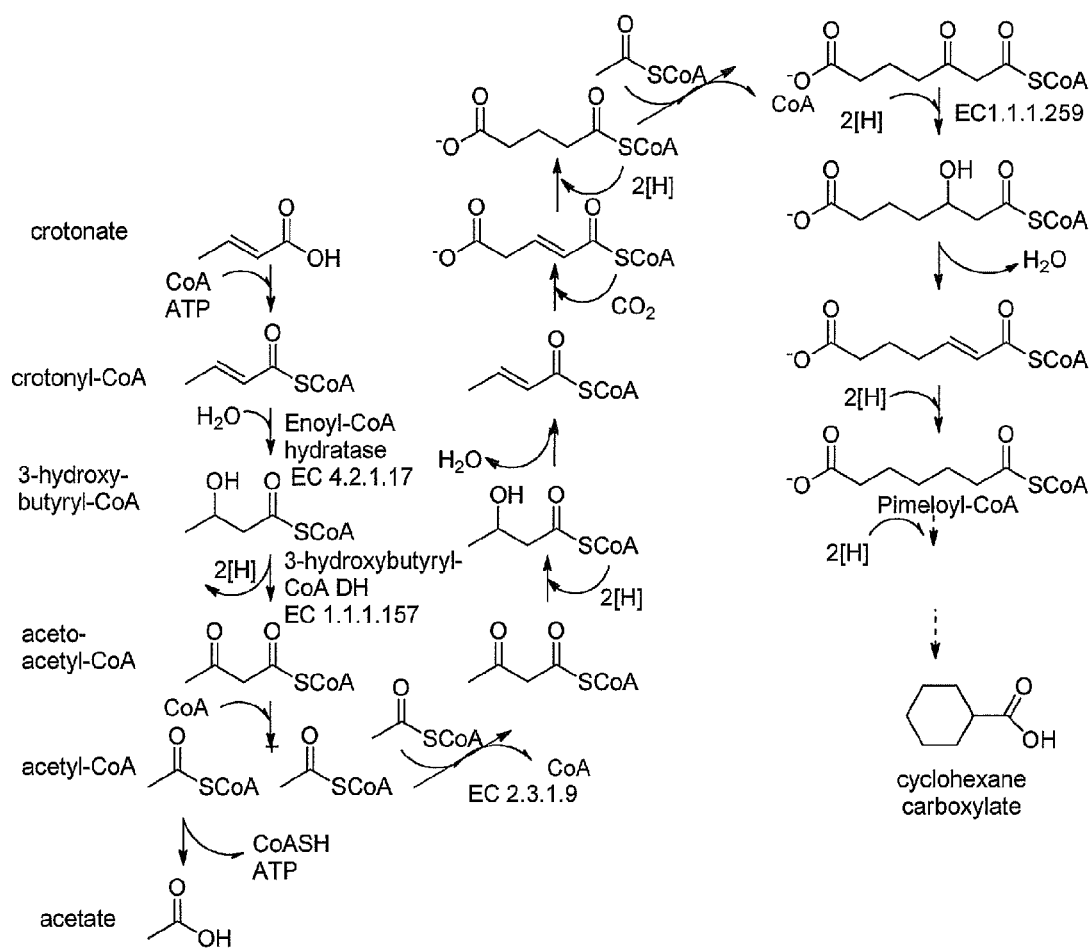

FIG. 9 is a scheme showing formation of pimeloyl-CoA in the cyclohexane carboxylate pathway from crotonate by methanogens. See Mouttaki et al., *Applied and Environmental Microbiology*, pages 930-938 (2001).

Figure 10:
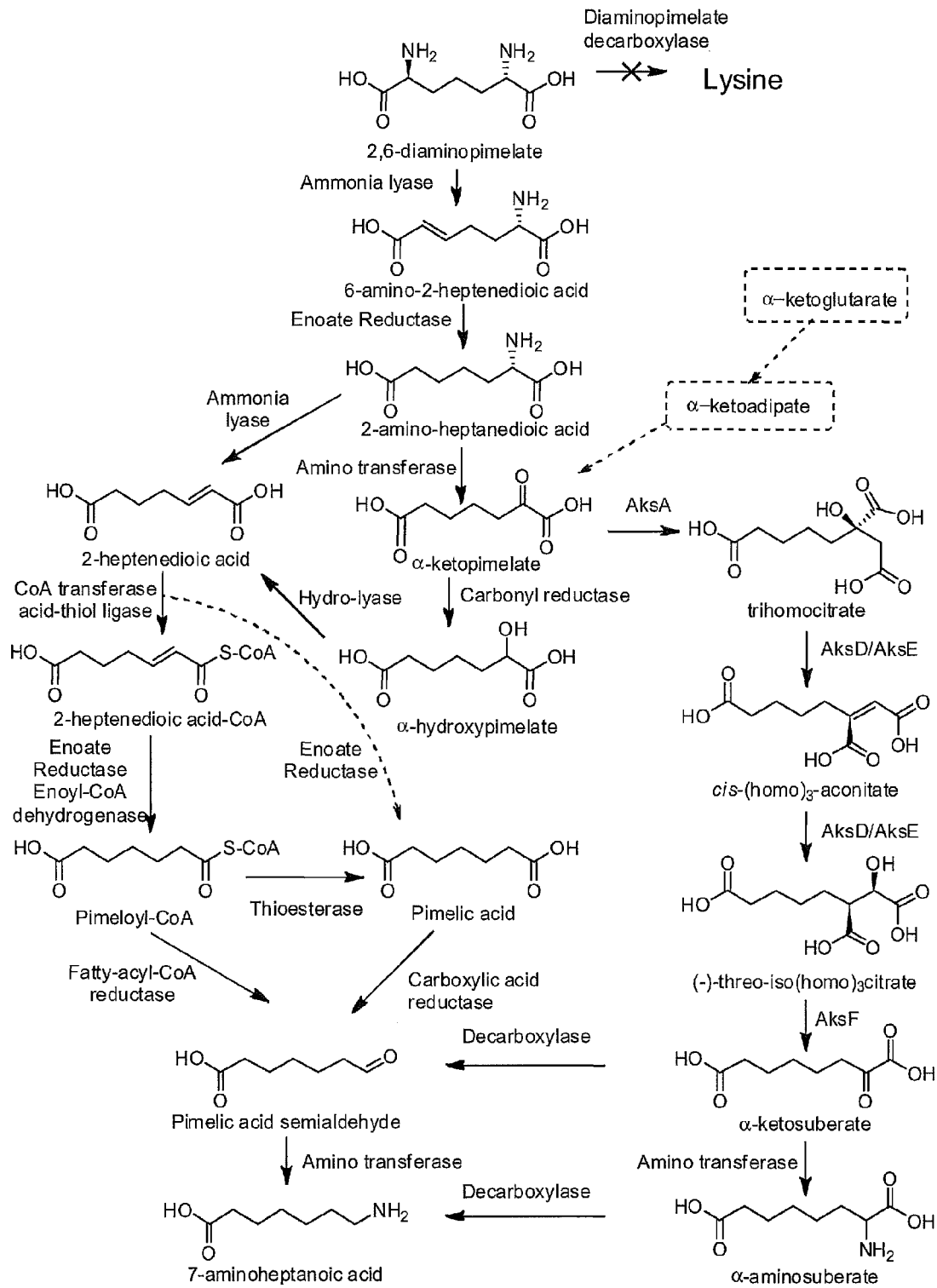

FIG. 10 is a schematic showing examples of engineered pathways to pimelic acid semialdehyde and 7-aminoheptanoic acid from D,L-diaminopimelate as a starting point via 2-aminoheptanedioic acid. There are 2 routes from 2-amino-heptanedioic acid to pimelic acid semialdehyde, either via reductive deamination by an ammonia lyase to 2-heptenedioic acid or via follnation of the α-keto-acid that can subsequently be converted to pimelic acid or its CoA ester. Alternatively, α-keto-pimelate derived from 2-aminoheptanedioic acid can undergo one round of chain elongation to α-keto-suberate, which can either be decarboxylated to form pimelic acid semialdehyde, or converted to α-aminosuberate, which will lead directly to 7-aminoheptanoic acid upon decarboxylation. α-keto-pimelate also can be derived from α-keto-adipate, which in turn can be derived from α-ketoglutarate, through two successive rounds of α-keto-acid chain elongation.

FIG. 11A shows an SDS-PAGE analysis on soluble and insoluble fractions from expression of the *Citrobacter amalonaticus* ammonia lyase protein.

FIG. 11B shows an SDS-PAGE analysis on soluble and insoluble fractions from expression of the *Clostridium tetanomorphum* (I5) and *Aspergillus oryzae* (I6) ammonia lyase proteins.

Figure 12:
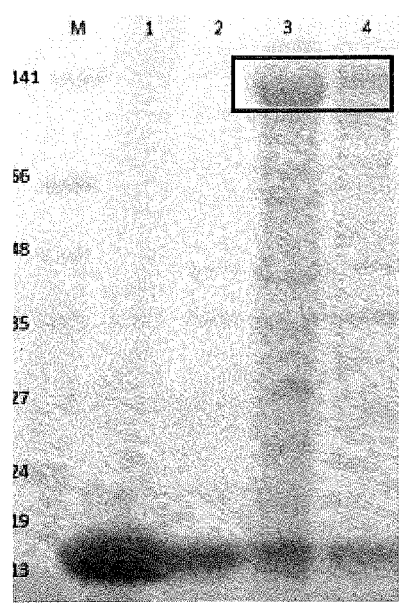

FIG. 12 shows an SDS-PAGE analysis on soluble and insoluble fractions from expression of the *Nocardia* sp. carboxylic acid reductase gene.

Figure 13:
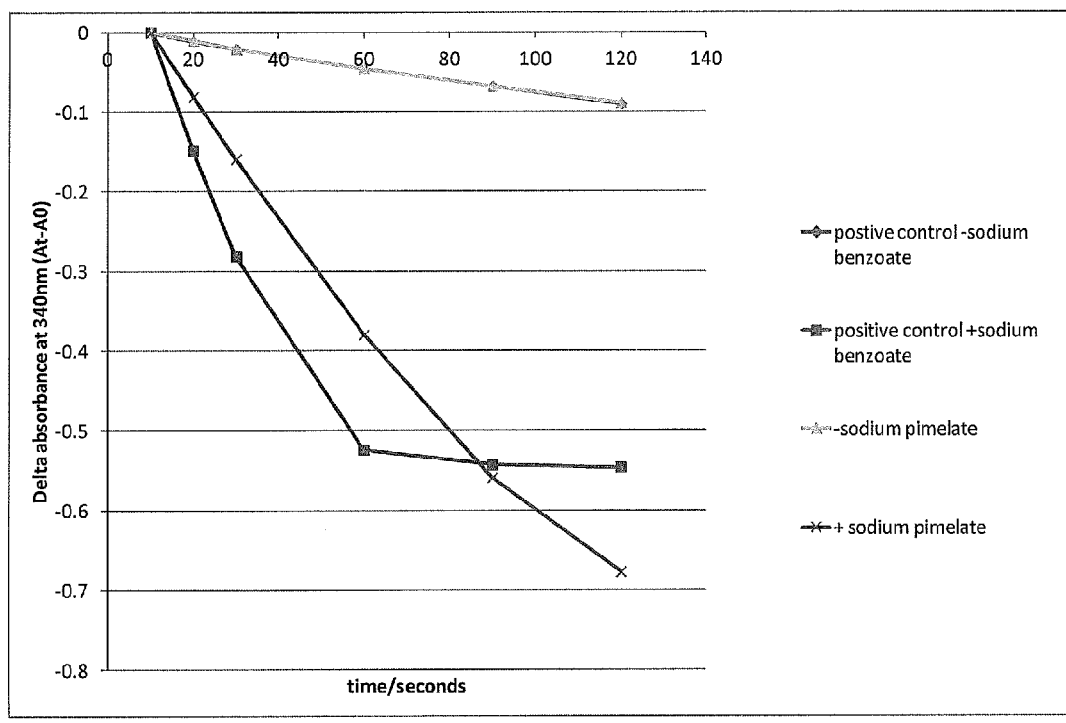

FIG. 13 shows a change in absorbance over time due to reduction of pimelic acid to pimelic acid semialdehyde by *Nocardia* CAR reductase activity.

FIG. 14 shows an SDS-PAGE analysis on soluble fraction and insoluble fraction from expression of the *Haemophilus influenzae* YciA thioesterase protein (I8)

FIG. 15 shows an SDS-PAGE analysis of the aminotransferase IlvE-Omega Vf fusion (pING2022) and IlvE-Ad optimized omega fusion (pING2030) proteins.

Figure 16:
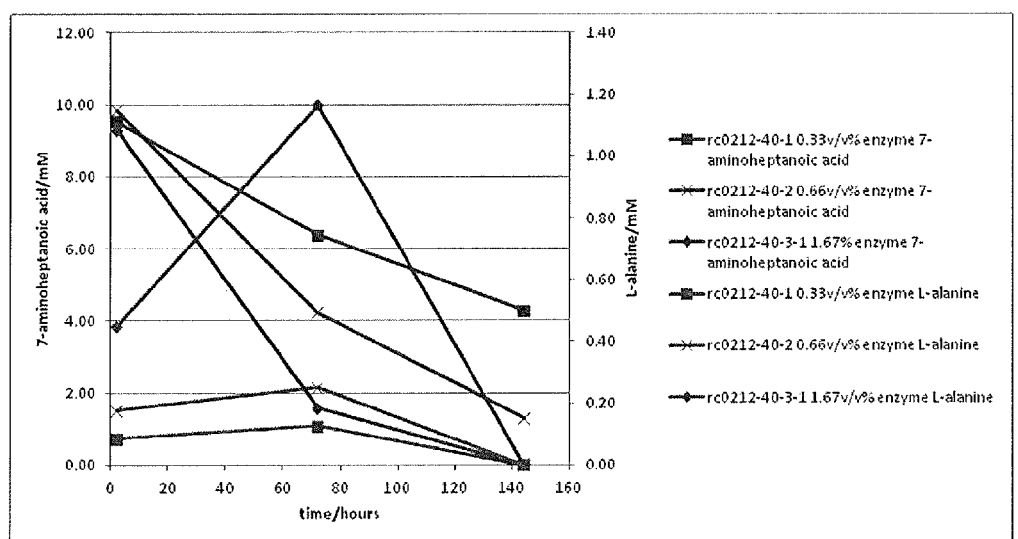

FIG. 16 shows Results of the biotransformation of sodium pyruvate and 7-aminoheptanoic acid with the measured concentrations of 7-aminoheptanoic acid substrate and L-alanine product.

Figure 17:
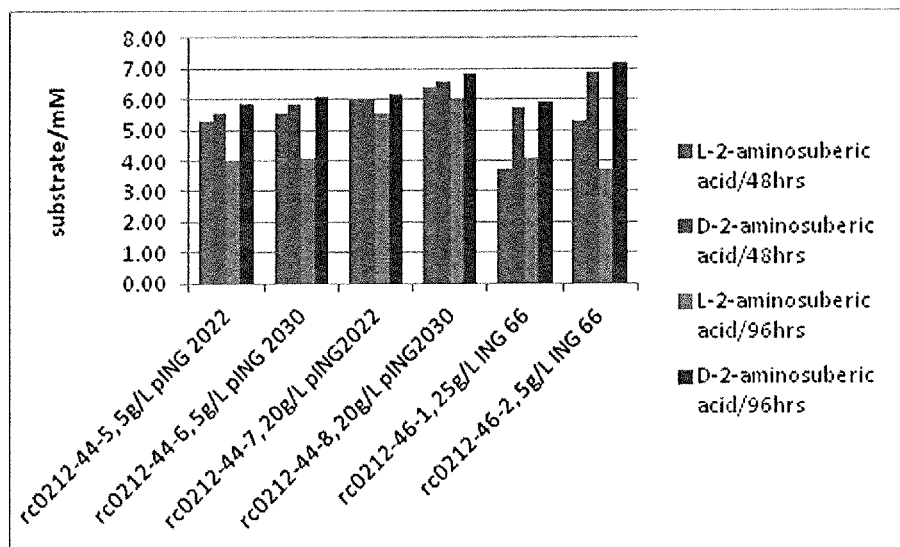

FIG. 17 shows a Summary of the HPLC results from the L- and D-2-aminosuberic acid enantiomer concentrations in the six biotransformations after 48 and 96 hours.

FIG. 18 shows an SDS-PAGE analysis on soluble and insoluble fractions from the bead lysis of expression of the *E. coli* GadA (I29), *E. coli* LysA (I30), *E. coli* GadA ilvE (I31) and *E. coli* LysA ilvE (I32) proteins.

FIG. 19 shows the formation of 7-aminoheptanoic acid from the decarboxylation of 2-aminosuberate.

FIG. 20 shows protein alignment using the ClustalW algorithm showing significant homology between MJ0277 (SEQ ID NO:22) and comD (SEQ ID NO:41)/comE (SEQ ID NO:42) proteins.

FIG. 21 shows homology of MJ0277 (SEQ ID NO:22) to LACLA acetolactate synthase from *Lactococcus lactis* (SEQ ID NO:43).

FIG. 22 shows an analysis of the functional domains in LACLA acetolactate synthese, comD/comE from *Methanocella paludicola* and the hypothetical acetolactate synthase MJ0277 showed that all of them have a similar structure containing a thiamine phosphate binding site.

Figure 23:
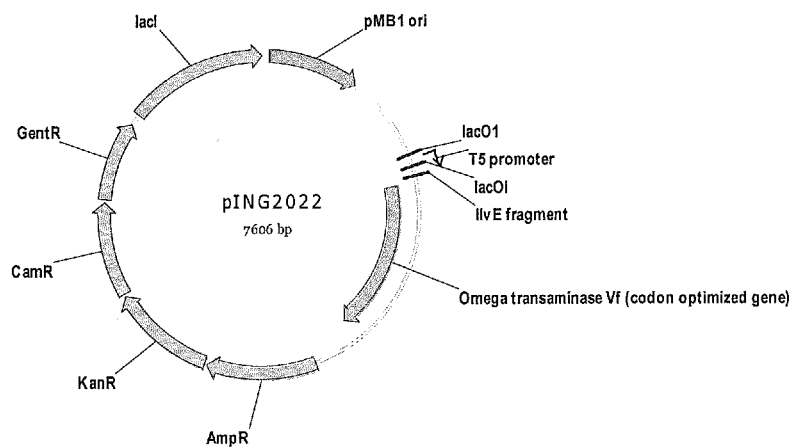

FIG. 23 depicts a map of pING2022 vector, containing the IlvE-Omega Vf fusion gene.

Figure 24:
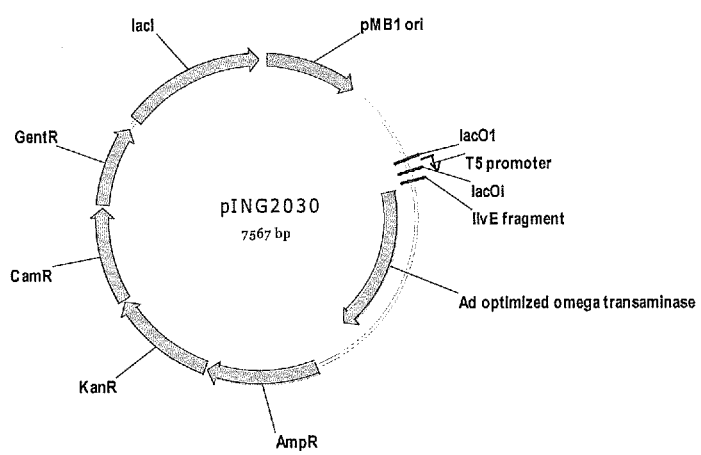

FIG. 24 depicts a map of pING2030 vector containing the IlvE-Ad optimized omega fusion gene.

FIG. 25 sets forth the SEQ. ID 1-40

DETAILED DESCRIPTION OF THE INVENTION

In general, this disclosure relates to methods and materials for biosynthetically producing di- or trifunctional C7 alkanes that are useful as intermediates in the production of nylon-7, nylon-7,x and nylon-x,7, as well as the production of polyesters.

In some embodiments, one or more (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) isolated enzymes (e.g., an ammonia lyase, enoate reductase, aminotransferase, CoA transferase, thioestesterase, acid-thiol ligase, hydro-lyase, carbonyl reductase, thioesterase, carboxylic acid reductase, fatty-acyl CoA reductase, ω-transaminase, α-keto acid decarboxylase, enzymes catalyzing α-keto acid chain elongation, acyl-ACP synthetase, FatA (fatty acyl-ACP thioesterase A), FatB (fatty acyl-ACP thioesterase B), or acyl-[acp] reductase) can be used to biosynthetically produce the di- or trifunctional C7 alkanes. Such enzymes can be isolated from recombinant cells expressing exogenous nucleic acids encoding the enzyme(s) or non-recombinant cells naturally expressing the enzymes.

In some embodiments, a recombinant host that includes one or more (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) exogenous nucleic acids encoding one or more (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) enzymes (e.g., one or more (as above) of an ammonia lyase, enoate reductase, aminotransferase, CoA transferase, thioestesterase, acid-thiol ligase, hydro-lyase, carbonyl reductase, thioesterase, carboxylic acid reductase, fatty-acyl CoA reductase, ω-transaminase, α-keto acid decarboxylase, enzymes catalyzing α-keto acid chain elongation, acyl-ACP synthetase, FatA, FatB, or acyl-[acp] reductase), or a lysate prepared from such a recombinant host or a non-recombinant cell naturally expressing the enzyme(s) can be used to biosynthetically produce the di- or trifunctional C7 alkanes. A recombinant host also may have a deficiency in one or more endogenous enzymes in order to divert metabolic intermediates towards the production of the di- or trifunctional C7 alkanes.

As described herein, the biosynthetically produced di- or trifunctional C7 alkanes can be used to produce nylon-7, nylon-7,x, or nylon-x,7, as well as polyesters. The term "nylon-7" is a polyamide produced by polymerization of the monomer 7-aminoheptanoic acid or by ring-opening condensation enantholactam. Nylon-7 also is known as "polyenanthamide" or "polyheptanamide."

The term "nylon-x,7" refers to the family of polyamides that are produced by the polymerization of heptane-1,7-dioic acid (also known as pimelic acid or pimelate) with a diamine. The integer x indicates the number of carbon atoms in the diamine with which the heptane-1,7-dioic acid is reacted. In some embodiments, the integer x is an integer greater than 3, e.g., greater than 5, greater than 7, or greater than 9. For example, nylon-5,7 is produced by reacting heptane-1,7-dioic acid and 1,5-pentanediamine. Nylon 7,7 is produced by reacting heptane-1,7-dioic acid and 1,7 diaminoheptane.

The term "nylon-7,x" refers to the family of polyamides that are produced by the polymerization reaction of heptamethylenediamine with a dicarboxylic acid. The integer x indicates the number of carbon atoms in the dicarboxylic acid with which the heptamethylenediamine is reacted. For example, nylon-7,5 is produced by the reaction of heptamethylenediamine (also known as 1,7-diaminoheptane or 1,7-heptanediamine) and pentane-1,5-dioic acid. In some embodiments, the integer x is an integer greater than 3, e.g., greater than 5, greater than 7 or greater than 9.

The term "polyester" refers to a category of polymers which contains an ester functional group in their main chain. Polyesters can be homopolymers, for example polycaprolactone, that is produced by ring-opening condensation of caprolactone. Copolymer polyesters are formed by the esterification condensation of polyfunctional alcohols and acids. For example, adipic acid and ethylene glycol are used to produce polyethylene adipate. Pimelic acid can be used in the place of adipic acid in such copolymers. Alternatively, 7-hydroxyheptanoic acid can be used to produce polyenantholactone.

The foregoing and other aspects of the present invention will now be described in more detail with respect to embodiments described herein. It should be appreciated that the invention can be embodied in different forms and should not be construed as limited to the embodiments set forth herein. Rather, these embodiments are provided so that this disclosure will be thorough and complete, and will convey the scope of the invention to those skilled in the art.

1.1 Definitions

The terminology used in the description of the invention herein is for the purpose of describing particular embodiments only and is not intended to be limiting of the invention. As used in the description of the embodiments of the invention and the appended claims, the singular forms "a," "an" and "the" are intended to include the plural forms as well, unless the context clearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention belongs.

As used herein, the term "enzyme" or "enzymes" refers to a protein catalyst capable of catalyzing a reaction. Herein, the term does not mean only an isolated enzyme, but also includes a host cell expressing that enzyme. Accordingly, the conversion of A to B by enzyme C should also be construed to encompass the conversion of A to B by a host cell expressing enzyme C.

As used herein, the term "difunctional C7 alkane" refers to straight or branched, saturated or unsaturated, hydrocarbon having seven carbon atoms and two functional groups. The functional groups may be positioned at any point along the hydrocarbon chain. In some embodiments, the functional groups are located at the terminal ends of the hydrocarbon chain (e.g., one functional group at each terminus). The term is also intended to encompass cyclic compounds such as enantholactam. Exemplary difunctional C7 alkanes include, but are not limited to, pimeloyl-CoA, pimeloyl-[acp], heptane-1,7-dioic acid (pimelic acid or pimelate), 7-aminoheptanoic acid, 7-hydroxyheptanoic acid, heptamethylenediamine, 1,7-heptanediol, 7-aminoheptanol, 7-aminoheptanal, enantholactam, pimelic acid semialdehyde (also known as 7-oxoheptanoate), 2-heptenediacid, and 2-heptene diacid-CoA.

As used herein, the terms "-oate" and "-oic acid", for example heptanoate and heptanoic acid, are used interchangeably. Moreover, it should be understood that "-ate", "-oate" and "-oic acid" can be used interchangeably throughout to refer to the compound in any of its neutral or ionized forms, and so-called "zwitterionic" forms.

As used herein, the term "trifunctional C7 alkane" refers to straight or branched, saturated or unsaturated, hydrocarbon having seven carbon atoms and three functional groups. The functional groups may be positioned at any point along the hydrocarbon chain. In some embodiments, two of the three functional groups are located at the terminal ends of the hydrocarbon (e.g., one functional group at each terminus). Exemplary trifunctional C7 alkanes include, but are not limited to, 2-oxopimelate (α-ketopimelate), 2-aminopimelate α-aminopimelate), 2-hydroxypimelate (α-hydroxypimelate), and 2-hydroxypimelate-CoA α-hydroxypimelate-CoA).

As used herein, the term "functional group" refers to an amine group, a carboxylic acid group, an aldehyde group, an alcohol group, a co-enzyme A group or a keto group. The term "amine group" refers to the radical —NH2. The term "carboxylic acid group" refers to the radical —COOH. The term "aldehyde group" refers to the radical —C(O)H. The term "alcohol group" refers to the radical —OH. The term "keto group" refers to the radical C(O).

The term "co-enzyme A group" refers to the organic cofactor, or prosthetic group (nonprotein portion of an enzyme), whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

The term "acp" or "acyl carrier protein" refers to a protein (which typically is active in fatty acid synthesis) that picks up acetyl and malonyl groups from acetyl coenzyme A and malonyl coenzyme A and links them by condensation to form β-keto acid acyl carrier protein, releasing carbon dioxide and the sulfhydryl form of the acyl carrier protein.

The functional groups on a di- or trifunctional C7 alkane can be the same or different. For example, in some embodiments with a difunctional C7 alkane, both functional groups can be amine groups, both functional groups can be carboxylic acid groups, or both functional groups can be alcohol groups.

In some embodiments, one of the functional groups on a difunctional C7 alkane is an amine group and the other is a carboxylic acid group. In some embodiments, one of the functional groups on a difunctional C7 alkane is an alcohol group and the other is a carboxylic acid group. In some embodiments, one of the functional groups on a difunctional C7 alkane is an alcohol group and the other is an amine group.

In some embodiments with a trifunctional C7 alkane, two of the functional groups are carboxylic acid groups and one functional group is a keto group or a hydroxyl group or an amino group.

The term "heterologous" is used herein to refer to any nucleic acid or polypeptide, that is not derived from a cell of the same species as the host cell. Accordingly, as used herein, "homologous" nucleic acids or proteins are those that occur in, or are produced by, a cell of the same species as the host cell.

The term "exogenous" as used herein with reference to nucleic acid and a particular host cell refers to any nucleic acid that does not occur in (and cannot be obtained from)

that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast y.

It will be clear from the above that "exogenous" nucleic acids can be "homologous" or "heterologous" nucleic acids. In contrast, the term "endogenous" as used herein with reference to nucleic acids or genes (or proteins encoded by the nucleic acids or genes) and a particular cell refers to any nucleic acid or gene that does occur in (and can be obtained from) that particular cell as found in nature.

As used herein, the term "recombinant host" refer to a host, the genome of which has been augmented by at least exogenous nucleic acid sequence. Such nucleic acid sequences include, but are not limited to, nucleic acids that are not naturally present in the host (i.e., a heterologous nucleic acid), DNA sequences that are not normally transcribed into RNA or translated into a protein ("expressed"), and other nucleic acid sequences which one desires to introduce into the non-recombinant host (e.g., a regulatory region to alter expression of a particular nucleic acid sequence). It will be appreciated that typically the genome of a recombinant host described herein is augmented through the stable introduction of one or more exogenous nucleic acids. Generally, the exogenous nucleic acid is not originally resident in the host that is the recipient of the DNA (i.e., it is a heterologous nucleic acid), but it is within the scope of the invention to isolate a nucleic acid from a given host, and to subsequently introduce one or more additional copies of that nucleic acid into the same host, e.g., to enhance production of an encoded product or alter the expression pattern of a nucleic acid. In some instances, the exogenous nucleic acid will modify or even replace an endogenous gene or DNA sequence by, e.g., homologous recombination or site-directed mutagenesis. Modification or replacement of an endogenous gene can result in a deficiency in a particular encoded product, e.g., an enzyme. Suitable recombinant hosts are described below. Recombinant hosts can also contain nucleic acids that are not incorporated into the genome of the host cell but exist (and preferably replicate) episomally in the cell.

As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. An enhancer, while typically at the 5' end of a coding region, can also be separate from a promoter sequence and can be, e.g., within an intronic region of a gene or 3' to the coding region of the gene.

As used herein, "operably linked" means incorporated into a genetic construct so that expression control sequences effectively control expression of a coding sequence of interest.

1.2 Feedstocks

A variety of different feedstocks can be used to produce di- or trifunctional alkanes. In some embodiments, a recombinant host cell, or a lysate prepared from a cell (e.g., a recombinant host cell), is contacted with a renewable feedstock to produce a di- or trifunctional C7 alkane, such as 7-aminoheptanoic acid. Examples of renewable feedstocks which may be used as a carbon source include, but are not limited to, cellulosic feedstocks, plant-derived carbohydrates and fatty acids. In some embodiments, the feedstock with which the recombinant host cell is contacted is glucose, sucrose, xylose, fatty acids or glycerol.

In addition to renewable feedstocks, such as those listed above, the recombinant host cell can be modified for growth on synthesis gas, also known as SynGas, as a source of carbon. In this specific embodiment, the recombinant host cells of the invention are engineered to provide an efficient metabolic pathway for utilization of SynGas, or other gaseous carbon sources, to produce di- or trifunctional C7 alkanes.

Additionally, recombinant hosts described herein, or a lysate prepared from a recombinant host cell, can be contacted with an aromatic hydrocarbon feedstock. The use of aromatic hydrocarbon feedstocks, rather than renewable feedstocks, provides a way to convert such petroleum derived materials to compounds that are more benign to the environment, reducing environmental impact. Examples of suitable aromatic hydrocarbon feedstocks include, but are not limited to, toluene, benzene, benzoic acid and shikimate.

1.3. Routes to Difunctional C7 Alkanes Comprising Enzyme-Catalyzed Steps

As stated above, embodiments of the present invention relate to methods for producing di- or trifunctional C7 alkanes in the presence of one or more isolated enzymes, in the presence of a recombinant host cell expressing that/those enzyme(s), or in the presence of a cell lysate (or a partially purified lysate) of cell (e.g., recombinant cell) that expresses the enzyme(s). In some embodiments, the production of the di- or trifunctional C7 alkanes starts with pimelate or pimeloyl-CoA and proceeds through a common intermediate, namely, pimelic acid semialdehyde. Specifically, in some embodiments, the invention relates to a method of producing the difunctional C7 alkane 7-aminoheptanoic acid by using an enzyme that catalyzes the semialdehyde amination of pimelic acid semialdehyde to 7-aminoheptanoic acid. See FIG. 1. A semialdehyde aminotransferase such as an ω-transanimase can be used. Exemplary transaminases include, but are not limited to transaminases classified under EC 2.6.1 such as EC 2.6.1.18; EC 2.6.1.19; EC 2.6.1.2; EC 2.6.1.7; EC 2.6.1.29; EC 2.6.1.36; EC 2.6.1.39; EC 2.6.1.42; and EC 2.6.1.68. In some embodiments, the aminotransferase is β-alanine aminotransferase classified in EC 2.6.1.18 from *V. fluvialis, B. weihenstephanensis, P. aureginosa, B. subtilis,* or *P. syringae.* See WO2011/031147, which is incorporated herein in its entirety.

In some embodiments, 7-aminoheptanal can be produced using an enzyme that catalyzes the aldehyde dehydrogenation of 7-aminoheptanoic acid to 7-aminoheptanal. See, FIG. 1. An aldehyde dehydrogenases classified under EC 1.2.1, such as EC 1.2.1.4 or EC 1.2.1.63, can be used to produce 7-aminoheptanal from 7-aminoheptanoic acid.

In some embodiments, heptamethylenediamine (also known as 1,7-diaminoheptane) can be produced from 7-aminoheptanal using an enzyme that catalyzes the transfer of an amino group. See FIG. 1. Suitable aminotransferases include, but are not limited to, aminotransferases in EC 2.6.1 such as EC 2.6.1.18; EC 2.6.1.19; EC 2.6.1.2; EC 2.6.1.7; EC 2.6.1.29; EC 2.6.1.36; EC 2.6.1.39; EC 2.6.1.42; and EC 2.6.1.68. In some embodiments, the aminotransferase is β-alanine aminotransferase classified in EC 2.6.1.18 from *V. fluvialis, B. weihenstephanensis, P. aureginosa, B. subtilis,* or *P. syringae.* See WO2011/031147, which is incorporated herein in its entirety.

In some embodiments, enantholactam can be produced from 7-aminoheptanoic acid using an enzyme that catalyzes the amide hydrolysis of 7-aminoheptanoic acid. See, FIG. 1. Suitable amidohydrolases include amidotransferases classified under EC 3.5.2 such as EC 3.5.2.12 or EC 3.5.2.11 can be used.

In some embodiments, 7-hydroxyheptanoate is produced from pimelic acid semialdehyde or 7-aminoheptanol is produced from 7-aminoheptanal using an enzyme that catalyzes the reduction of an aldehyde. See FIG. 1. For example, an alcohol dehydrogenase classified under EC 1.1.1 such as EC 1.1.1.21 can be used.

In some embodiments, 1,7 heptanediol can be produced from 7-hydroxyheptanoate using an aldehyde dehydrogenase and an alcohol dehydrogenase. A suitable aldehyde dehydrogenase can be classified under EC 1.2.1 (e.g., EC 1.2.1.4). See, FIG. 1. A suitable alcohol dehydrogenase can be classified under E.C. 1.1.1. such as EC 1.1.1.1

In embodiments in which the C7 di- or trifunctional alkanes may be toxic to the host (e.g., semialdehydes such as 7-oxoheptanoate or 7-aminoheptanal), the conversion to the toxic compound can be performed in vitro using isolated enzymes or a lysate from the recombinant host. In some embodiments, the toxic compound is produced by the host and then subsequently converted (using isolated enzymes, a recombinant host expressing an enzyme, or chemically converted) to enantholactam.

1.5 Biosynthetic Pathways to Pimelate and/or Pimeloyl-CoA

Pimelate and/or pimeloyl-CoA can be obtained via a number of different ways including: (i) α-ketosuberate produced from the α-keto acid chain elongation pathway, or (ii) the biotin biosynthesis pathway I; (iii) biotin biosynthesis pathway II; (iv) the condensation of three malonyl-CoA molecules into a single pimeloyl-CoA molecule; (v) the benzoate degradation pathway; (vi) cyclohexane carboxylate pathway, (vi) D,L-diaminopimelate pathway; and (vii) a biosynthetic pathway where the starting carbon source is crotonate. See FIG. 2. These pathways to pimelate and/or pimeloyl-CoA are described in greater detail below.

In any of these pathways, pimelate can be produced from pimeloyl-CoA using an enzyme that catalyzes the hydrolysis of a thioester. For example, enzymes that can hydrolyze a thioester include, but are not limited to, thioesterases, acid-thiol ligases, and CoA transferases. Suitable thioesterases include thioesterases classified in EC 3.1.2 such as EC 3.1.2.18; EC 3.1.2.19; or EC 3.1.2.20. For example, one of the following enzymes can be used: a thioester hydrolases/acyl-CoA thioesterase classified in EC 3.1.2 such as an ADP-dependent medium-chain-acyl-CoA hydrolase in EC 3.1.2.19 and 3.1.2.18, an acyl-CoA hydrolase in EC 3.1.2.20; or a hydrolase in EC 3.1.2.3. Suitable acid-thiol ligases include acid-thiol ligases classified in EC 6.2.1 such as EC 6.2.1.3; EC 6.2.1.14; and EC 6.2.1.23. Suitable CoA transferases include CoA transferases classified under EC 2.8.3 such as EC 2.8.3.6, EC 2.8.3.8, EC 2.8.3.12 or EC 2.8.3.13.

Heptane-1,7-dioic acid can be obtained from pimeloyl-[acp] by the use of enzymes acting on [acp]-thioesters, such as EC 2.3.1.38 ([acyl-carrier-protein] S-acetyltransferase) or hydrolases in EC 3.1.2.14, such as fatA and fatB. Alternatively, pimelic acid can be obtained form pimeloyl-[acp] methyl ester by hydrolysis of the ester bond by AaasaS (acyl-ACP synthetase), followed by removal of the methyl group by a lipase/esterase.

Pimelate can be transformed to pimelic acid semialdehyde using an enzyme that catalyzes the reduction of a carboxylic acid. Suitable reductases include, but are not limited to, carboxylic acid reductases classified in EC 1.2.99 or fatty acyl-CoA reductases classified in EC 1.2.1 such as EC 1.2.1.50. In some embodiments, a fatty-acyl-CoA reductase can directly convert pimeloyl-CoA or pimeloyl-[acp] to pimelic acid semialdehyde. Exemplary carbonyl reductases in EC 1.2.99 include, but are not limited to EC 1.2.99.6 from *Norcardia* sp. (Aimin et al., *Appl. Environ. Microbiol.* 70: 1874-1881 (2004), incorporated by reference) or *S. griseus* (Suzuki et al., *J. Antibiot.* (Tokyo) 60: 380-387 (2007) incorporated by reference). Exemplary carbonyl reductases in EC 1.2.1 include, but are not limited to EC 1.2.1.75 from, e.g., *C. aurantiacus* (Bugler, M, et al., *J Bacteriology* 184: 2404-2410 (2002), incorporated by reference), M sedula (Kockelkorn, D. and Fuchs, G., *J. Bacteriology* 191: 6352-6362 (2009), incorporated by reference), or *S. tokodai* (Alber, B. et al., *J. Bacteriology* 188: 8551-8559 (2006), incorporated by reference); and 1.2.1.50 from, e.g., *Acinetobacter* sp., *A. platyrhynchos* (Ishige, T., et al., *Appl. Envtl. Microbiology* 68: 1192-1195 (2002), incorporated by reference), *A. thaliana* (Doan, T. T., et al., *Journal Plant Physiology* 166: 787-796 (2009) and Hooks, M. A., et al., *Plant J.* 20:1-13 (1999), both of which are incorporated by reference); *Homo sapiens* (McAndrew, R. P. et al., *J. Biol. Chem.* 283: 9435-9443 (2008), incorporated by reference), *M. Musculis, P. leiognathi, P. phosphoreum, P. sativum,* or *S. chinesis.*

1.5.1 α-Keto Acid Chain Elongation

Difunctional alkanes can be produced from α-ketoglutarate via successive chain elongation reactions to α-ketoadipate, α-ketopimelate or α-ketosuberate known in the art. See, e.g., FIG. 3 and WO2010/068944. Decarboxylation of the α-keto dioic acid (Cn, n=5-8) or the corresponding 2-amino-dioic acid then provides precursors to α,ω-difunctional alkanes of Cn-1, e.g., $C_{4-7}$. These successive alpha-keto acid chain elongation reactions occur in the Coenzyme B biosynthesis pathway as elucidated in methanogenic bacteria such as *Methanocaldococcus jannaschii, Methanococcus voltae,* and *Methanosarcina thermophila.*

The three successive rounds of chain elongation from α-ketoglutarate (C5) to α-ketosuberate are catalyzed by the same three enzymes acting three times (and in the case of EC 4.2.1.114 (AksD (3-isopropylmalate dehydratase large subunit)/AksE (3-isopropylmalate dehydratase small subunit)) six times) on substrates, each time increasing chain length. See FIG. 3. These enzymes include, but are not limited to:

EC 2.3.3.14:homocitrate synthase/AksA (alpha-isopropylmalate synthase), which acts on α-ketoglutarate, α-ketoadipate, and α-ketopimelate; EC 4.2.1.114: homoaconitase or AksD/AksE, which catalyzes the dehydration reactions of (R)-homocitrate, dihomocitrate and trihomocitrate, as well as the hydration reactions of cis-homoaconitate, cis-(homo)$_2$ aconitate and cis-(homo)$_3$aconitate; and EC 1.1.1.87: homoisocitrate dehydrogenase or AksF (multifunctional 3-isopropylmalate dehydrogenase/D-malate dehydrogenase_, which catalyzes the NAD(P)+ dependent oxidative decarboxylation of homoisocitrate, threo-iso(homo)$_2$citrate and threo-iso(homo)$_3$citrate.

Exemplary AksA enzymes include, but are not limited to, those in EC 2.3.3 such as EC 2.3.13 or 2.3.3.14. Exemplary AksD enzymes include those in EC 4.2.1 such as EC 4.2.1.33. Exemplary AksF enzymes include, but are not limited to enzymes in EC 1.1.1 such as EC 1.1.1.85.

In some embodiments, the chain elongation enzyme is AksA MTH1630, AksD MTH1631, AksE MTH0829 or AksF MTH1388. See, e.g., WO2010/104391, which is incorporated by reference herein.

The advantage of this pathway is that it only requires the recombinant expression of three heterologous proteins in a host. Chain elongation from α-ketoglutarate to α-ketoadipate also occur in the lysine biosynthesis V pathway of archae, including *Aeropyrum pernix, Deinococcus radiodurans, Pyrococcus abyssi, Pyrococcus horikoshii, Sulfolobus solfataricus, Sulfolobus tokodaii,* and *Thermus thermophilus*; and in the lysine biosynthesis IV pathway of yeast and fungi including *Euglena gracilis, Aspergillus, Penicillium chrysogenum* and *Saccharomyces cerevisiae*.

In the lysine biosynthesis IV and V pathways, the reactions from α-ketoglutarate to α-ketoadipate are catalyzed by the consecutive action of four enzymes, namely: EC 2.3.3.14: homocitrate synthase (hcs/LYS20/LYS21/nifV); EC 4.2.1.114: methanogen HACN; EC 4.2.1.36: homoaconitase hydratase; and EC 1.1.1.87-homoisocitrate dehydrogenase (hicDH or LYS12).

1.5.3 Malonyl-CoA Condensation Pathway

In some embodiments, malonyl-CoA can be used as the source of pimeloyl-CoA as certain organisms are able to condense three malonyl-CoA molecules into a single pimeloyl-CoA molecule. See FIG. 4. See also Lin, S, and Cronan, J. E., *Molecular Biosystems* 7: 1811-21 (2011), which is incorporated by reference herein. Accordingly, a recombinant host can be produced in which pimeloyl-CoA is produced from malonyl-CoA. In some embodiments, the host cell is an organism other than *Achromobacter*. In some embodiments, the pimeloyl-CoA may be subsequently converted to pimelic acid or other difunctional C7 alkanes.

1.5.4 Biotin Biosynthesis Pathways I (Gram Negative Bacteria) and II (Gram Positive Bacteria)

In one embodiment, a recombinant host cell produces pimelic acid and/or pimeloyl-[acp] from acetyl-CoA derived from glycerol and/or fatty acids. See, e.g., Lin, S., *Nature Chem. Biol.* 6: 682-688 (2010); and Cronan, J. E. and Lin, S., *Current Opinion in Chem. Biology* 15: 1-7 (2011), both of which are incorporated by reference herein. FIG. 5 shows formation of pimeloyl-CoA from pimelic acid or other precursors in biotin biosynthesis II (gram positive bacteria). FIG. 6 shows formation of pimelyl-[acp] or its methyl esters in biotin biosynthesis I (gram negative bacteria). FIG. 6 also shows pathways for the conversion of pimeloyl-[acp] methyl ester into pimelate monomethyl ester. The pimelate monomethyl ester is subsequently converted to pimelic acid (heptane-1,7-dioic acid) in the presence of, e.g., a lipase in EC 3.1.1. FIG. 6 also shows the conversion of pimeloyl-[acp] methyl ester into pimeloyl-[acp] in the presence of an esterase (e.g., an enzyme in EC 3.1.1, such as EC 3.1.1.85, BioH). The pimeloyl-[acp] is subsequently converted into pimelic acid (heptane-1,7-dioic acid) in the presence of a thioesterase, e.g., an enzyme in EC 3.1.2.14, such as FatA or FatB. In some embodiments, the invention contemplates a recombinant host cell capable of producing pimelic acid (heptane-1,7-dioic acid) that comprises one or all of the enzymes shown in FIG. 6. In some embodiments, the recombinant host cell does has a deficiency in 7-keto-8-aminopelargonic acid synthetase, an enzyme capable of converting 6-carboxyhexanoyl-CoA (pimeloyl-CoA) into 7-keto-8-aminopelargonic acid (KAPA), and encoded by the BioF gene in host organisms with a native biotin biosynthesis pathway so that the pimeloyl-CoA cannot be shuttled into biotin biosynthesis.

Pimeloyl-[acp] methyl ester can also be produced as a result of the metabolism of long-chain acyl-[acp] and/or free fatty acids by BioI (for example BioI from *Bacillus subtilis*).

1.5.5 Eukaryotic Biosynthesis Pathway

Pimelic acid and/or pimeloyl-CoA can also be obtained from eukaryotic biotin biosynthesis pathways. See, e.g., Roje, S., *Phytochemistry* 68: 1904-1921 (2007); and Charles R. Hall, The Contribution of Horizontal Gene Transfer to the Evolution of Fungi (May 10, 2007) (unpublished Ph.D. dissertation, Duke University) (on file with Duke University Libraries), both of which are incorporated by reference herein. In the eukaryotic pathway, acetyl-CoA is biotransformed to acetoacetyl CoA using an enzyme classified under EC 2.3.1.9; acetoacetyl-CoA is biotransformed into (S)-3-hydroxybutanoyl-CoA using an enzyme classified under E.C. 1.1.1.157; (S)-3-hydroxybutanoyl-CoA is biotransfored to crotonyl-CoA using an enzyme classified under EC 4.2.1.17; crotonyl-CoA is biotransformed into glutaconyl-1-CoA using an enzyme classified under EC 4.1.1.70; glutaconyl-1-CoA is biotransformed to glutaryl-CoA using an enzyme classified under EC 1.3.99.7; glutaryl-CoA is biotranformed into 3-ketopimelyl-CoA using an enzyme classified under EC 2.3.1.43; 3-ketopimelyl-CoA is biotransformed into 3-hydroxypimelyl-CoA using an enzyme classified under EC 1.1.1.4259; 3-hydroxypimelyl-CoA is biotransformed into 2,3-didehydro-pimeloyl-CoA using an enzyme classified under EC 4.2.1.-, and 2,3-didehydropimeloyl-CoA is biotransformed into pimeloyl-CoA using an enzyme classified under EC 1.3.1.62. The pimeloyl-CoA is subsequently transformed into pimelic acid.

In some embodiments, acetyl-CoA can be fed into the tricarboxylic acid (TCA) cycle, in which acetyl-CoA is transformed into succinic acid (butan-1,4-dioic acid). The succinic acid is then diverted from the TCA cycle into a pathway for synthesizing pimelic acid starting with the biotransformation of 2-oxoglutarate into 2-hydroxy-1,2,4-butanetricarboxylic acid (homocitrate) (e.g., by an enzyme in EC 2.3.3.14); biotransformation of homocitrate to homo cis aconitase and homo cis aconitase to homoisocitrate using an enzyme classified under EC 4.2.1.36; biotransformation of homoisocitrate to oxaloglutarate using an enzyme classified under EC 1.1.1.87; biotransformation of oxaloglutarate to 2-oxoadipate using an enzyme classified under EC 1.1.1.87, and biotransformation of 2-oxoadipate to glutaryl-CoA using an enzyme classified under EC 1.2.4.2. Glutaryl-CoA can be converted to pomeloyl-CoA as discussed above. The homocitrate is ultimately converted to pimeloyl-CoA and, subsequently, into pimelic acid as described herein.

Thus, in some embodiments, the invention provides a recombinant host cell comprising the enzymes for converting acetyl CoA into heptane-1,7-dioic acid. In some embodiments, the recombinant host cell has a deficiency in 7-keto-8-aminopelargonic acid synthetase, an enzyme capable of converting 6-carboxyhexanoyl-CoA (pimeloyl-CoA) into 7-keto-8-aminopelargonic acid (KAPA), and encoded by the BioF gene in the host, if the host organisms has a native biotin biosynthesis pathway, so that the pimeloyl-CoA cannot be shuttled into biotin biosynthesis. The embodiments of the invention also provide a method of producing heptane-1,7-dioic acid comprising the use of such recombinant host cells.

1.5.6 Benzoyl-CoA Degradation Pathway

One additional source of pimeloyl-CoA and/or pimelic acid contemplated herein is the benzoate degradation pathway shown in FIG. 7. See, e.g., Bernsteinb, J. R., et al., *Metabolic Eng'g* 10: 131-140 (2008); Harwood, C. S., et al., *FEMS Microbiology Reviews* 22: 439-458 (1999); and Harrison, F. H. and Harwood, C. S., *Microbiology* 151: 727-736 (2005), all of which are incorporated by reference herein. A number of transformations are illustrated in FIG. 7, where benzoate is converted into benzoyl-CoA using an enzyme classified under EC 6.2.1.25, and ultimately into pimeloyl-CoA. Benzoyl-CoA is converted to cyclohexa-1,5-dienecarbonyl CoA using an enzyme classified under EC 1.3.99.15. In some embodiments, cyclohexa-1,5-dienecarbonyl CoA is biotransformed to 6-hydroxycyclohex-1-ene-1-carboxyl-CoA using an enzyme classified under EC 4.2.1.100; 6-hydroxycyclohex-1-ene-1-carboxyl-CoA is biotransformed to 6-ketoxycyclohex-1-ene-1-carboxyl-CoA using an enzyme classified under EC 1.1.1.-; 6-ketoxycyclohex-1-ene-1-carboxyl-CoA is biotransformed to 3-hydroxypimelyl-CoA using an enzyme classified under EC 3.7.1.-; 3-hydroxypimelyl-CoA is biotransformed to 6-carboxylhex-2-enoyl-CoA using an enzyme classified under EC 4.2.1.-; 3-hydroxypimelyl-CoA is biotransformed to pomelyol-CoA using an enzyme classified under EC 1.3.1.62. The pimeloyl-CoA, in turn, is converted into pimelic acid (heptane-1,7-dioic acid). In some embodiments, cyclohexa-1,5-dienecarbonyl CoA is biotransformed to cyclohex-1-ene-1-carboxyl-CoA, cyclohex-1-ene-1-carboxyl-CoA is biotransformed to 2-hydroxycyclohexane-1-carboxyl CoA using an enzyme classified under EC 4.2.1.-; 2-hydroxycyclohexane-1-carboxyl CoA is biotransformed to 2-ketocyclohexane-1-carboxyl-CoA using an enzyme classified under E.C. 1.1.1.-, and 2-ketocyclohexanecarboxyl-CoA is biotransformed to pimeloyl-CoA using an enzyme classified under EC 3.1.2.-_ (e.g., a-ketocyclohexanecarboxyl-CoA hydrolase Rp-badl, an enzyme classified under EC 3.1.2.-).

In some embodiments, the recombinant host cell capable of producing heptane-1,7-dioic acid includes one or more of the enzymes listed in FIG. 7 or in this section.

1.5.7 2,6-Diaminopimelate Pathway

Yet another source of pimelate is D,L diaminopimelate, also known as 2,6-diaminopimelate. D,L-diaminopimelate is an intermediate in the production of lysine. In some embodiments, an endogenous lysine pathway can be modified to preferentially produce pimelate by creating recombinant host cells that have a deficiency in diaminopimilate decarboxylase., See, e.g., FIG. 10. The D,L diaminopimelate can be biotransformed into an unsaturated monoaminopimelic acid by an enzyme that catalyzes the reductive deamination of D,L diaminopimelate to 6-amino-2-heptenedioic acid. Examples of enzymes that catalyze reductive deamination of D,L diaminopimilate include ammonia lyases classified in EC 4.3.1 such as EC 4.3.1.1; EC 4.3.1.2; EC 4.3.1.3; EC 4.3.1.12; EC 4.3.1.13; and EC 4.3.1.24. In some embodiments, the ammonia lyase is a methyl aspartate ammonia lyase classified under EC 4.3.1.2 from *C. ama-lonaticus, C. tetanomorphum* or *A. oryzae*. See, e.g., Botting, *Biochemistry* 27: 2953-2955 (1988); and Kato, *Appl. Microbial. Biotechnol.* 50: 468-474 (1998), the entireties of which are incorporated by reference herein.

6-amino-2-heptenedioic acid can be biotransformed into 2-amino-2-heptenedioic acid using an enzyme that catalyzes the enoate reduction of 6-amino-2-heptenedioic acid to 2-amino-2-heptanedioic acid (also known as 2-aminopimelic acid or alpha aminopimelate). Examples of enzymes that catalyze the enoate reduction of 6-amino-2-heptenedioic acid include enoate reductases classified in EC 1.3.1 such as EC 1.3.1.31. In some embodiments, the enoate reductase is YqjM or OPR1/3 in EC 1.3.1.31 from *B. subtilis* or *L. esculentum*, respectively. See, e.g., Stueckler, *Org. Lett.* 9: 5409-5411 (2007); Kitzing, *J. Biol. Chem.* 280: 27904-27913 (2005); Hall, *Angew. Chem. Int. Ed.* 46: 3934-3937 (2007); and Breithaupt, *Proc. Natl. Acad. Sci. USA* 103: 14337-14342 (2006), the entireties of which are incorporated by reference herein.

The 2-aminopimelic acid can be converted to the corresponding 2-heptenedioic acid (also known as 2,3-didehydropimelic acid) by an enzyme that catalyzes the reductive deamination of 2-aminopimelic acid. Examples of enzymes that catalyze reductive deamination of 2-aminopimelic acid include ammonia lyases classified in EC 4.3.1 such as EC 4.3.1.1; EC 4.3.1.2; EC 4.3.1.3; EC 4.3.1.12; EC 4.3.1.13; or EC 4.3.1.24 as described above. The 2-heptene dioic acid can be transformed to 2-heptene dioic acid CoA using a CoA transferase (e.g., a CoA transferase classified in EC2.8.3 such EC 2.8.3.12 or EC 2.8.3.13) and an acid thiol ligase (e.g., an acid-thiol ligases classified n EC 6.2.1 such as EC 6.2.1.3; EC 6.2.1.14; or EC 6.2.1.23).

2-heptene dioic acid CoA is then converted to pimelate-CoA by an enzyme that catalyzes the enoate reduction of 2-heptene dioic acid such as an enoate reductase enzyme classified in EC 1.3.1. Pimelate-CoA can be converted to pimelate as described above.

Figure 3:
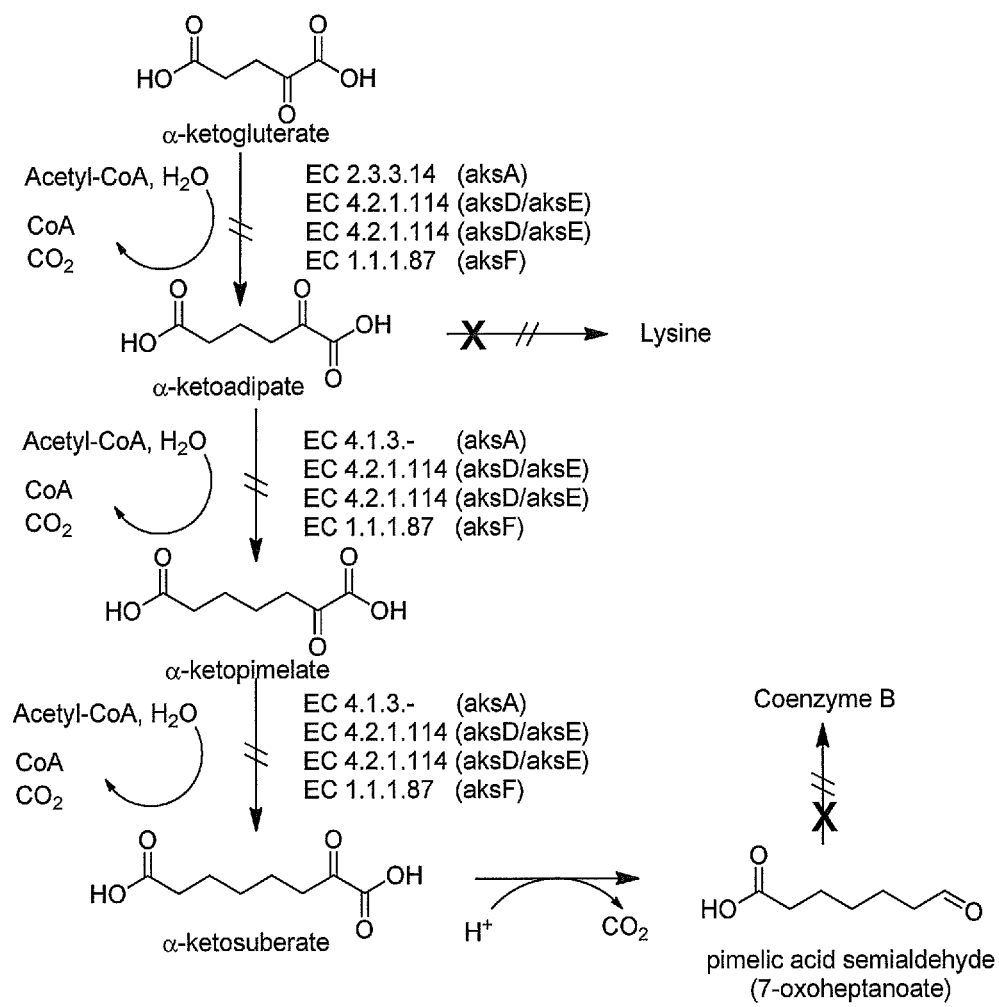
FIG. 3 is a schematic of the series of reactions in α-ketoacid chain elongation. Three basic reactions are involved: a condensation between an α-ketodiacid and acetyl-CoA to form a citrate homolog, isomerization of the citrate homolog to an isocitrate homolog, and oxidative decarboxylation of the isocitrate homolog to an α-ketodiacid containing an additional methylene group [Howell98: Howell D M, Harich K, Xu H, White RH (1998). Alpha-keto acid chain elongation reactions involved in the biosynthesis of coenzyme B (7-mercaptoheptanoyl threonine phosphate) in methanogenic Archaea." Biochemistry 1998; 37(28); 10108-17.]

As shown in FIG. 10 and in FIG. 3, a keto pimelate also can undergo one round of chain elongation to α-ketosuberate, which can either be decarboxylated to form pimelic acid semialdehyde, or converted to α-aminosuberate, which will lead directly to 7-aminoheptanoic acid upon decarboxylation. Exemplary decarboxylases include those in EC 4.1.1 such as EC 4.1.1.11; EC 4.1.1.15; EC 4.1.1.17; EC 4.1.1.18; EC 4.1.1.19; EC 4.1.1.20 and EC 4.1.1.86. In some embodiments, the decarboxylase comprises ketoisovalerate decarboxylase kivD in EC 4.1.1.1 from *L. lactis*; benzoylformate decarboxylase mdIC A460I or BFD in EC4.1.1.7 from *P. putida*; pyruvate decarboxylase isozymes 1 and 2 Pdc1 in EC 4.1.1.1 from *S. cereivisae*; pyruvate decarboxylase Pdc (I472A) from *Z. mobilis*; or branched chain alpha-keto acid decarboxylase kdcA in EC 4.1.1.72 from *L. lactis*, as described in WO2011/031147, the entirety of which is incorporated by reference herein.

The α-amino suberate can be converted to 7-aminoheptanoic acid using chain elongation enzymes, such as those present in methanogenic bacteria (e.g., *Methanobacterium autotrophicum*). Such chain elongation enzymes include, but are not limited to AksA, AksD, and AksE or F as discussed above. Exemplary AksA enzymes include, but are not limited to, those in EC 2.3.3. Exemplary enzymes in EC 2.3.3 include, but are not limited to EC 2.3.13 or 2.3.3.14. Exemplary AksD enzymes include those in EC 4.2.1. An exemplary enzyme in EC 4.2.1 includes, but is not limited to EC 4.2.1.33. Exemplary AksF enzymes include, but are not limited to enzymes in EC 1.1.1. An exemplary enzyme in EC 1.1.1 includes, but is not limited to EC 1.1.1.85. And, in this instance, the fourth set of enzymes comprises a decarboxylase. Exemplary decarboxylases include those in EC 4.1.1. Exemplary decarboxylases in EC 4.1.1 include, but are not limited to EC 4.1.1.11; EC 4.1.1.15; EC 4.1.1.17; EC 4.1.1.18; EC 4.1.1.19; EC 4.1.1.20 and EC 4.1.1.86.

In one embodiment, α keto pimelate can be contacted with one or more enzymes that catalyze the ketone reduction to α hydroxypimelate (e.g., a carbonyl reductase such as EC1.1.1.184), which in turn can be converted to α-hydroxypimelate CoA using an enzyme that catalyzes the transfer of CoA (e.g., a CoA transferase described above). The α-hydroxypimelate CoA can be converted to 2-heptene dioic acid CoA with an enzyme that catalyzes the dehydration of the α-hydroxypimelate-CoA (e.g., a hydrolyase classified under EC 4.2.1. such as EC 4.2.1.2, EC 4.2.1.59, EC 4.2.1.61). The 2-heptene dioic acid CoA can be converted to pimelic CoA using an enzyme that catalyzes the enoate reduction of 2-heptene dioic acid CoA. Suitable enoate reductases are described above.

In some embodiments, the invention provides a recombinant host cell comprising one or more enzymes necessary to convert D,L-diaminopimelate preferentially to pimelate.

1.5.8 Crotonate Pathway

A source of pimeloyl-CoA, and ultimately a source of pimelate, is a biosynthetic pathway where the starting carbon source is crotonate. That biosynthetic pathway is illustrated in FIG. 9. See, e.g., Mouttaki, H., et al., *Applied Envtl. Microbiology* 73: 930-938 (2001). The crotonate is broken down to acetyl-CoA. It has been reported that two thirds of the acetyl-CoA produced in the biosynthetic pathway shown in FIG. 9 is transformed into acetate. In some embodiments, the invention provides a recombinant host cell that is deficient in the enzymes that would convert acetyl-CoA into acetate (e.g., a phosphate acetyltransferase and acetate kinase such that the acetyl-CoA is instead converted to acetoacetyl-CoA and subsequently to glutaconyl-CoA in a number of metabolic steps as shown in FIG. 9. The glutaconyl-CoA is subsequently converted to glutaryl-CoA. The glutaryl-CoA is chain-extended to form 3-oxopimelyl-CoA. Following a reduction, dehydration, and a second reduction, pimelyl-CoA is obtained.

In the biosynthetic pathway shown in FIG. 9, the pimelyl-CoA is ultimately transformed into cyclohexane carboxylate. Such a biosynthetic pathway has been observed in *S. aciditrophicus*. Thus, in some embodiments, the invention provides a recombinant host cell in which the genes encoding the enzymes that would convert pimeloyl-CoA into cyclohex-1-ene-1-carboxyl-CoA and ultimately into cyclohexane carboxylate, are "knocked out", such that the metabolic pathway ends at pimeloyl-CoA.

1.5.9 Tetralin Degradation Pathway

In some embodiments, pimelic acid semialdehyde is produced using the tetralin (benzocyclohexane) degradation pathway from *Sphingomonas* and *Corynebacterium* spp. 7-oxoheptanoic acid is produced as an intermediate is the tetralin degradation pathway in *Sphingomonas macrogolitabid*. López-Sánchez, A., et al., *Appl. Environ. Microbiol.* 76:110-118 (2010). Tetralin is metabolized by cleavage of both aromatic rings yielding pyruvate and pimelic acid semialdehyde. Tetralin, an organic solvent, is a complex starting material that is derived from naphthalene. Naphthalene is currently produced from coal tar, but biosynthetic pathways for naphthalene synthesis are known to occur in termites, fungi and some types of plants. Chen, J. et al., *Nature* 392: 558-559 (1998); Daisy, B. H., et al., *Microbiology* 148: 3737-3741 (2002); and Azuma, H., et al., *Phytochemistry* 42: 999-1004 (1996). Pimelic acid semialdehyde can be converted to 7-amino heptanoic acid or 7-hydroxyheptanoic acid as discussed above.

1.11 Hexamethylenediamine from 2-oxopimelate

Some embodiments of the invention also provides a method of producing hexamethylenediamine from 2-oxopimelate comprising using recombinant host cells. 2-oxopimelate is a known intermediate in the Coenzyme B biosynthesis pathway in methanogenic Archae.

Thus the invention provides a recombinant host cell comprising: an enzyme capable of converting 2-oxopimelate into 2-aminopimelate (e.g., an aminotransferase enzyme in EC 2.6.1.67), an enzyme capable of converting 2-aminopimelate to 2-amino-7-oxoheptanoate (e.g., a reductase enzyme in EC 1.4.1), an enzyme capable of converting 2-amino-7-oxoheptanoate to 2,7-diaminoheptanoate (e.g., a 1-aminotransferase enzyme in EC 2.6.1), and an enzyme capable of converting 2,7-diaminoheptanoate to hexamethylenediamine (e.g., a decarboxylase enzyme in EC 4.1.1). In some embodiments, the recombinant host cell capable of producing hexamethylenediamine comprises any or all of these enzymes. Embodiments of the invention also provide a method of producing hexamethylenediamine comprising the use of these recombinant host cells.

In some embodiments, the invention provides a method for producing hexamethylenediamine from renewable feedstocks such as sugars, fatty acids, glycerol, and SynGas. In some embodiments, the non-naturally occurring host cell capable of producing hexamethylenediamine comprises any or all of the enzymes required to convert renewable feedstocks to hexamethylenediamine.

2.2 Recombinant Host Cells

This disclosure features recombinant host cells that recombinantly express one or more (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) of the enzymes used for producing a compound in one of the pathways described herein and methods of using such host cells to produce di- and trifunctional C7 alkanes. For example, a host cell can include one or more (as above) exogenous nucleic acids encoding one or more (as above) of the following: an enzyme that catalyzes the reductive deamination of D,L diaminopimelate or alpha-aminopimielate; an enzyme that catalyzes the enoate reduction of 2-heptenedioic acid to pimelic acid; an enzyme that catalyzes the carboxylic acid reduction of pimelic acid to pimelic acid semialdehyde, an enzyme that catalyzes the semialdehyde amination of pimelic acid semialdehyde to 7-aminoheptanoic acid, an enzyme that catalyzes the amido hydrolysis of 7-aminoheptanoic acid to enantholactam, an enzyme that catalyzes the aldehyde dehydrogenation of 7-aminoheptanoic acid to 7-aminoheptanal; an enzyme that catalyzes the transfer of an amino group to 7-aminoheptanal to produce 1,7-diaminoheptane; an enzyme that catalyzes the transfer of CoA to 2-heptenedioic acid to produce 2-heptene diacid-CoA; an enzyme that catalyzes the enoate reduction of 2-heptene dioic acid-CoA to pimeloyl-CoA; an enzyme that catalyzes the thioester hydrolysis of pimeloyl-CoA to produce pimelic acid; an enzyme that catalyzes the carboxylic acid reduction of pimelic acid to pimelic acid semialdehyde; an enzyme that catalyzes the transfer of an amino group from alpha amino pimelate to produce alpha keto pimelate; an enzyme that catalyzes the carbonyl reduction of alpha keto pimelate to alpha hydroxy pimelate; an enzyme that catalyzes the transfer of CoA to alpha hydroxy pimelate to produce alpha hydroxypimelate CoA; an enzyme that catalyzes the reduction of alpha hydroxypimelate to 2-heptenedioic acid; an enzyme that catalyzes the alpha keto acid chain elongation of alpha ketopimelate to alpha ketosuberate, an enzyme that catalyzes the transfer of an amino group to alpha ketosuberate to produce alpha-aminosuberate, an enzyme that catalyzes the alpha keto acid decarboxylation of alpha aminosuberate to 7-aminoheptanoic acid; an enzyme that catalyzes the alpha keto acid decarboylation of alpha ketosuberate to produce pimelic acid semialdehyde; an enzyme that catalyzes the enoate reduction of 6-amino-2-heptendioic acid to produce pimelic acid; or an enzyme that catalyzes the thioester hydrolysis of pimeloyl [ac[p] to pimelic acid. Recombinant host cells can contain any subgroup consisting of one or more (as above) nucleic acids encoding one or more of the above-listed enzymes.

The host cells that are used typically possess a number of properties: they may be easily genetically modified, are tolerant of the conditions used in the method of the invention, and grow to cells densities which are industrially useful.

Optionally the host cell may be a single celled microorganism, or may be a cell of a cell line. The host cell may be of a wild type genotype. In this instance, the enzyme that is used to catalyze one or more steps in the method of the invention is naturally present in the host cell and is expressed at a level that has industrial use in the methods of the invention. In an alternative, the host cell has been genetically modified to express the enzyme at a level that has industrial use in the methods of the embodiments of invention. The enzyme may be sourced from the cell in which it is expressed. In an alternative, the enzyme is sourced from a different strain or species of cell.

In one alternative, the host cell is a prokaryote. In another alternative it is a eukaryote. Typically single celled microorganisms are used.

The term prokaryotic cell includes gram positive and gram negative bacteria. Examples of suitable gram negative bacteria include *Escherichia coli, Rhodopseudomonas palustris, sphingomonads, pseudomonads*, and other bacteria belonging to *Corynebacterium, Salmonella, Burkholderia, Moraxella, Acaligenes, Psychrobacter, Thermotoga, Acinetobacteria, Rhodobacter, Azoarcus*, and *Rhodospirillum* genera. Examples of suitable gram positive bacteria include streptococci, lactobacilli, and other bacteria belonging to *Nocardia, Bacillus, Rhodococcus, Clostridium, Streptomyces*, and *Arthobacter* genera.

Eukaryotic host cells include those from yeast and other fungi, as well as, for example, insect, mouse, rat, primate, or human cells. Examples of suitable eukaryotic host cells include the yeasts *Yarrowia lipolytica, Candida* genera such as *Candida tropicalis, C. albicans, C. cloacae, C. guillermondii, C. intermedia, C. maltosa, C. parapsilosis, C. zeylenoides*, yeasts belonging to the *Rhodotorula, Rhizopus, Trichosporon*, and *Lipomyces* genera, and other fungi belonging to *Aspergillus*, Exophiala, *Mucor, Trichoderma, Cladosporium, Phanerochaete, Cladophialophora, Paecilomyces, Scedosporium*, and *Ophiostoma* genera.

The host cells may be provided in a variety of different forms. The cells may be resting cells. That is to say that the cells are grown up in cultures and removed from the culture medium before being employed as the biocatalyst. The cells may be used directly following growth, or they may be stored before use. Typical methods of storage include freezing. In an alternative, the cells are lyophilized prior to use. In a further alternative, the cells are growing cells. That is to say that the cells perform their biocatalytic action while being cultured. If the substrate for a particular biocatalytic reaction cannot cross the cell membrane to be transformed by host cells, then in one alternative, a crude lysate may be used. A crude lysate is the initial suspension of cellular components produced following lysis of the cells. Lysis of the cells may be performed by any means, including chemical or mechanical. Further methods of lysis will be evident to the skilled person in light of their general knowledge and the teachings herein. In another alternative, a clarified lysate may be used. A clarified lysate may be prepared by centrifuging the crude lysate to pellet unlysed cells and other cellular debris.

In some embodiments, substantially pure cultures of recombinant host cells are provided. As used herein, a "substantially pure culture" of a recombinant cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant cells, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of recombinant cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In one embodiment, the recombinant cells of this disclosure can be harvested from a fermentation process by conventional methods such as filtration or centrifugation and formulated into a dry pellet or dry powder formulation while maintaining high activity. Processes for production of a dry powder whole recombinant cell composition exhibiting one or more of the activities disclosed herein can include spray-drying, freeze-drying, fluidised bed drying, vacuum drum drying, or agglomeration and the like. The compositions can be a shelf-stable, dry biocatalyst composition suitable for the biosynthetic methods described herein. Drying methods such as freeze-drying, fluidised bed drying or a method employing extrusion/spheronisation pelleting followed by fluidised bed drying can be particularly useful. Temperatures for these processes may be <100° C. but typically <70° C. to maintain high residual activity and stereoselectivity. The dry powder formulation should have a water content of 0-10% w/w, typically 2-5% w/w. Stabilising additives such as salts (e.g. KCl), sugars, proteins and the like may be included to improve thermal tolerance or improve the drying characteristics of the recombinant cells during the drying process.

In some embodiments, partially or wholly purified enzymes may be used instead of or in combination with recombinant hosts or lysates of recombinant or non-recombinant cells. Wholly or partially purified enzymes can be wholly or partially purified lysates of any of the recombinant cells described here or non-recombinant cells. Methods of purification are well known in the art. Partial or complete purification has the advantage that the enzyme of interest is separated from other cellular components which may interfere with the reaction catalyzed by that enzyme (either by also reacting with the substrate or by converting intermediates or the desired product to an unwanted compound).

Purification does add further steps to any biocatalyst preparation, however, and therefore may not be suitable in all instances. The determination of the suitability of the use of partially or wholly purified enzymes will be well within the grasp of the skilled person following the teaching herein.

In some embodiments one or more of the conversions in the method of the invention will be performed by the biocatalyst under aerobic conditions. In an alternative one or more of the conversions in the method of the invention will be performed under anaerobic conditions. In a further alternative, some steps of the method of the invention will be performed under aerobic conditions and some steps will be performed under anaerobic conditions.

2.3 Modification of Whole Cell Biocatalysts

The biocatalysts used in the methods of the invention may be unmodified host cells of the species in which the enzyme naturally occurs. Typically, however, it is necessary to modify genetically the host cell to produce a non-naturally occurring (i.e., recombinant or engineered) host cell.

2.4 Chromosomal Modification of the Host Cell Genome

In some embodiments, the chromosome of the whole cell biocatalyst (i.e., the host cell) has been modified. This modification may be an insertion, a deletion or a substitution of a nucleic acid in the chromosome. Methods of effecting modifications to the chromosome of a cell are well known, e.g., transposon mutagenesis, Cre-Lox mediated recombination, lambda Red and RecET mediated recombination.

Stable integration into the chromosome of a nucleic acid is advantageous because it allows the maintenance of the nucleic acid without the need for a selectable marker.

By performing repeated insertions, it is possible to integrate stably a number of different nucleic acids into a host cell biocatalyst's chromosome. Stable integration means that the host cell can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

2.5 Episomal Modification of the Host Cell Biocatalyst's Genome

In some embodiments, the episomal composition of the host cell genome is modified. By episome is meant any autonomously replicating element, for example a plasmid (which may be linear or circular), a cosmid, a yeast artificial chromosome (YAC), etc. Episomal elements frequently place a metabolic load on their host cell, and accordingly, in the absence of any active partitioning mechanism to ensure that at least one copy of the episome is present in each daughter cell following cell division it is necessary to include a selectable marker.

2.6 Introduced Nucleic Acid Sequences

The nucleic acids introduced into the cell may comprise one or more (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) of a number of elements. Typically one of the elements encodes an enzyme that is used to produce di- or trifunctional C7 alkanes or precursors to such molecules. In some alternatives, the nucleic acid encodes a protein which is not an enzyme that functions in the method of the invention.

Typically, a promoter is operably linked to a nucleic acid. The choice of promoter will depend on the intended application, and can readily be determined by the skilled person. For example, if an enzyme catalyzed reaction may be detrimental to a particular host cell, it may be desirable to use a regulated or inducible promoter, such that gene expression can be turned on or off as necessary. Alternatively, it may be preferred to have expression driven by either a weak or strong constitutive promoter to ensure that the enzyme is expressed at all stages of growth. Exemplary promoters suitable for eukaryotic cell systems include the SV40 early promoter, the cytomegalovirus (CMV) promoter, the mouse mammary tumor virus (MMTV) steroid-inducible promoter, and the Moloney murineleukemia virus (MMLV) promoter. Exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Other suitable promoters in yeast are known to those skilled in the art. Exemplary promoters suitable for bacterial cell systems include but are not limited to: T7, T3, SP6, lac and trp promoters.

If necessary to ensure expression, the introduced nucleic acid also can be operably linked to comprise 5' untranslated region (UTR), 3' UTR, enhancer and/or teiminator regions, as required. Such elements will be known to the skilled person.

2.7 Expression of Multiple Enzymes in a Host Cell

In some embodiments, a single strain of host cell is used to express more than one (e.g., two or more; three or more; four or more; five or more; six or more; seven or more; eight or more; nine or more; ten or more; eleven or more; twelve or more; thirteen or more; fourteen or more; fifteen or more; sixteen or more; seventeen or more; eighteen or more; nineteen or more; twenty or more; or even more) of the enzymes used in the methods of the invention. In this instance, the multiple enzymes may be encoded by the same introduced nucleic acid. In an alternative, the enzymes may be encoded on separate introduced nucleic acid fragments. The enzymes may all be expressed from a single promoter (for example by arranging the enzymes in the form of an operon). In an alternative, the enzymes may be expressed from multiple separate promoters. In some instances, the multiple separate promoters may be induced by the same chemical (for example, each of the multiple enzymes may be expressed from the yeast GAL promoter, thus meaning that each gene is inducible with galactose). Other suitable promoters are known in the art. In an alternative, each of the genes encoding an enzyme used in the method of the invention is under the control of a different promoter. Thus, different enzymes can be introduced individually through the use of different inducing compounds. In another alternative, an intermediate approach is used, wherein a number of enzymes are under the control of the same promoter, and a number of enzymes are under the control of different promoters. This alternative may be particularly advantageous when numerous enzyme pathways have been generated in a host cell and it is desirous to control each member of a pathway in concert with the other pathway members, but to control each pathway separately.

Further considerations can be made with regard to whether the multiple enzymes are expressed from the chromosome or from the plasmid. In instances where the enzyme is expressed from the plasmid, advantageously each plasmid comprises a different origin and/or a different selectable marker.

The expression of multiple enzymes in a single cell is advantageous because, if the co-expressed enzymes act directly after one another in a reaction pathway, it ensures that the product of the upstream enzyme reaction is immediately available to be acted upon by the downstream enzyme. This avoids the need for either (i) purification of the intermediate and the setting up of second reaction vessel to perform the second reaction; or (ii) the need for the product to be exported from the cell comprising the upstream enzyme into the culture medium where it may be acted upon by a cell comprising the downstream enzyme.

2.8 Chaperone Systems

When a cell has been engineered to express a protein under non-natural conditions (for example, when a protein that is native to a species is expressed at levels above the natural level, or in an alternative, when a protein from a different species is expressed in a host cell) in some instances that protein will not be expressed in an active form. Instead it may fold incorrectly, and accumulate as a non-functional "inclusion body" aggregates. In this instance, the cells used to express the protein may be subjected to genetic modification to further express chaperone proteins which are able either to prevent the mis-folding of the protein, or are able to refold it from the aggregated state. The inclusion of such chaperone proteins is advantageous because it increases the quantity of active protein per cell, and therefore increases the overall efficiency of the method of the invention. The expressed chaperone may be a chaperone protein of the host cell. In an alternative, the chaperone may be from the same species/strain as the protein. Typical chaperone proteins for expression include members of the GroEL/GroES family, and members of the DnaJ/DnaK/GrpE family. Homologs of the archetypal *E. coli* GroEL/GroES and DnaJ/DnaK/GrpE proteins have been identified in other prokaryotic species (see, for example), and eukaryotic homologs are also known (GroEL and GroES correspond to the eukaryotic proteins Hsp60 and Hsp10, and DnaJ, DnaK and GrpE correspond to the eukaryotic proteins Hsp70, Hsp40 and Hsp24, respectively). These proteins have been identified in a number of species of yeast (for example, *Saccharomyces cerevisiae*). The choice of appropriate chaperone proteins for coexpression with an enzyme used in the method of the invention will be evident to the skilled person following the teachings herein.

2.9 Metabolic Engineering of Host Cells

Metabolic engineering is the process of optimizing the parameters in a host cell in order to increase the ability of a cell to produce a compound. The host cells used in the method of the present invention optionally have been engineered to optimize the output of the difunctional C7 alkanes discussed above.

Metabolic engineering to increase the ability of a cell to produce a compound is principally performed via two avenues. The first is to optimize the enzymes in the pathway producing the desired product from the starting material. In a multi-enzyme pathway resulting in the production of a difunctional C7 alkanes (as shown in the figures and described in the preceding sections), it is possible to determine the concentration of each intermediate in the pathway using techniques known to the skilled person (for example, two dimensional electrophoresis, the use of isotopically labeled precursors, and nuclear magnetic resonance (NMR) spectroscopy), and therefore determine which of the enzyme conversions is the rate limiting step—that is to say which step in the reaction scheme is the slowest. This can be determined by observing a build up of an intermediate, which indicates that the enzyme acting upon this intermediate is limiting the overall rate of conversion. In this instance, the rate at which this intermediate is reacted should therefore be increased. This can be performed by a number of means. Firstly, the expression level of the limiting enzyme may be increased. Optionally this may be achieved by placing the gene encoding the enzyme under the control of a strong promoter, e.g., the T7 promoter if the enzyme is being expressed in *E. coli* or the TEF promoter if the enzyme is being expressed in yeast. The second option is to increase the number of copies of the gene encoding the enzyme that are present in cell, for instance by placing the gene on a multicopy plasmid, or by incorporating multiple copies of the gene into the chromosome of the host cell (these copies may be incorporated at the same location in the chromosome or in different locations in the chromosome).

The production of difunctional C7 alkanes (as shown in the figures and described in the preceding sections) can also be increased by inactivating or reducing the activity of any enzymes which are capable of diverting the substrate, any of the intermediates, or the product into a metabolic pathway other than that which is the aim of the method. Therefore, the activity of the enzyme may be lowered to increase the yield of the difunctional C7 alkanes. Thus in some embodiments, the recombinant host cells disclosed herein can have a deficiency in one or more enzymes (e.g., by deleting the nucleic acid encoding an enzyme of interest or reducing expression of the nucleic acid) that are capable of diverting the starting material of the method of the invention, or any intermediates produced in the reaction pathway producing difunctional C7 alkanes, to a different, unwanted, end product. In an alternative, the enzyme is not deleted, but is instead altered so that it can acts against the substrate, intermediates, or product, at a rate that is less than the rate of the wild type enzyme. In the instance where the enzyme catalyses a reversible reaction, then the enzyme should be altered so that it acts only in the desired direction of reaction.

For example, in some embodiments, a recombinant host cell can have a deficiency in an enzyme capable of converting pimeloyl-[acp] into 7-keto-8-aminopelargonic acid (KAPA) or converting 6-carboxyhexanoyl-CoA (pimeloyl-CoA) into KAPA (e.g., a deletion or inactivation of BioF, the gene encoding 7-keto-8-aminopelargonic acid synthetase (E.C. 2.3.1.47).

In some embodiments, a recombinant host cell can have a deficiency in diaminopimilate decarboxylase, which creates a lysine auxotroph. A lysine auxotroph can be particularly useful for deregulating carbon flux to D,L diaminopimelate, the immediate precursor to lysine. A lysine auxotroph would require fed-batch fermentation.

2.10 Growing Whole Cell Biocatalysts

In some embodiments of the invention, host cells are used which are growing (L e., dividing) at the time the cells perform the conversions in the method of the invention. In these embodiments the cells are cultured under conditions which optimize the production of desired difunctional C7 alkane. Any of the recombinant host cells described herein can be cultured to produce and/or secrete the biosynthetic products of the invention. As used herein, the term culture is equivalent with fermentor and bioreactor.

2.10.1 Media

In some instances, the carbon source used for growth will be provided in the form of a nutrient broth, for example Luria medium or yeast extract medium. In other instances, a defined medium (that is to say, a medium in which the concentration of each component is known) appropriate for growth of the host cell may be used. In one alternative, the growth medium comprises glucose as a carbon source. In another alternative, the carbon source used by the host cells in the medium is glucose, sucrose, xylose, fatty acids and glycerol.

2.10.2 Growth of Multiple Strains in the Same Culture

In some embodiments, the enzymes which catalyze the conversions in the method of the invention are present in more than one strain/species of cell, wherein those more than one strain/species of cell are used simultaneously. In the instance where the multiple strains/species are growing when the conversions in the method of the invention are performed (i.e., the cells are in co-culture), then the strains/species that are chosen must be selected such that one strain does not outcompete the other strain. Such a relationship can be obtained by introducing an artificial symbiosis into the co-culture. That is to say that the two stains/species that are used are each auxotrophic for an essential nutrient, but for different nutrients. Furthermore, the other strain should be engineered to produce an excess of that nutrient so that both strains can survive together in a culture when the growth medium of the culture does not comprise the two essential nutrients. Selection of appropriate auxotrophies will be well within the grasp of the skilled person following the teachings herein.

2.10.3 Fermentations

The culture conditions described herein can be scaled up and grown continuously for manufacturing of heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of di- and trifunctional C7 alkanes. Generally, and as with non continuous culture procedures, the continuous and/or near-continuous production of heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam described previously include culturing a recombinant host cell producing heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam described herein in the presence of sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, recombinant cells can be cultured for hours, if suitable for a particular application. It is to be understood that the continuous and/or near-continuous culture conditions also can include all time intervals in between these exemplary periods. It is further understood that the time of culturing the host cell of the invention is for a sufficient period of time to produce a sufficient amount of product for a desired purpose.

Fermentation procedures are well known in the art. Briefly, fermentation for the biosynthetic production of heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam described previously can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam producers described herein for continuous production of substantial quantities of these, the heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol or enantholactam producers also can be, for example, simultaneously subjected to further procedures to convert the product to other compounds or the product can be separated from the fermentation culture and sequentially subjected to chemical or biocatalytic conversions to convert the product to other compounds, if desired.

2.11 Compositions of the Invention

The invention also provides compositions comprising recombinant host cells according to the invention and heptane-1,7-dioic acid, 7-oxoheptanoic acid, 7-hydroxyheptanoic acid, 7-hydroxyheptanal, 7-aminoheptanoic acid, heptamethylenediamine, 1,7-heptandiol, 7-aminoheptanal, 7-aminoheptanol and enantholactam. The invention also provides a composition comprising a recombinant host cell according to the invention and a feedstock. In some embodiments the feedstock is a renewable feedstock, for example wherein the feedstock is selected from the group consisting of glucose, sucrose, xylose, fatty acids and glycerol. In some embodiments the feedstock is a polyaromatic hydrocarbon, for example benzene, toluene or shikimate.

3.1 Examples

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

3.1.1 Conversion of 2,6-diaminopimelate to 2-amino-5,6-dehydro Pimelic Acid (6-amino-2-heptene Dioic Acid) and of 2-aminoheptanedioic Acid to 2-heptenedioic Acid by Ammonia Lyases (EC 4.3.1.-) (See, FIG. 10)

3.1.1.1 Selection of MAL Enzyme Gene Targets

Upon identification of the pathways involved in conversion of 2,6-diamino pimelic acid into pimelic acid, which is used in the production of nylon 7,7, and conversion of pimelic acid into 7-amino heptaonic acid, gene targets from these pathways were selected. In particular, enzyme targets were selected from the ammonia lyase family (EC 4.3.1), including methylaspartate ammonia lyase (MAL; EC 4.3.1.2), based on its broad substrate specificity, presence in a wide range of hosts, ability to be cloned and expressed exogenously, and available crystal structure for rational design protein engineering. The MAL genes from *Citrobacter amalonaticus, Clostridium tetanomorphum* and *Aspergillus oryzae* were selected. The MAL enzymes encoded by *C. amalonaticus* (GeneBank AB005294; fragment 1641-2882878596.879060NM_NM) and *C. tetanomorphum* (GeneBank 548141; fragment 756-1997) have significant dissimilarity (57% identity). The *Aspergillus oryzae* MAL gene (GeneBank XM_001827609) is evolutionarily divergent (44% identity with *Citrobacter amalonaticus* MAL, 39% identity with *Clostridium tetanomorphum* MAL), which may show different catalytic properties and/or selectivities. Another unusual ammonia lyase that is a potential enzyme for the reductive deamination of 2,6-diaminopimelate and 2-aminoheptanedioic acid, is the D-glucosaminate ammonia lyase (EC 4.3.1.9) from *Pseudomonas fluorescens* (accession number BAD69624). This is an unusual ammonia lyase that catalyzes an α,β-elimination:

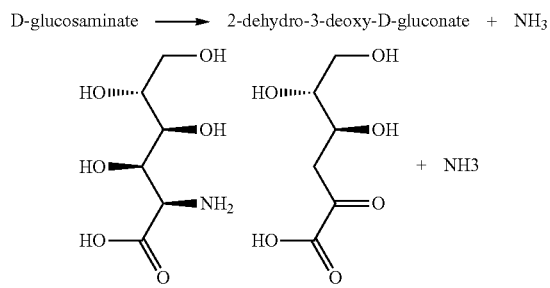

3.1.1.2 Cloning Expression Vectors Containing Gene Targets

The selected MAL gene targets from *Citrobacter amalonaticus*, *Clostridium tetanomorphum*, and *Aspergillus oryzae* were then cloned into the IPTG inducible pET21-a backbone using in ABLE technology to generate I4 (pET21-a with the *Citrobacter amalonaticus* MAL gene), I5 (pET21-a with the *Clostridium tetanomorphum* MAL gene), and I6 (pET21-a with the *Aspergillus oryzae* MAL gene). First, the gene and vector DNA are split into truncated parts using software analysis. Potential restriction enzyme, e.g., EarI, sites in the selected MAL genes and pET21 vector were identified and disrupted by introducing mutations. EarI restriction sites located within coding sequences were disrupted, e.g., by incorporation of a silent mutation, as to avoid altering the encoded protein sequence. The resulting DNA was free of EarI sites, and was used the input sequence for software analysis to design corresponding truncated parts flanked by EarI (ordered through DNA 2.0), long and short linker oligonucleotides (ordered through Sigma-Aldrich), and long and short part oligonucleotides (ordered through Sigma-Aldrich). The 5'-end of the part and linker oligonucleotides were phosphorylated by incubating the primer in the present of T4 kinase under suitable reaction conditions (6 µM oligo, 1 PNK buffer, 1 mM ATP, 10 U T4 kinase, 5 mM DTT, 5% (w/v) PEG8000) at 37° C. for 30 minutes, followed by inactivation of the enzyme at 65° C. for 20 minutes.

Next, the phosphorylated linker oligos and phosphorylated part oligos were annealed by mixing equimolar amounts of each oligo (50 µL at 6 µM) and then heating the mixture to 65° C. in a thermocycler before gradually lowering the temperature down to 20° C. to form partially double-strand part oligos and partially double-strand linker oligos having specific 16 bp overhangs (melting temperature above 75° C.). The resulting annealed part oligos (POA) and annealed linker oligos (LOA) were then diluted to a final concentration of 1 µM with TE buffer (Tris-EDTA).

Then, the part/linker fragments corresponding to the selected genes (*Citrobacter amalonaticus*, *Clostridium tetanomorphum* and *Aspergillus oryzae* MAL) were generated by successive cycles of EarI digestion of the cloned truncated parts followed by ligation of their respective annealed part oligos (POA28, POA29 or POA30), their truncated part (TP28, TP29 or TP30), and the annealed linker oligos from the vector backbone (LOA31). Part linker fusions corresponding to the vector backbone were prepared by ligation of its annealed part oligos (POA31), its truncated part (TP31) and the annealed linker oligos from either genes (LOA28, LOA29 or LOA30). Ten and twenty-fold molar excesses of LOA and POA compared to the truncated part were used in the gene and vector reactions respectively to favor ligation between the truncated part and the oligonucleotides during each EarI digestion/ligation cycle. The reactions were performed in a total volume of 50 µL and were incubated in a thermocycler (Eppendorf Mastercycler Gradient). Cycles of EarI digestion/ligation were achieved by alternating the temperature between 37° C. and 16° C., which correspond to the optimum temperatures for the EarI digestion and for the ligation using the T4 DNA ligase respectively. The samples were loaded on a 0.7% agarose gel, and the part linker was purified from the residual backbone through agarose gel separation and gel extraction (QIAGEN QIAquick Gel Extraction Kit). Expected size fragments were observed after agarose gel electrophoresis for the preparation of part linker fragments. Ligation of the digested fragment with the annealed oligonucleotides displaying compatible 3 bp overhangs resulted in the formation of a non-cleavable part/linker fragment.

The gene part/linker fusions were then combined with their respective vector part/linker fusion using a 2-part assembly to construct an *E. coli* expression vector using the part linkers previously generated. The gene and vector part linker fusions were mixed together in an equimolar amount (0.1 µmol each), which resulted in the expected DNA fragment assembly due to the specific complementary overhangs formed in the annealed part oligonucleotide and the annealed linker oligonucleotide from each part. Reactions were incubated at room temperature for 30 min prior to transformation of high efficiency chemically competent NEB10β *E. coli* cells using 2 µl of the assembly reaction and 10 µl of the competent cells. Transformed cells were plated on LB-Amp-agar and incubated at 37° C. overnight. Five hundred clones were obtained for each assembly. Two random clones were then picked from each assembly and the corresponding vectors were isolated using the QIAGEN QIAprep Miniprep Kit.

Restriction analysis was performed on the previously isolated vectors to confirm the construction of the correct assembly, e.g., assembly of the *Citrobacter amalonaticus* gene into the pET21-a backbone. Clones obtained from the assembly of the *Citrobacter amalonaticus* gene into the *E. coli* expression vector were analyzed using PvuI and BmgBI to identify positive clones for the insertion. Clones obtained from the assembly of the *Clostridium tetanomorphum* gene into the *E. coli* expression vector were analyzed using PstI and AlwNI (Figure 30, Table 10) to identify positive clones for the insertion. Clones obtained from the assembly of the *Aspergillus oryzae* gene into the *E. coli* expression vector were analyzed using SphI and EcoRV to identify positive clones for the insertion. The restriction products from each sample were analyzed using agarose gel electrophoresis. The expected band pattern was observed for both clones from each assembly confirming the construction of *E. coli* expression vectors harbouring the *Citrobacter amalonaticus*, *Clostridium tetanomorphum* and *Aspergillus oryzae* MAL genes. Assembly of the I7 negative control vector (pET21-a control) was performed using the part/linker fusion pET21-a part/pET21-a linker was performed as a negative control, and clones from the generation of the negative control gene-free construct were analyzed using XmnI and AlwNI. To further confirm proper assembly of the expression vectors, the part junctions between the 3'-end of the vector backbone and the 5'-end of the genes as well as between the 3'-end of the gene and the 5'-end of the vector backbone were sequenced from one of the two clones from each assembly.

3.1.1.3 Expression of Exogenous MAL Genes in *E. coli*

The *E. coli* constructs previously obtained were used to study the expression of the *Citrobacter amalonaticus*, *Clostridium tetanomorphum* and *Aspergillus oryzae* MAL genes in *E. coli*. The vectors (10 ng DNA from each assembly) were used to transform electrocompetent BL21 (DE3) *E. coli* cells, and transformation samples were plated on LB-Amp-Agar. Transformants were obtained after overnight incubation at 37° C.

A single clone was picked from each assembly plate, and was used to inoculate 5 ml of LB-Amp medium as a starting culture. The $OD_{600}$ was measured after overnight incubation at 37° C. and 250 rpm. Two mL of each starting culture (approximately $4.5 \times 10^7$-$6.2 \times 10^7$ cells) were used to inoculate 100 mL of LB-Amp, and the cultures were incubated in a 500 mL baffled shake flask at 37° C. and 250 rpm until an $OD_{600}$ of 0.6 to 0.8 was reached. Protein expression, which is controlled by the T7 promoter in pET21-a, was induced by addition of 1 mM IPTG (final concentration) and cultures were further incubated at 37° C. and 250 rpm. 1 mL of each sample was taken prior to induction, 4 h post-induction, and 24 h post-induction. Cell growth was checked by measuring $OD_{600}$. The remaining culture left after 24 h post-induction incubation was transferred to a 50 mL falcon tube, harvested by centrifugation at 5000 rpm for 10 minutes and the cell pellets stored at −20° C.

Next, the time-point samples from each assembly were processed for SDS-PAGE analysis. The samples were centrifuged at 13000 rpm for 2 min before the supernatant was removed and the cells were lysed using the Bugbuster protein extraction reagent supplemented with lysozyme (15 mg/mL) and benzonase (3.4 U/µL). The lysis reactions were then centrifuged at 13000 rpm for 2 min, and the soluble fraction was transferred to a new tube and the insoluble fraction was re-suspended in water. 20 µl of each fraction was mixed with 80 µl SDS-Sample buffer (SDS-Loading Buffer, 9% DTT and water) and the mixture was heated in a heatblock for 5 minutes at 95° C. 10 µl of each sample was then loaded on SDS-PAGE 4-20% Tricene gels to analyze the protein content of the soluble and insoluble fractions. A protein band at the expected size (45 kDa) was clearly visible in the soluble fraction after IPTG induction. No corresponding protein was observed in the negative control experiment suggesting that the expected 45 kDa *Citrobacter amalonaticus* MAL protein and 45 kDa *Clostridium tetanomorphum* MAL protein were successfully expressed as soluble proteins in *E. coli* from the assembled expression vector constructs No significant protein was observed in the insoluble fraction of any sample after induction. The 45 kDa *Aspergillus oryzae* MAL protein was also expressed in *E. coli* from the assembled expression vector construct, but it was expressed as an insoluble protein (a 45 kDa band was visible in the insoluble fraction after induction) (See, FIGS. 11A and 11B).

In order to improve the solubility of the *Aspergillus oryzae* MAL protein, the temperature of induction and/or the concentration of inducer was reduced, which in some cases has been shown to result in increased protein solubility due to a slower rate in protein synthesis and therefore a higher efficiency in protein folding. These parameters were reduced using the same expression and induction procedure described above, but SDS-PAGE analysis shows that the *Aspergillus oryzae* MAL protein was still insoluble (a 45 kDa band was visible in the insoluble fraction after induction). A yeast expression vector containing the *Aspergillus oryzae* MAL protein may be used to express the protein in soluble form.

Cultures of *E. coli* expressing the *Citrobacter amalonaticus* or *Clostridium tetanomorphum* MAL genes were scaled up to increase production of the soluble proteins for use in enzymatic assays. The cultures were grown, induced, and harvested as previously described. Briefly, a single clone was picked from each transformation plate previously prepared, and 20 ml of LB-Amp medium were inoculated as starting cultures. The $OD_{600}$ was measured after overnight incubation at 37° C. and 250 rpm. 16 mL of each starting culture (approximately $4.4 \times 10^8$ cells) were used to inoculate 800 mL of LB-Amp, and the cultures were incubated in a 2 L baffled shake flask at 37° C. and 250 rpm until an $OD_{600}$ of 0.6 to 0.8 was reached. Protein expression was induced by addition of 1 mM IPTG (final concentration), and cultures were further incubated at 37° C. and 250 rpm. After 24 h post-induction incubation, the remaining culture was transferred to four 50 mL falcon tubes, harvested by repeated centrifugation at 5000 rpm for 10 minutes (4 rounds of centrifugation per tube; 50 mL of medium per round) and the cell pellets stored at −20° C.

Glass bead lysis was used to disrupt the cells for collecting the *Citrobacter amalonaticus*, *Clostridium tetanomorphum* and *Aspergillus oryzae* MAL protein. Cell pellets from the 24 hour post-induction samples were re-suspended in bead lysis buffer consisting of 0.1 mM Tris, 1 mg/ml Pepstatin A and 200 mM PMSF protease inhibitors. Acid washed 212-300 µm glass beads (0.4 g per 1 mL of lysis buffer) were added to each tube, and lysed in a sonicating water bath in parallel. 250 µl samples from each of the 4 tubes were taken prior to sonication and after 5 minutes and 10 minutes of cell lysis. The 250 µl samples from each time point were pooled to give a total sample of 1 mL. Cell free extracts were prepared by centrifugation for 10 minutes at 5000 rpm and transfer of the supernatants to new tubes. Insoluble samples were prepared after re-suspension of the cell pellet isolated after 10 min of sonication with an equivalent volume of water. The remaining pellets and supernatant were stored at −20° C. 20 µl of each pooled fraction was mixed with 80 µl SDS-Sample buffer (SDS-loading buffer, 9% DTT and water) and the mixture was heated in a heatblock for 5 minutes at 95° C. 10 µl of each SDS-sample preparation was then loaded on SDS-PAGE 4-20% Tricene gels to analyze the protein content of the soluble and insoluble fractions. Protein bands were clearly detected in the samples from expression of the *Citrobacter amalonaticus* MAL and the *Clostridium tetanomorphum* MAL.

3.1.1.4 Functionality of Exogenously Expressed MAL

The activity of the methyl aspartate ammonia lyase derived from *Citrobacter amalonaticus*, *Clostridium tetanomorphum*, and *Aspergillus oryzae* was assayed using the I4, I5, and I6 strains towards beta-methyl aspartate, in the first place. In subsequent studies described herein, the activity of these strains were assayed in the context of different substrates, namely, 2-aminopimelate, D,L-lysine, and, finally, 2,6-diaminopimelic acid. A negative control biotransformation of 2-aminopimelate with I17 was also conducted.

3.1.1.4.1 Biotransformation Screening of I4, I5, and I6 Strains Toward beta-methyl Aspartate

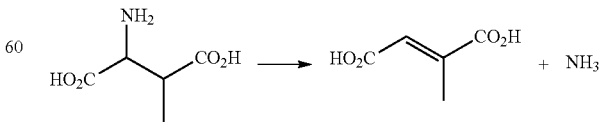

Six biotransformations were prepared at either 5 g/L or 20 g/L whole cell equivalent of the I4, I5 and I6 lyase strains. The enzyme concentration was calculated based on whole cell equivalent which is the pelleted cell mass after centrifugation (wet cell weight) divided by the volume of buffer used to resuspend the cells during lysis. The biotransformations were conducted in 3 ml volumes with 10 mM DL-threo-beta methyl aspartate.

Reactions were incubated at 30° C. in an orbital incubator and samples removed for analysis by HPLC after 1, 5 and 18 hours. The 1 ml aliquots were prepared for analysis by heat treatment to remove heat labile proteins. The samples were subsequently centrifuged at 10,000 rpm for 2 minutes and filtered through a 0.2 micron filter. Analysis of the samples was carried out by HPLC using a Phenomenex Rezex column with 5 mM sulfuric acid mobile phase using RID and UV detection. Confirmation of lyase activity was affirmed by detection of mesaconic acid in the samples. The concentration of mesaconic acid formed in each biotransformation was determined by measurement of an external standard mesaconic acid from Aldrich.

Mesaconic acid was detected in all the I4 and I5 strain biotransformations, confirming functional expression of the lyase enzyme was present in these cell extracts. No activity was observed in the I6 strain which is consistent with the results observed by SDS PAGE analysis of the expressed protein which showed the protein was expressed in insoluble form. The yield of mesaconic acid in all samples analyzed from the I4 and I5 strains was ~5 mM, which is consistent with the anticipated activity on 10 mM DL-threo-beta methyl aspartate, since the wild type enzyme is L-enantioselective. In the I4 and I5 strains complete conversion was observed after just 1 hour incubation.

3.1.1.4.2 Biotransformation Screening of I4 and I5 Strains Toward 2-aminopimelate

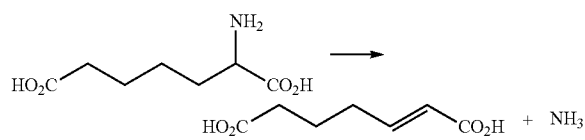

Eight biotransformations were prepared varying levels of enzyme and substrate concentrations (2 variable, 2 level stat design) to examine I4 and I5 enzyme activity towards 2-aminopimelate. The biotransformations were conducted in 3 ml volumes with varying loadings as indicated below:

I4 strain 5 g/L; 2-aminopimelate concentration 5 mM
I4 strain 5 g/L; 2-aminopimelate concentration 10 mM
I4 strain 20 g/L; 2-aminopimelate concentration 5 mM
I4 strain 20 g/L; 2-aminopimelate concentration 10 mM
I5 strain 5 g/L; 2-aminopimelate concentration 5 mM
I5 strain 5 g/L; 2-aminopimelate concentration 10 mM
I5 strain 20 g/L; 2-aminopimelate concentration 5 mM
I5 strain 20 g/L; 2-aminopimelate concentration 10 mM The biotransformations were placed in a falcon tube at 30° C. in a shaker incubator. Aliquots (1 ml) were removed from the biotransformations after 7, 14 and 21 days. Prolonged incubation was operated to provide best possible chance of observing lyase activity. The 1 ml aliquots were prepared for analysis by heat treatment to remove heat labile proteins. The samples were subsequently centrifuged at 10,000 rpm for 2 minutes and filtered through a 0.2 micron filter. Analysis of the samples was carried out by HPLC using a precolumn derivatisation method. This method comprises forming a chiral adduct with a Boc-cysteine and ortho-phthaldehyde reagent to form a diastereomeric pair of L- and D-2-aminopimelate derivatives. The diastereomers (representing the enantiomers of 2-aminopimelate) can then be separated by HPLC using a C18 column and a 5 mM potassium phosphate buffer pH 7.0 and acetonitrile gradient at 338 nm. The peak areas for L- and D-2-aminopimelate signals in each sample were recorded and observed decrease in the L-2-aminopimelate standard is expressed as % relative to the D-2-aminopimelate.

The data show L-2-aminopimelate being degraded in all the biotransformations. The increase in enantiomeric excess is consistent with the natural L-enantioselectivity expeected for these lyase enzymes which preferentially acts on L-beta-methyl aspartate. The lower substrate loadings (5 mM) also showed a greater enantio-enrichment (ie higher conversion of the available substrate) compared to the higher substrate loadings which is consistent with the anticipated lyase activity.

The presence of unreacted 2-aminopimelate was confirmed via mass spectrometry. The M+H equal to 176.09 was observed in the sample and matched the simulated mass spectrum for $C_7H_{13}NO_4$. On the full sweep mass spectrum, the enoic acid product (M+H=159.06) was not observed. However, when the MS accumulated ions for 20 seconds over a 20 m/z wide mass isolation the correct product signal was observed and matched with the simulated mass spectrum for $C_7H_{10}O_4$.

A sample of the rac-2-aminopimelic acid starting material was also analyzed. Using the same MS methods carried out on this standard clearly displayed the expected molecular ion for 2-aminopimelate. However, repeating the MS ion accumulation for 20 seconds over a 20 m/z wide mass isolation (as had been carried out on the previous biotransformation sample) revealed the presence of the enoic acid product as a mass fragment.

3.1.1.4.3 Negative Control Biotransformation of 2-aminopimelate with I17 Strain

Four biotransformations were prepared with varying level of cell extract and substrate to match the levels used in the experiment described in 3.1.1.4.1. The biotransformations were conducted in 3 ml reaction volumes as indicated below:

I7 strain 5 g/L; 2-aminopimelate concentration 5 mM
I7 strain 5 g/L; 2-aminopimelate concentration 10 mM
I7 strain 20 g/L; 2-aminopimelate concentration 5 mM
I7 strain 20 g/L; 2-aminopimelate concentration 10 mM The biotransformations were incubated at 30° C. in a shaker incubator and samples taken after 8, 13 and 21 days. Analysis of the reaction was carried out by HPLC following the method described in the experiment described above in 3.1.1.4.1.

The data show there is some loss of the L-enantiomer in the I17 strain. However the relative decrease in the L-enantiomer is less than the equivalent biotransformations with the I4 and I5 strains, particular when the second time points incubating for 2 weeks are compared. The trend depicted below clearly shows the I4 and I5 strains in the biotransformations have a consistently higher level of L-2-aminopimelate degradation compared to the I17 negative control strain across the 2×2 statistical design experiment examining cell extract and substrate loadings.

3.1.1.4.4 Biotransformation Screening of I4 and I5 CFE with DL-lysine

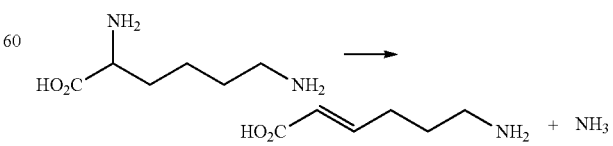

Eight biotransformations were prepared in a similar fashion as used to test for lyase activity towards 2-aminopimelate. The I4 and I5 lyase strains were tested at varying concentrations of cell extract and DL-lysine substrate as follows:

I4 strain 5 g/L; DL-lysine concentration 5 mM
I4 strain 5 g/L; DL-lysine concentration 10 mM
I4 strain 20 g/L; DL-lysine concentration 5 mM
I4 strain 20 g/L; DL-lysine concentration 10 mM
I5 strain 5 g/L; DL-lysine concentration 5 mM
I5 strain 5 g/L; DL-lysine concentration 10 mM
I5 strain 20 g/L; DL-lysine concentration 5 mM
I5 strain 20 g/L; DL-lysine concentration 10 mM The biotransformations were placed in a falcon tube at 30° C. in a shaker incubator. Aliquots (1 ml) were removed from the biotransformations after 7, 14 and 21 days. Prolonged incubation was operated to provide best possible chance of observing lyase activity. The 1 ml aliquots were prepared for analysis by heat treatment to remove heat labile proteins. The samples were subsequently centrifuged at 10,000 rpm for 2 minutes and filtered through a 0.2 micron filter. DL-lysine samples were analyzed using a chiral HPLC column (Chirobiotic T2 Astec) to monitor enantiomer ratios to determine lyase activity. Samples were removed from the biotransformations after 7, 14 and 21 days.

The results indicate loss of L-lysine in all the biotransformations with 5 mM lysine. Some variations in enantioselective action on DL-lysine was observed, where the concentration of L-lysine exceeded the concentration of D-lysine. Owing to the poor UV absorbance (detector set to 210 nm) and low signal to noise ratio of lysine in the HPLC chromatogram the possibility of a false positive L-lysine detection cannot be excluded from these results. However, in general degradation of L-lysine from DL-lysine was observed across the eight biotransformations which is consistent with the expected stereoselectivity of potential lytic activity arising from lyase functioning in the I4 and I5 strains.

In order to gather further evidence to support the functioning of lyase activity in these biotransformations, a sample was analyzed by MS to attempt to detect the desired enoic acid product in the sample. The MS signal corresponding to the unreacted lysine (M+H=176.09) was observed in the sample and matched the simulated mass spectrum for $C_6H_{14}N_2O_2$.

On the full sweep mass spectrum, the enoic acid product (M+H=130.09) was not observed. However, as for the amino-pimelic acid reactions, when the MS accumulated ions for 20 seconds over a 20 m/z wide mass isolation the correct product signal was observed and matched with the simulated mass spectrum for $C_6H_{11}NO_2$.

A sample of the DL-lysine starting material was also analyzed. Using the same MS methods carried out on this standard clearly displayed the expected molecular ion for DL-lysine. However, repeating the MS ion accumulation for 20 seconds over a 20 m/z wide mass isolation (as had been carried out on the previous biotransformation sample) revealed the presence of the enoic acid product as a mass fragment.

3.1.1.4.5 Biotransformation Screening of I4 and I5 CFE with meso-2,6-diaminopimelic acid

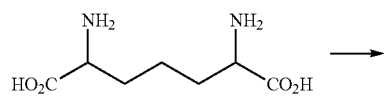

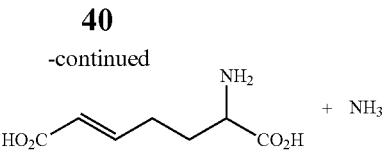

Six biotransformations were prepared to test for lyase activity towards meso-2,6-diaminopimelic acid. The I4, I5 and I7 strains were tested with 5 mM meso-2,6-diaminopimelic acid. Varying concentrations of cell extract were examined as follows:

I4 strain 5 g/L; meso-2,6-diaminopimelic acid concentration 5 mM
I4 strain 20 g/L; meso-2,6-diaminopimelic acid concentration 5 mM
I5 strain 5 g/L; meso-2,6-diaminopimelic acid concentration 5 mM
I5 strain 20 g/L; meso-2,6-diaminopimelic acid concentration 5 mM
I17 strain 5 g/L; meso-2,6-diaminopimelic acid concentration 5 mM
I17 strain 20 g/L; meso-2,6-diaminopimelic acid concentration 5 mM The biotransformations were placed in a falcon tube at 30° C. in a shaker incubator. Aliquots (1 ml) aliquots were removed from the biotransformations after 4 days, further sample acquisitions are pending prior to HPLC analysis.

A sample acquired after 4 days was analyzed by MS. The analysis confirmed the presence of meso-2,6-diaminopimelic acid which matched the simulated mass signal for $C_7H_{14}N_2O_4$.

The desired enoic acid signal was not observed in this mass spectrum in the biotransformation sample. However, when ion accumulation was introduced for 0.5 sec then the corresponding enoic acid signal (M+H=174.08) was observed in one of the samples.

3.1.2 Conversion of 2-amino-5,6-dehydro Pimelic Acid (6-amino-2-heptenedioic acid) to 2-amino-heptane Dioic Acid and 2-heptenedioic Acid or its CoA ester to Pimelic acid or its CoA Ester by Enoate Reductases (EC 1.3.1.31) or Enoyl-CoA Dehydrogenases (EC 1.3.1.62) (See, FIG. 10)

3.1.2.1 Selection of Enoate Reductase Targets

Upon identification of the pathways involved in the conversion of two unsaturated intermediates of pimelic acid, i.e., 2-amino-5,6-dehydro pimelic acid and 2-heptenedioic acid, into their corresponding saturated compounds 2-aminoheptanedioic acid and pimelic acid, enzyme targets were selected from the enoate reductase family (EC 1.3.1), such as EC 1.3.1.31, based on to their different substrate specificity towards α,β-unsaturated carboxylic acids and their stability (Stereocomplementary bioreduction of α,β-unsaturated dicarboxylic acids and dimethyl esters using enoate reductases—Enzyme- and substrate-based stereocontrol: Stueckler et al. Org. Lett. 2007, 9, 5409-5411).

In particular, the enoatereductase genes from *Bacillus subtilis* (YqjM) (GeneBank D84432; fragment 242791-243807) and *Solanum lycopersicum* (OPR1 and OPR3) (GeneBank NM_001247852, fragment 108-1238 and GeneBank NM_001246944; fragment 94-1284, respectively) were selected because they had been previously cloned and successfully expressed in *E. coli*, crystal structures of the YqjM and OPR3 enzymes were reported, which enables protein engineering through rational design (The 1.3 A crystal structure of the flavoprotein YqjM reveals a novel class of old yellow enzyme: Kitzing et al. *J. Biol. Chem.* 2005, 280, 27904-27913; Asymmetric bioreduction of activated alkenes using cloned 12-oxophytodienoate reductase isoenzymes OPR-1 and OPR-3 from *Lycopersicon esculentum* (Tomato): A striking switch of stereopreference: Hall et al. *Angew. Chem. Int. Ed.* 2007, 46, 3934-3937; Crystal structure of 12-oxophytodienoate reductase 3 from tomato—Self inhibition by dimerization: Breithaupt et al. *PNAS* 2006, 103, 14337-14342).

Enoate reductases from *Clostridium* species are also considered due to their broad substrate specificity (Chiral compounds synthesized by biocatalytic reductions: Simon et al. *Angew. Chem. Ed. Engl.* 1985, 24, 539-553; Properties and mechanistic aspects of newly found redox enzymes from anaerobes suitable for bioconversions on preparatory scales: Simon et al. *Pure & Appl. Chem.* 1992, 64, 1181-1186). However, those enzymes were not cloned and expressed for initial proof of concept due to their high sensitivity towards oxygen (Enoate reductases of *Clostridia*—Cloning, sequencing and expression: Rohdich et al. *J. Biol. Chem.* 2001, 276, 5779-5787), but may be useful catalysts for the final pathway construction in an anaerobic host. In particular, the following enoate reductases should be useful for the reduction of the double bonds in the target 2-enoyl C7 compounds:

enr 2-Enoate reductase (Y16137) EC 1.3.1.31 from *Clostridium kluyveri*: Whole cells of *Clostridium kluyveri* were found to reduce a broad range of 2-enoates in the presence of molecular hydrogen. The substrates were: tiglic acid, acrylic acid, methacrylic acid, dimethylacrylic acid, (E)-pentenoic acid, (E)-hexenoic acid, sorbic acid, cinnamic acid [19], (E)-2-butenoic acid and (E)-2-methyl-2-butenoic acid, (E)- and (Z)-3-methyl-2-pentenoic acid, p-methoxy-cinnamic acid and p-nitro-cinnamic acid [Bühler, M., Giesel, H., Tischer, W. and Simon, H. (1980) Occurrence and the possible physiological role of 2-enoate reductases. *FEBS Lett.* 109, 244-246]. A partial sequence of the gene encoding the enzyme was identified [Rohdich, F., Wiese, A., Feicht, R., Simon, H. and Bacher, A. (2001) Enoate reductases of Clostridia. Cloning, sequencing, and expression. *J. Biol. Chem.* 276, 5779-5787]. Since the genome of *C. kluyveri* has been sequenced, we found the full sequence of the gene (YP_001394144.1, GENEBANK).

enr 2-Enoate reductase (Y09960) EC 1.3.1.31 from *C. tyrobutyricum* (previously *Clostridium* sp. La 1): 2-Enoate reductase was found in *Clostridium* sp. growing on (E)-butenoate and purified to homogeneity. It accepted (E)-2-methylbutenoate and cinnamate [Elshahed M S, Bhupathiraju V K, Wofford N Q, Nanny M A, McInerney M J. (2001) Metabolism of benzoate, cyclohex-1-ene carboxylate, and cyclohexane carboxylate by "*Syntrophus aciditrophicus*" strain SB in syntrophic association with H(2)-using microorganisms. Appl Environ Microbiol. 67: 1728-1738], (E)-alpha-formylamino-cinnamate, and 4-methyl-2-pentenoate [Bühler, M., Giesel, H., Tischer, W. and Simon, H. (1980) Occurrence and the possible physiological role of 2-enoate reductases. *FEBS Lett.* 109, 244-246]. The gene encoding enr reductase was identified and the enzyme was overexpressed in *E. coli* under anaerobic conditions [Rohdich, F., Wiese, A., Feicht, R., Simon, H. and Bacher, A. (2001) Enoate reductases of Clostridia. Cloning, sequencing, and expression. *J. Biol. Chem.* 276, 5779-5787].

enr 2-Enoate reductase (Y16136) EC 1.3.1.31 from *Moorella thermoacetica* (previously *Clostridium thermoaceticum*): An antiserum against enoate reductase from *C. tyrobutyricum* cross-reacted with a protein of the thermophilic *Clostridium thermoaceticum*. The gene encoding the reductase was identified and the enzyme was successfully overexpressed in *E. coli* [Rohdich, 2001].

Other potential enoate reductase candidates were identified from *Saccharomyces cerevisiae* and *Pseudomonas putida* but no evidence of gene characterization and no activity towards α,β-unsaturated carboxylic acids were reported respectively for those two enzymes.

In addition to enoate reductases, pimeloyl-CoA dehydrogenases (EC 1.3.1.62) should catalyse the reduction of the double bond in 2-heptenedioic acids and the corresponding CoA esters. Pimeloyl-CoA dehydrogenase activity was found in cell extracts of *Syntrophus aciditrophicus* grown in a co-culture with *Desulfovibrio* sp. strain G11 with benzoate or in a pure culture with crotonate and is involved in the benzoate degradation pathway (Elshahed M S, Bhupathiraju V K, Wofford N Q, Nanny M A, McInerney M J. (2001) Metabolism of benzoate, cyclohex-1-ene carboxylate, and cyclohexane carboxylate by "*Syntrophus aciditrophicus*" strain SB in syntrophic association with H(2)-using microorganisms. *Appl Environ Microbiol.* 67: 1728-1738). Other hypothetical pimeloyl-CoA dehydrogenases found in databases include ThnJ (D9PTN0) and ThnK (D9PTM9) from *Sphingomonas macrogolitabida*—found in the gene cluster for tetralin degradation via the beta-oxidation pathway, PimC (Q6N3I0) and PimD (Q6N3I1) from *Rhodopseudomonas palustris* and PimC (A5ES10) and PimD (A5ES09) from *Bradyrhizobium* sp.

Other dehydrogenases useful to the invention include GDH Glutaryl-Coenzyme A Dehydrogenase *Desulfococcus multivorans*, a non-decarboxylating glutaconyl-coenzyme A-forming glutaryl-coenzyme A dehydrogenase was characterized in the obligately anaerobic bacteria Desulfococcus multivorans [Wischgoll S, Demmer U, Warkentin E, Günther R, Boll M, Ermler U. (2010) Structural basis for promoting and preventing decarboxylation in glutaryl-coenzyme A dehydrogenases. Biochemistry. 49: 5350-5357]. The enzyme was overexpressed and its crystal structure was determined.

3.1.2.2 Cloning Expression Vectors Containing Gene Targets

The selected YqjM, OPR1, and OPR3 gene targets from *Bacillus subtilis* and *Solanum lycopersicum* were then cloned into the IPTG inducible pET21-a backbone using in ABLE technology, as described in detail in Section 3.1.1.2) to generate I1 (*Bacillus subtilis* YqjM gene in pET21-a), I2 (*Solanum lycopersicum* OPR1 gene in pET21-a), and I3 (*Solanum lycopersicum* OPR3 gene in pET21-a).

Briefly, potential EarI sites in the selected genes and the vector backbone were disrupted to prevent interference with the part/linker fusion preparation involving EarI digestion/ligation cycles. No EarI sites were observed in the *Bacillus subtilis* YqjM enoate reductase gene, but one and two EarI sites were detected in the *Solanum lycopersicum* OPR1 and OPR3 genes, respectively, which were disrupted by incorporating silent mutation(s) in the restriction site. Disruption of the EarI sites 1 and 2 in the *Solanum lycopersicum* OPR3 gene sequence resulted in an inadvertent EarI site being created, which was only discovered after the sequences were synthesized. The residual EarI site was removed using the Quikchange single-site directed mutagenesis kit from Stratagene. Forward and reverse primers were designed to disrupt the residual EarI site, and the primers were phosphorylated as described in the section 3.1.1.2 prior to the Quikchange reaction. The Quikchange and the negative control reactions were prepared as follows:

| Reagent | TP27 Quikchange | Negative control |
|---|---|---|
| 10x Pfu turbo Reaction Buffer | 5 µl | 5 µl |
| TP27 | 1 µl | 1 µl |
| Forward Primer | 3 µl | 3 µl |
| Reverse Primer | 3 µl | 3 µl |
| dNTP solution | 5 µl | 5 µl |
| Molecular Biology Grade Water | 32 µl | 33 µl |
| Pfu turbo enyme | 1 µl | — |
| Total Volume | 50 µl | 50 µl |

The reactions were run in a thermocycler (95° C. 0.5 minutes; 35 cycles of 95° C. 0.5 minutes, 55° C. 1 minute, 68° C. 10 minutes; 68° C. 1 minutes, 4° C. hold), and then treated with DpnI (1 µL) to digest the methylated parental DNA at 37° C. for 2 hours. The digestion reactions (3 µL) were used to transform TOP10 electrocompetent *E. coli* cells, and the transformation samples (100 µL) were plated onto LB-Kan-Agar. About 100 clones were obtained on the Quikchange reaction plate compared to none on the negative control plate after overnight incubation at 37° C. Ten clones were picked from the plate, the corresponding plasmids were purified, and analyzed by EarI digestion. The absence of a 300 bp band on the agarose gel indicated that the EarI site located in the OPR3 gene was deleted. EarI digestion showed that several clones were positive for the removal of the residual EarI site. DNA sequencing confirmed the clone's sequence.

Vector from clone 3 (a clone positive for removal of EarI) was used to transform electrocompetent TOP10 *E. coli* cells. QIAGEN Hi-Speed Plasmid Purification Midi Kit was used to prepare a large DNA stock from the culture, and the DNA sample was subsequently concentrated using the QIAGEN PCR purification kit. The final DNA concentration and the volume of the sample was 470.0 ng/µl in 120 µl (DNA conc. 199.8 nM).

Three EarI sites were detected in the vector backbone pET21-a, which were disrupted by mutating the last guanidine base of the restriction site into a thymine (corresponding to the first cytosine into an adenine on the reverse complement sequence).

The EarI free sequences were then used as input sequences in the part designer software to design the corresponding truncated parts flanked by EarI sites, as discussed in Section 3.1.1.2. The synthesized *Bacillus subtilis* YqjM (TP25), *Solanum lycopersicum* OPR1 (TP26), and *Solanum lycopersicum* OPR3 (TP27) truncated parts were inserted into the DNA2.0 pJ201 vector. The pET21-a truncated part vector was fully synthesized with introduction of a fragment including the chloramphenicol resistance gene to produce the vector TP31.

Phosphorylation and subsequent annealing of the in ABLE oligonucleotides were performed as described in section 3.1.1.2.

Next, part linker fusions were prepared by ligating the 5'-end of the truncated part with its corresponding part oligo annealed fragment, and the 3'-end of the truncated part with the linker oligo annealed fragment, as previously described in section 3.1.1.2. Part linker fusions corresponding to the *Bacillus subtilis* YqjM, *Solanum lycopersicum* OPR1 and *Solanum lycopersicum* OPR3 genes were prepared by ligation of their respective annealed part oligos, their truncated part, and the annealed linker oligos from the vector backbone. Part linker fusions corresponding to the vector backbone were prepared by ligation of its annealed part oligos, its truncated part, and the annealed linker oligos from either genes. A negative control gene-free assembly was also prepared by ligation of the vector backbone annealed part oligos, its truncated part, and its annealed linker oligos, resulting in self-assembly of the vector backbone.

A ten and twenty-fold molar excesses of linker and part oligos to the truncated part was used in the gene and vector reactions to favor ligation between the truncated part and the oligonucleotides during each EarI digestion/ligation cycle. The 50 µL EarI digestion/ligation reactions were incubated in a thermocycler (Eppendorf Mastercycler Gradient), alternating the temperature between 37° C. and 16° C. Upon completion of the cycles, samples were loaded on a 0.7% agarose gels, and the expected size fragments were observed for preparation of the part/linker fusions, e.g., *Bacillus subtilis* YqjM part/pET21-a linker and *Solanum lycopersicum* OPR1 part/pET21-a linker as well as the 3 kb vector backbone; or pET21-a part/*Solanum lycopersicum* OPR3 linker—5.3 kb and *Solanum lycopersicum* OPR3 part/pET21-a linker—1.2 kb as well as a 1.8 kb band corresponding to the vector backbone. The correct size bands were then excised from the gel, and the DNA was gel extracted using the QIAGEN QIAquick Gel Extraction Kit. The DNA concentration ranged from 14.4 ng/µl to 49.6 µg/µl in a total volume of 30 µl (DNA conc. range 5.4 nM to 35.6 nM).

Combination of the gene part/linker fusions with their respective vector part/linker fusion was then carried out through a 2-part assembly as described in section 3.1.1.2. Briefly, the gene part linkers and the vector part linkers were incubated at room temperature for 30 min prior to transformation of high efficiency OPR3 chemically competent NEB10β *E. coli* cells using 2 µl of the assembly reaction and 10 µl of the competent cells. Transformed cells were plated on LB-Amp-agar, and incubated at 37° C. overnight. Five hundred clones were obtained for each assembly. One or two random clones were selected from each assembly, and the corresponding vectors were isolated using the QIAGEN QIAprep Miniprep Kit.

Restriction was performed to confirm vector construction, as described in section 3.1.1.2. Briefly, clones obtained from the assembly I1 were analyzed using PstI and HincII to identify positive clones for the insertion of the *Bacillus subtilis* YqjM gene into the *E. coli* pET21-1 expression vector, clones obtained from the assembly I2 were analyzed using PvuI and PsiI, and clones obtained from the assembly I3 were analyzed using BglII and MluI. The restriction products were run on an agarose gel, and the expected band pattern was observed for the clones tested from each assembly, confirming the construction of *E. coli* pET21-a expression vectors harbouring the *Bacillus subtilis* YqjM, the *Solanum lycopersicum* OPR1 and *Solanum lycopersicum* OPR3 enoate reductase genes. In addition, the part junctions between the 3'-end of the vector backbone and the 5'-end of the genes as well as between the 3'-end of the gene and the 5'-end of the vector backbone were sequenced to confirm the construction.

3.1.2.3 Expression of Exogenous Enoate Reducatase Genes in E. coli

Initially, the cloned enoate reductase genes were expressed in E. coli using 1 mM IPTG and 37° induction temperature, as described above in Section 3.1.1.3. Briefly, the OD600 was measured for each culture pre-induction and at various time points after induction. The remaining culture left after 24 h post-induction incubation was transferred to a 50 mL falcon tube, harvested by centrifugation at 5000 rpm for 10 minutes, and the protein content of the samples were analyzed using SDS-PAGE. A large protein band at the expected size (35 kDa) was clearly visible in the soluble fraction from the expression study of the Bacillus subtilis YqjM enaoate reductase after IPTG induction. A large band was visible in the insoluble fraction from the expression of the Solanum lycopersicum OPR1 enoate reducatase after IPTG induction, suggesting that the expected 42 kDa OPR1 protein expressed from 12 was insoluble in E. coli. A protein band at the expected size (44 kDa) was clearly detected in the soluble portion after IPTG induction of Solanum lycopersicum OPR3 enoate reductase I3, as well as in the insoluble fraction, suggesting that the expected 44 kDa Solanum lycopersicum OPR3 enoate reductase protein was expressed in E. coli as partial soluble form.

Based on reports of expression functional expression of the Solanum lycopersicum OPR1 enoate reductase in E. coli optimized in the literature, the conditions for IPTG concentration (range of 0.1-1 mM IPTG) and induction temperature (range of 16-37° C.) were optimized in an attempt to improve the solubility of Solanum lycopersicum OPR1 enoate reductase in E. coli. (Strassner et al. JBC 1999, 274, p. 35067-35073; Hall et al. Angew. Chem. Int. Ed. 2007, 46, p. 3934-3937). The same expression protocol and the same SDS-PAGE sample preparation as described in section 3.1.1.3. was used for the solubility optimization experiments.

The time-point samples from each assembly were then processed for and analyzed using SDS-PAGE analysis, as described in section 3.1.1.3, which showed that lowering the induction temperature to 16° C. and the inducer concentration to 0.1 mM was effective to partially solubilize the Solanum lycopersicum OPR1 enoate reductase expressed in E. coli.

E. coli strains expressing the 3 enoate reductases were scaled up to 800 ml cultures and assayed for activity.

Figure 2:
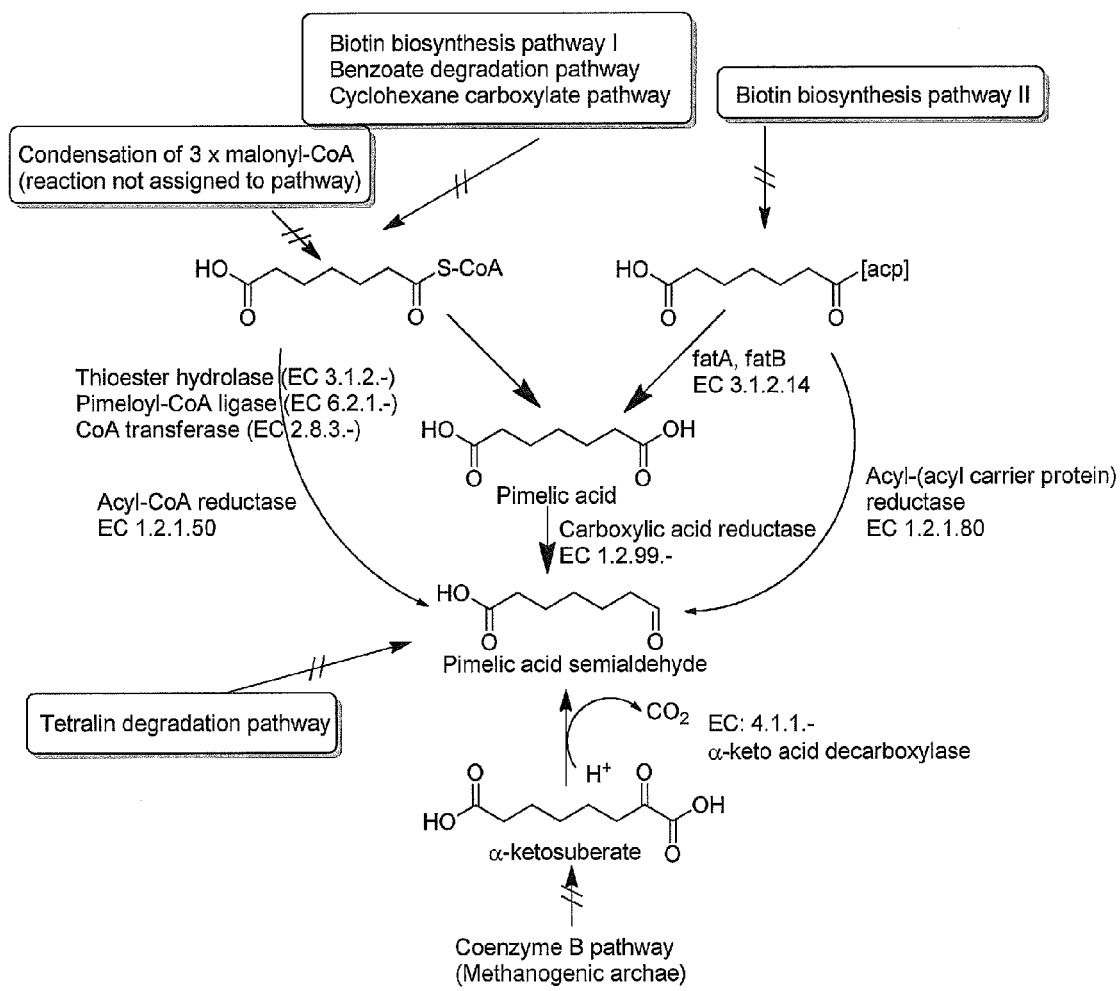
FIG. 2 is a schematic of the formation of pimelic acid semialdehyde from pimeloyl-CoA, pimeloyl-[acp], or α-ketosuberate, all of which are intermediates in naturally occurring pathways as indicated.

3.1.3 Conversion of pimeloyl-CoA and pimeloyl-[acp] to Pimelic Acid Semialdehyde by Fatty acyl-CoA Reductases (Aldehyde Forming FAR) (EC 1.2.1.50) or acyl-[acp] Reductases (EC 1.2.1.80) (See, FIG. 2).

3.1.3.1 Selection of Target Enzymes

Fatty acyl CoA reductases are involved in wax ester synthesis in plants and other higher eukaryotes for cuticle wax formation. In Archaea and bacteria, these enzymes are involved in long-chain alkane biosynthesis, although their physiological function in these organisms is still not always clear. The formation of wax esters in plants begins with the elongation of acyl CoAs to form long-chain fatty acids (LFCA) (or fatty acyl-CoAs), which are then reduced via the decarbonylation pathway or acyl CoA reduction pathways (Cheesbrough and Kolattukudy, 1984).

Hydrocarbons are formed via the decarbonylation pathway. This pathway is initiated by a fatty acyl-CoA reductase-catalysed reaction to produce the aldehyde, followed by decarbonylation catalysed by an aldehyde decarbonylase to yield the [Cn-1] alkane (Cheesbrough and Kolattukudy, 1984).

The acyl CoA reduction pathway is also initiated by a reduction of LCFAs to aldehydes, followed by a further reduction of aldehydes by an aldehyde reductase to produce even-chained primary alcohols (Millar et al., 1999) (Kolattukudy, 1971). Similar pathways are thought to exist in prokaryotes (Schirmer et al., 2010).

Both pathways are initiated by reduction of long-chain acyl-CoAs to aldehydes catalysed by fatty acyl-CoA reductase (FAR; EC 1.2.1.50) in a reversible reaction. In the acyl CoA reduction pathway, the aldehydes are reduced further to the alcohols. This can be achieved in either one or two steps, depending on the organism. The two step reduction is initiated using the acyl-CoA reductase-catalysed reaction, which releases the fatty aldehyde for a second reduction catalysed by a fatty aldehyde reductase. The one step reduction is catalysed by a bi-functional acyl CoA reductase which reduces the acyl CoA directly to the alcohol without releasing the aldehyde intermediate. Thus, fatty acyl CoA reductases can be broadly divided into two types: (1) alcohol-forming acyl-CoA reductases and (2) aldehyde generating acyl-CoA reductases. There are examples of both types in prokaryotes and eukaryotes. Since the target is pimelic semialdehyde, the aldehyde-generating fatty acyl CoA reductases are the most promising candidates for reduction of pimeloyl CoA.

Preliminary literature and database searches revealed that the overwhelming majority of acyl-CoA reductases studied or identified by sequence homology were alcohol-forming FARs in both eukaryotes and prokaryotes. However, one of the early examples of an aldehyde-generating reductase came from Acinetobacter calcoaceticus—Acr1. Therefore, the primary sequence of this enzyme was used in database searches for other aldehyde-generating enzymes.

A general rule for acyl-CoA reductases seems to be that the shorter proteins (295-350 aa) tend to be aldehyde-generating enzymes, whereas longer polypeptides (500+ aa) are alcohol producers. However, most of the shorter enzymes deposited in databases had putative or hypothetical annotations with no further information beyond sequence data and, for this reason, they were not considered.

The candidates were chosen using the following criteria:—(1) The enzyme must generate aldehyde only or there must be scope to eliminate alcohol formation by protein engineering; (2) The must be evidence of existence of the protein i.e. protein has been identified and purified or isolated in cellular fractions; (3) The enzyme was tested using acyl-CoA or acyl-ACP substrates; (4) The enzyme must not be part of multi-enzyme complex unless activity has been demonstrated independently of the complex. Once candidates were identified, further bioinformatics and literature searches were perfoinied to provide additional data to rank the selections.

Table 1 shows the results of database searches carried out against a known aldehyde-forming enzyme (Acr1). Each of the candidates has been purified and assayed in vitro. The candidates were ranked and grouped according to their suitability. The top ranking enzymes (1-3) are considered the best candidates for further study, the intermediate ranked enzymes (4 and 5) are considered to be good candidates but may require further investigation and the lower ranked enzyme (6) would require more effort to obtain enzyme activity data, due to the absence of the protein sequence and the lack of a sequenced genome.

TABLE 1

Candidate Acyl-CoA reductases from various organisms.

| Rank | Protein name or Pubmed accession number | Organism | Shortest substrate tested (no. carbon atoms) | No. of amino acids | Reduction to alcohol | Level of Evidence* |
|---|---|---|---|---|---|---|
| 1 | P94129 | Acinetobacter calcoaceticus | 14 | 295 | No | Enzyme activity |
| 2 | YP_400611 | Synechococcus elongatus PCC 7942 | 18 | 341 | No | Enzyme activity |
| 3 | BAF92773 | Photobacterium phosphoreum | 14 | 488 | No | Enzyme activity |
| 4 | YP_959769 | Marinobacter aquaoelei VT8 | 8 | 661 | Yes, but may be possible to truncate | Enzyme activity |
| 5 | YP_959486 | Marinobacter aquaoelei VT8 | ND | 513 | Yes, but may be possible to truncate | Enzyme activity |
| 6 | AAB35106 (partial) | Botryococcus braunii | 16 | 26 | No | Enzyme activity |

*Level of evidence - Enzyme activity means enzyme has been purified either heterologously or homologously, or activity has been measured in crude extracts or other cellular fractions Acinetobacter calcoaceticus Acr1 (P94129) (Reiser, S., and Somerville, C. (1997): Isolation of mutants of Acinetobacter calcoaceticus deficient in wax ester synthesis and complementation of one mutation with a gene encoding a fatty acyl coenzyme A reductase. J Bacteriol 179, 2969-2975): An aldehyde-generating acyl-CoA reductase has been purified and contains 295 amino acids, with a molecular weight of 32.5 kDa. This enzyme has been expressed in E. coli and cell-free extracts were shown to contain acyl-CoA reductase activity. Acyl-CoA substrates ranging from C12 to C24 in length were assayed (but not the C-odd substrates). The corresponding aldehyde was generated in all cases except for the C12 substrate. It would be worth examining the substrate range of this enzyme further and testing its activity on shorter length acyl-CoAs. Even if pimeloyl CoA is not a substrate, there is scope for directed evolution to extend the substrate range. This enzyme has been named directly in a patent about enhancing production of fatty acid derivatives (US20110256599).

AAR from Synechococcus elongatus PCC 7942 (YP_400611) (Schirmer, A., Rude, M. A., Li, X., Popova, E., and Del Cardayre, S. B. (2010). Microbial Biosynthesis of Alkanes. Science 329, 559-562): This acyl-ACP reductase is in the cyanobacterium S. elongatus and designated AAR. The enzyme is thought to be involved in alkane biosynthesis. It has been expressed and purified in E. coli MG1655. Both CoA and ACP derivatives are substrates. Thus, octadecanal is formed from either oleoyl-CoA and oleoyl-ACP without fatty alcohol formation. However, oleoyl-ACP was the preferred substrate, with a KM of 8 μM compared to 130 μM for oleoyl-CoA. The enzyme is NADPH-dependent and requires magnesium for activity. No other substrates have been tested. The selectivity for aldehyde formation and the activity with CoA derivatives makes this enzyme a good candidate for testing for pimeloyl-CoA reduction. Furthermore, there are a number of orthologues of this gene in closely related organisms (Schirmer et al., 2010), although AAR is the best studied. The following patents are associated with the work from (Schirmer et al., 2010): WO 2009/140695 and WO 2009/140696.

LuxC (BAF92773) from Photobacterium phosphoreum (Boylan, M., Miyamoto, C., Wall, L., Graham, A., and Meighen, E. (1989). Lux C, D and E genes of the Vibrio fischeri luminescence operon code for the reductase, transferase, and synthetase enzymes involved in aldehyde biosynthesis. Photochemistry and photobiology 49, 681-688; Lee, C. Y., and Meighen, E. A. (1997). Cysteine-286 as the site of acylation of the Lux-specific fatty acyl-CoA reductase. Biochim Biophys Acta 1338, 215-222; Wang, X., and Kolattukudy, P. E. (1995). Solubilization and purification of aldehyde-generating fatty acyl-CoA reductase from green alga Botryococcus braunii. FEBS Lett 370, 15-18): LuxC is part of a multi-enzyme complex (LuxCDE) consisting of a fatty acyl-CoA reductase, fatty acyl synthetase and fatty acyl thioesterase, and is involved in bioluminescence. LuxC is a well-studied enzyme and has been cloned, expressed and purified in E. coli. The enzyme exhibits acyl-CoA reductase activity with the C14 substrate, tetradecanoyl-CoA (myristoyl-CoA), which is reduced to the corresponding aldehyde, tetradecanal. No other substrates have been tested. Although the LuxC is part of a multisubunit complex in vivo, the enzyme has been successfully purified from the wild-type organism and has been expressed and partially purified from E. coli. In both cases, LuxC was active independently of the other subunits. This makes LuxC a good candidate to convert pimeloyl-CoA to pimelic acid semialdehyde.

FAcoAR from Marinobacter aquaeolei VT8 (YP_959769.1) (Willis, R. M., Wahlen, B. D., Seefeldt, L. C., and Barney, B. M. (2011). Characterization of a fatty acyl-CoA reductase from Marinobacter aquaeolei VT8: a bacterial enzyme catalyzing the reduction of fatty acyl-CoA to fatty alcohol. Biochemistry 50, 10550-10558): This fatty acyl CoA reductase (designated FAcoAR) was recently discovered in the gamma proteobacterium Marinobacter aquaeolei VT8. It is the first prokaryotic example of a bi-functional acyl-CoA reductase, catalyzing reduction of acyl-CoA derivatives to alcohol. Crucially it is the only enzyme that has been tested with substrates below C12, and shows activity with octanoyl-CoA in vitro (Willis et al., 2011). Although this enzyme generates alcohol from acyl-CoA, the rationale for its inclusion is that there is clear evidence that it has a broad substrate range from octanoyl-CoA (C8) to arachidonoyl-CoA (C20). Furthermore, the C-terminal end shows high sequence homology to the Acr1 enzyme, so the N-terminal region may be the alcohol-forming domain. Therefore, it would be worthwhile to test the effect of removing the portion of the gene coding for the N-terminal region of the polypeptide, with the aim of generating a functional, aldehyde-generating enzyme. A potential problem with this approach is that the enzyme might be inactive or the aldehyde may not be released from the truncated enzyme complex. This enzyme has not been tested for activity against acyl ACP derivatives.

FAR from *Marinobacter aquaeolei* VT8 (YP_959486) (Hofvander, P., Doan, T. T. P., and Hamberg, M. (2011). A prokaryotic acyl-CoA reductase performing reduction of fatty acyl-CoA to fatty alcohol. FEBS Letters 585, 3538-3543): This fatty acyl CoA reductase (designated FAR) was originally identified as a fatty aldehyde reductase (Wahlen, B. D., Oswald, W. S., Seefeldt, L. C., and Barney, B. M. (2009). Purification, characterization, and potential bacterial wax production role of an NADPH-dependent fatty aldehyde reductase from *Marinobacter aquaeolei* VT8. Appl Environ Microbiol 75, 2758-2764), but has since been shown to have acyl-CoA reductase activity (Hofvander, P., Doan, T. T. P., and Hamberg, M. (2011). A prokaryotic acyl-CoA reductase performing reduction of fatty acyl-CoA to fatty alcohol. FEBS Letters 585, 3538-3543). It is very similar to the fatty acyl-CoA reductase described above, but it is also known to act on acyl ACP derivatives Activity was observed with C16-CoA up to C20-CoA, but has not been tested with shorter substrates. The enzyme is 513 amino acids long and has the same C-terminal domain associated with aldehyde generation as Acr1. It is possible that this enzyme could also be truncated, which would mean cleaving off the N-terminal region as described previously. It is not clear whether or not FAR and FAcoR are entirely different enzymes, since two separate (and competing) research groups have studied them.

Aldehyde-generating acyl-CoA reductase from *Botryococcus braunii* (AAB35106) (Wang, X., and Kolattukudy, P. E. (1995). Solubilization and purification of aldehyde-generating fatty acyl-CoA reductase from green alga *Botryococcus braunii*. FEBS Left 370, 15-18): This enzyme is an aldehyde-generating acyl-CoA reductase from the microalga, *Botryococcus braunii*. The enzyme has been purified from the wild-type organism and assayed using labeled activated fatty acid, [1-14C]-palmitoyl-CoA. The enzyme was shown to produce the corresponding aldehyde and was NADH-dependent. The substrate range has not been studied and this would need to be addressed. Furthermore, the protein needs to be cloned, expressed and purified in *E. coli*. Accession number AAB35106 refers to a partial 26 amino acid N-terminal sequence from the purified enzyme. The full protein sequence is not deposited on UNIPROT, BRENDA or NCBl databases. Sequencing of the genome is underway. There might be scope to isolate the gene using primers for the N terminal sequence, but the general lack of information about the enzyme may complicate its exploitation for metabolic engineering.

Thus, a number of acyl-CoA reductases have been identified that are suitable candidates to be tested for reduction of pimeloyl-CoA to pimelic semialdehyde. The enzyme from *Acinetobacter calcoaceticus*, Acr1, appears to be the best candidate, as it is the best characterized of the enzymes identified even though there is no information on activity with short chain, C-odd substrates. If initial tests turn out to be negative, the enzyme would still be a good target for directed evolution to obtain pimeloyl CoA reduction.

AAR from *S. elongatus* and its orthologues as well as LuxC are also promising candidates. Although these enzymes operate on relatively long chain fatty acyl CoA substrates, they have not been tested with short chain substrates. Again, directed evolution may provide a promising route to obtain the desired substrate selectivity if the initial tests are negative.

The two enzymes from *M. aquaeolei* VT8 may also be promising, although some protein engineering is likely to be required to prevent oxidation of the aldehyde. These enzymes are suitable candidates because they are known to act on the shortest chain fatty acyl CoAs out of all the fatty acyl CoA reductases identified. The gene encoding the enzyme from *B. braunii* has not yet been identified. This makes it the most difficult of the enzymes to work with, but it could be investigated if other options are not successful. Similar enzymes are also known in higher plants (e.g. *Pisum sativum*) and provide further options for testing, but, again, are not well characterised.

Thus, the above six enzymes have been selected because there are literature reports that they have been prepared, purified (partially of fully) either recombinantly or natively in cellular fractions and assayed in vitro. Their nucleotide and primary amino acid sequences are deposited on the main protein databases BRENDA and UNIPROT, except for the enzyme from *Botyrococcus braunii*. Results from the studies have been published in peer-reviewed journals. The substrates tested range from octanoyl-CoA (C8) up to arachinadoyl-CoA (C20) and also included acyl-ACP as substrate in the case of AAR from Synechococcus elongates. The corresponding aldehydes are formed as products. However, to date, none of the enzymes have been tested with pimeloyl-CoA or any other C-odd number substrates, presumably because the metabolism of these substrates is invariably assumed to follow the same pattern as the C-even number substrates and, until now, there has been no reason to test them against these substrates. Therefore, it is highly likely that the enzymes will catalyse the reduction of pimeloyl-CoA. Even if pimeloyl CoA is not a substrate, the enzymes would provide a good starting points for directed evolution or targeted protein engineering.

Other candidates amongst the long fatty acyl-CoA reductase for the conversion of pimeloyl-CoA to pimelic acid semialdehyde include, but is not limited to, reductases from the following organisms: *Pisum sativum* (Vioque et al., 1997. Resolution and purification of an aldehyde-generating and an alcohol-generating fatty acyl-CoA reductase from Pea leaves (*Pisum sativum* L.), Archives of Biochemistry and Biophysics, 340 (1), 64-72); *Vibrio fischeri* (P12748) (Boylan et al., 1985. Functional identification of the fatty acid reductase components encoded in the luminescence operon of *Vibrio fischeri*, Journal of Bacteriology, 163(3), 1186-1190); *Brassica oleracea* and *B. napus* (Q39342) (Kolattukudy, 1971. Enzymatic synthesis of fatty alcohols in *Brassica oleracea*. Archives of Biochemistry and Biophysics, 142(2), 701-709); *Clostridium butyricum* (Day et al., 1978. Partial purification and properties of acyl-CoA reductase from *Clostridium butyricum*, Archives of Biochemistry and Biophysics, 190(1), 322-331); *Anas platyrhynchos* (Ishige, T.; Tani, A.; Takabe, K.; Kawasaki, K.; Sakai, Y.; Kato, N. Wax Ester Production from n-Alkanes by *Acinetobacter* sp. Strain M-1: Ultrastructure of Cellular Inclusions and Role of Acyl Coenzyme A Reductase. Appl Environ Microbiol 2002, 68, 1192-1195); *Arabidopsis thaliana* (Doan, T. T. P.; Carlsson, A. S.; Bamberg, M.; Bülow, L.; Stymne, S.; Olsson, P. Functional expression of five *Arabidopsis* fatty acyl-CoA reductase genes in *Escherichia coli*. Journal of plant physiology 2009, 166, 787-796; Hooks, M. A.; Kellas, F.; Graham, I. A. Long-chain acyl-CoA oxidases of *Arabidopsis*. Plant J. 1999, 20, 1-13); *Homo sapiens*, R. P.; Wang, Y.; Mohsen, A. W.; He, M.; Vockley, J.; Kim, J. J. P. Structural basis for substrate fatty acyl chain specificity: crystal structure of human very-long-chain acyl-CoA dehydrogenase. J Biol Chem 2008, 283, 9435-9443); *Simmondsia chinensis* (Q9XGY7), and *Mus musculus* (Q7TNT2, Q922J9).

3.1.4 Conversion of Pimelic Acid to Pimelic Acid Semialdehyde by Carboxylaic Acid Reductases (EC 1.2.99.-)

3.1.4.1 Selection, Cloning, and Expression of Carboxylic Acid Reducatse Targets Enzyme targets for the reduction of pimelic acid into pimelic acid semialdehyde were selected from the carboxylic acid reductase family (EC 1.2.99.-, such as EC 1.2.99.6). In particular, the *Nocardia* carboxylic acid reducatse is a monomeric enzyme that displays a large substrate specificity towards aromatic substrates and was successfully cloned and expressed in *E. coli* (*Nocardia* sp. Carboxylic acid reductase: Cloning, expression, and characterization of a new aldehyde oxidoreductase family: He et al. *Appl. Environ. Microbiol.* 2004, 70, 1874-1881). The enzyme was therefore a good candidate for an initial screening to monitor conversion of pimelic acid to pimelic acid semialdehyde.

The *Nocardia* sp. carboxylic acid reductase (CAR) gene (GeneBank AY495697) was previously cloned into the pHAT-10 vector (Clontech). The *E. coli* strain BL-21 (DE3) RP 1pPV2-85 harbouring the carboxylic acid reductase from *Nocardia* species was used (He et al. (2004). Expression study was then initiated using standard conditions (1 mM IPTG, 37° C. pre- and post-induction temperatures) and was expressed in *E. coli* under IPTG induction according to the previously reported protocol, and scaled up to produce enough protein for the activity assay.

3.1.4.2 Cell Lysis and SDS-PAGE Analysis

The cell pellet was lysed to provide material for the activity assays. Due to the large scale glass bead lysis in conjunction with lysozyme treatment was employed to break the cells. The cell pellet from the 4 hour post-induction sample was re-suspended in bead lysis buffer consisting of 0.1 mM Tris, 1 mg/ml Pepstatin A and 200 mM PMSF protease inhibitors (161 μL of the mixture should be used for the lysis of the cell pellet from 1 mL of culture at an OD600 of 5) supplemented with 1.5 mg/mL lysozyme. Acid washed 212-300 μm glass beads (0.4 g per 1 mL of lysis buffer) were added to each sample, and lysed by vortexing (cycles of 30 s vortex and 30 s on ice for 10 cycles). The lysis reaction was then centrifuged at 13000 rpm for 20 min. The soluble fraction was transferred to a new tube and the insoluble fraction re-suspended in the same volume of water as the volume of lysis buffer previously used. 20 μl of each fraction was mixed with 80 μl SDS-Sample buffer (SDS-Loading Buffer, 9% DTT and water) and the mixture was heated in a heatblock for 5 minutes at 95° C. 20 μl of each SDS-sample preparation was then loaded on SDS-PAGE 4-20% Tricene gels to analyze the protein content of the soluble and insoluble fractions (FIG. 12).

Figure 1:
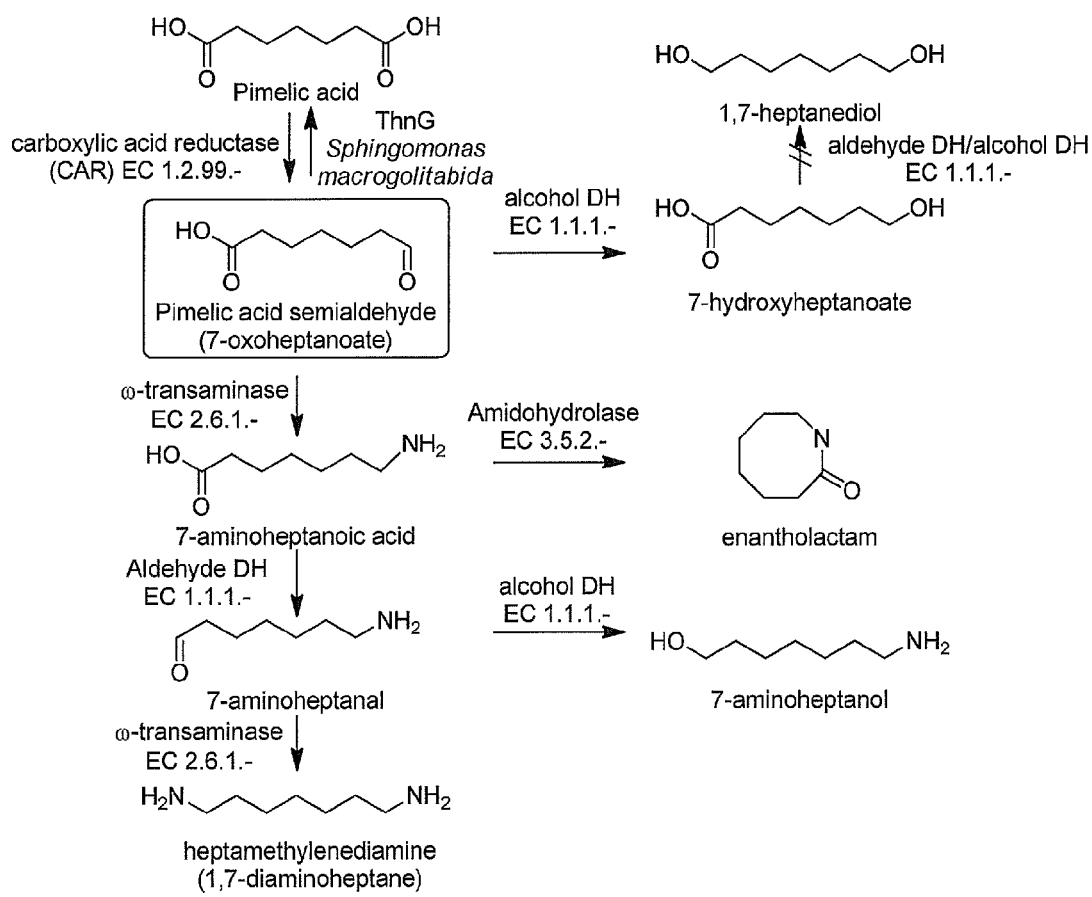
FIG. 1 is a schematic showing the biotransformation of pimelic acid semialdehyde, to various difunctional C7 alkanes useful for nylon 7, nylon 7,7 and nylon 7,x production, as well as polyesters.

Protein bands at the expected size (128 kDa) were clearly visible in the soluble and insoluble fractions (FIG. 1: Lanes 3 and 4 respectively) after 4 h post-induction. A larger amount of expressed proteins was observed in the soluble fractions (FIG. 12: Lane 3) showing that a large fraction of the protein was expressed in soluble form.

3.1.4.3 Activity Assays

The activity assay was based on spectrophotometric detection of CAR activity towards sodium benzoate as positive control and sodium pimelate. The conditions for the assay were taken from Applied and Environmental Microbiology 2004, 70, p 1874-1881.

The following stock solutions were prepared: 50 mM sodium benzoate, 50 mM sodium pimelate, 100 mM $MgCl_2$, 50 mM Tris.HCl pH7.5 with 1 mM DTT, 1 mM EDTA in 10 v/v % glycerol buffer, 10 mM ATP, 1.5 mM NADPH (reduced form).

In a quartz cuvette the following reagents were added: 100 μL $MgCl_2$, 100 μL ATP, 100 μl NADPH, 2004 Tris.HCl buffer. The absorbance at 340 nm was measured and recorded and 100 μL of CAR cell free extract was added. The absorbance was monitored and recorded. After 2 minutes 100 μL of 100 mM of either sodium benzoate or sodium pimelate was added, and the absorbance was again monitored and recorded. The absorbance monitored over time was subtracted from the initial measurement. The best line fit for the data was plotted to generate a gradient of the rate of change in absorbance at 340 nm and is presented in FIG. 13 and Table 2 below to determine the relative rate of change in absorbance compared to that of benzoic acid:

TABLE 2

| Substrate | gradient of trend line | Adjusted for background | Relative rate % compared to benzoate |
| --- | --- | --- | --- |
| sodium benzoate | 0.0141 | 0.00133 | 100% |
| sodium pimelate | 0.0076 | 0.0068 | 51.1% |

Thus, CAR from *Nocardia* catalysed the reduction of pimelic acid to pimelic acid semialdehyde with >50% of the activity for benzoic acid. Other suitable enzymes for the reduction of pimelic acid from EC 1.2.99.6 include for example that of *Streptomyces griseus* (Suzuki et al., 2007. GriC and GriD constitute a carboxylic acid reductase involved in grixazone biosynthesis in *Streptomyces griseus*. J Antibiot (Tokyo). Jun; 60(6):380-7).

3.1.5 Conversion of Pimeloyl-CoA to Pimelic Acid by Thioester Hydrolases (EC 3.2.1.-), Pimeloyl-CoA Ligases (EC 6.2.1.-) such as EC 6.2.1.14 and 6.2.1.23, or CoA Transferases, (EC 2.8.3.-) and Pimeloyl-[acp] to Pimelic Acid by oleoyl-[acp] hydrolase (EC 3.1.2.14)

Enzymes that are able to catalyse the hydrolysis or transfer of CoASH include thioester hydrolases from EC 3.2.1.-, such as EC 3.1.2.2, EC 3.1.2.3, EC 3.1.2.18; 3.1.2.19, 3.1.2.20 EC 3.1.2.21, EC 3.1.2.27, acid-thiol ligases from EC 6.2.1.-, such as EC 6.2.1.3, EC 6.2.1.14, EC 6.2.1.23 and CoA transferases from EC 2.8.3.-, such as EC 2.8.3.12 and EC 2.8.3.13. Amongst those three families, thioesterases present the best candidates for the hydrolysis of pimeloyl-CoA due to the large number of characterized enzymes and their broad substrate specificity in terms of chain length (C-3 to C-26) and in terms of functional groups (Dicarboxylyl-CoA substrate).

3.1.5.1 Acid-thiol Ligases

Acid thiol ligases catalyse the formation of carbon-sulfur bonds with concomitant hydrolysis of adenosine triphosphate (ATP). Hydrolysis of Acyl-CoA would therefore require the generation of ATP during the acid thiol ligase-catalysed reaction which is thermodynamically disfavored compared to the reverse reaction:

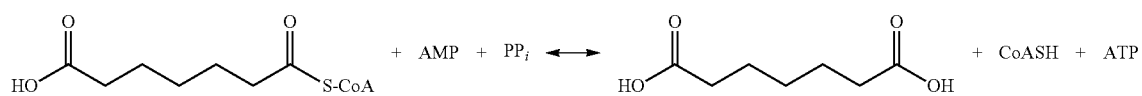

However, these enzymes are still useful and several CoA ligases are known to act on pimeloyl-CoA:

| Enzyme | EC | Source | Reaction | Gene | Size | Over-expression | Purification |
|---|---|---|---|---|---|---|---|
| bioW (P22822) | 6.2.1.14 6-carboxy-hexanoate--CoA ligase AMP forming (pimeloyl-CoA synthase) | Lysinibacillus (Bacillus sphaericus) | pimelic acid → pimeloyl-CoA | Yes | 28 kDA | Yes, E. coli | Yes, homogeneity |
| pauA (AJ012480) | 6.2.1.n catabolic pimeloyl-CoA synthase | Pseudomonas mendocina35 | pimelic acid → pimeloyl-CoA adipic acid → adipoyl-CoA azelaic acid → azelaoyl-CoA | Yes | 74 kDa | Yes, E. coli | Yes, homogeneity |
| ?? | 6.2.1.n pimeloyl-CoA synthetase | Bacillus megaterium | pimelic acid → pimeloyl-CoA | No | ? | No | Yes, 34-fold |
| ?? | pimeloyl-CoA synthase | Lavandula vera L. | pimelic acid → pimeloyl-CoA | No | ? | No | No |
| ?? | plant soluble acyl-CoA synthetase | Pisum sativum L. | pimelic acid → pimeloyl-CoA azelaic acid → azelaoyl-CoA | No | 53 kDa | No | No |
| ?? | plant peroxisomal acyl-CoA synthetase | Pisum sativum L. | pimelic acid → pimeloyl-CoA | No | ? | No | No |
| ?? | 6.2.1.23 - microsomal dicarboxylate-CoA ligase | Rattus norvegicus | C5-C16 dicarboxylates → CoA esters | No | ? | No | No |
| ?? | 6.2.1.23 pimeloyl-CoA synthetase | LP-1 strain | pimelic acid → pimeloyl-CoA | No | ? | No | No |

BioW (Uniprot:P22822)—from *Lysinibacillus sphaericus* (*Bacillus sphaericus*)

Pimelic acid CoA synthase (6-carboxyhexanoate-CoA ligase) was discovered in *Bacillus sphaericus* using cell free extracts. It is involved in the biotin biosynthesis pathway. The enzyme activity was determined indirectly by a reaction coupled with 7-keto-8-aminopelargonic acid synthetase and microbiological assay using *Saccharomyces cerevisiae*[1]. The gene encoding pimelic acid CoA synthase (bioW) was identified together with 7-keto-8-aminopelargonic acid synthetase (bioF) by complementation studies of *E. coli* mutants with the library carrying sequences from the *B. sphaericus* genome [Gloeckler R, Ohsawa I, Speck D, Ledoux C, Bernard S, Zinsius M, Villeval D, Kisou T, Kamogawa K, Lemoine Y. (1990) Cloning and characterization of the *Bacillus sphaericus* genes controlling the bioconversion of pimelate into dethiobiotin. *Gene*. 87:63-70]. BioW was overexpressed in *E. coli* and purified to homogeneity [Ploux O, Soularue P, Marquet A, Gloeckler R, Lemoine Y. (1992) Investigation of the first step of biotin biosynthesis in *Bacillus sphaericus*. Purification and characterization of the pimeloyl-CoA synthase, and uptake of pimelate. *Biochem J*. 287: 685-690]. The enzyme was active in the presence of disodium pimelate, ATP, CoASH and MgCl$_2$. The products of the reaction were pimeloyl-CoA and AMP, no ADP was detected. The enzyme was specific only for ATP and pimelate. Other nucleotides (such as GTP, AMP) and alternative substrates (succinate, glutarate, adipate, suberate) were not accepted.

PauA (GenBank: AJ012480.1) from *Pseudomonas mendocina* 35

Catabolic pimeloyl-CoA ligase, pauA, is involved in degradation of dicarboxylic acids (C6-C10) in *Pseudomonas mendocina* 35 [Binieda A, Fuhrmann M, Lehner B, Rey-Berthod C, Frutiger-Hughes S, Hughes G, Shaw N M. (1999) Purification, characterization, DNA sequence and cloning of a pimeloyl-CoA synthetase from *Pseudomonas mendocina* 35. *Biochem J*. 340:793-801]. The enzyme activates dicarboxylic acids which are subsequently metabolized via the beta-oxidation pathway. The enzyme was purified to homogeneity and the partial amino acid sequence was determined. PauA showed a broader substrate range than bioW, and accepts pimelate (100% relative activity), adipate (72%) and azelate (18%). The enzyme was between one and two orders of magnitude more active than bioW involved in the biotin biosynthesis pathways. The gene pauA was identified and the ligase was successfully overexpressed in *E. coli*.

Pimeloyl-CoA Synthetase from *Bacillus megaterium*

The enzyme was purified about 34-fold with 79% recovery [Izumi Y, Morita H, Tani Y, Ogata K. (1974) The pimeloyl-CoA synthetase responsible for the first step in biotin biosynthesis by microorganisms. *Agr. Biol. Chem*. 38, 2257-2262]. The reaction required pimelate, ATP, CoASH and MgCl$_2$. The enzyme was specific towards pimelate only, and other dicarboxylic acids were not accepted. Interestingly, ATP could be replaced with ADP, suggesting that pyrophosphate cleavage is not essential. The amino acid and nucleotide sequences are not known. However three complete genomes of *Bacillus megaterium* have been published since 1974. Therefore, a BLAST search for bioW homologs was undertaken. Unfortunately, this did not show any matches.

Plant Pimeloyl-CoA Synthase from *Lavandula vera* L.

Pimeloyl-CoA synthase activity in lavender cell cultures has been described [6]. Although [$^3$H]-pimelic acid was found to be a precursor in biotin biosynthesis, there are no data available about the enzyme or the gene.

Plant Soluble acyl-CoA Synthetase from *Pisum sativum* L.

The activity was found in the soluble fraction of pea protein extracts [7]. The enzyme required ATP/Mg$^{2+}$ and CoASH. The molecular weight of the ligase was determined by western blot technique using polyclonal antibodies against the ligase from *Lysinibacillus sphaericus*. The enzyme accepted pimelic acid as well as azelaic acid, but not nonanoic acid. GTP could be used instead of ATP, but no reaction was observed for ADP. The gene encoding the soluble pimeloyl-CoA synthetase was not identified.

Plant Peroxisomal acyl-CoA Synthetase from *Pisum sativum* L.

The enzyme was located in the peroxisomal protein fraction [GerblingH, AxiotisS, Douce R. (1994) A new acyl-CoA synthetase, located in higher plant cytosol. *J Plant Physiol.* 143: 561-564.]. Pimelic acid was activated to pimeloyl-CoA and subsequently degraded to acetyl-CoA and malonyl-CoA by the beta-oxidation pathway. The substrate range of this enzyme was not tested. It showed a higher pH-optimum than soluble acyl-CoA synthetase from the same organism.

Dicarboxylate-CoA Ligase from *Rattus norvegicus*

Dicarboxylic acids (C5-C16) were converted into their CoA esters by a dicarboxylyl-CoA synthetase from the microsomal protein fraction from a rat liver [Vamecq J, de Hoffmann E, Van Hoof F. (1985) The microsomal dicarboxylyl-CoA synthetase. *Biochem J.* 230:683-693.]. The enzyme uses ATP, but not GTP. The reaction is inhibited by its products, and AMP is more inhibitory than pyrophosphate. The enzyme showed the highest activity for the C12 substrate. In some assays of dicarboxylyl-CoA synthetase, the plateau of CoA consumption was followed by CoA release. This is an important observation because it suggests that the reaction might be reversible. However, this suggestion should be treated with some caution, because the protein sample may have been contaminated with CoA thioesterase. Whilst this enzyme may be promising, BLAST searching of the *R. norvegicus* genome sequence did not reveal any bioW or pauA homologues. An alternative approach would be needed to identify the gene, for example, enzyme purification, N-terminal sequencing, primer design and PCR amplification.

Pimeloyl-CoA Synthetase from Unidentified Bacterium, LP-1 Strain

The activity was found in environmental cultures of denitrifying bacteria from activated sludge enriched to grow on sodium nitrate and pimelate [Gallus C, Schink B. (1994) Anaerobic degradation of pimelate by newly isolated denitrifying bacteria. *Microbiology.* 140: 409-416.]. The enzyme was active in the presence of ATP and Mg$^{2+}$. The product of the reaction was AMP rather than ADP. The enzyme did not accept benzoic acid.

The CoA ligases have not been tested rigorously or systematically for reversibility. No crystal structures are available, so the active site structure is not known. Therefore, it is not clear whether AMP, pyrophosphate or magnesium ions would be needed for the reverse reaction, and in vitro assays should be done in the presence and absence of combinations of these cofactors. Of course, the ultimate goal is to obtain the reverse reaction in whole cells, and this might be more challenging. The later reactions in the pathway will, of course, pull the equilibrium in the thiolytic direction. Nevertheless, this might be a difficult reaction to reverse because the hydrolysis of ATP and subsequent hydrolysis of pyrophosphate make the forward reaction exergonic. Therefore, it is important to measure the effect of different ATP:AMP ratios on reversibility of the reaction in vitro before attempting to engineer the cells. If the ATP:AMP ratio is critical, it might be necessary to manipulate the cellular energy charge to make the intracellular ATP concentration low enough to allow the reverse reaction to proceed. This, in turn, may cause further difficulties with obtaining good productivity, since it might be necessary to use ATP synthase inhibitors or uncouplers to achieve low enough ATP concentrations. In principle, none of these problems is insurmountable, but development of the engineered biocatalysts might become complicated. Therefore, simpler enzyme systems such as thioesterases were investigated as a higher priority.

3.1.5.2 CoA Transferases (EC 2.8.3.-)

CoA transferases are less attractive candidates than thioesterases, due to either a narrow substrate specificity or a lack of gene/protein characterization such as for the succinate-hydroxymethylglutarate CoA transferase despite showing activity towards the C-6 derivative of pimeloyl-CoA, adipyl-CoA (EC 2.8.3.13—Substrate specificity of a dicarboxyl-CoA:dicarboxylic acid coenzyme A transferase from rat liver mitochondria: Deana et al. *Biochem Int.* 1992, 26, 767-773). Some enzymes from this family may still be useful, since it had been possible to change the activity of the enzyme glutaconate CoA transferase from *Acidaminococcus fermentans* (EC 2.8.3.12-Glutaconate CoA-transferase from *Acidaminococcus fermentans*: Buckel et al. Eur. J. Biochem. 1981, 118, 315-321) from a CoA transferase to CoA esterase by site-directed mutagenesis (Mack M, Buckel W. (1997) Conversion of glutaconate CoA-transferase from *Acidaminococcus fermentans* into an acyl-CoA hydrolase by site-directed mutagenesis. *FEBS Lett.* 405: 209-212). This enzyme was successfully expressed in *E. coli* and used for enzymatic biosynthesis of glutaconyl-CoA, 3-methylglutaconyl-CoA, butynedioyl-CoA, 2-hydroxyadpioyl-CoA, oxalocrotonyl-CoA and muconyl-CoA (Parthasarthy A, Pierik A, Kahnt J, Zelder O, Buckel W. (2011) Substrate specificity of 2-hydroxyglutaryl-CoA dehydratase from *Clostiridium symbiosum*: Toward a bio-based production of adipic acid. *Biochemistry.* 50: 3540-35500). The crystal structure of GctAB was also published (Jacob U, Mack M, Clausen T, Huber R, Buckel W, Messerschmidt A., (1997) Glutaconate CoA-transferase from *Acidaminococcus fermentans*: the crystal structure reveals homology with other CoA-transferases. Structure. 5:415-426). This transferase binds the terminal carboxylate anion via several hydrogen bonds to serine residues, which may adjust to the different chain lengths. The CoA transferase from *Rattus norvegious* (Succinate-hydroxymethylglutarate CoA-transferase EC 2.8.3.13) is also a good candidate, since it accepts adipyl-CoA as substrate, with higher affinity than that observed for succinyl-CoA, malonyl-CoA, glutaryl-CoA (Substrate specificity of a dicarboxyl-CoA:dicarboxylic acid coenzyme A transferase from rat liver mitochondria (Deana Biochem Int. 1992, 26, 767-773).

3.1.5.3 Thioester Hydrolases (EC 2.3.1.-)
3.1.5.3.1 Selection of Suitable Enzymes Thioesterases are hydrolytic enzymes that catalyze the hydrolysis of thioesters:

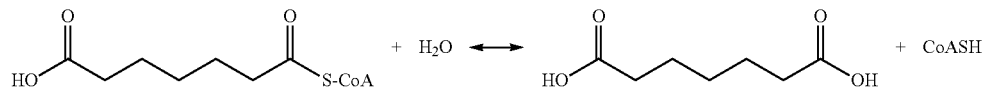

There are very large numbers of thioesterases listed in the databases, but it seems that only two thioesterases (ACOT8 and ACOT4) have been tested for activity towards dicarboxylyl-mono-CoA esters.

| Enzyme | EC | Source | Substrates | Gene | Size (kDa) | Over-expression | Purification |
|---|---|---|---|---|---|---|---|
| ACOT8 (PTE-2) | 3.1.2.27 | Mus musculus | Broad range straight-CoA, bile acids CoA and branched-chain acyl-CoA | Yes | 50 | Yes | Yes, his-tag fusion, homogeneity |
| ACOT5 (PTE-1c) | 3.1.2.2 palmitoyl-CoA hydrolase | Mus musculus | Medium chain acyl-CoA | Yes | 46.6 | Yes | Yes, his-tag fusion, homogeneity |
| ACOT3 (PTE-1a) | 3.1.2.2 palmitoyl-CoA hydrolase | Mus musculus | Long chain acyl-CoAs | Yes | 47.4 | Yes | Yes, his-tag fusion, homogeneity |
| ACOT4 (PTE-1b) | 3.1.2.3 Succinyl-CoA thioester-ase | Mus musculus | Succinyl-CoA and glutaryl-CoA ONLY. | Yes | 36 (active as dimer) | Yes | Yes, his-tag fusion, homogeneity |

ACOT8 Peroxisomal acyl-CoA Thioesterase 8 (Formerly PTE-2) from *Mus musculus*

ACOT8 is a homologue of human PET1 thioesterase. The enzyme was overexpressed as a His-Tag fusion protein in *E. coli* and purified to homogeneity using HisTrap column chromatography [Westin M A, Hunt M C, Alexson S E. (2005) The identification of a succinyl-CoA thioesterase suggests a novel pathway for succinate production in peroxisomes. *J Biol. Chem.* 280: 38125-38132]. The activity was inhibited at substrate concentrations >5-10 µM for long-chain acyl-CoAs, but addition of BSA prevented inhibition. The substrate range of the thioesterase was tested using saturated and unsaturated straight-chain acyl-CoAs (C2-C20). The highest activity was for C10-C18, bile acids (trihydroxycoprostanoyl-CoA, choloyl-CoA and chenodeoxycholoyl-CoA and branched-chain acyl-CoAs. $K_m$ values for most of the substrates tested were rather low, strongly suggesting that ACOT8 has very broad substrate specificity and can accept most of them. ACOT8 was strongly inhibited by CoASH with an $IC_{50}$ of 10-15 µM. ACOT8 was also tested for activity towards dicarboxylyl-mono-CoA derivatives and preferentially hydrolyzed the longer-chain substrates (activity increase with C chain length from C3 to C12) [Hunt M C, Solaas K, Kase B F, Alexson S E. (2002) Characterization of an acyl-coA thioesterase that functions as a major regulator of peroxisomal lipid metabolism. *J Biol. Chem.* 277: 1128-1138].

ACOT3 (Formerly PTE-1a) from *Mus musculus*

ACOT3 was expressed in *E. coli* and purified to homogeneity [19]. The enzyme showed activity for monocarboxylic acid esters from C8 to C26, with the highest activity towards longer chain substrates (C16). The enzyme did not accept bile acid esters. There was no inhibition with free CoASH. Dicarboxylic acid esters were not tested.

ACOT5 (Formerly PTE-1c) from *Mus musculus*

ACOT5 was expressed in *E. coli* and purified to homogeneity [Westin M A, Alexson S E, Hunt M C. (2004) Molecular cloning and characterization of two mouse peroxisome proliferator-activated receptor alpha (PPARalpha)-regulated peroxisomal acyl-CoA thioesterases. *J Biol Chem.* 279: 21841-21848]. The enzyme showed activity for monocarboxylic acid esters from C6 to C20, with the highest activity towards medium chain substrates (C10). The enzyme did not accept bile acid esters. There was no inhibition with free CoASH. Dicarboxylic acid esters were not tested.

ACOT4 Peroxisomal acyl-CoA Thioesterase 4 (Formerly PTE-1b) from *Mus musculus*

ACOT4 was expressed in *E. coli* and purified to homogeneity [18]. The enzyme showed a narrow substrate range, accepting succinyl-CoA and glutaryl-CoA. The reaction was not inhibited by CoASH at concentrations up to 500 µM.

ACOT8, ACOT5 and ACOT3 are thus excellent candidates for the hydrolysis of dicarboxylyl-CoAs and other acyl-CoAs that are involved in the pimelic acid biosynthesis pathway.

3.1.5.3.2 Cloning, Expression and Biotransformations with Selected Thioesterases Thioesterases from *Mus musculus* Acot8 (WT mRNA sequence GeneBank NM_133240; mRNA fragment 65-1027) and the *Haemophilus influenzae* YciA (WT gene sequence (GeneBank L42023 fragment 878596-879060)

were selected as examples for the conversion of pimeloyl-CoA to pimelic acid, due their specificity towards dicarboxylyl-CoA substrates (The identification of a succinyl-CoA thioesterase suggests a novel pathway for succinate production in peroxisomes: Westin J. et al. Biol. Chem. 2005, 280, 38125-38132; Divergence of function in the hot dog fold enzyme superfamily—the bacterial thioesterase YciA: Zhuang et al. Biochemistry 2008, 47, 2789-2796). Both genes were identified from their respective host genome and successfully cloned and expressed in *Escherichia coli* (Characterization of an acyl-CoA thioesterase that functions as a major regulator of peroxisomal lipid metabolism: Hunt et al. J. Biol. Chem. 277, 1128-1138; Divergence of function in the hot dog fold enzyme superfamily—the bacterial thioesterase YciA: Zhuang et al. Biochemistry 2008, 47, 2789-2796).

Both genes were selected as wild-type sequences for the construction of the corresponding *E. coli* expression vectors and used to transform *E. coli* BL21 (DE3). Expression of *Haemophilus influenzae* YciA thioesterase was achieved in *E. coli*, (FIG. 14*h*) but not of the *Mus musculus* Acot8 thioesterase. A protein band at the expected size (17 kDa) was clearly detected after IPTG induction in the soluble fraction (Lanes 2 to 3) and in the insoluble fraction (Lanes 6 and 7). No corresponding protein was observed in the negative control experiment (Lanes 4 and 8) suggesting that the expected 17 kDa *Haemophilus influenzae* YciA thioesterase protein was successfully expressed in *E. coli* from the assembly construct I8. Soluble expression of the YciA protein appeared to increase over time between 4 h and 24 h post-induction incubation (Lanes 2 and 3) whereas insoluble expression appeared to decrease in the same period (Lanes 6 and 7). Therefore, the 24 h soluble sample seemed to be the best candidate for monitoring activity of the *Haemophilus influenzae* YciA thioesterase.

Since no expression of the *Mus musculus* Acot8 protein was detected in *E. coli* using the pET21-a/IPTG expression system, *Saccharomyces cerevisiae* was selected as an alternative system to produce and test the thioesterase enzyme. Transformation with the *S. cerevisiae* expression vector was carried out and expression from the constitutive promoter ADH1p was monitored on SDS-PAGE after cell lysis.

3.1.6 Conversion of Pimelic Acid Semialdehyde to 7-aminoheptanoic Acid and Conversion of α-ketosuberate to α-aminosuberate by Aminotransferases (EC 2.6.1.19; EC 2.6.1.39)

Transaminases or aminotransferases are enzymes that catalyse the reaction between an amino acid and a keto acid. This reaction involves removing the amino group from the amino donor, leaving behind an α-keto acid, and transferring it to the acceptor α-keto acid and converting it into an amino acid. They are important enzymes in the synthesis of amino acids and are ubiquitous throughout nature. Many of these enzymes contain pyridoxal-phosphate (PLP) as cofactor. These enzymes belong to a large diverse family covering a wide range of cellular functions, using a wide range of substrates.

3.1.6.1 Conversion of Pimelic Acid Semialdehyde to 7-aminoheptanoic Acid

A number of candidates, identified by literature searching, BLAST searching and protein database searching are suitable enzymes for to conversion of pimelic acid semialdehyde to 7-aminoheptanoic acid.

| Enzyme Name/EC No. | Accession number | Source | Gene available | Protein purified |
|---|---|---|---|---|
| EC 2.6.1.19 | YP_001823341.1 | *Streptomyces griseus* | Yes | Yes |
| LysN | Q72LL6 | *Thermus thermophillus* | Yes | Yes |
| AADaT | Q64602 | *Rattus norvegicus* | Yes | Yes |

EC 2.6.1.19

4-Aminobutyrate Transaminase from *Streptomyces griseus*

This enzyme was first studied in 1985 and was found to catalyse the reaction 4-aminobutanoate+2-oxoglutarate→4-oxobutanoate+glutamate.

The enzyme has a relatively wide substrate range, including 6-aminohexanoate and 7-aminoheptanoate, using 2-oxoglutatarate as the amino acceptor, and forming the corresponding semialdehydes (Yonaha, K., K. Suzuki, and S. Toyama, 4-*Aminobutyrate:2-oxoglutarate aminotransferase of Streptomyces griseus: purification and properties*. Eur J Biochem, 1985. 146(1): p. 101-6). Although this is very promising, the reversibility of these reactions has not been tested. Therefore, the reverse reactions are tested in vitro, using glutamate as the amino donor, since this would provide 7-aminoheptanoic acid from 7-oxoheptanoate. The enzyme was purified in *S. griseus* IFO 3102 (*S. griseus* subsp. *griseus*) and was found to be 100 kDa, consisting of two identical subunits approx. 50 kDa each. The cofactor is pyridoxal 5'-phosphate. A protein is deposited on the Pubmed database (Table 1). The gene encoding this (SGR_1829), annotated as a putative 4-aminotransferase, is present in the genome sequence of *S. griseus* IFO 13350, which is closely related to IFO 3102. Although not clear, it is highly likely that this protein is a close homologue of the enzyme described and studied (Yonaha, K., K. Suzuki, and S. Toyama, 4-*Aminobutyrate:2-oxoglutarate aminotransferase of Streptomyces griseus: purification and properties*. Eur J Biochem, 1985. 146(1): p. 101-6). In light of the substrate range data available, this protein is a very good candidate for testing as a suitable aminotransferase enzyme.

EC 2.6.1.39

Aminoadipate Transaminase from *Thermus thermophilus* (Q72LL6)

This is an enzyme with homology to the alpha-aminoadipate aminotransferases (AAAAT) from mammals and is thought to be involved in lysine synthesis in the bacterium *Thermus thermophilus* HB27 [2, 3]. Kinetic data are available for substrates such as 2-oxoadipate, 2-oxoisocaproate, alpha-aminoadipate and even aromatic amino acids [3]. The protein has been expressed and purified in *E. coli* and was found to exist in vitro mainly as a homodimer, with each subunit ~44 kDa in size (Miyazaki, T., et al., *alpha-Aminoadipate aminotransferase from an extremely thermophilic bacterium, Thermus thermophilus*. Microbiology, 2004. 150 (Pt 7): p. 2327-34). The broad substrate specificity, its prokaryotic origin and the availability of the encoding gene suggest that it may be a good candidate for testing with 1. It is a very well studied enzyme and its crystal structure is available (PDB ID: 2ZP7), which offers mechanistic insights into substrate specificity (Ouchi, T., et al., *Dual roles of a conserved pair, Arg23 and Ser20, in recognition of multiple substrates in alpha-aminoadipate aminotransferase from Thermus thermophilus*. Biochem Biophys Res Commun, 2009. 388(1): p. 21-7; Tomita, T., et al., *Mechanism for* multiple-substrates recognition of alpha-aminoadipate aminotransferase from Thermus thermophilus. Proteins, 2009. 75(2): p. 348-59).

Aminoadipate Aminotransferase from *Rattus norvegicus* (Q64602)

This enzyme is similar to the enzyme from *Thermus thermophilus* described previously. It is annotated as a kynurenine/aminoadipate aminotransferase, although there is some evidence to suggest that two distinct proteins carry out these reactions (Mawal, M. R. and D. R. Deshmukh, *Alpha-aminoadipate and kynurenine aminotransferase activities from rat kidney. Evidence for separate identity*. J Biol Chem, 1991. 266(4): p. 2573-5). The protein has been purified from rat kidney and expressed in human embryonic kidney fibroblast cells and was found to be around 100 kDa in size. The enzyme can accept 2-oxoadipate as a substrate. Earlier studies (presumably on the same enzyme) indicate that it is able to use DL-2-aminopimelic acid as an amino donor, with 2-oxoglutarate as acceptor in a reaction that is apparently reversible (Deshmukh, D. R. and S. M. Mungre, Purification and properties of 2-aminoadipate: 2-oxoglutarate aminotransferase from bovine kidney. Biochem J, 1989. 261(3): p. 761-8). The same paper indicated that pimelic acid may be an inhibitor of activity with a 30% reduction in activity in the presence of pimelic acid.

The above three enzymes should be suitable for the final transamination to yield 7-aminoheptanoic acid. The enzyme from *S. griseus* is a good candidate and the process of cloning, expression and purification would not be particularly difficult. The same is true of LysN from *T. thermophiles*, which seems to have a broad substrate range. The enzyme from *Rattus norvegicus* would be more challenging but activity data suggest that this enzyme may be able to use the specific substrates required.

A further 5 genes (*Bacillus weihenstephanensis* KBAB4, *Pseudomonas aeruginosa* (gi9951072), *Bacillus subtilis* (gi16078032), *Pseudomonas syringae* class III, *Rhodobacter sphaeroides* class III) were selected (DSM patent (Preparation of 6-aminocaproic acid from 5-formyl valeric acid: DSM—US2011-0171699 A1 patent). These enzymes showed some activity in the conversion of α-keto pimelic acid into α-amino pimelic acid and may also be active in the conversion of pimelic acid semialdehyde into 7-amino heptanoic acid. (See, SEQ ID 5-14).

SDS-PAGE analysis of IlvE-Omega Vf fusion (pING2022) (FIG. 23) and IlvE-Ad optimized omega fusion (pING2030) (FIG. 24) proteins expressed in *E. coli* BL21 as before. A clear band of the expected size is observed in both the IlvE-Omega Vf fusion (pING2022) (FIG. 15, Lanes 5 and 6) and IlvE-Ad optimized omega fusion (pING2030) (FIG. 15, Lanes 8 and 9) proteins. There is no corresponding band in the negative control, confirming the expression of the IlvE-Omega Vf fusion and the IlvE-Ad optimized omega fusion proteins.

Activity assay of IlvE-Omega Vf Fusion (pING2022) and IlvE-Ad Optimized Omega Fusion (pING2030) Aminotransferase Proteins Recombinant Vf aminotransferase was used to assay for activity on 7-aminoheptanoic acid. Three biotransformations were prepared examining the effect of enzyme loading on conversion of 7-aminoheptanoic acid and sodium pyruvate to L-alanine. Detection of L-alanine in the biotransformation would provide positive evidence for the desired aminotransferase specificity on 7-aminoheptanoic acid. The reaction scheme depicting aminotransferase conversion of 7-aminoheptanoic acid to pimelic acid semialdehyde is depicted below:.

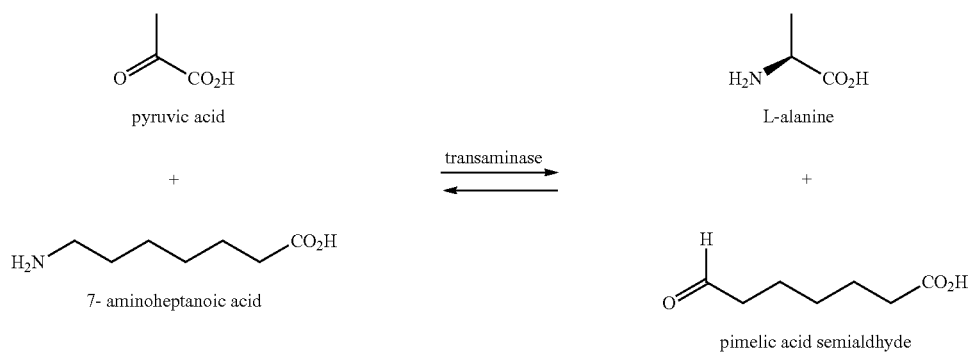

3.1.6.2 Expression of Selected Aminotransferases

Two genes were selected for the conversion of both pimelic acid semialdehyde to 7-aminoheptanoic acid, and the conversion of α-ketosuberate to α-aminosuberate: (1) IlvE-Omega Vf fusion (SEQ ID 1 and 2) and (2) IlvE-Ad optimized omega fusion (SEQ ID 3 and 4). These genes were prepared in plasmids that incorporate fusion of the omega aminotransferase with the 5'-end of the branched chain amino transferase IlvE, which previously showed high expression level in *E. coli* (See, FIG. 23 and FIG. 24). It was demonstrated that introduction of the IlvE fragment increases significantly the expression of the aminotransferase genes. Another heat induced plasmid containing a branched chain aminotransferase gene with the IlvE fragment was also tested (ING66) in the activity assays.

The three biotransformations (3 ml volume) contained 50 mM sodium pyruvate and 10 mM 7-aminoheptanoic acid. The reactions were held in a 30° C. orbital incubator and aliquots removed periodically from the biotransformations for analysis.

| Sample ID | sodium pyruvate/mM | 7-aminoheptanoic acid/mM | Enzyme loading v/v % |
| --- | --- | --- | --- |
| rc0212-40-1 | 50 | 10 | 0.33 |
| rc0212-40-2 | 50 | 10 | 0.66 |
| rc0212-40-3 | 50 | 10 | 1.67 |

The aliquots (1 ml) were removed from the biotransformations and heat to 95° C. for 5 minutes to precipitate soluble protein. The sample was subsequently centrifuged and the supernatant filtered through a 0.2 micron filter prior to HPLC analysis. The HPLC analysis used a precolumn derivatisation method based on chemical adduct formation with beta-mercaptoethanol and orthophthaldehyde. External standards of L-alanine and 7-aminoheptanoic acid were used to determine the concentration of 7-aminoheptanoic acid and L-alanine in the biotransformations.

The results (FIG. 16) clearly show the formation of L-alanine in the biotransformation providing compelling evidence for aminotransferase activity and specificity with Vf aminotransferase. The 7-aminoheptanoic acid concentration decreases over time which is consistent with the expected aminotransferase activity. The rate of 7-aminoheptanoic acid increases with increased concentration of enzyme which is again consistent with expected transaminase activity. The amount of L-alanine formed is not matched by the 7-aminoheptanoic consumed, this could be caused by alternative biochemical degradation of the L-alanine formed by other non-aminotransferase enzymes present in the E. coli extract.

A further examination of the aminotransferases was performed to assess for activity towards 2-aminosuberate.

through a 0.2 micron filter prior to HPLC analysis. The HPLC analysis used a precolumn derivatisation method based on chemical adduct formation with Boc-cysteine and orthophthaldehyde. External standards of DL-2-aminosuberic acid and L-alanine were used to determine the retention times of the 2-aminosuberic acid enantiomers.

The results indicate a reduction in the L-2-aminosuberic acid concentration and an enantioenrichment in the D-2-aminosuberic acid across all six biotransformations. This effect is consistent with the action of the aminotransferase on the L-enantiomer, since the aminotransferases tested here are known to exhibit L-stereoselectivity. No measurable L-alanine was observed by HPLC which should result from the transamination of pyruvate, however it is likely that the L-alanine formed has been degraded further by the other host proteins present in the biotransformation as has been previously observed in the 7-aminoheptanoic acid reactions.

The ING66 biotransformations (rc0212-46-1 and -2) showed significantly higher levels of L-2-aminosuberic acid degradation compared to the pING2022 and pING2030 aminotransferases. ING 66 branched chain aminoacid aminotransferase is already known to exhibit excellent selec-

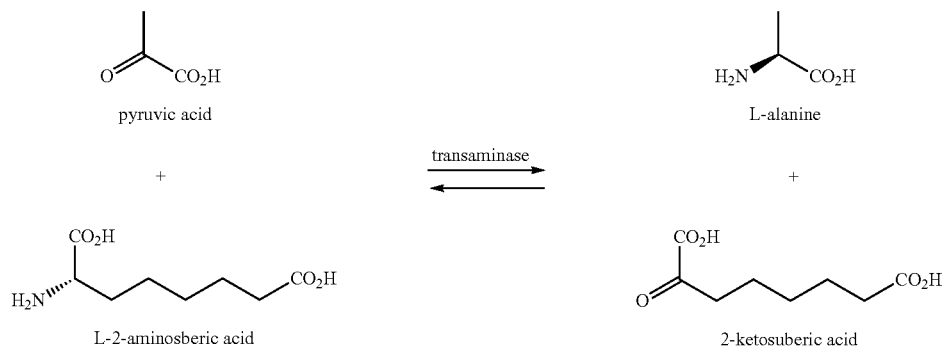
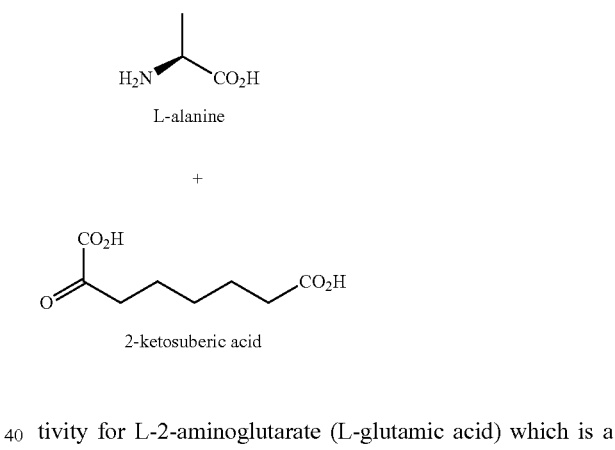

An aminotransferase conversion of L-2-aminosuberic acid to 2-ketosuberic acid provides an opportunity to modulate biotransformations.

Six biotransformations were carried out examining pING 2022, pING2030 and ING66 (Ilve branched chain aminotransferase, E.C.2.6.1.42, construct already in strain collection). Each biotransformation contained 10 mM DL-2-aminosuberic acid, 50 mM sodium pyruvate and high or low loading of cell free extract (CFE) as indicated below, N.B. ING 66 used as whole cells:

| lab book ID | aminotransferase | whole cell equivalents g/L |
| --- | --- | --- |
| rc0212-44-5 | pING2022 | 5 |
| rc0212-44-6 | pING2030 | 5 |
| rc0212-44-7 | pING2022 | 20 |
| rc0212-44-8 | pING2030 | 20 |
| rc0212-46-1 | ING66 | 25 |
| rc0212-46-2 | ING66 | 5 |

The six biotransformations (3 ml volume) were held in a 30° C. orbital incubator and aliquots removed periodically from the biotransformations for analysis. The aliquots (1 ml) were removed from the biotransformations and heat to 95° C. for 5 minutes to precipitate soluble protein. The sample was subsequently centrifuged and the supernatant filtered tivity for L-2-aminoglutarate (L-glutamic acid) which is a shorter (C5) homologue of L-2-aminosuberic acid so this preference in activity for ING 66 is not unexpected.

3.1.7 Conversion of α-amino Suberic Acid to 7-amino Heptanoic Acid by α-amino decarboxylases (EC 4.1.1.-) (See, FIG. 10)

Suitable catalysts were selected from the α-amino acid decarboxylases as candidates for the decarboxylation of α-amino suberic acid, in particular the aspartate 4-decarboxylase (EC 4.1.1.11), the glutamate decarboxylase (EC 4.1.1.15), the lysine decarboxylase (EC 4.1.1.18), the diaminopimelate decarboxylase (EC 4.1.1.20), and the diaminobutyrate decarboxylase (EC 4.1.1.86).

The Escherichia coli GadA glutamate decarboxylase and Escherichia coli LysA diaminopimelate decarboxylase were initially selected from those groups of proteins. Other suitable enzymes include LysA from Methanocaldococcus jannaschii (AAB99100) (EC 4.1.1.20) (Ray, S. S., et al., Cocrystal structures of diaminopimelate decarboxylase: mechanism, evolution, and inhibition of an antibiotic resistance accessory factor. Structure, 2002. 10(11): p. 1499-1508), and the lysine decarboxylases present in E. coli: CadA (AAA23536), which is inducible under anaerobic conditions and by lysine, and has a very high activity and Ldc (accession D87518) that is constitutively expressed but has lower activity for lysine (Kikuchi, Y., et al., Characterization of a second lysine decarboxylase isolated from Escherichia coli. J Bacteriol, 1997. 179(14): p. 4486-9).

The DNA sequences corresponding to the selected genes as well as their related protein sequence are shown in SEQ ID 15-18. Sequence of the *Escherichia coli* LysA diaminopimelate decarboxylase was selected as an *E. coli* codon optimized gene as previously described (Preparation of 6-aminocaproic acid from 5-formyl valeric acid: DSM—US2011-0171699 A1 patent). The *Escherichia coli* GadA glutamate decarboxylase was selected as wild type sequence. The genes were cloned and expressed using methods described in previous examples.

In addition to the previously prepared constructs (I29: pET21-GadA and I30:pET21-LysA, 2 further constructs were prepared by introduction of the ilvE fragment (assemblies I31 and I32 below) using the in ABLE technology. Introduction of the 15 amino acid Nter peptide of the *E. coli* branched amino acid aminotransferase (IlvE) upstream of the protein of interest has previously been shown to result in an increase in expression of some protein targets in *E. coli*.

The expression results are summarized below:

| | | Soluble fraction | | Insoluble fraction | |
|---|---|---|---|---|---|
| Assembly | Protein | 4 h | 24 h | 4 h | 24 h |
| I29 | *E. coli* GadA | ++ | + | +++ | +++ |
| I30 | *E. coli* LysA | + | + | + | + |
| I31 | *E. coli* GadA ilvE | + | ++ | +++ | ++ |
| I32 | *E. coli* LysA ilvE | +++ | ++ | + | + |

Preparation of Protein Extracts for Activity Assay

The previously frozen cell pellets from the 24 hour post-induction samples were re-suspended in bead lysis buffer consisting of 0.1 mM Tris, 1 mg/ml Pepstatin A and 200 mM PMSF protease inhibitors (161 μL of the mixture should be used for the lysis of the cell pellet from 1 mL of culture at an $OD_{600}$ of 5), supplemented with 1.5 mg lysozyme. Acid washed 212-300 μm glass beads (0.4 g per 1 mL of lysis buffer) were added to each sample. Lysis was performed by 30 second bursts of vortexing on full speed, followed by 30 second incubation on ice, repeated to a total time of 10 minutes.

1 mL samples were taken and the remainder of the culture used for the activity assays. The 1 mL samples were centrifuged at 13000 rpm, for 2 minutes and the supernatant separated. SDS samples were prepared and analyzed on SDS-PAGE gels as described above (FIG. 18). Following lysis, there is a large band in the soluble fraction for the *E. coli* GadA ilvE (I31) protein (FIG. 18, Lane 4) that was not present in the 1 mL sample, lysed by bugbuster. The *E. coli* LysA (I32) protein, which showed high soluble expression previously, did not show much soluble expression in the bead lysis (FIG. 18, Lane 5). This may indicate a large variability in the lysis methods. Crude cell extracts were then used to monitor the activity of proteins expressed from the 4 constructs I29 to I32.

Biotransformations were performed to assay activity for 2-aminosuberate. Each biotransformation comprised of 1 mM 2-mercaptoethanol and 10 □g/ml pyridoxal phosphate as described (Biochem. J. (1965) 96, 75). All substrates included in the biotransformations were at 10 mM concentration and crude cell extract loading was at 20 g/L whole cell equivalent. Biotransformations were incubated in falcon tubes at 37 degC and 250 rpm.

Samples were removed after 18 and 24 hours incubation. The aliquots were heated to 95 degC for 5 minutes to denatured the soluble protein. Any precipitates were removed by centrifugation at 12,000 rpm and 0.2 micron filtration of the supernatant. The filtered samples were analysed by HPLC in order to confirm whether decarboxylation of the relevant substrates had occurred.

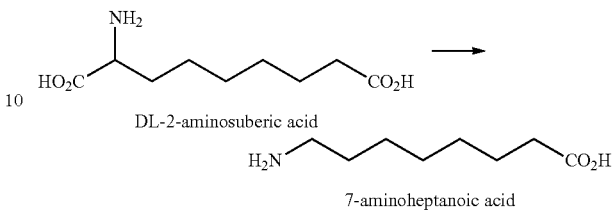

The conversion of DL-2-aminosuberic acid should yield 7-aminoheptanoic acid by the action of α-amino acid decarboxylase. The HPLC traces showed little change in the DL-2-aminosuberic acid concentration over the duration of this experiment. A peak corresponding to 7-aminoheptanoic acid however was observed in the 24 hour aliquots. The concentration of the observed peak corresponding to 7-aminoheptanoic acid is shown in FIG. 19.

3.1.8 Conversion of α-keto Suberic Acid to Pimelic Acid Semialdehyde by α-keto Decarboxylases (EC 4.1.1.-)

3.1.8.1 Selection of Suitable Catalysts

Amongst the family of decarboxylase, the α-keto acid decarboxylases emerged as the best candidates for the decarboxylation of α-keto suberic acid, in particular the pyruvate decarboxylase EC 4.1.1.1), the benzoylformate decarboxylase (EC 4.1.1.7) and the branched-chain-2-oxoacid decarboxylase (EC 4.1.1.72).

Genes encoding proteins from each of those four groups have been identified from a broad range of hosts and their products characterized biochemically and in some cases structurally (The crystal structure of benzoylformate decarboxylase at 1.6 A resolution—Diversity of catalytic residues in ThDP-dependent enzymes: Hasson et al. *Biochemistry* 1998, 37, 9918-9930; High resolution crystal structure of pyruvate decarboxylase from *Zymomonas mobilis*: Dobritzsch et al. J. Biol. Chem. 1998, 273, 20196-20204; Structure of the branched-chain keto acid decarboxylase (KdcA) from *Lactococcus lactis* provides insights into the structural basis for the chemoselective and enantioselective carboligation reaction: Berthold et al. *Acta Crystallographica Sec. D* 2007. D63, 1217-1224).

The following enzymes were then selected amongst those groups according to their substrate specificity: *Lactococcus lactis* kivD 2-ketoisovalerate decarboxylase (GeneBank JA114157); *Lactococcus lactis* kdcA branched chain alpha-keto acid decarboxylase (GeneBank JA114154), *Saccharomyces cerevisiae* pdc1 pyruvate decarboxylase (GeneBank JA114148), *Zymomonas mobilis* pdc (I472A) pyruvate decarboxylase mutant (GeneBank JA114151), *Pseudomonas putida* mdlC (A460I) benzoylformate mutant (GeneBank AY143338; fragment 2860-4446).

The first four enzymes previously showed some activity in the decarboxylation of the α-keto pimelic acid, the C-7 derivative of the target compound, α-keto suberic acid (Preparation of 6-aminocaproic acid from 5-formyl valeric acid: DSM—US2011-0171699 A1 patent).

Characterization of the A460I mutant of the benzoylformate decarboxylase from *Pseudomonas putida* displayed increased selectivity towards 2-keto hexanoic acid (Exchanging the substrate specificities of pyruvate decarboxylase from *Zymomonas mobilis* and benzoylformate decarboxylase from *Pseudomonas putida*: Siegert et al. *Port. Eng. Des. Sel.* 2005, 18, 345-357) compared to the wild-type enzyme which showed low activity towards 2-keto octanoic acid (Comparative characterisation of ThPP-dependent decarboxylases: Gocke et al. *J. Mol. Cat. B: Enzymatic* 2009, 61, 30-35).

3.1.8.1 Synthesis of 2-ketopimelic Acid and 2-ketosuberic Acid

In order to characterise the alpha-keto acid decarboxylase activity of 2-ketosuberate and 2-ketopimelate these substrates were synthesised since they are not commercially available. The route and method used was taken from *JOC* 1986 51, p 2389-2391, 3.77 g of 2-ketosuberic acid and 1.72 grams of 2-ketopimelic acid were prepared. The chemical structure of the two respective products was determined by $^1$H and $^{13}$C-NMR.

genic bacteria, Biochemistry, 28: 9417-9423; White R H (1994) Biosynthesis of 7-mercaptoheptanoylthreonine phosphate, Biochemistry, 33: 7077-7081]. The genes encoding enzymes responsible for the some of the steps of the pathway (aksA, aksD, aksE and aksF) have been identified, cloned and expressed in *E. coli*, but not the gene encoding 2-ketosuberic acid decarboxylase [Howell D M, Harich K, Xu H, White R H. (1998) Alpha-keto acid chain elongation reactions involved in the biosynthesis of coenzyme B (7-mercaptoheptanoyl threonine phosphate) in methanogenic Archaea. Biochemistry, 37: 10108-10117; Howell D M, Graupner M, Xu H, White R H. (2000) Identification of enzymes homologous to isocitrate dehydrogenase that are involved in coenzyme B and leucine biosynthesis in methanoarchaea. J Bacteriol. 182: 5013-5016; Drevland R M, Jia Y, Palmer D R, Graham D E. (2008) Methanogen homoa-

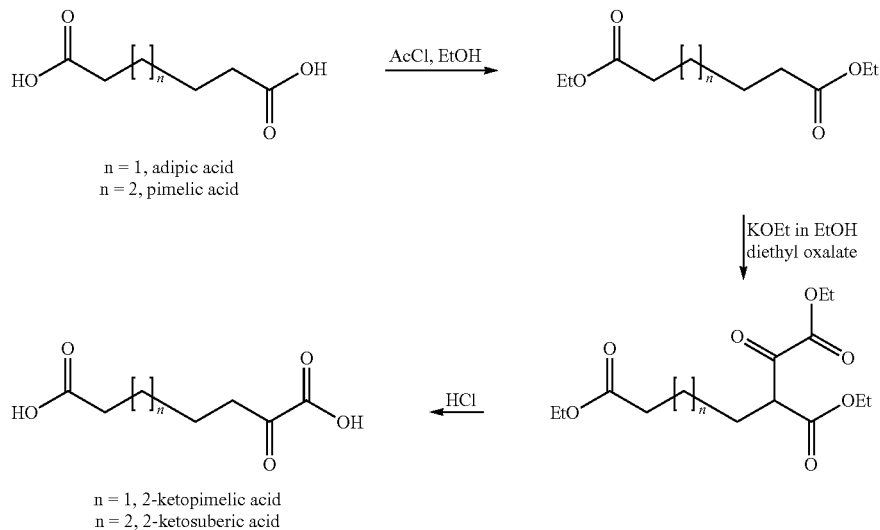

n = 1, adipic acid
n = 2, pimelic acid n = 1, 2-ketopimelic acid
n = 2, 2-ketosuberic acid 3.1.9 Conversion of α-ketosuberic Acid to Pimelic Acid Semialdehyde by α-keto Decarboxylases (EC 4.1.1.-)

The pathway for synthesis of coenzyme B [(7-hercaptoheptanoyl)threonine phosphate] has been postulated by White [White R H (1989) Biosynthesis of the 7-mercaptoheptanoic acid subunit of component B [(7-mercaptoheptanoyl)threonine phosphate] of methanogenic bacteria, Biochemistry, 28: 860-865] based on the analysis of other metabolic pathways in Archea and the mass spectroscopic analysis of incorporation of 2H and 13C labeled precursors into the final product. The pathway contains a nonoxidative decarboxylation step of 2-ketosuberic acid to 7-oxoheptanoic acid (pimelate semialdehyde) mediated by a postulated 2-ketoacid decarboxylase. In the next step, 7-mercaptoheptanoic acid is formed. Since this product only is formed (and not the C5 and C6 equivalents), this indicates that at least one of the upstream enzymes in the pathway will only accept C8, but not C6 and C7 substrates.

The pathway was verified by confirmation of the 2-ketodicarboxylic acid elongation reaction from 2-ketoglutarate to 2-ketosuberate using GC-MS [White R H (1989) A novel biosynthesis of medium chain length alpha-ketodicarboxylic acids in methanogenic archaebacteria. Archivers of Biochemistry and Biophysics, 270: 691-697] and synthesis of 7-mercaptoheptanoic acid and coenzyme B from 7-oxoheptanoic acid [White R H (1989) Steps in the conversion of a-ketosuberate to 7-mercaptoheptanoic acid in methanoconitase catalyzes both hydrolyase reactions in coenzyme B biosynthesis. J Biol Chem. 283: 28888-28896], Nothing is known about nonoxidative decarboxylation of 2-ketosuberic acid to 7-oxoheptanoic acid and this activity has not been reported in vitro. However 2-ketosuberic acid was converted to coenzyme B by whole cells [White R H (1989)].

Methodology

Work done by White and Graham showed that Archaebacteria (like *Methanocaldococcus jannaschii*) are likely to possess an enzyme responsible for nonoxidative decarboxylation of 2-ketosuberic acid to 7-oxoheptanoic acid. Other enzymes involved in the coenzyme B pathway were identified by analysis of the genomes of *M. jannaschii* [Bult C J, White O, Olsen G J, Zhou L, Fleischmann R D, Sutton G G, Blake J A, FitzGerald L M, Clayton R A, Gocayne J D, Kerlavage A R, Dougherty B A, Tomb J F, Adams M D, Reich C I, Overbeek R, Kirkness E F, Weinstock K G, Merrick J M, Glodek A, Scott J L, Geoghagen N S, Venter J C. (1996) Complete genome sequence of the methanogenicarchaeon, *Methanococcus jannaschii*. Science. 273: 1058-1073] and *Methanobacterium thermoautotrophicum* ΔH [Smith D R, Doucette-Stamm L A, Deloughery C, Lee H, Dubois J, Aldredge T, Bashirzadeh R, Blakely D, Cook R, Gilbert K, Harrison D, Hoang L, Keagle P, Lumm W, Pothier B, Qiu D, Spadafora R, Vicaire R, Wang Y, Wierzbowski J, Gibson R, Jiwani N, Caruso A, Bush D, Reeve J N, (1997) Complete genome sequence of *Methanobacterium*

*thermoautotrophicum* deltaH: functional analysis and comparative genomics. J Bacteriol. 179: 7135-7155]. The genomes were analyzed for the presence of the target gene clusters and were BLAST searched for proteins showing homology to existing enzymes. We took a similar approach to identify the gene encoding 2-ketosuberic acid decarboxylase.

Results

Analysis of the Gene Clusters

Bacterial genomes can show a high level of organization in which genes encoding enzymes playing a role in specific pathways are localized in operons and/or gene clusters. Because other enzymes of the coenzyme B pathway have been identified and the sequences of some archaebacterial genomes are published, an attempt was made to identify 2-ketosuberic acid decarboxylase. The table below shows the genes and enzymes involved in the pathway.

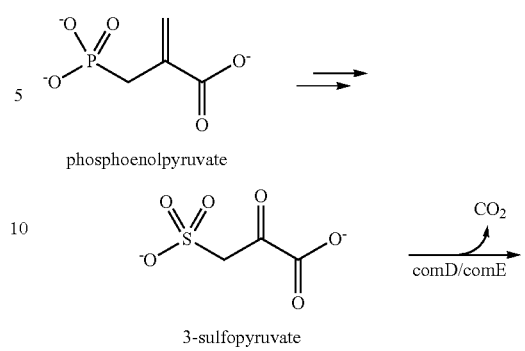

|  |  | Genes | |
| --- | --- | --- | --- |
| Enzyme | Reaction | *Methanocaldococcus jannaschii* | *Methanobacterium thermoautotrophicum* |
| AksA (R)-homocitrate synthase | condensation of α-ketoglutarate and acetyl-CoA; condensation of α-ketoadipate and α-ketopimelate to acetyl-CoA; | MJ0503 | MTH1630 |
| AksDAksE homocitrate synthase/ dehydratase and cis-homoaconitatehydratase | dehydration of (R)-homocitrate and analogs to cis-homoaconitate or the respective analogs, and the hydration of the products to homoisocitrate and its respective analog | MJ1003 MJ1271 | MTH1113 MTH1631 |
| AksF NAD-dependent threo-isocitrate dehydrogenase | NAD-dependent decarboxylation of (-)-threo-isohomocitrate, (-)-threo-iso(homo)$_2$citrate and (-)-threo-iso(homo)$_3$citrate | MJ1596 | MTH0184 |
| 2-ketosuberic acid decarboxylase | 2-ketosuberic acid decarboxylation | ?? | ?? |
| mercaptoheptanoate synthase |  | ?? | ?? |
| mercaptoheptanoylthreonine synthase |  | ?? | ?? |
| N-(7-mercaptoheptanoyl)-3-O-phosphono-L-threonine synthase |  | ?? | ?? |

The coenzyme B biosynthetic genes from *M. jannaschii* and *M. thermoautotrophicum* did not appear to reside in gene clusters, except for the genes encoding (R)-homocitrate synthase (MTH1630) and homocitrate synthase/dehydratase large subunit (MTH1631) in *M. thermoautotrophicum*. The analysis of hypothetical operons containing any of the genes listed above did not show the presence of any protein with homology to known decarboxylases. Therefore, a search was made for analogous decarboxylations in related metabolic pathways in *M. jannaschii*.

Analysis of *Methanocaldococcus jannaschii* Genome

Analysis of other metabolic pathways in *M. jannaschii* showed that a similar decarboxylation is present in the coenzyme M pathway [Graupner M, Xu H and White R H. (2000) Identification of the gene encoding sulfopyruvate decarboxylase, an enzyme involved in biosynthesis of coenzyme M. *J Bacteriol.* 182: 4862-4867].

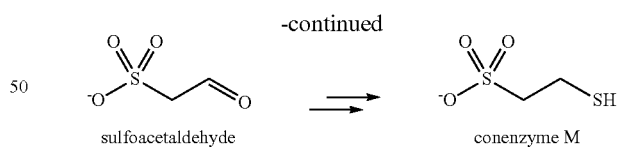

Nonoxidative decarboxylation of 3-sulfopyruvate to sulfoacetaldehyde is catalyzed by sulfopyruvate decarboxylase (EC.4.1.1.79) containing two subunits, comD (SEQ ID 19) and comE (SEQ ID 20). As both coenzyme B and coenzyme M are involved in methanogenesis and the reactions downstream of the decarboxylation are analogous, it is possible that the decarboxylases evolved together and show high homology to each other.

ComD, comE and their orthologues found in the BRENDA database were used as queries to BLAST search the *Methanocaldococcus jannaschii*. The best match was obtained using comD/comE decarboxylase from *Methanocella paludicola* (SEQ ID 21).

Only two open reading frames (MJ0277 and MJ0663) encoded by the *M. jannaschii* genome showed significant homology to comD/comE with the E-value <0.0001. Both of them were annotated as acetolactate synthases (SEQ ID 22 and SEQ ID 23).

Another search was performed using sequences of decarboxylases accepting similar substrates that are deposited in the BRENDA database (2-ketoglutarate decarboxylase, oxaloacetate decarboxylase, α-ketoisovalerate decarboxylase, transaminated amino acid decarboxylase, benzoylformate decarboxylase, 2-ketoarginine decarboxylase, phosphonopyruvate decarboxylase, pyruvate decarboxylase and indole-3-pyruvate decarboxylase).

ClustalW algorithm showed significant homology between MJ0277 and comD/comE proteins (FIG. 20). However, MJ0277 showed even higher homology to LACLA acetolactate synthase from *Lactococcus lactis* (FIG. 21).

Analysis of the functional domains in LACLA acetolactate synthese, comD/comE from *Methanocella paludicola* and the hypothetical acetolactate synthase MJ0277 showed that all of them have a similar structure containing a thiamine phosphate binding site (FIG. 22). Almost identical results were obtained for the second open reading frame MJ0663 from *Methanocaldococcus jannaschii*.

| QUERY (Name & UNIPROT entry) | Substrate | Source | Hits (E-value <$10^{-4}$) |
|---|---|---|---|
| Kgd Q9CC97 | 2-ketoglutarate decarboxylase 4.1.1.71 | *Mycobacterium leprae* | No hits |
| citM Q7X4Z5 | oxaloacetate decarboxylase | *Lactococcus lactis* | No hits |
| kivd Q684J7 | α-ketoisovalerate decarboxylase 4.1.1.1 | *Lactococcus lactis* | NP_247250.1 acetolactate synthase catalytic subunit E-value: 8e−29 NP_247647.1 acetolactate synthase large subunit IlvB5e−19 |
| ARO10 Q06408 | transaminated amino acid decarboxylase 4.1.1.- | *Saccharomyces cerevisiae* | NP_247250.1 acetolactate synthase catalytic subunit 2e−17 NP_247647.1 acetolactate synthase large subunit IlvB9e−12 P58416.1 Sulfopyruvate decarboxylase subunit beta 4e−04 |
| MdlC Q97XR3 | benzoylformate decarboxylase 4.1.1.7 | *Sulfolobus solfataricus* | NP_247250.1 acetolactate synthase catalytic subunit 3e−23 NP_247065.1 signal recognition particle protein Srp54 6e−04 2V3C_C Crystal Structure Of The Srp54-Srp19-7s.S SrpRna6e−04 3NDB_B Crystal Structure Of A Signal Sequence Bound To The Signal 6e−04 |
| aruI B7V368 | 2-ketoarginine decarboxylase | *Pseudomonas aeruginosa* | NP_247250.1 acetolactate synthase catalytic subunit 4e−71 NP_247647.1 acetolactate synthase large subunit 2e−38 NP_248425.1cobyrinic acid a,c-diamide synthase 4e−05 |
| fom2 Q6D9X5 | phosphonopyruvate decarboxylase | *Erwinia carotovora* subsp. *atroseptica* (*Pectobacterium atrosepticum*) | P58416.1 Sulfopyruvate decarboxylase subunit beta 3e−20 P58415.1Sulfopyravate decarboxylase subunit alpha 2e−11 NP_247516.1 2-oxoglutarate ferredoxinoxidoreductase subunit beta 2e−05 NP_247250.1 acetolactate synthase catalytic subunit 6e−04 |
| PDC6 P26263 | Pyruvate decarboxylase isozyme 3 4.1.1.1 | *Saccharomyces cerevisiae* | NP_247250.1 acetolactate synthase catalytic subunit 6e−23 NP_247647.1 acetolactate synthase large subunit IlvB9e−14 P58416.1Sulfopyruvate decarboxylase subunit beta 6e−04 NP_247310.1 hypothetical protein MJ_0337 9e−04 |
| IpdC F2EPZ5 | Indole-3-pyruvate decarboxylase | *Pantoea ananatis* | NP_247250.1 acetolactate synthase catalytic subunit 6e−22 NP_247647.1 acetolactate synthase large subunit 7e−12 NP_247516.1 2-oxoglutarate ferredoxinoxidoreductase subunit beta 9e−05 |

MJ0277 (accession number NP_247250) and MJ0663 (NP_247647) were good hits for almost all the queries used to search the genome. The protein alignment using the The acetolactate synthase (ALS) enzyme (also known as acetohydroxy acid synthase) catalyzes the conversion of pyruvate to α-acetolactate.

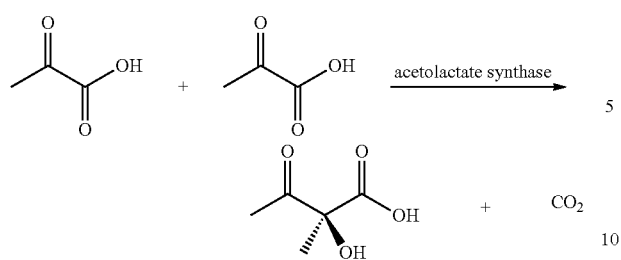

The first step of the reaction is decarboxylation of pyruvate (which is a 2-ketoacid) to an enzyme-bound intermediate that is further condensed with the second pyruvate molecule resulting in acetolactate. Thus, 2-ketoacid decarboxylases and acetolactate synthases are likely to show high homology to each other.

Conclusions

Analysis of the M. jannaschii genome showed the presence of two proteins annotated as acetolactate synthases (MJ0277 and MJ0663) that may be the previously unidentified 2-ketosuberic acid nonoxidative decarboxylase involved in coenzyme B biosynthesis. It is very likely that one of them is the real acetolactate synthase. This enzymatic activity has been shown in many archaebacteria, and M. jannaschii encodes the acetolactate synthase regulatory subunit, MJ0161. However, one of the enzymes may be the unidentified 2-ketoacid decarboxylase and has simply been misannotated. Alternatively, 2-ketosuberic acid might be decarboxylated by the enzyme responsible for decarboxylation of 3-sulfopyruvate in the coenzyme M pathway. Therefore, comD/comE decarboxylase should also be considered as a target enzyme.

The proteins annotated as acetolactate synthases MJ0277 (NP_247250) and MJ0663 (NP_247647) were identified as prime candidates for nonoxidative decarboxylation of 2-ketoadipic acid, 2-ketopimelic acid and 2-ketosuberic acid. In addition: 3-sulfopyruvate decarboxylase comD/comE (P58415/P58416), Kgd (Q9CC97), citM (Q7X4Z5), kivd (Q684J7), ARO10 (Q06408), MdlC (Q97XR3), aruI (B7V368), fom2 (Q6D9x5), PDC6 (P26263) and IpdC (F2EPZ5) are excellent candidates for the conversion of 2-ketosuberic acid to pimelic acid semialdehyde (SEQ ID 24-40).

3.1.10 Conversion of α-keto Pimelic Acid to α-keto Suberic Acid by α-keto Acid Chain Elongation (See, FIG. 10)

3.1.10.1 Selection of Enzyme Gene Targets

Conversion of α-ketopimelic acid into α-ketosuberic acid was previously reported to be part of the biosynthesis of the Coenzyme B in methanogenic archaebacteria, such as *Methanocaldococcus janaschii*, *Methanocaldococcus vannielii*, *Methanocaldococcus maripaludis*, *Methanobacterium thermoautotrophicum*, *Methanosarcina termophila* and others (White, Arch. Biochem. Biophys. 270: 691-697 (1989)). Genes encoding the enzymes involved in the multi cycles of chain elongation from α-ketoglutaric acid to suberic acid, homologous to enzymes involved in the leucin and lysine biosynthesis, were idientifed from *Methanocaldococcus janaschii* and their corresponding proteins characterized α-keto acid chain elongation reactions involved in the biosynthesis of coenzyme B (7-mercaptoheptanoyl threonine phosphate) in Howell et al., Biochemistry 37: 10108-10117 (1998); Drevland et al., Bacteriol. 189: 4391-4400 (2007); Howell et al., J. Bacteriol. 182: 5013-5016 (2000); Drevland et al., J. Biol. Chem. 283: 28888-28896 (2008); and Jeyakanthan et al., Biochemistry 49: 2687-2696 (2010).

Orthologous genes were also identified from *Methanobacterium thermoautotrophicum*, but their products have not been characterized yet. At least two isogenes were reported in this archaebacteria for each of the required activity (AskA, AksD/E and AksF) as previously reported in *Methanocaldococcus janaschii* (Smith et al. 1997, 179, 7135-7155). The table below presents the orthology of the corresponding *Methanobacterium thermoautotrophicum* proteins with the well-characterized *Methanocaldococcus janaschii* proteins based on the literature previously mentioned and their potential deduced function

| Enzyme activity | M. janaschii proteins | Functions of M. janaschii proteins | Orthologous M. thermoautotrophicum proteins |
| --- | --- | --- | --- |
| AksA: 2-isopropylmalate synthase/homocitrate synthase | MJ0503 | Condensation of α-ketoglutarate and acetyl-CoA to form trans-homoaconitate; functions in the α-ketosuberate synthesis | MTH1630 |
|  | MJ1195 | Formation of 2-isopropylmalate from acetyl-CoA and 2-oxoisovalerate in leucine biosynthesis | MTH1481 |
| AksD: 3-isopropylmalate dehydratase/homoaconitase (Large subunit) | MJ1003 | Formation of cis-homo$_n$ aconitate (n = 1-4) when coupled with MJ1271; involved in the production of α-keto suberic acid | MTH1631 |
|  | MJ0499 | Involved in the leucine biosynthesis | MTH1386 |
| AksE: 3-isopropylmalate dehydratase or isomerase/homoaconitase (Small subunit) | MJ1271 | Formation of cis-homo$_n$ aconitate (n = 1-4) when coupled with MJ1003; involved in the production of α-keto suberic acid | MTH0829: Contains the YLTR consensus sequence characteristic of homoaconitase |
|  | MJ1277 | Involved in the leucine biosynthesis | MTH1387: Contains the YLVM consensus sequence characteristic of |

-continued

| Enzyme activity | M. janaschii proteins | Functions of M. janaschii proteins | Orthologous M. thermoautotrophicum proteins |
|---|---|---|---|
| AksF: 3-isopropylmalate dehydrogenase/homoisocitrate dehydrogenase | MJ1596 | Involved in the production of α-keto suberic acid | isopropylmalate isomerase MTH1388 |
|  | MJ0720 | Involved in the leucine biosynthesis | MTH0184 |

Identification of orthologs to the chain elongation proteins in *Methanobacterium thermoautotrophicum* was reported in the literature from comparative genomics data between *Methanocaldococcus janaschii* and *Methanobacterium thermoautotrophicum* genomes, sequence analysis of the corresponding proteins and activity assay. Potential application of the alternative *Methanobacterium thermoautotrophicum* gene products and their corresponding *Methanocaldococcus janaschii* orthologs for the synthesis of alpha-keto pimelic acid was reported (WO2010-104391 A2). Therefore, eight *Methanobacterium thermoautotrophicum* proteins were selected for the exemplification of the chain elongation reaction between pimelic acid and suberic acid, i.e., AksA 2-isopropylmalate synthase/homocitrate synthases MTH1630 and MTH1481, fragment 1337346-1338863; AksD 3-isopropylmalate dehydratase/homoaconitases (Large subunit) MTH1386 fragment 1253910-1255169; and MTH1631 (fragment 1495715-1497001; AksE 3-isopropylmalate dehydratase or isomerase/homoaconitases (Small subunit) MTH 0829 fragment 752586-753098; and MTH1387 fragment 1255181-1255669; and AksF 3-isopropylmalate dehydrogenase/homoisocitrate dehydrogenases MTH0184 fragment 130396-131391; and MTH 1388 fragment 1255666-1256655.

Wild-type genes were selected for the construction of the corresponding *E. coli* expression vectors, except for the genes AksA(1)-MTH1630, AksD(2)-MTH1631 and AksF (2)-MTH1388 in which the starting codons GTG or TTG were changed to ATG.

3.1.10.2 Cloning Expression Vectors Containing Gene Targets

The selected gene targets from *Methanobacterium thermoautotrophicum* were then cloned into the IPTG inducible pET21-a backbone using in ABLE technology, as described in detail in Section 3.1.1.2) to generate I9 (*M. thermoautotrophicum* AksA(1)-MTH1630 gene in pET21-a), I10 (*M. thermoautotrophicum* AksA(2)-MTH1481 gene in pET21-a), I11 (*M. thermoautotrophicum* AksD(1)-MTH1386 gene pET21-a gene in pET21-a), I12 (*M. thermoautotrophicum* AksD(2)-MTH1631 gene in pET21-a), I13 (*M. thermoautotrophicum* AksE(1)-MTH0829 gene in pET21-a), I14 (*M. thermoautotrophicum* AksE(2)-MTH1387 gene in pET21-a), I15 (*M. thermoautotrophicum* AksF(1)-MTH0184 gene in pET21-a), and I16 (*M. thermoautotrophicum* AksF(2)-MTH1388 gene in pET21-a).

Briefly, potential EarI sites in the selected genes and the vector backbone were disrupted to prevent interference with the part/linker fusion preparation involving EarI digestion/ligation cycles. No EarI sites were observed in AksD(1)-MTH1386, AksD(2)-MTH1631 and AksE(2)-MTH1387. One EarI site was observed in each of the AksA(1)-MTH1630, AksA(2)-MTH1481, AksE(1)-MTH0829 and AksF(2)-MTH1388 genes, and two EarI sites were observed in the AksF(1)-MTH0184 gene three EarI sites were detected in the vector backbone pET21-a. The EarI sites were disrupted by introducing a silent mutation(s) into the restriction site. The three EarI sites in the vector were disrupted by mutating the last guanidine base of the restriction site into a thymine.

The EarI free sequences were then used as input sequences in the part designer software to design the corresponding truncated parts flanked by EarI sites, as discussed in Section 3.1.1.2. The synthesized *Methanobacterium thermoautotrophicum* AksA(1)-MTH1630 (TP48), AksA(2)-MTH1481 (TP49), AksD(1)-MTH1386 (TP50), AksD(2)-MTH1631 (TP51), AksE(1)-MTH0829 (TP52), AksE(2)-MTH1387 (TP53), AksF(1)-MTH0184 (TP54) and AksF(2)-MTH1388 (TP55) truncated parts were inserted into the DNA2.0 pJ201 vector. The pET21-a truncated part vector was fully synthesized with introduction of a fragment including the chloramphenicol resistance gene to produce the vector TP31.

Phosphorylation and subsequent annealing of the in ABLE oligonucleotides were performed as described in section 3.1.1.2. Briefly, the oligos were incubated with T4 kinase at 37° C. for 30 minutes, followed by inactivation of the enzyme at 65° C. for 20 minutes.

Next, part linker fusions were prepared by ligating the 5'-end of the truncated part with its corresponding part oligo annealed fragment, and the 3'-end of the truncated part with the linker oligo annealed fragment, as previously described in section 3.1.1.2. Part linker fusions corresponding to the selected genes (*Methanobacterium thermoautotrophicum* AksA(1)-MTH1630, AksA(2)-MTH1481, AksD(1)-MTH1386, AksD(2)-MTH1631, AksE(1)-MTH0829, AksE(2)-MTH1387, AksF(1)-MTH0184 and AksF(2)-MTH1388) were prepared by ligation of their respective annealed part oligos (POA48, POA49, POA50, POA51, POA52, POA53, POA54 or POA55), their truncated part (TP48, TP49, TP50, TP51, TP52, TP53, TP54 or TP55) and the annealed linker oligos from the vector backbone. Part linker fusions corresponding to the vector backbone were prepared by ligation of its annealed part oligos, its truncated part, and the annealed linker oligos from either genes. A negative control gene-free assembly was also prepared by ligation of the vector backbone annealed part oligos, its truncated part, and its annealed linker oligos, resulting in self-assembly of the vector backbone.

A ten and twenty-fold molar excesses of linker and part oligos to the truncated part was used in the gene and vector reactions to favor ligation between the truncated part and the oligonucleotides during each EarI digestion/ligation cycle. The 50 μL EarI digestion/ligation reactions were incubated in a thermocycler (Eppendorf Mastercycler Gradient), alternating the temperature between 37° C. and 16° C. Upon completion of the cycles, samples were loaded on a 0.7% agarose gels, and the expected size fragments were observed for preparation of the part/linker fusions. The correct size bands were then excised from the gel, and the DNA was gel extracted using the QIAGEN QIAquick Gel Extraction Kit. The DNA concentration ranged from 13.6 ng/µl to 24.8 µg/µl in a total volume of 30 µl (DNA conc. range 4.9 nM to 53.9 nM). Self-assembly of the part/linker fusion (pET21-a part/pET21-a linker) for the generation of the negative control gene-free construct was also performed.

Combination of the gene part/linker fusions with their respective vector part/linker fusion was then carried out through a 2-part assembly, as described in section 3.1.1.2. Briefly, the gene part linkers and the vector part linkers were incubated at room temperature for 30 min prior to transformation of high efficiency chemically competent NEB10β E. coli cells using 2 µl of the assembly reaction and 10 µl of the competent cells. Transformed cells were plated on LB-Amp-agar, and incubated at 37° C. overnight. About one thousand clones were obtained for each assembly. Two random clones were selected from each assembly, and the corresponding vectors were isolated using the QIAGEN QIAprep Miniprep Kit.

Restriction was performed to confirm vector construction, as described in section 3.1.1.2. Briefly, clones obtained from I9 were analyzed using BglII and XmnI to identify positive clones for the insertion of the *Methanobacterium thermoautotrophicum* AksA(1)-MTH1630 gene into pET21-a, clones obtained from I10 assembly were analyzed using PstI and XmaI/XbaI to identify insertion of AksA(2)-MTH1481 gene into pET21-a, clones obtained from I11 assembly were analyzed using HindIII and AlwNI to identify insertion of AksD(1)-MTH1386 gene, clones obtained from I12 assembly were analyzed using NcoI and BglII to identify insertion of AksD(2)-MTH1631 gene, clones obtained from I13 assembly I13 were analyzed using MluI and XmnI to identify insertion of AksE(1)-MTH0829 into pET21-a, clones obtained from I14 assembly I14 were analyzed using PsiI and XmaI/AlwNI to identify insertion of AksE(2)-MTH1387 gene into the *E. coli* expression vector, clones obtained from I15 assembly were analyzed using AlwNI and HincII to identify insertion of AksF(1)-MTH0184 gene into the *E. coli* expression vector, and clones obtained from 116 assembly were analyzed using BsaI and HindIII/AlwN1 to identify insertion of the AksF(2)-MTH1388. The restriction products were am on an agarose gel, and the expected band pattern was observed for the clones tested from each assembly, confirming the construction of *E. coli* pET21-a expression vectors harbouring the *Methanobacterium thermoautotrophicum* chain elongation genes. In addition, the part junctions between the 3'-end of the vector backbone and the 5'-end of the genes as well as between the 3'-end of the gene and the 5'-end of the vector backbone were sequenced to confirm the construction.

3.1.10.3 Expression of Exogenous Thioesterase Genes in *E. coli*

Expression of exogenous *Methanobacterium thermoautotrophicum* AksA(1)-MTH1630, AksA(2)-MTH1481, AksD(1)-MTH1386, AksD(2)-MTH1631, AksE(1)-MTH0829, AksE(2)-MTH1387, AksF(1)-MTH0184 and AksF(1)-MTH0184 chain elongation genes gene products in *E. coli* was performed as described in section 3.1.1.3. Briefly, electrocompetent BL21 (DE3) cells were transformed with 10 ng DNA, and the transformation samples were plated on LB-Amp-Agar. Transformants were obtained after overnight incubation at 37° C. A single clone was picked from each assembly, and 5 ml of LB-Amp medium were inoculated as a starting culture. The $OD_{600}$ of the culture was measured after overnight incubation at 37° C. and 250 rpm, 2 mL culture (approximately $8 \times 10^7$) were used to inoculate 100 mL of LB-Amp, which were incubated in a 500 mL baffled shake flask at 37° C. and 250 rpm.

Protein expression was induced by addition of 1 mM IPTG (final conc.), and cultures were incubated at 37° C. and 250 rpm. A 1 mL sample was taken prior to induction and after 4 h and 24 h post-induction incubation, and the $OD_{600}$ measured to determine cell growth. After 24 h post-induction incubation, the remaining culture was transferred to a 50 mL falcon tube, harvested by centrifugation at 5000 rpm for 10 minutes, and the cell pellets used for further analysis or stored at −20° C.

For SDS-PAGE analysis, the samples were centrifuged at 13000 rpm for 2 min, the supernatant was removed, and the cells were lysed using the Bugbuster protein extraction reagent supplemented with lysozyme (15 mg/mL) and benzonase (3.4 U/µL). The lysis reactions were then centrifuged at 13000 rpm for 2 min, the soluble fraction was transferred to a new tube, and the insoluble fraction re-suspended in water. 20 µl of each fraction was mixed with 80 µl SDS-Sample buffer (SDS-Loading Buffer, 9% DTT and water), heated in a heatblock for 5 minutes at 95° C., and 10 µl of each SDS-sample preparation was then loaded on SDS-PAGE 4-20% Tricene gels to analyze the protein content of the soluble and insoluble fractions.

Only the AksE(2)-MTH1387 protein was successfully expressed in soluble form, i.e., an 18 kD bank in the soluble fraction after IPTG induction. The AksA(1)-MTH1630, AksD(2)-MTH1631, AksF(1)-MTH0184 and AksF(2)-MTH1388 proteins were expressed in insoluble forms, i.e., a 44, 36, and 46 kD bands, respectively, were detected in the insoluble portion. No expression was detected for the AksA (2)-MTH1481, AksD(1)-MTH1386 and AksE(2)-MTH1387 proteins. Therefore, expression optimization was performed for AksA(1)-MTH1630, AksD(2)-MTH1631, AksF(1)-MTH0184, AksF(2)-MTH1388, AksA(2)-MTH1481, AksD (1)-MTH1386, and AksE(2)-MTH1387, based on reports of successful expression of *Methanocaldococcus jannaschii* orthologs in the literature. In particular, literature data on the expression of the M janaschii orthologs revealed a set of different conditions in particular in terms of inducer concentration and induction temperature. The IPTG conc. was varied between 0.1 and 1 mM (initial conditions 1 mM) and the temperature of induction was varied between 16 and 37 C (initial conditions 37 C). The same expression protocol and the same SDS-PAGE sample preparation, as described in the section 3.1.1.3 was used for the solubility optimization experiments.

The level of AksA(1)-MTH1630 protein expression was improved after decreasing 10-fold the IPTG concentration, but the protein remained insoluble; optimization of the temperature did not affect expression or solubility. No significant improvement in AksD(2)-MTH1631 and AksF (2)-MTH1388 solubility by lowering 10-fold the IPTG concentration since both proteins were only visible in the insoluble fractions after induction. No significant improvement in solubility was observed for AksD(2)-MTH1631 and AksF(2)-MTH1388 by lowering the induction temperature to 16° C. since both proteins were only visible in the insoluble fractions after induction. However, AksF(1)-MTH0184 solubility was improved by lowering the induction temperature to 30° C. Therefore, AksA(1)-MTH1630 (19), AksD(2)-MTH1631 (112) and AksF(2)-MTH1388 (116) may be expressed in different hosts, e.g., eukaryotic system like *Saccharomyces cerevisiae* or in a thermophile bacteria like *Bacillus stearothermophilus*.

Since the *Methanobacterium thermoautotrophicum* AksA(1)-MTH1630, AksA(2)-MTH1481, AksD(2)-MTH1631 and AksE(1)-MTH0829 gene products were not expressed in a soluble foiin in *E. coli* using the pET21-a/IPTG expression system, these genes was cloned for expression using the *Saccharomyces cerevisiae* expression system. The expression vector was assembled using the in ABLE technology described above, except the SapI restriction enzyme instead of EarI in the preparation of the part/linker fusion of the yeast vector backbone, comprising the constitutive promoter ADH1p, the transcription terminator CYC1t, and the high copy number vector backbone derived from the YEplac195 plasmid. Electrocompetent TOP10 *E. coli* cells were transformed with each part/linker assembly and a large DNA stock for was prepared using the QIAGEN Hi-Speed Plasmid Purification Midi Kit (67.4-173.0 nM in 120 µl). The expected size fragment was observed for the preparation of the yeast vector part/ADH1 promoter linker, despite the use of SapI, after agarose gel electrophoresis. The correct bands were then excised from the gel, and the DNA was gel extracted using the QIAGEN QIAquick Gel Extraction Kit (14.1-138.1 nM in 30 µl).

The final constructs were then prepared incubating the 4-part assembly reaction, i.e., the ADH1 promoter, each of the *Methanobacterium thermoautotrophicum* genes AksA(1)-MTH1630, AksA(2)-MTH1481, AksD(2)-MTH1631 and AksE(1)-MTH0829, the CYC1 terminator and the yeast vector backbone, at 37° C. Then, 10 µl high efficiency chemically competent NEB10β *E. coli* cells were transformed with 2 µl of the assembly reaction, plated on LB-Kan-agar, and incubated at 37° C. overnight. Between two hundred and two hundred and fifty clones were obtained for the 4-part assemblies. Five random clones were then picked from the plates, and the corresponding vectors were isolated using the QIAGEN QIAprep Miniprep Kit.

The isolated constructs were analyzed using restriction analysis. A preliminary analysis was performed using PmeI/SapI to identify any truncated vector contaminants. The clones did not contain truncated vector contaminants, so they were then analyzed using the restriction enzymes XhoI/NdeI, BsaI and MluI in order to confirm the insertion of the 4 part/linker fusions. The expected band pattern was observed for both clones confirming the construction of *S. cerevisiae* expression vector harbouring the ADH1 promoter, the gene of interest, the CYC1 terminator and the yeast vector backbone. Lastly, the junctions between the 4 parts were sequenced to confirm proper assembly.

Transformation with the *S. cerevisiae* I24-I27 expression vectors can be performed as described herein, and expression from the constitutive promoter ADH1p can monitored after cell lysis using SDS-PAGE. The I24 construct includes the ADH1 promoter, the *Methanobacterium thermoautotrophicum* AksA(1)-MTH1630 gene, and the CYC1 terminator inserted in the yeast vector backbone. The I25 construct includes the ADH1 promoter, the *Methanobacterium thermoautotrophicum* AksA(2)-MTH1481 gene, and the CYC1 terminator. The I26 construct includes the ADH1 promoter, the *Methanobacterium thermoautotrophicum* AksD(2)-MTH1631 gene, and the CYC1 terminator. The I27 construct includes the ADH1 promoter, the *Methanobacterium thermoautotrophicum* AksE(1)-MTH0829 gene, and the CYC1 terminator.

Patents, patent applications, publications, product descriptions, and protocols cited throughout this application are incorporated herein by reference in their entireties for all purposes.

We claim:

1. A method of converting a compound, the method comprising (a) contacting pimeloyl acyl carrier protein (PACP) with an enzyme that catalyzes the thioester hydrolysis of PACP to pimelic acid (PA), wherein PA is produced, and
   (b) further contacting the PA with an enzyme that catalyzes the carboxylic acid reduction of PA to pimelic acid semialdehyde (PAS), wherein PAS is produced.

2. The method of claim 1, wherein the enzyme that catalyzes the thioester hydrolysis of PACP to PA is a thioesterase, an acid-thiol ligase, or a CoA transferase.

3. The method of claim 2, wherein:
   the thioesterase is a thioesterase in EC 3.1.2;
   the acid-thiol ligase is an acid-thiol ligase in EC 6.2.1, and
   the CoA transferase is a CoA transferase in EC 2.8.3.

4. The method of claim 3, wherein:
   the thioesterase in EC 3.1.2 is one more of
      the thioesterase in EC 3.1.2.18, EC 3.1.2.19, or EC 3.1.2.20,
      the gene product of yciA,
      a thioesterase in EC 3.1.2.14, and
      the gene product of fatA or fatB;
   the acid-thiol ligase in EC 6.2,1 is
      an acid-thiol ligase in EC 6.2,1,14, or EC 6.2.1.23; and
   the CoA transferase in EC 2.8.3 is
      a CoA transferase in EC 2.8.3.12, EC 2.8.3.13, or EC 2.8.3.14.

5. The method of claim 1, wherein the PACP is produced by a process comprising one or more steps of the biotin biosynthesis pathway I (see FIG. 6).

6. The method of claim 1, wherein the enzyme that catalyzes the carboxylic acid reduction of PA to PAS is one or more of
a carboxylic acid reductase, and
a carboxylic acid reductase in EC 1.2.99.

7. The method of claim 6, wherein the carboxylic acid reductase in EC 1.2.99 is a carboxylic acid reductase in EC 1.2.99.6.

8. The method of claim 1, the method further comprising contacting PACP with an enzyme that catalyzes the reduction of PACP to PAS, wherein PAS is produced.

9. The method of claim 8, wherein the enzyme that catalyzes the reduction of PACP to PAS is one or more of
a fatty-acyl-CoA reductase or an aldehyde dehydrogenase;
a fatty-acyl-CoA reductase or an aldehyde dehydrogenase is a reductase in EC 1.2.1,
a fatty-acyl-CoA reductase or aldehyde dehydrogenase in EC 1.2.1.4, EC 1.2.1.50, EC 1.2.1.83, or EC 1.2.1.80.

10. The method of claim 8, wherein the PACP is produced by a process comprising one or more steps of:
the biotin biosynthesis pathway I (see FIG. 6).

11. The method of claim 8, wherein the enzyme, or one or more enzymes, is or are:
(i) isolated; (ii) in cell lysate, a partially purified cell lysate, cell lysates, or partially purified cell lysates; or (iii) in one or more host cell strains recombinantly expressing it or them.

12. The method of claim 1, the method further comprising contacting α-ketosuberate (AKS) with an enzyme that catalyzes the α-keto decarboxylation of AKA to PAS, wherein PAS is produced.

13. The method of claim 12, wherein the enzyme that catalyzes the α-keto decarboxylation of AKS to PAS is one or more of
a decarboxylase or an acetolactate synthase, and
an enzyme in EC.4.1.1.

14. The method of claim 13, wherein the AKS is produced by a process comprising one or more steps of:
(a) a pathway shown in FIG. 10; or
(b) the coenzyme B pathway of methanogenic archae (see FIG. 3).

15. The method of claim 12, wherein the AKS is produced by a process comprising one or more steps of:
(a) a pathway shown in FIG. 10; or
(b) the coenzyme B pathway of methanogenic archae (see FIG. 3).

16. The method of claim 12, wherein the enzyme, or one or more enzymes, is or are:
(i) isolated; (ii) in a cell lysate or partially purified cell lysate; or (iii) in a host cell recombinantly expressing it or them.

17. The method of claim 1, the method further comprising contacting AKS with an enzyme that catalyzes the transfer of an amino group to the AKS to produce α-amino suberate (AAS), wherein AAS is produced.

18. The method of claim 17, wherein the enzyme that catalyzes the transfer of an amino group to the AKS to produce α-amino suberate (AAS) is one or more of
an amino acid aminotransferase,
an aminotransferase in EC 2.6.1, or
an amino acid aminotransferase in EC 2.6.1.39, EC 2.6.1.42, or EC 2.6.1.67.

19. The method of claim 17, further comprising contacting the AAS with an enzyme that catalyzes the α-amino acid decarboxylation of the AAS to 7-amino-heptanoic acid (7 AHA), wherein 7 AHA is produced.

20. The method of claim 19, wherein the enzyme that catalyzes the α-amino acid decarboxylation of the AAS to 7-amino-heptanoic acid (7 AHA) is one or more of
a decarboxylase or an acetolactate synthase, or
an enzyme in EC.4.1.1.

21. The method of claim 19, further comprising contacting the 7 AHA with an enzyme that catalyzes the amide hydrolysis of the 7 AHA to enantholactam (ENTL), wherein ENTL is produced.

22. The method of claim 19, further comprising contacting the 7 AHA with an enzyme that catalyzes the aldehyde dehydrogenation of the 7 AHA to 7-amino-heptanal (7 AHT), wherein 7 AHT is produced.

23. The method of claim 22, further comprising contacting the 7 AHT with an enzyme that catalyzes the transfer of an amino group to the 7 AHT to produce 1,7-diaminoheptane (1,7 DAH), wherein 1,7 DAH is produced.

24. The method of claim 17, wherein the enzyme, or one or more enzymes, is or are:
(i) isolated; (ii) in a cell lysate or partially purified cell lysate; or (iii) in a host cell recombinantly expressing it or them.

25. The method of claim 1, the method further comprising contacting PAS with an enzyme that catalyzes the semialdehyde amination of the PAS to 7-amino-heptanoic acid (7 AHA), wherein 7 AHA is produced.

26. The method of claim 25, further comprising contacting the 7 AHA with an enzyme that catalyzes the amide hydrolysis of the 7 AHA to enantholactam (ENTL), wherein ENTL is produced.

27. The method of claim 25, further comprising:
contacting the 7 AHA with an enzyme that catalyzes the aldehyde dehydrogenation of the 7 AHA to 7-amino-heptanal (7 AHT), wherein AHT is produced; and
contacting the 7 AHT with an enzyme that catalyzes the transfer of an amino group to the 7 AHT to produce 1,7-diaminoheptane (1,7 DAH), wherein 1,7 DAH is produced.

28. The method of claim 25, wherein the PAS is produced by a process comprising:
(1) contacting a-ketosuberate (AKS) with an enzyme that catalyzes the α-keto decarboxylation of AKS to PAS; or
(2) one or more steps of the Tetralin degradation pathway (see FIG. 8).

29. The method of claim 25, wherein the enzyme, or one or more enzymes, is or are:
(i) isolated; (ii) in a cell lysate or partially purified cell lysate; or (iii) in a host cell recombinantly expressing it or them.

30. The method of claim 1, the method further comprising contacting 7 AHT with an enzyme that catalyzes the transfer of an amino group to the 7 AHT to produce 1,7-diaminoheptane (1,7 DAH), wherein 1,7 DAH is produced.

31. The method of claim 30, wherein the enzyme that catalyzes the transfer of an amino group to the 7 AHT to produce 1,7-diaminoheptane (1,7 DAH) is one or more of
an amino acid aminotransferase or an ω-transaminase,
an amino acid aminotransferase in EC 2.6.1 or an ω-transaminase in EC.2.6.1,
an amino acid aminotransferase in EC 2.6.1.39, EC 2.6.1.42, or EC 2.6.1.67, and
an ω-transaminase in EC 2.6.1.18, EC 2.6.1.19, or EC 2.6.1.39.

32. The method of claim 30, wherein the 7 AHT is produced by aldehyde dehydrogenation of 7 AHA, which is produced by one or steps of a pathway shown in FIG. 10.

33. The method of claim 30, wherein the enzyme, or one or more enzymes, is or are:
  (i) isolated; (ii) in a cell lysate or partially purified cell lysate; or (iii) in a host cell recombinantly expressing it or them.

34. The method of claim 1, wherein the enzyme in (a) or (b) is:
  (i) isolated; (ii) in a cell lysate or partially purified cell lysate; or (iii) in a host cell recombinantly expressing it.

35. An isolated cell comprising one or more exogenous nucleic acid encoding:
  (a) (I) a thiosterase, an acid thiol ligase, or a CoA transferase that catalyzes the thioester hydrolysis of PACP to PA; and (ii) a carboxylic acid reductase that catalyzes the carboxylic acid reduction of PA to PAS; and comprising PACP; and
  optionally further comprising one or more exogenous nucleic acid encoding:
  (b) (i) a fatty-acyl-CoA reductase or an aldehyde dehydrogenase; and (ii) an enzyme that catalyzes a reaction whose product is PACP;
  (c) (i) a keto add decarboxylase or an acetolactate synthase; and (ii) and enzyme that catalyzes a reaction whose product is AKS;
  (d) (i) an aminotransferase; and (ii) a decarboxylase or an acetolactate synthase; or
  (e) (i) an aminotransferase or a ω-transaminase; and (ii) an enzyme that catalyzes a reaction whose product is 7 AHT.

36. The cell of claim 35, wherein the cell is a prokaryotic cell or a eukaryotic cell.

37. The isolated cell of claim 35, wherein the exogenous nucleic acid encoding the thiosterase is selected from the group consisting of fatA and fatB; and wherein the exogenous nucleic acid encoding the carboxylic acid reductase is car from *Nocardia*.

38. The isolated cell of claim 37, wherein the isolated cell is a prokaryotic cell or a eukaryotic cell.

39. A method of converting a compound, the method comprising contacting PACP with an enzyme that catalyzes the thioester hydrolysis of PACP to PA, wherein the enzyme is the gene product of fatA or fatB.

40. The method of claim 39, wherein the PACP is produced by a process comprising one or more steps of the biotin biosynthesis pathway I (see FIG. 6).

41. The method of claim 39, further comprising contacting the PA with the gene product of car that catalyzes the carboxylic acid reduction of PA to PAS, wherein PAS is produced.

42. The method of claim 39 wherein the enzyme is: (i) isolated; (ii) in a cell lysate or partially purified cell lysate; or (iii) in a host cell recombinantly expressing it.

* * * * *

UNITED STATES PATENT AND TRADEMARK OFFICE
CERTIFICATE OF CORRECTION

PATENT NO. : 9,650,653 B2
APPLICATION NO. : 14/130117
DATED : May 16, 2017
INVENTOR(S) : Paul S. Pearlman et al.

Page 1 of 1

It is certified that error appears in the above-identified patent and that said Letters Patent is hereby corrected as shown below:

On the Title Page

Item [74], Attorney, Agent, or Firm, "Finnegan Henderson, Farabow, Garrett & Dunner, LLP; Carla A. Mouta-Bellum" should read -- William J. Simmons; Carla A. Mouta-Bellum, Ph.D. --.

In the Claims

Claim 4, Column 170, Line 52-53, "is one more of the thioesterase" should read -- is one or more of a thioesterase --.

Claim 4, Column 170, Line 59, "EC 6.2,1" should read -- EC 6.2.1 --.

Claim 4, Column 170, Line 60, "EC 6.2,1,14," should read -- EC 6.2.1.14, --.

Claim 32, Column 172, Line 67, "produced by one or steps" should read -- produced by one or more steps --.

Claim 35, Column 173, Line 23, "a keto add" should read -- keto acid --.

Signed and Sealed this
Nineteenth Day of December, 2017

Joseph Matal
*Performing the Functions and Duties of the
Under Secretary of Commerce for Intellectual Property and
Director of the United States Patent and Trademark Office*